(12) United States Patent
Shepard et al.

(10) Patent No.: US 11,926,616 B2
(45) Date of Patent: *Mar. 12, 2024

(54) AMINOPYRAZINE DIOL COMPOUNDS AS PI3K-γ INHIBITORS

(71) Applicant: Incyte Corporation, Wilmington, DE (US)

(72) Inventors: Stacey Shepard, Wilmington, DE (US); Andrew P. Combs, Kennett Square, PA (US); Nikoo Falahatpisheh, Wilmington, DE (US); Lixin Shao, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/540,860

(22) Filed: Dec. 2, 2021

(65) Prior Publication Data

US 2022/0213065 A1 Jul. 7, 2022

Related U.S. Application Data

(63) Continuation of application No. 16/847,975, filed on Apr. 14, 2020, now abandoned, which is a continuation of application No. 16/295,705, filed on Mar. 7, 2019, now Pat. No. 10,669,262.

(60) Provisional application No. 62/745,873, filed on Oct. 15, 2018, provisional application No. 62/702,230, filed on Jul. 23, 2018, provisional application No. 62/640,276, filed on Mar. 8, 2018.

(51) Int. Cl.
| | |
|---|---|
| *A61P 37/02* | (2006.01) |
| *A61P 9/00* | (2006.01) |
| *A61P 25/28* | (2006.01) |
| *A61P 35/00* | (2006.01) |
| *C07B 59/00* | (2006.01) |
| *C07D 241/20* | (2006.01) |
| *C07D 241/28* | (2006.01) |
| *C07D 403/04* | (2006.01) |
| *C07D 403/08* | (2006.01) |
| *C07D 403/14* | (2006.01) |
| *C07D 405/12* | (2006.01) |
| *C07D 413/04* | (2006.01) |
| *C07D 417/04* | (2006.01) |

(52) U.S. Cl.
CPC .............. *C07D 403/04* (2013.01); *A61P 9/00* (2018.01); *A61P 25/28* (2018.01); *A61P 35/00* (2018.01); *A61P 37/02* (2018.01); *C07B 59/002* (2013.01); *C07D 241/20* (2013.01); *C07D 241/28* (2013.01); *C07D 403/08* (2013.01); *C07D 403/14* (2013.01); *C07D 405/12* (2013.01); *C07D 413/04* (2013.01); *C07D 417/04* (2013.01); *C07B 2200/05* (2013.01)

(58) Field of Classification Search
CPC .. A61P 37/02; A61P 25/28; A61P 9/00; A61P 35/00

See application file for complete search history.

(56) References Cited

U.S. PATENT DOCUMENTS

| | | |
|---|---|---|
| 4,705,853 A | 11/1987 | Cale |
| 4,861,884 A | 8/1989 | Treybig |
| 4,921,860 A | 5/1990 | Cliffe |
| 4,971,909 A | 11/1990 | Kaneoya et al. |
| 5,025,096 A | 6/1991 | Chiu et al. |
| 5,155,117 A | 10/1992 | Reitz |
| 5,232,945 A | 8/1993 | Hulin |
| 5,252,737 A | 10/1993 | Stern et al. |
| 5,315,043 A | 5/1994 | Fernandez et al. |
| 5,393,860 A | 2/1995 | Kvakovszky et al. |
| 5,430,123 A | 7/1995 | Kvakovszky et al. |
| 5,436,134 A | 7/1995 | Haugland et al. |
| 5,459,266 A | 10/1995 | Kvakovszky et al. |
| 5,521,056 A | 5/1996 | Buchanan et al. |
| 5,521,184 A | 5/1996 | Zimmerman |

(Continued)

FOREIGN PATENT DOCUMENTS

| | | |
|---|---|---|
| AR | 86653 | 1/2014 |
| CA | 2464604 | 10/2004 |

(Continued)

OTHER PUBLICATIONS

Office Action in Colombian Appln. No. NC2020/0012169, dated Mar. 31, 2023, 6 pages (with machine translation).

(Continued)

*Primary Examiner* — Bruck Kifle
(74) *Attorney, Agent, or Firm* — Fish & Richardson P.C.

(57) ABSTRACT

This application relates to compounds of Formula (I):

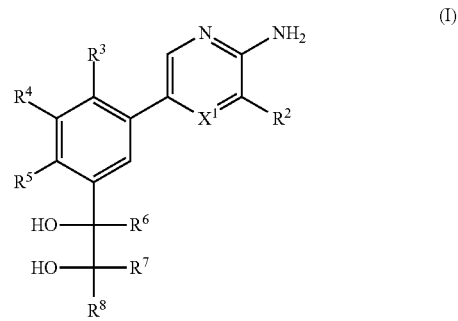

or pharmaceutically acceptable salts thereof, which are inhibitors of PI3K-γ which are useful for the treatment of disorders such as autoimmune diseases, cancer, cardiovascular diseases, and neurodegenerative diseases.

30 Claims, No Drawings

(56) References Cited

U.S. PATENT DOCUMENTS

| | | |
|---|---|---|
| 5,534,416 A | 7/1996 | Millard et al. |
| 5,545,535 A | 8/1996 | Ruth et al. |
| 5,602,156 A | 2/1997 | Kohn et al. |
| 5,621,027 A | 4/1997 | Roschger et al. |
| 5,656,449 A | 8/1997 | Yue |
| 5,672,592 A | 9/1997 | Jackson et al. |
| 5,677,459 A | 10/1997 | McDonald et al. |
| 5,705,512 A | 1/1998 | McDonald et al. |
| 5,716,971 A | 2/1998 | Shiraishi et al. |
| 5,723,477 A | 3/1998 | McDonald et al. |
| 5,756,508 A | 5/1998 | Thompson et al. |
| 5,811,442 A | 9/1998 | Bencherif et al. |
| 5,863,903 A | 1/1999 | Lundgren et al. |
| 5,869,487 A | 2/1999 | Coburn et al. |
| 5,880,137 A | 3/1999 | Miller et al. |
| 5,883,106 A | 3/1999 | Stevens et al. |
| 5,929,075 A | 7/1999 | Heeres et al. |
| 6,172,084 B1 | 1/2001 | Cuny et al. |
| 6,197,798 B1 | 3/2001 | Fink et al. |
| 6,207,679 B1 | 3/2001 | Cuny et al. |
| 6,274,598 B1 | 8/2001 | Ellis et al. |
| 6,559,167 B1 | 5/2003 | Garst et al. |
| 7,745,437 B2 | 6/2010 | Ren et al. |
| 7,872,031 B2 | 1/2011 | Lauffer et al. |
| 8,232,406 B2 | 7/2012 | Lauffer et al. |
| 8,410,112 B2 | 4/2013 | Charrier et al. |
| 8,741,931 B2 | 6/2014 | Jimenez et al. |
| 8,841,308 B2 | 9/2014 | Charrier et al. |
| 8,841,337 B2 | 9/2014 | Charrier et al. |
| 8,841,450 B2 | 9/2014 | Charrier et al. |
| 8,846,917 B2 | 9/2014 | Charrier et al. |
| 8,846,918 B2 | 9/2014 | Charrier et al. |
| 8,962,623 B2 | 2/2015 | Shetty et al. |
| 8,969,356 B2 | 3/2015 | Charrier et al. |
| 9,035,053 B2 | 5/2015 | Charrier et al. |
| 9,096,584 B2 | 8/2015 | Charrier et al. |
| 9,365,557 B2 | 6/2016 | Charrier et al. |
| 9,701,674 B2 | 7/2017 | Charrier et al. |
| 10,669,262 B2 | 6/2020 | Shepard et al. |
| 11,046,658 B2 | 6/2021 | Douty et al. |
| 2002/0103141 A1 | 8/2002 | McKearn et al. |
| 2002/0115678 A1 | 8/2002 | Ellis et al. |
| 2002/0169072 A1 | 11/2002 | Nakayama et al. |
| 2003/0008828 A1 | 1/2003 | Priestley et al. |
| 2003/0027798 A1 | 2/2003 | Druzgala et al. |
| 2003/0225142 A1 | 12/2003 | Crooks et al. |
| 2004/0082641 A1 | 4/2004 | Rytved et al. |
| 2004/0106621 A1 | 6/2004 | Wu et al. |
| 2004/0127519 A1 | 7/2004 | Reinhard et al. |
| 2004/0127719 A1 | 7/2004 | Yang et al. |
| 2004/0158065 A1 | 8/2004 | Berth et al. |
| 2004/0229873 A1 | 11/2004 | Harbige et al. |
| 2005/0048312 A1 | 3/2005 | Herron et al. |
| 2005/0069551 A1 | 3/2005 | Shoji et al. |
| 2005/0234046 A1 | 10/2005 | Zhao et al. |
| 2005/0234389 A1 | 10/2005 | Bouwstra et al. |
| 2005/0239826 A1 | 10/2005 | Stenkamp et al. |
| 2005/0282825 A1 | 12/2005 | Malamas et al. |
| 2005/0282826 A1 | 12/2005 | Malamas et al. |
| 2006/0205736 A1 | 9/2006 | Noble et al. |
| 2006/0270686 A1 | 11/2006 | Kelly et al. |
| 2007/0010573 A1 | 1/2007 | Kong et al. |
| 2007/0015752 A1 | 1/2007 | Hangauer |
| 2007/0039644 A1 | 2/2007 | Lee et al. |
| 2007/0060613 A1 | 3/2007 | Kim |
| 2007/0066619 A1 | 3/2007 | Hamilton et al. |
| 2007/0143936 A1 | 6/2007 | Lagrange |
| 2007/0190358 A1 | 8/2007 | Byun et al. |
| 2008/0009527 A1 | 1/2008 | Dumas et al. |
| 2008/0103074 A1 | 5/2008 | Stokes et al. |
| 2008/0184495 A1 | 8/2008 | Brun et al. |
| 2008/0255389 A1 | 10/2008 | Coggan et al. |
| 2008/0280891 A1 | 11/2008 | Kelly et al. |
| 2008/0281075 A1 | 11/2008 | Harwood et al. |
| 2008/0293739 A1 | 11/2008 | Trede |
| 2008/0300419 A1 | 12/2008 | Chen et al. |
| 2009/0011991 A1 | 1/2009 | Shoji et al. |
| 2009/0048280 A1 | 2/2009 | Burgoon, Jr. et al. |
| 2009/0093479 A1 | 4/2009 | Kelly et al. |
| 2009/0124602 A1 | 5/2009 | Maltais et al. |
| 2009/0124805 A1 | 5/2009 | Alleyne |
| 2009/0149653 A1 | 6/2009 | Cheng et al. |
| 2009/0163463 A1 | 6/2009 | Bruce et al. |
| 2009/0272946 A1 | 11/2009 | Lu |
| 2010/0036172 A1 | 2/2010 | Hung et al. |
| 2010/0056576 A1 | 3/2010 | Burger et al. |
| 2010/0099825 A1 | 4/2010 | Schmitz et al. |
| 2010/0160669 A1 | 6/2010 | Liu et al. |
| 2010/0184986 A1 | 7/2010 | Carter et al. |
| 2010/0273764 A1 | 10/2010 | Andrews et al. |
| 2011/0049497 A1 | 3/2011 | Ise |
| 2011/0082165 A1 | 4/2011 | Ellsworth et al. |
| 2011/0124663 A1 | 5/2011 | Conn et al. |
| 2011/0277841 A1 | 11/2011 | Chi et al. |
| 2011/0306707 A1 | 12/2011 | Benton et al. |
| 2012/0122708 A1 | 5/2012 | Castells et al. |
| 2012/0129888 A1 | 5/2012 | Castells et al. |
| 2012/0142930 A1 | 6/2012 | Castells et al. |
| 2012/0289481 A1 | 11/2012 | D'Neil et al. |
| 2013/0004859 A1 | 1/2013 | Yu et al. |
| 2013/0035323 A1 | 2/2013 | Amberg et al. |
| 2013/0056716 A1 | 3/2013 | Cheng et al. |
| 2013/0066029 A1 | 3/2013 | Radlauer et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0158031 A1 | 6/2013 | Cai et al. |
| 2013/0158067 A1 | 6/2013 | Woller et al. |
| 2013/0224121 A1 | 8/2013 | Fukui et al. |
| 2013/0261106 A1 | 10/2013 | Carry et al. |
| 2013/0267521 A1 | 10/2013 | Castro et al. |
| 2014/0088117 A1 | 3/2014 | Burch et al. |
| 2014/0117318 A1 | 5/2014 | Choi et al. |
| 2014/0148484 A1 | 5/2014 | Schnapp et al. |
| 2014/0171525 A1 | 6/2014 | Yu et al. |
| 2014/0178815 A1 | 6/2014 | Jung et al. |
| 2014/0200227 A1 | 7/2014 | Xue et al. |
| 2014/0249132 A1 | 9/2014 | Li et al. |
| 2014/0275070 A1 | 9/2014 | Grembecka et al. |
| 2014/0275167 A1 | 9/2014 | Hartman |
| 2014/0288067 A1 | 9/2014 | Chesworth et al. |
| 2015/0057300 A1 | 2/2015 | Tafesse et al. |
| 2015/0137096 A1 | 5/2015 | Xia et al. |
| 2015/0141434 A1 | 5/2015 | Park |
| 2015/0171349 A1 | 6/2015 | Ma et al. |
| 2015/0197513 A1 | 7/2015 | Wrasidlo et al. |
| 2015/0249222 A1 | 9/2015 | Szigethy et al. |
| 2015/0306227 A1 | 10/2015 | Cruise et al. |
| 2015/0322076 A1 | 11/2015 | Chen et al. |
| 2015/0342951 A1 | 12/2015 | Cooke et al. |
| 2015/0359797 A1 | 12/2015 | Helleday et al. |
| 2016/0122302 A1 | 5/2016 | Silverman et al. |
| 2016/0176857 A1 | 6/2016 | Ly |
| 2016/0200731 A1 | 7/2016 | Mickle et al. |
| 2016/0246152 A1 | 8/2016 | Igawa et al. |
| 2016/0311809 A1 | 10/2016 | Charrier et al. |
| 2016/0340311 A1 | 11/2016 | Biswas et al. |
| 2016/0359122 A1 | 12/2016 | Boudreault et al. |
| 2017/0092880 A1 | 3/2017 | Boudreault et al. |
| 2017/0101394 A1 | 4/2017 | Zhang |
| 2017/0101395 A1 | 4/2017 | Zhang |
| 2017/0101403 A1 | 4/2017 | Zhang |
| 2017/0186964 A1 | 6/2017 | Cho et al. |
| 2017/0186975 A1 | 6/2017 | Kim et al. |
| 2017/0190689 A1 | 7/2017 | Sparks et al. |
| 2017/0204080 A1 | 7/2017 | Chen et al. |
| 2017/0232016 A1 | 8/2017 | Zou et al. |
| 2017/0275278 A1 | 9/2017 | Silverman et al. |
| 2017/0294597 A1 | 10/2017 | Tsai et al. |
| 2017/0305861 A1 | 10/2017 | Kim et al. |
| 2018/0086709 A1 | 3/2018 | Choi et al. |
| 2018/0173922 A1 | 6/2018 | Ghavanini et al. |
| 2019/0276435 A1 | 9/2019 | Shepard et al. |

(56) References Cited

U.S. PATENT DOCUMENTS

| | | | |
|---|---|---|---|
| 2020/0002295 | A1 | 1/2020 | Douty et al. |
| 2020/0339542 | A1 | 10/2020 | Shepard et al. |
| 2022/0411383 | A1 | 12/2022 | Douty et al. |

FOREIGN PATENT DOCUMENTS

| | | |
|---|---|---|
| CA | 2956996 | 2/2016 |
| CL | 201400517 | 8/2014 |
| CL | 201400498 | 12/2014 |
| CN | 1374306 | 10/2002 |
| CN | 101058577 | 10/2007 |
| CN | 101384586 | 3/2009 |
| CN | 101513584 | 8/2009 |
| CN | 101591332 | 12/2009 |
| CN | 101712809 | 5/2010 |
| CN | 101781200 | 7/2010 |
| CN | 102125875 | 7/2011 |
| CN | 102260218 | 11/2011 |
| CN | 102428087 | 4/2012 |
| CN | 102548984 | 7/2012 |
| CN | 102850328 | 1/2013 |
| CN | 103087050 | 5/2013 |
| CN | 103193702 | 7/2013 |
| CN | 103524372 | 1/2014 |
| CN | 103588771 | 2/2014 |
| CN | 103664878 | 3/2014 |
| CN | 103694236 | 4/2014 |
| CN | 103804312 | 5/2014 |
| CN | 103848838 | 6/2014 |
| CN | 103923085 | 7/2014 |
| CN | 104004026 | 8/2014 |
| CN | 104557863 | 4/2015 |
| CN | 104703979 | 6/2015 |
| CN | 104744348 | 7/2015 |
| CN | 104926788 | 9/2015 |
| CN | 104927742 | 9/2015 |
| CN | 105175202 | 12/2015 |
| CN | 105315199 | 2/2016 |
| CN | 106831735 | 6/2017 |
| CN | 106905299 | 6/2017 |
| CO | 6331431 | 10/2011 |
| CO | 6640285 | 3/2013 |
| DE | 3628223 | 2/1987 |
| DE | 19509353 | 10/1995 |
| DE | 19718742 | 11/1998 |
| DE | 102009055828 | 7/2010 |
| DE | 102010054892 | 6/2012 |
| DE | 102012006896 | 10/2013 |
| EP | 0553009 | 7/1993 |
| EP | 0695743 | 2/1996 |
| EP | 0808838 | 11/1997 |
| EP | 0827135 | 3/1998 |
| EP | 0879814 | 11/1998 |
| EP | 0930302 | 7/1999 |
| EP | 1837330 | 9/2007 |
| EP | 2396307 | 12/2011 |
| EP | 2524918 | 11/2012 |
| EP | 2723722 | 4/2014 |
| EP | 3051604 | 8/2016 |
| EP | 3116506 | 1/2017 |
| EP | 3128041 | 2/2017 |
| ES | 2379919 | 5/2012 |
| GB | 2290489 | 1/1996 |
| IN | 110DEL2012 | 5/2015 |
| IT | 2006MI0895 | 8/2006 |
| IT | MI20110208 | 8/2012 |
| JP | 05058997 | 3/1993 |
| JP | 06001776 | 1/1994 |
| JP | H06256327 | 9/1994 |
| JP | H06340642 | 12/1994 |
| JP | 07082249 | 3/1995 |
| JP | H08175994 | 7/1996 |
| JP | H08337583 | 12/1996 |
| JP | H10188264 | 7/1998 |
| JP | H10324687 | 12/1998 |
| JP | H11292883 | 10/1999 |
| JP | 2000073094 | 3/2000 |
| JP | 2000076640 | 3/2000 |
| JP | 2000076642 | 3/2000 |
| JP | 2000076643 | 3/2000 |
| JP | 2001072660 | 3/2001 |
| JP | 2001089460 | 4/2001 |
| JP | 2001247548 | 9/2001 |
| JP | 2002338837 | 11/2002 |
| JP | 2003012645 | 1/2003 |
| JP | 2003040809 | 2/2003 |
| JP | 2003212706 | 7/2003 |
| JP | 2003292408 | 10/2003 |
| JP | 3502629 | 3/2004 |
| JP | 2004067540 | 3/2004 |
| JP | 2004123617 | 4/2004 |
| JP | 2004143061 | 5/2004 |
| JP | 2004143163 | 5/2004 |
| JP | 2004196670 | 7/2004 |
| JP | 2005029500 | 2/2005 |
| JP | 2005126586 | 5/2005 |
| JP | 2006041020 | 2/2006 |
| JP | 2007039388 | 2/2007 |
| JP | 2007145819 | 6/2007 |
| JP | 2007161674 | 6/2007 |
| JP | 2009001742 | 1/2009 |
| JP | 2009007342 | 1/2009 |
| JP | 2009023986 | 2/2009 |
| JP | 2010143829 | 7/2010 |
| JP | 2012036125 | 2/2012 |
| JP | 2013129651 | 7/2013 |
| JP | 2013129653 | 7/2013 |
| JP | 2014001205 | 1/2014 |
| JP | 2014015447 | 1/2014 |
| JP | 2014037382 | 2/2014 |
| JP | 2014078381 | 5/2014 |
| JP | 2014078382 | 5/2014 |
| JP | 2014111559 | 6/2014 |
| JP | 2014198841 | 10/2014 |
| JP | 2014198843 | 10/2014 |
| JP | 2014198844 | 10/2014 |
| JP | 2015003895 | 1/2015 |
| JP | 2015017236 | 1/2015 |
| JP | 2015043445 | 3/2015 |
| JP | 2015122247 | 7/2015 |
| JP | 2015125845 | 7/2015 |
| JP | 2015141806 | 8/2015 |
| JP | 2015193569 | 11/2015 |
| JP | 2016124730 | 7/2016 |
| JP | 2017019789 | 1/2017 |
| KR | RD 371041 | 3/1995 |
| KR | 20080049767 | 6/2008 |
| KR | 20100001274 | 1/2010 |
| KR | 20120063028 | 6/2012 |
| KR | 20130122361 | 11/2013 |
| KR | 20160126792 | 11/2016 |
| KR | 20170036233 | 4/2017 |
| KR | 20170093273 | 8/2017 |
| TW | I388566 | 3/2013 |
| WO | WO 98/29114 | 7/1988 |
| WO | WO 91/17979 | 11/1991 |
| WO | WO 94/22853 | 10/1994 |
| WO | WO 94/24213 | 10/1994 |
| WO | WO 94/25425 | 11/1994 |
| WO | WO 95/07695 | 3/1995 |
| WO | WO 95/08327 | 3/1995 |
| WO | WO 95/24391 | 9/1995 |
| WO | WO 95/29155 | 11/1995 |
| WO | WO 95/34564 | 12/1995 |
| WO | WO 96/11910 | 4/1996 |
| WO | WO 96/11911 | 4/1996 |
| WO | WO 96/13499 | 5/1996 |
| WO | WO 96/15123 | 5/1996 |
| WO | WO 96/18394 | 6/1996 |
| WO | WO 96/21651 | 7/1996 |
| WO | WO 96/37486 | 11/1996 |
| WO | WO 97/01538 | 1/1997 |
| WO | WO 97/11943 | 4/1997 |
| WO | WO 97/12864 | 4/1997 |

(56) References Cited

FOREIGN PATENT DOCUMENTS

| | | |
|---|---|---|
| WO | WO 97/16187 | 5/1997 |
| WO | WO 97/16192 | 5/1997 |
| WO | WO 97/21702 | 6/1997 |
| WO | WO 97/26258 | 7/1997 |
| WO | WO 97/33872 | 9/1997 |
| WO | WO 97/43267 | 11/1997 |
| WO | WO 98/05642 | 2/1998 |
| WO | WO 98/07702 | 2/1998 |
| WO | WO 98/13361 | 4/1998 |
| WO | WO 98/14436 | 4/1998 |
| WO | WO 98/17274 | 4/1998 |
| WO | WO 98/18326 | 5/1998 |
| WO | WO 98/27098 | 6/1998 |
| WO | WO 98/35961 | 8/1998 |
| WO | WO 98/55480 | 12/1998 |
| WO | WO 99/01453 | 1/1999 |
| WO | WO 99/02503 | 1/1999 |
| WO | WO 99/15169 | 4/1999 |
| WO | WO 99/27930 | 6/1999 |
| WO | WO 99/32110 | 7/1999 |
| WO | WO 99/32117 | 7/1999 |
| WO | WO 99/32455 | 7/1999 |
| WO | WO 99/33810 | 7/1999 |
| WO | WO 99/38829 | 8/1999 |
| WO | WO 99/55313 | 11/1999 |
| WO | WO 99/57113 | 11/1999 |
| WO | WO 99/63984 | 12/1999 |
| WO | WO 99/64407 | 12/1999 |
| WO | WO 00/05201 | 2/2000 |
| WO | WO 00/009495 | 2/2000 |
| WO | WO 00/09498 | 2/2000 |
| WO | WO 00/15615 | 3/2000 |
| WO | WO 00/25139 | 5/2000 |
| WO | WO 00/34230 | 6/2000 |
| WO | WO 00/34277 | 6/2000 |
| WO | WO 00/39094 | 7/2000 |
| WO | WO 00/43405 | 7/2000 |
| WO | WO 00/053595 | 9/2000 |
| WO | WO 01/04076 | 1/2001 |
| WO | WO 01/07407 | 2/2001 |
| WO | WO 01/014402 | 3/2001 |
| WO | WO 01/16122 | 3/2001 |
| WO | WO 01/32658 | 5/2001 |
| WO | WO 01/36415 | 5/2001 |
| WO | WO 01/40188 | 6/2001 |
| WO | WO 01/064655 | 9/2001 |
| WO | WO 01/81328 | 11/2001 |
| WO | WO 01/87853 | 11/2001 |
| WO | WO 02/000196 | 1/2002 |
| WO | WO 02/00648 | 1/2002 |
| WO | WO 02/06271 | 1/2002 |
| WO | WO 02/08199 | 1/2002 |
| WO | WO 02/09759 | 2/2002 |
| WO | WO 02/20501 | 3/2002 |
| WO | WO 02/24689 | 3/2002 |
| WO | WO 02/038628 | 5/2002 |
| WO | WO 02/042272 | 5/2002 |
| WO | WO 02/042306 | 5/2002 |
| WO | WO 02/046162 | 6/2002 |
| WO | WO 02/060877 | 8/2002 |
| WO | WO 02/069712 | 9/2002 |
| WO | WO 02/070514 | 9/2002 |
| WO | WO 02/072543 | 9/2002 |
| WO | WO 02/076395 | 10/2002 |
| WO | WO 02/079143 | 10/2002 |
| WO | WO 02/089738 | 11/2002 |
| WO | WO 03/004475 | 1/2003 |
| WO | WO 03/024441 | 3/2003 |
| WO | WO 03/024967 | 3/2003 |
| WO | WO 03/028684 | 4/2003 |
| WO | WO 03/034824 | 5/2003 |
| WO | WO 03/037347 | 5/2003 |
| WO | WO 03/040257 | 5/2003 |
| WO | WO 03/044015 | 5/2003 |
| WO | WO 03/053441 | 7/2003 |
| WO | WO 03/059348 | 7/2003 |
| WO | WO 03/059886 | 7/2003 |
| WO | WO 03/062201 | 7/2003 |
| WO | WO 03/062215 | 7/2003 |
| WO | WO 2003/057205 | 7/2003 |
| WO | WO 03/072548 | 9/2003 |
| WO | WO 03/074148 | 9/2003 |
| WO | WO 03/092889 | 11/2003 |
| WO | WO 2003/093258 | 11/2003 |
| WO | WO 2003/097644 | 11/2003 |
| WO | WO 03/099771 | 12/2003 |
| WO | WO 03/104220 | 12/2003 |
| WO | WO 2004/002948 | 1/2004 |
| WO | WO 2004/005281 | 1/2004 |
| WO | WO 2004/012726 | 2/2004 |
| WO | WO 2004/016600 | 2/2004 |
| WO | WO 2004/017920 | 3/2004 |
| WO | WO 2004/019863 | 3/2004 |
| WO | WO 2004/020413 | 3/2004 |
| WO | WO 2004/033444 | 4/2004 |
| WO | WO 2004/043443 | 5/2004 |
| WO | WO 2004/043956 | 5/2004 |
| WO | WO 2004/046120 | 6/2004 |
| WO | WO 2004/047840 | 6/2004 |
| WO | WO 2004/052890 | 6/2004 |
| WO | WO 04/056786 | 7/2004 |
| WO | WO 2004/054505 | 7/2004 |
| WO | WO 2004/055006 | 7/2004 |
| WO | WO 2004/055015 | 7/2004 |
| WO | WO 2004/056786 | 7/2004 |
| WO | WO 2004/058778 | 7/2004 |
| WO | WO 2004/064755 | 8/2004 |
| WO | WO 2004/065388 | 8/2004 |
| WO | WO 2004/069160 | 8/2004 |
| WO | WO 2004/069805 | 8/2004 |
| WO | WO 2004/069808 | 8/2004 |
| WO | WO 04/080980 | 9/2004 |
| WO | WO 2004/080980 | 9/2004 |
| WO | WO 2004/089910 | 10/2004 |
| WO | WO 2004/094372 | 11/2004 |
| WO | WO 2004/094405 | 11/2004 |
| WO | WO 2004/094406 | 11/2004 |
| WO | WO 2004/094416 | 11/2004 |
| WO | WO 2004/100943 | 11/2004 |
| WO | WO 2004/104052 | 12/2004 |
| WO | WO 2004/108673 | 12/2004 |
| WO | WO 2004/108686 | 12/2004 |
| WO | WO 2004/113258 | 12/2004 |
| WO | WO 2004/113277 | 12/2004 |
| WO | WO 2005/000309 | 1/2005 |
| WO | WO 2005/005382 | 1/2005 |
| WO | WO 2005/012298 | 2/2005 |
| WO | WO 05/028444 | 3/2005 |
| WO | WO 2005/025623 | 3/2005 |
| WO | WO 2005/026166 | 3/2005 |
| WO | WO 2005/028444 | 3/2005 |
| WO | WO 2005/030766 | 4/2005 |
| WO | WO 2005/047215 | 5/2005 |
| WO | WO 2005/049619 | 6/2005 |
| WO | WO 2005/054232 | 6/2005 |
| WO | WO 2005/058876 | 6/2005 |
| WO | WO 2005/066162 | 7/2005 |
| WO | WO 2005/074940 | 8/2005 |
| WO | WO 2005/075452 | 8/2005 |
| WO | WO 2005/079802 | 9/2005 |
| WO | WO 2005/092836 | 10/2005 |
| WO | WO 2005/099688 | 10/2005 |
| WO | WO 2005/105790 | 11/2005 |
| WO | WO 2005/115994 | 12/2005 |
| WO | WO 2006/002823 | 1/2006 |
| WO | WO 2006/010546 | 2/2006 |
| WO | WO 2006/038606 | 4/2006 |
| WO | WO 2006/047772 | 5/2006 |
| WO | WO 2006/051704 | 5/2006 |
| WO | WO 2006/051937 | 5/2006 |
| WO | WO 2006/055187 | 5/2006 |
| WO | WO 2006/055725 | 5/2006 |
| WO | WO 2006/056399 | 6/2006 |
| WO | WO 2006/056854 | 6/2006 |

(56) References Cited

FOREIGN PATENT DOCUMENTS

| | | |
|---|---|---|
| WO | WO 2006/060762 | 6/2006 |
| WO | WO 2006/069287 | 6/2006 |
| WO | WO 2006/070195 | 7/2006 |
| WO | WO 2006/080884 | 8/2006 |
| WO | WO 2006/082001 | 8/2006 |
| WO | WO 2006/084773 | 8/2006 |
| WO | WO 2006/088836 | 8/2006 |
| WO | WO 2006/103254 | 10/2006 |
| WO | WO 2006/114401 | 11/2006 |
| WO | WO 2006/124874 | 11/2006 |
| WO | WO 2006/128563 | 12/2006 |
| WO | WO 2006/138166 | 12/2006 |
| WO | WO 2007/000250 | 1/2007 |
| WO | WO 2007/006380 | 1/2007 |
| WO | WO 2007/009083 | 1/2007 |
| WO | WO 2007/009389 | 1/2007 |
| WO | WO 2007/011721 | 1/2007 |
| WO | WO 2007/016674 | 2/2007 |
| WO | WO 2007/023186 | 3/2007 |
| WO | WO 2007/025169 | 3/2007 |
| WO | WO 2007/031828 | 3/2007 |
| WO | WO 2007/033781 | 3/2007 |
| WO | WO 2007/038459 | 4/2007 |
| WO | WO 2007/044779 | 4/2007 |
| WO | WO 2007/049098 | 5/2007 |
| WO | WO 2007/051981 | 5/2007 |
| WO | WO 2007/055183 | 5/2007 |
| WO | WO 2007/063935 | 6/2007 |
| WO | WO 2007/064914 | 6/2007 |
| WO | WO 2007/073855 | 7/2007 |
| WO | WO 2007/077048 | 7/2007 |
| WO | WO 2007/077057 | 7/2007 |
| WO | WO 2007/077435 | 7/2007 |
| WO | WO 2007/085718 | 8/2007 |
| WO | WO 2007/091110 | 8/2007 |
| WO | WO 2007/101531 | 9/2007 |
| WO | WO 2007/107543 | 9/2007 |
| WO | WO 2007/109238 | 9/2007 |
| WO | WO 2007/111904 | 10/2007 |
| WO | WO 2007/112347 | 10/2007 |
| WO | WO 2007/113258 | 10/2007 |
| WO | WO 2007/120655 | 10/2007 |
| WO | WO 2007/120718 | 10/2007 |
| WO | WO 2007/124849 | 11/2007 |
| WO | WO 2007/125061 | 11/2007 |
| WO | WO 2007/129664 | 11/2007 |
| WO | WO 2007/137790 | 12/2007 |
| WO | WO 2007/147874 | 12/2007 |
| WO | WO 2008/002676 | 1/2008 |
| WO | WO 2008/004942 | 1/2008 |
| WO | WO 2008/005937 | 1/2008 |
| WO | WO 2008/006663 | 1/2008 |
| WO | WO 2008/007900 | 1/2008 |
| WO | WO 2008/008453 | 1/2008 |
| WO | WO 2008/016968 | 2/2008 |
| WO | WO 2008/025820 | 3/2008 |
| WO | WO 2008/034600 | 3/2008 |
| WO | WO 2008/038010 | 4/2008 |
| WO | WO 2008/038955 | 4/2008 |
| WO | WO 2008/043533 | 4/2008 |
| WO | WO 2008/044713 | 4/2008 |
| WO | WO 2008/046527 | 4/2008 |
| WO | WO 2008/052733 | 5/2008 |
| WO | WO 2008/054117 | 5/2008 |
| WO | WO 2008/070908 | 6/2008 |
| WO | WO 2008/071937 | 6/2008 |
| WO | WO 2008/073480 | 6/2008 |
| WO | WO 2008/073933 | 6/2008 |
| WO | WO 2008/074997 | 6/2008 |
| WO | WO 2008/077625 | 7/2008 |
| WO | WO 2008/080504 | 7/2008 |
| WO | WO 2008/094992 | 8/2008 |
| WO | WO 2008/095785 | 8/2008 |
| WO | WO 2008/100620 | 8/2008 |
| WO | WO 2008/116665 | 10/2008 |
| WO | WO 2008/116671 | 10/2008 |
| WO | WO 2008/124092 | 10/2008 |
| WO | WO 2008/127727 | 10/2008 |
| WO | WO 2008/127728 | 10/2008 |
| WO | WO 2008/132091 | 11/2008 |
| WO | WO 2008/137128 | 11/2008 |
| WO | WO 2008/143440 | 11/2008 |
| WO | WO 2008/144464 | 11/2008 |
| WO | WO 2008/145335 | 12/2008 |
| WO | WO 2008/147154 | 12/2008 |
| WO | WO 2008/150899 | 12/2008 |
| WO | WO 2008/151211 | 12/2008 |
| WO | WO 2009/002970 | 12/2008 |
| WO | WO 2009/007390 | 1/2009 |
| WO | WO 2009/013348 | 1/2009 |
| WO | WO 2009/014637 | 1/2009 |
| WO | WO 2009/051705 | 4/2009 |
| WO | WO 2009/054941 | 4/2009 |
| WO | WO 2009/057978 | 5/2009 |
| WO | WO 2009/071701 | 6/2009 |
| WO | WO 2009/073246 | 6/2009 |
| WO | WO 2009/086731 | 7/2009 |
| WO | WO 2009/087305 | 7/2009 |
| WO | WO 2009/088103 | 7/2009 |
| WO | WO 2009/092590 | 7/2009 |
| WO | WO 2009/093082 | 7/2009 |
| WO | WO 2009/100130 | 8/2009 |
| WO | WO 2009/102588 | 8/2009 |
| WO | WO 2009/105717 | 8/2009 |
| WO | WO 2009/109539 | 9/2009 |
| WO | WO 2009/112461 | 9/2009 |
| WO | WO 2009/112826 | 9/2009 |
| WO | WO 2009/112839 | 9/2009 |
| WO | WO 2009/114173 | 9/2009 |
| WO | WO 2009/115517 | 9/2009 |
| WO | WO 2009/120872 | 10/2009 |
| WO | WO 2009/123241 | 10/2009 |
| WO | WO 2009/135590 | 11/2009 |
| WO | WO 2009/141532 | 11/2009 |
| WO | WO 2009/144961 | 12/2009 |
| WO | WO 2009/147190 | 12/2009 |
| WO | WO 2009/148052 | 12/2009 |
| WO | WO 2009/158257 | 12/2009 |
| WO | WO 2009/158467 | 12/2009 |
| WO | WO 2009144394 | 12/2009 |
| WO | WO 2010/000198 | 1/2010 |
| WO | WO 2010/019930 | 2/2010 |
| WO | WO 2010/027583 | 3/2010 |
| WO | WO 2010/028151 | 3/2010 |
| WO | WO 2010/029082 | 3/2010 |
| WO | WO 2010/029300 | 3/2010 |
| WO | WO 2010/033168 | 3/2010 |
| WO | WO 2010/034500 | 4/2010 |
| WO | WO 2010/042500 | 4/2010 |
| WO | WO 2010/042799 | 4/2010 |
| WO | WO 2010/043784 | 4/2010 |
| WO | WO 2010/047712 | 4/2010 |
| WO | WO 2010/048131 | 4/2010 |
| WO | WO 2010/054398 | 5/2010 |
| WO | WO 2010/056992 | 5/2010 |
| WO | WO 2010/061903 | 6/2010 |
| WO | WO 2010/065333 | 6/2010 |
| WO | WO 2010/071837 | 6/2010 |
| WO | WO 2010/080488 | 7/2010 |
| WO | WO 2010/091384 | 8/2010 |
| WO | WO 2010/100475 | 9/2010 |
| WO | WO 2010/111573 | 9/2010 |
| WO | WO 2010/137302 | 12/2010 |
| WO | WO 2010/138901 | 12/2010 |
| WO | WO 2010/148351 | 12/2010 |
| WO | WO 2010/149819 | 12/2010 |
| WO | WO 2010/150204 | 12/2010 |
| WO | WO 2011/000992 | 1/2011 |
| WO | WO 2011/002991 | 1/2011 |
| WO | WO 2011/005786 | 1/2011 |
| WO | WO 2011/005793 | 1/2011 |
| WO | WO 2011/005842 | 1/2011 |
| WO | WO 2011/006074 | 1/2011 |
| WO | WO 2011/013681 | 2/2011 |

(56) References Cited

FOREIGN PATENT DOCUMENTS

| | | |
|---|---|---|
| WO | WO 2011/027289 | 3/2011 |
| WO | WO 2011/028638 | 3/2011 |
| WO | WO 2011/032034 | 3/2011 |
| WO | WO 2011/032277 | 3/2011 |
| WO | WO 2011/035855 | 3/2011 |
| WO | WO 2011/036461 | 3/2011 |
| WO | WO 2011/049150 | 4/2011 |
| WO | WO 2011/050323 | 4/2011 |
| WO | WO 2011/071109 | 6/2011 |
| WO | WO 2011/071860 | 6/2011 |
| WO | WO 2011/072064 | 6/2011 |
| WO | WO 2011/072791 | 6/2011 |
| WO | WO 2011/081937 | 7/2011 |
| WO | WO 2011/081945 | 7/2011 |
| WO | WO 2011/082488 | 7/2011 |
| WO | WO 2011/083304 | 7/2011 |
| WO | WO 2011/086531 | 7/2011 |
| WO | WO 2011/092140 | 8/2011 |
| WO | WO 2011/095196 | 8/2011 |
| WO | WO 2011/115940 | 9/2011 |
| WO | WO 2011/124580 | 10/2011 |
| WO | WO 2011/129936 | 10/2011 |
| WO | WO 2011/141642 | 11/2011 |
| WO | WO 2011/143365 | 11/2011 |
| WO | WO 2011/143422 | 11/2011 |
| WO | WO 2011/147038 | 12/2011 |
| WO | WO 2011/161612 | 12/2011 |
| WO | WO 2012/003189 | 1/2012 |
| WO | WO 2012/003912 | 1/2012 |
| WO | WO 2012/007869 | 1/2012 |
| WO | WO 2012/007877 | 1/2012 |
| WO | WO 2012/009227 | 1/2012 |
| WO | WO 2012/032065 | 3/2012 |
| WO | WO 2012/036278 | 3/2012 |
| WO | WO 2012/069852 | 5/2012 |
| WO | WO 2012/072620 | 6/2012 |
| WO | WO 2012/074869 | 6/2012 |
| WO | WO 2012/108879 | 8/2012 |
| WO | WO 2012/108881 | 8/2012 |
| WO | WO 2012/112956 | 8/2012 |
| WO | WO 2012/116137 | 8/2012 |
| WO | WO 2012/125629 | 9/2012 |
| WO | WO 2012/136111 | 10/2012 |
| WO | WO 2012/138938 | 10/2012 |
| WO | WO 2012/141487 | 10/2012 |
| WO | WO 2012/151355 | 11/2012 |
| WO | WO 2012/162334 | 11/2012 |
| WO | WO 2012/163489 | 12/2012 |
| WO | WO 2012/177639 | 12/2012 |
| WO | WO 2012/178123 | 12/2012 |
| WO | WO 2012/178125 | 12/2012 |
| WO | WO 2013/007707 | 1/2013 |
| WO | WO 2013/021276 | 2/2013 |
| WO | WO 2013/024003 | 2/2013 |
| WO | WO 2013/024005 | 2/2013 |
| WO | WO 2013/024169 | 2/2013 |
| WO | WO 2013/025805 | 2/2013 |
| WO | WO 2013/033569 | 3/2013 |
| WO | WO 2013/042137 | 3/2013 |
| WO | WO 2013/043764 | 3/2013 |
| WO | WO 2013/043765 | 3/2013 |
| WO | WO 2013/043767 | 3/2013 |
| WO | WO 2013/043797 | 3/2013 |
| WO | WO 2013/043799 | 3/2013 |
| WO | WO 2013/043825 | 3/2013 |
| WO | WO 2013/043846 | 3/2013 |
| WO | WO 2013/043874 | 3/2013 |
| WO | WO 2013/043912 | 3/2013 |
| WO | WO 2013/049726 | 4/2013 |
| WO | WO 2013/052391 | 4/2013 |
| WO | WO 2013/054764 | 4/2013 |
| WO | WO 2013/059194 | 4/2013 |
| WO | WO 2013/063204 | 5/2013 |
| WO | WO 2013/063549 | 5/2013 |
| WO | WO 2013/069242 | 5/2013 |
| WO | WO 2013/072758 | 5/2013 |
| WO | WO 2013/076092 | 5/2013 |
| WO | WO 2013/088315 | 6/2013 |
| WO | WO 2013/092936 | 6/2013 |
| WO | WO 2013/092939 | 6/2013 |
| WO | WO 2013/096226 | 6/2013 |
| WO | WO 2013/099867 | 7/2013 |
| WO | WO 2013/102826 | 7/2013 |
| WO | WO 2013/115280 | 8/2013 |
| WO | WO 2013/117649 | 8/2013 |
| WO | WO 2013/134079 | 9/2013 |
| WO | WO 2013/148227 | 10/2013 |
| WO | WO 2013/152727 | 10/2013 |
| WO | WO 2013/161929 | 10/2013 |
| WO | WO 2013/162061 | 10/2013 |
| WO | WO 2013/164769 | 11/2013 |
| WO | WO 2013/171729 | 11/2013 |
| WO | WO 2013/179049 | 12/2013 |
| WO | WO 2013/184794 | 12/2013 |
| WO | WO 2013/189848 | 12/2013 |
| WO | WO 2014/007395 | 1/2014 |
| WO | WO 2014/011768 | 1/2014 |
| WO | WO 2014/018741 | 1/2014 |
| WO | WO 2014/033631 | 3/2014 |
| WO | WO 2014/039714 | 3/2014 |
| WO | WO 2014/057078 | 4/2014 |
| WO | WO 2014/065073 | 5/2014 |
| WO | WO 2014/065209 | 5/2014 |
| WO | WO 2014/065236 | 5/2014 |
| WO | WO 2014/077285 | 5/2014 |
| WO | WO 2014/090147 | 6/2014 |
| WO | WO 2014/098831 | 6/2014 |
| WO | WO 2014/099834 | 6/2014 |
| WO | WO 2014/099836 | 6/2014 |
| WO | WO 2014/101295 | 7/2014 |
| WO | WO 2014/104387 | 7/2014 |
| WO | WO 2014/110297 | 7/2014 |
| WO | WO 2014/117718 | 8/2014 |
| WO | WO 2014/128591 | 8/2014 |
| WO | WO 2014/130582 | 8/2014 |
| WO | WO 2014/135617 | 9/2014 |
| WO | WO 2014/147021 | 9/2014 |
| WO | WO 2014/152588 | 9/2014 |
| WO | WO 2014/157994 | 10/2014 |
| WO | WO 2014/160185 | 10/2014 |
| WO | WO 2014/167084 | 10/2014 |
| WO | WO 2014/170873 | 10/2014 |
| WO | WO 2014/184343 | 11/2014 |
| WO | WO 2014/186450 | 11/2014 |
| WO | WO 2014/192902 | 12/2014 |
| WO | WO 2014/200882 | 12/2014 |
| WO | WO 2014/209034 | 12/2014 |
| WO | WO 2015/004029 | 1/2015 |
| WO | WO 2015/014900 | 2/2015 |
| WO | WO 2015/015993 | 2/2015 |
| WO | WO 2015/023664 | 2/2015 |
| WO | WO 2015/025172 | 2/2015 |
| WO | WO 2015/025962 | 2/2015 |
| WO | WO 2015/031561 | 3/2015 |
| WO | WO 2015/049034 | 4/2015 |
| WO | WO 2015/051071 | 4/2015 |
| WO | WO 2015/066188 | 5/2015 |
| WO | WO 2015/066697 | 5/2015 |
| WO | WO 2015/080904 | 6/2015 |
| WO | WO 2015/084842 | 6/2015 |
| WO | WO 2015/089634 | 6/2015 |
| WO | WO 2015/089809 | 6/2015 |
| WO | WO 2015/092009 | 6/2015 |
| WO | WO 2015/094118 | 6/2015 |
| WO | WO 2015/095256 | 6/2015 |
| WO | WO 2015/095701 | 6/2015 |
| WO | WO 2015/103317 | 7/2015 |
| WO | WO 2015/109109 | 7/2015 |
| WO | WO 2015/139621 | 9/2015 |
| WO | WO 2015/140133 | 9/2015 |
| WO | WO 2015/142903 | 9/2015 |
| WO | WO 2015/143185 | 9/2015 |
| WO | WO 2015/158689 | 10/2015 |
| WO | WO 2015/158690 | 10/2015 |

(56) References Cited

FOREIGN PATENT DOCUMENTS

| WO | WO 2015/158692 | 10/2015 |
|---|---|---|
| WO | WO 2015/160636 | 10/2015 |
| WO | WO 2015/162461 | 10/2015 |
| WO | WO 2015/179563 | 11/2015 |
| WO | WO 2015/184983 | 12/2015 |
| WO | WO 2015/193219 | 12/2015 |
| WO | WO 2015/198045 | 12/2015 |
| WO | WO 2015/198046 | 12/2015 |
| WO | WO 2016/006511 | 1/2016 |
| WO | WO 2016/006512 | 1/2016 |
| WO | WO 2016/008381 | 1/2016 |
| WO | WO 2016/012958 | 1/2016 |
| WO | WO 2016/012965 | 1/2016 |
| WO | WO 2016/020864 | 2/2016 |
| WO | WO 2016/022464 | 2/2016 |
| WO | WO 2016/024745 | 2/2016 |
| WO | WO 2016/040305 | 3/2016 |
| WO | WO 2016/044171 | 3/2016 |
| WO | WO 2016/049524 | 3/2016 |
| WO | WO 2016/049565 | 3/2016 |
| WO | WO 2016/054406 | 4/2016 |
| WO | WO 2016/055786 | 4/2016 |
| WO | WO 2016/055790 | 4/2016 |
| WO | WO 2016/073470 | 5/2016 |
| WO | WO 2016/074757 | 5/2016 |
| WO | WO 2016/088354 | 6/2016 |
| WO | WO 2016/095581 | 6/2016 |
| WO | WO 2016/097918 | 6/2016 |
| WO | WO 2016/116517 | 7/2016 |
| WO | WO 2016/125560 | 8/2016 |
| WO | WO 2016/138363 | 9/2016 |
| WO | WO 2016/140973 | 9/2016 |
| WO | WO 2016/144702 | 9/2016 |
| WO | WO 2016/160833 | 10/2016 |
| WO | WO 2016/161145 | 10/2016 |
| WO | WO 2016/162785 | 10/2016 |
| WO | WO 2016/173557 | 11/2016 |
| WO | WO 2016/177845 | 11/2016 |
| WO | WO 2016/178110 | 11/2016 |
| WO | WO 2016/181772 | 11/2016 |
| WO | WO 2017/011279 | 1/2017 |
| WO | WO 2017/052187 | 3/2017 |
| WO | WO 2017/058728 | 4/2017 |
| WO | WO 2017/058807 | 4/2017 |
| WO | WO 2017/059357 | 4/2017 |
| WO | WO 2017/059434 | 4/2017 |
| WO | WO 2017/060406 | 4/2017 |
| WO | WO 2017/061581 | 4/2017 |
| WO | WO 2017/070003 | 4/2017 |
| WO | WO 2017/079641 | 5/2017 |
| WO | WO 2017/087695 | 5/2017 |
| WO | WO 2017/097216 | 6/2017 |
| WO | WO 2017/100644 | 6/2017 |
| WO | WO 2017/106818 | 6/2017 |
| WO | WO 2017/118734 | 7/2017 |
| WO | WO 2017/127637 | 7/2017 |
| WO | WO 2017/130828 | 8/2017 |
| WO | WO 2017/170765 | 10/2017 |
| WO | WO 2017/185034 | 10/2017 |
| WO | WO 2017/189569 | 11/2017 |
| WO | WO 2017/192961 | 11/2017 |
| WO | WO 2017/197046 | 11/2017 |
| WO | WO 2017/223414 | 12/2017 |
| WO | WO 2018/006795 | 1/2018 |
| WO | WO 2018/033019 | 2/2018 |
| WO | WO 2018/037058 | 3/2018 |
| WO | WO 2018/042362 | 3/2018 |
| WO | WO 2018/056643 | 3/2018 |
| WO | WO 2018/056644 | 3/2018 |

OTHER PUBLICATIONS

Atzrodt et al., "The Renaissance of H/D Exchange," Angew Chem Int Ed., 2007, 46:7744-7765.
Barber et al., "PI3Kgamma inhibition blocks glomerulonephritis and extends lifespan in a mouse model of systemic lupus," Nat. Medicine, 2005, 11(9):933-935.
Bennani et al., "A short route to a moshe'rs acid precursor via catalytic asymmetric dihydroxylation (AD)," Tetrahedron: Asymmetry, 1994, 5(8):1413-1476.
Bennet et al., "Oncology," Cecil Textbook of Medicine, 20th edition, 1996, 1:1004-1010.
Berge et al., "Pharmaceutical Salts," Journal of Pharmaceutical Science, 1977, 66:1-19.
Berod et al., "PI3Kγ deficiency delays the onset of experimental autoimmune encephalomyelitis and ameliorates its clinical outcome," Euro. J Immunol., Mar. 2011, 41(3):833-844.
Blom et al., "Optimizing Preparative LC-MS Configurations and Methods for Parallel Synthesis Purification," J Comb Chem., Jul. 39, 2003, 5(5):670-683.
Blom et al., "Preparative LC-MS Purification: Improved Compound Specific Method Optimization," J Comb Chem., Sep. 11, 2004, 6(6):874-883.
Blom et al., "Two-Pump at Column Dilution Configuration for Preparative LC-MS," J Comb Chem., Jul.-Aug. 2002, 4(4):295-301.
Blunt et al., "Pharmacological targeting of PI3K isoforms as a therapeutic strategy in chronic lymphocytic leukaemia," Leukemia Research Reports, 2015, 4(2):60-63.
Brock et al., "Roles of GBβγ in membrane recruitment and activation of p110γ/p101 phosphoinositide 3-kinase γ," J Cell Biol., 2003, 160(1):89-99.
Camps et al., "Blockade of PI3Kγ suppresses joint inflammation and damage in mouse models of rheumatoid arthritis," Nat. Medicine, 2005, 11(9):936-943.
Cantley et al., "The Phosphoinositide 3-Kinase Pathway," Science, 2002, 296(5573): 1655-1657.
Carter et al., "Prioritization of driver mutations in pancreatic cancer using cancer-specific high-throughput annotation of somatic mutations (CHASM)," Cancer Biol. Ther. 2010, 10(6):582-587.
Cheung et al., "Mild and phosphine-free iron-catalyzed cross-coupling of nonactivated secondary alkyl halides with alkynyl Grignard reagents," Org. Lett., May 2, 2014, 16(9):2566-2569.
Chilean Office Action in Chilean Application No. 2275-2020, dated Nov. 14, 2021, 15 pages.
Choudhury-Mukherjee et al., "Design, Synthesis, and Evaluation of Analogues of 3,3,3-Trifluoro-2-Hydroxy-2-Phenyl-Propionamide as Orally Available General Anesthetics," J Med. Chem. 2003, 46(12):2494-2501.
Cohen et al., "Physicians' Desk Reference," Arch Intern Med., Jul. 8, 1996, 516: 6 pages.
Cohen et al., "The development and therapeutic potential of protein kinase inhibitors," Current Opinion in Chemical Biology, 1999, 3:459-465.
Comerford et al., "PI3Kγ Drives Priming and Survival of Autoreactive CD4+ T Cells during Experimental Autoimmune Encephalomyelitis," PLOS one, 2012, 7(9):e45095.
Dermer et al., "Another Anniversary for the War on Cancer," Bio/Technology, 1994, 12:320.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," J Pharmacol. Exp Ther. 2009, 328(3):758-765.
Doukas et al., "Phosphoinositide 3-kinase γ/δ inhibition limits infarct size after myocardial ischemia/reperfusion injury," Proc. Natl. Acad. Sci. USA, 2006, 103(52): 19866-19871.
El Khoury et al., "Ccr2 deficiency impairs microglial accumulation and accelerates progression of Alzheimer-like disease," Nat. Med., 2007, 13(4):432-438.
Ellman et al., "N-tert-Butanesulfinyl Imines: Versatile Intermediates for the Asymmetric Synthesis of Amines," Acc. Chem. Res., 2002, 35(11):984-995.
Eurasian Office Action in Eurasian Application No. 202092082, dated Oct. 22, 2021, 6 pages.
Falasca et al., "Targeting p110gamma in gastrointestinal cancers: attack on multiple fronts," Frontiers in Physiology, 2014, 5(391): 1-10.

(56) References Cited

OTHER PUBLICATIONS

Freshney et al., "Culture of Animal Cells," A Manual of Basic Technique, 1983, New York, chapter 1, pp. 1-6.
Gennaro, "Remington's Pharmaceutical Sciences," Mack Publishing Company, Easton, Pa., 1985, 17th ed., p. 1418.
Giri et al., "Mechanism of amyloid peptide induced CCR5 expression in monocytes and its inhibition by siRNA for Egr-1," Am. J. Physiol. Cell Physiol., 2005, 289:C264-C276.
Golub et al., "Molecular classification of cancer: class discovery and class prediction by gene expression monitoring," Science, Oct. 15, 1999, 286(5439):531-537.
Gonzalez-Garcia et al., "Phosphatidylinositol 3-Kinase γ Inhibition Ameliorates Inflammation and Tumor Growth in a Model of Colitis-Associated Cancer," Gastroenterology, 2010, 138:1374-1384.
Hanahan et al., "Hallmarks of Cancer: The Next Generation," Cell, 2011, 144:646-674.
Hayer et al., "PI3Kγ regulates cartilage damage in chronic inflammatory arthritis," FASEB Journal, 2009, 23:4288-4298.
Hulikal "Deuterium Labeled Compounds in Drug Discovery Process," Bioorganics and Applied Marerials Pvt Ltd., 2010, Abstract L15 (Abstract Only).
International Preliminary Report on Patentability in International Application No. PCT/US2019/021186, dated Sep. 8, 2020, 7 pages.
International Preliminary Report on Patentability in International Application No. PCT/US2019/040147, dated Jan. 14, 2021, 7 pages.
International Search Report and Written Opinion in International Application No. PCT/US2019/021186, dated Nov. 25, 2019, 12 pages.
International Search Report and Written Opinion in International Application No. PCT/US2019/040147, dated Sep. 13, 2019, 13 pages.
India Office Action in Indian Application No. 202017038998, dated Mar. 1, 2022, 5 pages.
Jimenez, et al., "The p85 Regulatory Subunit Controls Sequential Activation of Phosphoinositide 3-Kinase by Tyr Kinases and Ras," J Biol Chem., 2002, 277(44):41556-41562.
Kaneda et al., "Abstract 3650: PI3-kinase gamma controls the macrophage M1-M2 switch, thereby promoting tumor immunosuppression and progression," Cancer Res., 2014, 74:(Suppl 19:Abstact 3650).
Kendell and McKenzie, "B-Bromopropionic Acid," Org Synth Coll., 1941, 1:131.
Kerekes et al., "Aurora Kinase Inhibitors Based on the Imidazo[1,2-a]pyrazine Core: Fluorine and Deuterium Incorporation Improve Oral Absorption and Exposure," J Med Chem., 2011, 54(1):201-210.
Khoury et al., "Ccr2 deficiency impairs microglial accumulation and accelerates progression of Alzheimer-like disease," Nat. Med., 2007, 13(4):432-438.
Kolb et al., "Catalytic Asymmetric Dihydroxylation," Chem Rev., 1994, 94(8):2483-2547.
Laffargue et al., "Phosphoinositide 3-Kinase γ is an Essential Amplifier of Mast Cell Function," Immunity, 2002, 16:441-451.
Lebel et al., "Highly Chemoselective Rhodium-Catalyzed Methylenation of Fluorine-Containing Ketones," Organic Letters, 2002, 4(10):1671-1674.
Li al., "PI3Kγ Inhibition Alleviates Symptoms and Increases Axon Number in Experimental Autoimmune Encephalomyelitis Mice," Neuroscience, 2013, 253:89-99.
Lupia et al., "Ablation of Phosphoinositide 3-Kinase-Reduces the Severity of Acute Pancreatitis," Am. J Pathology, 2004, 165(6):2003-2011.
Luzung et al., "Rhenium-Catalyzed Coupling of Propargyl Alcohols and Allyl Silanes," J Am. Chem. Soc., 2003, 125(51):15760-15761.
Manning et al., "An innovative and efficient synthesis of stable isotope labelled 1-methyl-5-(4,4,5,5-tetramethyl-1,3,2-dioxaborolan-2-yl)-1H-pyrazole via [$^{13}C_4{}^2H_3$]N-methylpyrazole," Journal of Labelled Compounds and Radiopharmaceuticals, Nov. 2012, 55(13):467-469.

Martin et al., "PI3Kγ Mediates Kaposi's Sarcoma Associated Herpesvirus vGPCR-Induced Sarcomagenesis," Cancer Cell, 2011, 19(6):805-813.
Marvel and Tuley, "Glutaric Acid," Org Synth Coll., 1941, 1:289.
Moreno-Dorado et al., "Enantioselective synthesis of arylmethoxyacetic acid derivatives," Tetrahedron: Asymmetry, Feb. 21, 2003, 14(4):503-510.
Passos et al., "Involvement of phosphoinositide 3-kinase gamma in the neuro-inflammatory response and cognitive impairments induced by beta-amyloid 1-40 peptide in mice," Brain Behav. Immun. 2010, 24:493-501.
Pinho et al., "Phosphoinositide-3 kinases critically regulate the recruitment and survival of eosinophils in vivo: importance for the resolution of allergic inflammation," Journal of Leukocyte Biology, 2005, 77:800-810.
Prete et al., "Defective dendritic cell migration and activation of adaptive immunity in PI3Kc-deficient mice," The EMBO Journal, 2004, 23:3505-3515.
Randis et al., "Role of PI3Kδ and PI3Kγ in inflammatory arthritis and tissue localization of neutrophils," Eur. J Immunol, 2008, 38(5):1215-1224.
Read, "B-Hydroxypropianic Acid," Org Synth Coll., 1941, 1:321.
Remington's Pharmaceutical Sciences, 17th ed., Mack Publishing Company Easton, Pa., 1985, Chapter 76, 18 pages.
Robak et al., "Synthesis and Applications of tert-Butanesulfinamide," Chem. Rev. 2010, 110(6):3600-3740.
Rodrigues et al., "Absence of PI3Kγ leads to increased leukocyte apoptosis and diminished severity of experimental autoimmune encephalomyelitis," J Neuroimmunol. 2010, 222:90-94.
Ruckle et al., "PI3Kγ inhibition: towards an 'aspirin of the 21st century'?" Nat. Rev. Drug Discovery, 2006, 5:903-918.
Saito et al., "Direct Dehydroxylative Coupling Reaction of Alcohols with Organosilanes through Si-X Bond Activation by Halogen Bonding," Org. Lett. 2015, 17(12):3000-3003.
Schmid et al., "Receptor tyrosine kinases and TLR/ILIRs unexpectedly activate myeloid cell PI3Kγ, a single convergent point promoting tumor inflammation and progression," Cancer Cell, 2011, 19(6):715-727.
Schmidt al., "Abstract 411: PI3 Kinase gamma control of Arginase-1 expression promotes tumor immunosuppression," Cancer Res. 2012, 72:(Suppl 1: Abstract 411).
Sharpless et al., "The osmium-catalyzed asymmetric dihydroxylation: a new ligand class and a process improvement," J Org Chem., May 1, 1992, 57(10):2768-2771.
Sigmaaldrich.com, "L-α-Phosphatidyl-D-myo-inositol 4,5-diphosphate, dioctanoyl," CAS 204858-53-7, Retrieved on Jul. 6, 2020, 3 pages.
Subramanjam et al., "Targeting Nonclassical Oncogenes for Therapy in T-ALL," Cancer Cell, 2012, 21:459-472.
Thomas et al., "Airway inflammation: chemokine-induced neutrophilia and the class I phosphoinositide 3-kinases," Eur. J Immunol., 2005, 35:1283-1291.
Vanhaesebroeck et al., "Signalling by PI3K isoforms: insights from gene-targeted mice," Trends Biochem Sci., 2005, 30(4):194-204.
Vecchione et al., "Protection from angiotensin II-mediated vasculotoxic and hypertensive response in mice lacking PI3Kγ," J Exp. Med., 2005, 201(8):1217-1228.
Winterfeldt, "Applications of Diisobutylaluminium Hydride (DIBAH) and Triisobutylaluminium (TIBA) as Reducing Agents in Organic Synthesis," Synthesis, 1975, 10:617-630.
Xu et al., "Design, synthesis and biological evaluation of deuterated nintedanib for improving pharmacokinetic properties," J Label Compd Radiopharm., Jun. 15, 2015, 58(7):308-312.
Yang et al., "Kumada-Corriu Reactions of Alkyl Halides with Alkynyl Nucleophiles," Org. Lett., 2004, 6(9):1461-1463.
Eurasian Office Action in Eurasian Application No. 202092082, dated Jun. 20, 2022, 5 pages.
Colombia Office Action in Colombia Application No. NC2020/0012169, dated Oct. 27, 2022, 14 pages.
Elmenier et al., "Phosphatidylinositol 3 kinase (PI3K) inhibitors as new weapon to combat cancer," European Journal of Medicinal Chemistry, 2019, 111718.

(56) References Cited

OTHER PUBLICATIONS

Lu et al., "Rationally Designed PI3Kα Mutants to Mimic ATR and Their Use to Understand Binding Specificity of ATR Inhibitors," Journal of Molecular Biology, 2017, 429(11):1684-1704.

Pemberton et al., "Discovery of Highly Isoform Selective Orally Bioavailable Phosphoinositide 3-Kinase (PI3K)-γ Inhibitors," Journal of Medicinal Chemistry, 2018, 61(12):5435-5441.

Scott et al., "Discovery and SAR of Novel 2,3-Dihydroimidazo [1,2-c]quinazoline PI3K Inhibitors: Identification of Copanlisib (BAY 80-6946)," ChemMedChem, 2016, 11(14):1517-1530.

Indonesian Office Action in Indonesian Application No. P00202006480, dated Sep. 9, 2022, 8 pages.

Office Action and Search Report in Chinese Appln. No. 201980030125.X, dated Feb. 27, 2023, 15 pages (with English translation).

Office Action in Taiwanese Appln No. 108107573, dated Mar. 2, 2023, 7 pages (with English translation).

Australian Office Action in Australian Application No. 2019272342, dated Jul. 12, 2023, 3 pages.

Chinese Office Action in Chinese Application No. 201980030125-X, dated Aug. 30, 2023, 9 pages (with English Translation).

Ukraine Office Action in Ukraine Application No. a202006471, dated Jun. 18, 2023, 10 pages (with English Translation).

AMINOPYRAZINE DIOL COMPOUNDS AS PI3K-γ INHIBITORS

TECHNICAL FIELD

The present invention provides aminopyrazine diol compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinophils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J Immunol. 2005, 35, 1283-1291; Doukas et al., J Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Gir et al., Am. J. Physiol. Cell Physiol., 2005, 289, C264-C276; E1 Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophages at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., Cancer Res.

2012, 72 (Suppl 1: Abstract, 411; Kaneda et al., *Cancer Res.*, 74 (Suppl 19: Abstract 3650)).

In addition to its potential role in promoting protumorigenic microenvironment, PI3Kγ may play a direct role in cancer cells. PI3Kγ is reported to be required for signaling from the Kaposi's sarcoma-associated herpesvirus encoded vGPCR oncogene and tumor growth in a mouse model of sarcoma (Martin et al., *Cancer Cell*, 2011, 19, 805-813). PI3Kγ was also suggested to be required for growth of T-ALL (Subramanjam et al., *Cancer Cell*, 2012, 21, 459-472), PDAC and HCC cells (Falasca and Maffucci, *Frontiers in Physiology*, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotensin-evoked smooth muscle contraction and, therefore, protect mice from angiotensin-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA*, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention relates to, inter alia, compounds of Formula (I):

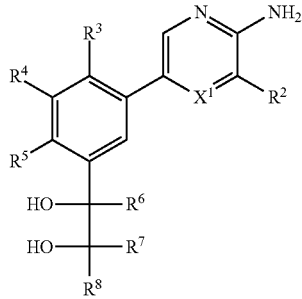

or pharmaceutically acceptable salts thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of PI3Kγ kinase comprising contacting the kinase with a compound of Formula (I), or a pharmaceutically acceptable salt thereof.

The present invention further provides methods of treating a disease or a disorder associated with abnormal PI3Kγ kinase expression or activity in a patient by administering to a patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

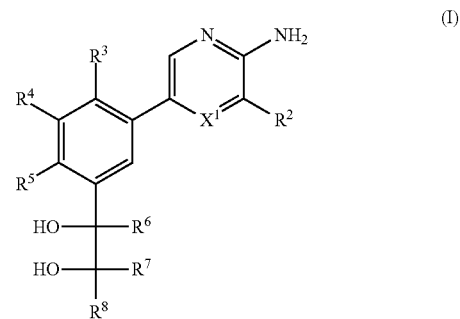

or a pharmaceutically acceptable salt thereof, wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;

$R^2$ is selected from H, D, halo, $C_{1-6}$ alkyl, $C_{1-6}$ haloalkyl, $C_{2-6}$ alkenyl, $C_{2-6}$ alkynyl, Cy, Cy-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{a1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{a1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{a1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, and $C_{2-6}$ alkynyl of $R^2$ are each optionally substituted with 1, 2, 3, 4, 5, 6, 7, or 8 independently selected $R^4$ substituents;

Cy is selected from $C_{6-14}$ aryl, $C_{3-14}$ cycloalkyl, 5-14 membered heteroaryl, and 4-14 membered heterocycloalkyl, each of which are optionally substituted with 1, 2, 3, 4, 5, 6, 7, or 8 independently selected $R^4$ substituents;

$R^3$, $R^4$ and $R^5$ are each independently selected from H, D, halo, CN, OH, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, amino, $C_{1-6}$ alkylamino, di($C_{1-6}$ alkyl)amino, and $C(O)NR^cR^d$, wherein the $C_{1-6}$ alkyl is optionally substituted by 1, 2, 3, 4, 5, or 6 D;

$R^6$, $R^7$ and $R^8$ are each independently selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b3}$, $C(O)NR^{c3}R^{d3}$, $C(O)NR^{c3}(OR^{a3})$, $C(O)OR^{a3}$, $C(=NR^{c3})R^{b3}$, $C(=NOH)R^{b3}$, $C(=NCN)R^{b3}$, and $C(=NR^{e3})NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$, $R^7$, and $R^8$ are each optionally substituted with 1, 2, 3, 4, 5, 6, 7, or 8 independently selected $R^B$ substituents; and wherein the $C_{1-6}$ haloalkyl of $R^6$, $R^7$, or $R^8$ is optionally substituted by 1, 2, 3, or 4 independently selected Y substituents;

each Y is independently selected from D, halo, $C_{1-6}$ alkyl, and $C_{1-6}$ haloalkyl;

or $R^6$ and $R^7$ substituents, together with the ring atoms to which they are attached, form a $C_{3-10}$ cycloalkyl or 4-7 membered heterocycloalkyl, each of which is optionally substituted with 1, 2, 3, or 4 independently selected R substituents;

or $R^7$ and $R^8$ substituents, together with the ring atoms to which they are attached, form a $C_{3-10}$ cycloalkyl or 4-7 membered heterocycloalkyl, each of which is optionally substituted with 1, 2, 3, or 4 independently selected R substituents;

$R^c$ and $R^d$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R and R, are each optionally substituted with 1, 2, 3, 4, 5, 6, 7, or 8 independently selected $R^M$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$, and $R^{d1}$, are each optionally substituted with 1, 2, 3, 4, 5, 6, 7, or 8 independently selected $R^A$ substituents;

or, any $R^{c1}$ and $R^{d1}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^A$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{b3}$, $R^{c3}$, and $R^{d3}$ are each optionally substituted with 1, 2, 3, 4, 5, 6, 7, or 8 independently selected R substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}C(=NOH)NR^{c4}R^{d4}$, $NR^{c4}C$ (=NCN)NR$^{c4}$R$^{d4}$, NR$^{c4}$S(O)R$^{b4}$, NR$^{c4}$S(O)NR$^{c4}$R$^{d4}$, NR$^{c4}$S(O)$_2$R$^{b4}$, NR$^{c4}$S(O)$_2$NR$^{e4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, OS(O)(=NR$^{e4}$)R$^{b4}$, OS(O)$_2$R$^{b4}$, SF$_5$, P(O)R$^{f1}$R$^{g4}$, OP(O)(OR$^{h4}$)(OR$^{i4}$), P(O)(OR$^{h4}$)(OR$^{i4}$), and BR$^{j4}$R$^{k4}$, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^A$ is optionally substituted with 1, 2, 3, 4, 5, 6, 7, or 8 independently selected R$^D$ substituents;

each R$^B$ is independently selected from D, halo, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a2}$, SR$^{a2}$, NHOR$^{a2}$, C(O)R$^{b2}$, C(O)NR$^{c2}$R$^{d2}$, C(O)NR$^{c2}$(OR$^{b2}$), C(O)OR$^{a2}$, OC(O)R$^{b2}$, OC(O)NR$^{c2}$R$^{d2}$, NR$^{c2}$R$^{d2}$, NR$^{c2}$NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NOH)R$^{b2}$, C(=NCN)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$C(=NR$^{e2}$)R$^{b2}$, NR$^{c2}$C(=NOH)NR$^{c2}$R$^{d2}$, NR$^{c2}$C(=NCN)NR$^{c2}$R$^{d2}$, NR$^{c2}$S(O)R$^{b2}$, NR$^{c2}$S(O)NR$^{c2}$R$^{d2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, OS(O)(=NR$^{e2}$)R$^{b2}$, OS(O)$_2$R$^{b2}$, SF$_5$, P(O)R$^{h1}$R$^{g2}$, OP(O)(OR$^{h2}$)(OR$^{i2}$), P(O)(OR$^{h2}$)(OR$^{i2}$), and BR$^{j2}$R$^{k2}$, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^B$ is optionally substituted with 1, 2, 3, 4, 5, 6, 7, or 8 independently selected R$^M$ substituents;

each R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a2}$, R$^{b2}$, R$^2$, and R$^{d2}$ are each optionally substituted with 1, 2, 3, 4, 5, 6, 7, or 8 independently selected R$^M$ substituents;

or, any R$^{c2}$ and R$^{d2}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^M$ substituents;

each R$^{e2}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{f2}$ and R$^{g2}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{h2}$ and R$^{i2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{j2}$ and R$^{k2}$ is independently selected from OH, C$_{1-6}$ alkoxy, and C$_{1-6}$ haloalkoxy;

or any R$^{j2}$ and R$^{k2}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a4}$, R$^{b4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a4}$, R$^{b4}$, R$^{c4}$, and R$^{d4}$ are each optionally substituted with 1, 2, 3, 4, 5, 6, 7, or 8 independently selected R$^D$ substituents;

or, any R$^{c4}$ and R$^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^D$ substituents;

each R$^{e4}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{f4}$ and R$^{g4}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{h4}$ and R$^{i4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{j4}$ and R$^{k4}$ is independently selected from OH, C$_{1-6}$ alkoxy, and C$_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{b5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOH)R^{b5}$, $C(=NCN)R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}C(=NOH)NR^{c5}R^{d5}$, $NR^{c5}(=NCN)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{c5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, 4, 5, 6, 7, or 8 independently selected $R^E$ substituents;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, 4, 5, 6, 7, or 8 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^E$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$ and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, 4, 5, 6, 7, or 8 independently selected $R^G$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, and $R^{d6}$ are each optionally substituted with 1, 2, 3, 4, 5, 6, 7, or 8 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^G$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^G$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl; and each $R^M$ is independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;

$R^2$ is selected from H, D, halo, $C_{1-6}$ alkyl, $C_{1-6}$ haloalkyl, $C_{2-6}$ alkenyl, $C_{2-6}$ alkynyl, Cy, Cy-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, and $C_{2-6}$ alkynyl of $R^2$ are each optionally substituted with 1, 2, 3, 4, 5, 6, 7, or 8 independently selected $R^A$ substituents;

Cy is selected from $C_{6-14}$ aryl, $C_{3-14}$ cycloalkyl, 5-14 membered heteroaryl, and 4-14 membered heterocycloalkyl, each of which are optionally substituted with 1, 2, 3, 4, 5, 6, 7, or 8 independently selected $R^A$ substituents;

$R^3$, $R^4$ and R are each independently selected from H, D, halo, CN, OH, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, amino, $C_{1-6}$ alkylamino, di($C_{1-6}$ alkyl)amino, and $C(O)NR^cR^d$, wherein said $C_{1-6}$ alkyl can be optionally substituted by 1, 2, 3, 4, 5, or 6 D;

$R^6$, $R^7$ and $R^8$ are each independently selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b3}$, $C(O)NR^{c3}R^{d3}$, $C(O)NR^{c3}(OR^{a3})$, $C(O)OR^{a3}$, $C(=NR^{e3})R^{b3}$, $C(=NOH)R^{b3}$, $C(=NCN)R^{b3}$, and $C(=NR^{e3})NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$, $R^7$, and $R^8$ are each optionally substituted with 1, 2, 3, 4, 5, 6, 7, or 8 independently selected $R^B$ substituents; and wherein said $C_{1-6}$ haloalkyl of $R^6$, $R^7$, or $R^8$ is optionally substituted by 1, 2, 3, or 4 independently selected Y substituents;

each Y is independently selected from D, halo, $C_{1-6}$ alkyl, and $C_{1-6}$ haloalkyl;

or $R^6$ and $R^7$ substituents, together with the ring atoms to which they are attached, form a $C_{3-10}$ cycloalkyl or 4-7 membered heterocycloalkyl, each of which is optionally substituted with 1, 2, 3, or 4 independently selected R substituents;

or $R^7$ and $R^8$ substituents, together with the ring atoms to which they are attached, form a $C_{3-10}$ cycloalkyl or 4-7 membered heterocycloalkyl, each of which is optionally substituted with 1, 2, 3, or 4 independently selected R substituents;

$R^c$ and $R^d$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^c$ and $R^d$, are each optionally substituted with 1, 2, 3, 4, 5, 6, 7, or 8 independently selected $R^M$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$, and $R^{d1}$, are each optionally substituted with 1, 2, 3, 4, 5, 6, 7, or 8 independently selected $R^A$ substituents;

or, any $R^{c1}$ and $R^{d1}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^A$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{b3}$, $R^{c3}$, and $R^{d3}$ are each optionally substituted with 1, 2, 3, 4, 5, 6, 7, or 8 independently selected $R^B$ substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^B$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^4NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^4C(=NR^{e4})R^{b4}$, $NR^{c4}C(=NOH)NR^{c4}R^{d4}$, $NR^{c4}C(=NCN)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{c4})R^{b4}$, $OS(O)_2R^{b4}$, $SF_5$, $P(O)R^{f4}R^{g4}$, $OP(O)(OR^{h4})(OR^{c4})$, $P(O)(OR^{h4})(OR^4)$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ is optionally substituted with 1, 2, 3, 4, 5, 6, 7, or 8 independently selected $R^D$ substituents;

each $R^B$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{b2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}C(=NOH)NR^{e2}R^{c2}$, $NR^{e2}C(=NCN)NR^{e2}R^{a2}$, $NR^{c2}S(O)R^{b2}$, $NR^{c2}S(O)NR^{c2}R^{d2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ is optionally substituted with 1, 2, 3, 4, 5, 6, 7, or 8 independently selected $R^M$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$, and $R^{d2}$ are each optionally substituted with 1, 2, 3, 4, 5, 6, 7, or 8 independently selected $R^M$ substituents;

or, any $R^{c2}$ and $R^{d2}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^M$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$$C(O)NR^{c5}R^{d5}$, $C(O)NR^{c5}(OR^{b5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{c5})R^{b5}$, $C(=NOH)R^{b5}$, $C(=NCN)R^{b5}$, $C(=NR^{c5})NR^{c5}R^{d5}$, $NR^{c5}C(=NR^{e5})NR^{c5}R^{d5}$, $NR^{c5}C(=NR^{e5})R^{b5}$, $NR^{c5}C(=NOH)NR^{c5}R^{d5}$, $NR^{c5}C(=NCN)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{c5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, or 4 independently selected $R^E$ substituents;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, or 4 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}C(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$ and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, or 4 independently selected $R^G$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, and $R^{d6}$ are each optionally substituted with 1, 2, 3, or 4 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^G$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^G$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl; and each $R^M$ is independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments,

X is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;

$R^2$ is selected from H, D, halo, $C_{1-6}$ alkyl, $C_{1-6}$ haloalkyl, $C_{2-6}$ alkenyl, $C_{2-6}$ alkynyl, Cy, Cy-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, and $C_{2-6}$ alkynyl of $R^2$ are each optionally substituted with 1, 2, 3, 4, 5, 6, 7, or 8 independently selected $R^A$ substituents;

Cy is selected from $C_{6-14}$ aryl, $C_{3-14}$ cycloalkyl, 5-14 membered heteroaryl, and 4-14 membered heterocycloalkyl, each of which are optionally substituted with 1, 2, 3, 4, 5, 6, 7, or 8 independently selected $R^A$ substituents;

$R^3$, $R^4$ and $R^5$ are each independently selected from H, D, halo, CN, OH, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, amino, $C_{1-6}$ alkylamino, di($C_{1-6}$ alkyl)amino, and $C(O)NR^cR^d$, wherein the $C_{1-6}$ alkyl is optionally substituted by 1, 2, 3, 4, 5, or 6 D;

$R^6$, $R^7$ and $R^8$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OH, COOH and $NH_2$;

$R^c$ and $R^d$ are each independently selected from H and $C_{1-6}$ alkyl;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$, and $R^{d1}$, are each optionally substituted with 1, 2, 3, 4, 5, 6, 7, or 8 independently selected $R^A$ substituents;

or, any $R^{c1}$ and $R^{d1}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^A$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}C(=NOH)NR^{c4}R^{d4}$, $NR^{c4}C(=NCN)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ is optionally substituted with 1, 2, 3, 4, 5, 6, 7, or 8 independently selected $R^D$ substituents;

each $R^B$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{b2})$, $C(O)OR^{a2}$, $OC(O)R^{b2}$, $OC(O)NR^{c2}R^{a2}$, $NR^{c2}R^{a2}$, $NR^{c2}NR^{c2}R^{a2}$, NR$^{c2}$C(O)R$^{b2}$, NR$^{c2}$C(O)OR$^{a2}$, NR$^{c2}$C(O)NR$^{c2}$R$^{a2}$, C(=NR$^{e2}$)R$^{b2}$, C(=NOH)R$^{b2}$, C(=NCN)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$C(=NR$^{e2}$)R$^{b2}$, NR$^{c2}$C(=NOH)NR$^{c2}$R$^{d2}$, NR$^{c2}$C(=NCN)NR$^{c2}$R$^{d2}$, NR$^{c2}$S(O)R$^{b2}$, NR$^{c2}$S(O)NR$^{c2}$R$^{d2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, OS(O)(=NR$^{e2}$)R$^{b2}$, OS(O)$_2$R$^{b2}$, SF$_5$, P(O)R$^{h2}$R$^{g2}$, OP(O)(OR$^{h2}$)(OR$^{i2}$), P(O)(OR$^{h2}$)(OR$^{i2}$), and BR$^{j2}$R$^{k2}$, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^B$ is optionally substituted with 1, 2, 3, 4, 5, 6, 7, or 8 independently selected R$^M$ substituents;

each R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a2}$, R$^{b2}$, R$^{c2}$, and R$^{d2}$ are each optionally substituted with 1, 2, 3, 4, 5, 6, 7, or 8 independently selected R$^M$ substituents;

or, any R$^{c2}$ and R$^{d2}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^M$ substituents;

each R$^{e2}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{f2}$ and R$^{g2}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{h2}$ and R$^{i2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{j2}$ and R$^{k2}$ is independently selected from OH, C$_{1-6}$ alkoxy, and C$_{1-6}$ haloalkoxy;

or any R$^{j2}$ and R$^{k2}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a4}$, R$^{b4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a4}$, R$^{b4}$, R$^{c4}$, and R$^{d4}$ are each optionally substituted with 1, 2, 3, 4, 5, 6, 7, or 8 independently selected R$^D$ substituents;

or, any R$^{c4}$ and R$^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^D$ substituents;

each R$^{e4}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{f4}$ and R$^{g4}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{h4}$ and R$^{i4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{j4}$ and R$^{k4}$ is independently selected from OH, C$_{1-6}$ alkoxy, and C$_{1-6}$ haloalkoxy;

or any R$^{j4}$ and R$^{k4}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^D$ is independently selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a5}$, SR$^{a5}$, NHOR$^{a5}$, C(O)R$^{b5}$, C(O)NR$^{c5}$R$^{d5}$, C(O)NR$^{c5}$(OR$^{b5}$), C(O)OR$^{a5}$, OC(O)R$^{b5}$, OC(O)NR$^{c5}$R$^{d5}$, NR$^{c5}$R$^{d5}$, NR$^{c5}$NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NOH)R$^{b5}$, C(=NCN)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$C(=NOH)NR$^{c5}$R$^{d5}$, NR$^{c5}$C(=NCN)NR$^{c5}$R$^{d5}$, NR$^{c5}$S(O)R$^{b5}$, NR$^{c5}$S(O)NR$^{c5}$R$^{d5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{c5}$, S(O)$_2$NR$^{c5}$R$^{d5}$, OS(O)(=NR$^{e5}$)

$R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, or 4 independently selected $R^E$ substituents;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, or 4 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}C(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$ and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, or 4 independently selected $R^G$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, and $R^{d6}$ are each optionally substituted with 1, 2, 3, or 4 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^G$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^G$ is independently selected from H, D, halo, CN, NO$_2$, SF$_5$, C$_{1-6}$ alkyl, C$_{1-6}$ alkoxy, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl; and each $R^M$ is independently selected from H, D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-4}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the compound of Formula (I) is a compound of Formula (II):

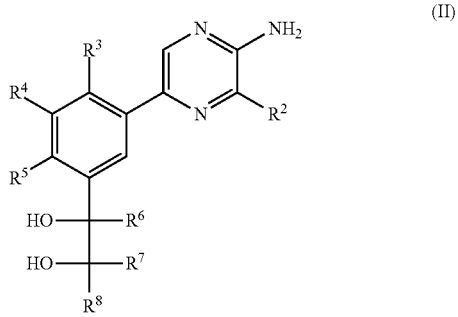

(II)

or a pharmaceutically acceptable salt thereof.

In some embodiments, the compound of Formula (I) is a compound of Formula (III):

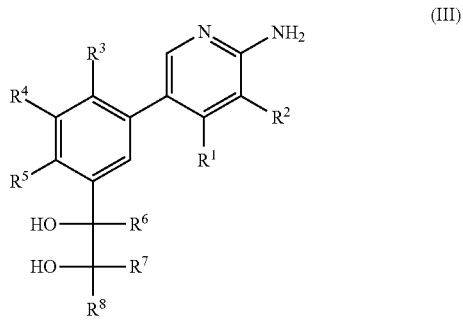

(III)

or a pharmaceutically acceptable salt thereof.

In some embodiments, $R^1$ is H, D or C$_{1-6}$ alkyl.
In some embodiments, $R^1$ is H, D or methyl.
In some embodiments, $R^1$ is H.

In some embodiments, $R^2$ is selected from H, D, halo, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-, C(O)NR$^{c1}$R$^{d1}$, C(O)OR$^{a1}$, CN, NO$_2$, OH, COOH and NH$_2$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of $R^2$ are each optionally substituted with 1, 2, 3, or 4 independently selected $R^4$ substituents.

In some embodiments, $R^2$ is selected from H, D, halo, C$_{1-6}$ alkyl, C$_{1-6}$ haloalkyl, C$_{2-6}$ alkenyl, C$_{2-6}$ alkynyl, Cy, Cy-C$_{1-6}$ alkyl-, C(O)NR$^{c1}$R$^{d1}$, C(O)OR$^{a1}$, CN, NO$_2$, OH, COOH and NH$_2$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of $R^2$ are each optionally substituted with 1, 2, 3, or 4 independently selected $R^4$ substituents.

In some embodiments, $R^2$ is selected from Cy, Cy-C$_{1-6}$ alkyl, C$_{1-6}$ haloalkyl, C(O)NR$^{c1}$R$^{d1}$, and C(O)OR$^{a1}$; and Cy is selected from C$_{3-14}$ cycloalkyl, 5-14 membered heteroaryl, and 4-14 membered heterocycloalkyl, each of which are optionally substituted with 1, 2, 3, 4, 5, 6, 7, or 8 independently selected $R^4$ substituents;

In some embodiments, $R^2$ is C(O)NR$^{c1}$R$^{d1}$ or C(O)OR$^{a1}$.

In some embodiments, $R^2$ is Cy, C(O)NR$^{c1}$R$^{d1}$ or NR$^c$C(O)R$^{b1}$.

In some embodiments, $R^2$ is C(O)NR$^{c1}$R$^{d1}$ or NR$^c$C(O)R$^{b1}$.

In some embodiments, $R^2$ is C(O)NR$^{c1}$R$^{d1}$.

In some embodiments, $R^2$ is Cy.

In some embodiments, $R^2$ is C(O)NR$^{c1}$R$^{d1}$ or NR$^{c1}$C(O)R$^{b1}$, wherein R$^{c1}$ is H; and R$^{b1}$ and R$^{d1}$ are each independently selected from C$_{1-6}$ alkyl, C$_{3-7}$ cycloalkyl, 4-10 membered heterocycloalkyl, C$_{3-10}$ cycloalkyl-C$_{1-6}$ alkyl-, and (4-10 membered heterocycloalkyl)-C$_{1-6}$ alkyl-, each of which is optionally substituted by 1, 2, 3, or 4 independently selected $R^4$ substituents.

In some embodiments, $R^2$ is C(O)NR$^{c1}$R$^{d1}$, wherein R$^{c1}$ is H; and R$^{d1}$ is selected from C$_{1-6}$ alkyl, C$_{3-7}$ cycloalkyl, 4-10 membered heterocycloalkyl, C$_{3-10}$ cycloalkyl-C$_{1-6}$ alkyl-, and (4-10 membered heterocycloalkyl)-C$_{1-6}$ alkyl-, each of which is optionally substituted by 1, 2, 3, or 4 independently selected $R^4$ substituents.

In some embodiments, $R^2$ is C(O)NR$^{c1}$R$^{d1}$; and each R$^{c1}$ and R$^{d1}$ is independently selected from H, C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{c1}$ and R$^{d1}$ are each optionally substituted with 1, 2, 3, or 4 independently selected $R^4$ substituents;

or, any R$^{c1}$ and R$^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^A$ substituents.

In some embodiments, $R^2$ is $C(O)NR^{c1}R^{d1}$; each $R^{c1}$ and $R^{d1}$ is independently selected from H, $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, or 4 independently selected $R^A$ substituents;
  or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^A$ substituents; and
  each $R^A$ is independently selected from D, halo, oxo, $C_{1-6}$ alkyl, $C_{1-6}$ haloalkyl, $C_{2-6}$ alkenyl, and $C_{2-6}$ alkynyl, CN, $NO_2$, and $OR^{a4}$, wherein the $C_{1-6}$ alkyl, $C_{2-6}$ alkenyl, and $C_{2-6}$ alkynyl of $R^A$ is optionally substituted with 1, 2, or 3 independently selected $R^D$ substituents.

In some embodiments, $R^2$ is $C(O)NR^{c1}R^{d1}$; each $R^{c1}$ and $R^{d1}$ is independently selected from H, $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, or 4 independently selected $R^A$ substituents;
  or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^A$ substituents;
  each $R^A$ is independently selected from D, halo, oxo, $C_{1-6}$ alkyl, $C_{1-6}$ haloalkyl, $C_{2-6}$ alkenyl, and $C_{2-6}$ alkynyl, CN, $NO_2$, and $OR^{a4}$, wherein the $C_{1-6}$ alkyl, $C_{2-6}$ alkenyl, and $C_{2-6}$ alkynyl of $R^A$ is optionally substituted with 1, 2, or 3 independently selected $R^D$ substituents;
  each $R^{a4}$ is independently selected from H and $C_{1-6}$ alkyl, wherein the $C_{1-6}$ alkyl is optionally substituted CN, $NO_2$, or OH; and
  each $R^D$ is OH.

In some embodiments, $R^2$ is $C(O)NR^{c1}R^{d1}$; and
$R^{c1}$ is H; and
$R^{d1}$ is selected from $C_{1-6}$ alkyl, $C_{3-7}$ cycloalkyl, 4-7 membered heterocycloalkyl, phenyl-$C_{1-4}$ alkyl-, and $C_{3-7}$ cycloalkyl-$C_{1-4}$ alkyl-, wherein the $C_{1-6}$ alkyl, $C_{3-7}$ cycloalkyl, 4-7 membered heterocycloalkyl, phenyl-$C_{1-4}$ alkyl-, and $C_{3-7}$ cycloalkyl-$C_{1-4}$ alkyl- of $R^{c1}$ and $R^{d1}$ are each optionally substituted with 1, 2, or 3 independently selected $R^A$ substituents;
  or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, or 3 independently selected $R^A$ substituents.

In some embodiments, $R^2$ is $C(O)NR^{c1}R^{d1}$; and
$R^{c1}$ is H; and
$R^{d1}$ is selected from ethyl, propyl, isopropyl, butyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclobutyl, methyl-phenyl, ethyl-phenyl, oxetanyl, tetrahydrofuranyl, tetrahydropyranyl, pyrrolidinyl, and thianyl, wherein the ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclobutyl, methyl-phenyl, ethyl-phenyl, oxetanyl, tetrahydrofuranyl, tetrahydropyranyl, pyrrolidinyl and thianyl of $R^{d1}$ are each optionally substituted with 1, 2, or 3 independently selected $R^A$ substituents;
  or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1, 2, or 3 independently selected $R^A$ substituents.

In some embodiments, $R^2$ is $C(O)NR^{c1}R^{d1}$; and
$R^{c1}$ is H; and
$R^{d1}$ is selected from ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl, and thianyl, wherein the ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl and thianyl of $R^{d1}$ are each optionally substituted with 1, 2, or 3 independently selected $R^A$ substituents;
  or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1, 2, or 3 independently selected $R^A$ substituents.

In some embodiments, $R^2$ is $C(O)NR^{c1}R^{d1}$;
$R^{c1}$ is H;
$R^{d1}$ is selected from $C_{1-6}$ alkyl, $C_{3-7}$ cycloalkyl, 4-7 membered heterocycloalkyl, phenyl-$C_{1-4}$ alkyl-, and $C_{3-7}$ cycloalkyl-$C_{1-4}$ alkyl-, wherein the $C_{1-6}$ alkyl, $C_{3-7}$ cycloalkyl, 4-7 membered heterocycloalkyl, phenyl-$C_{1-4}$ alkyl-, and $C_{3-7}$ cycloalkyl-$C_{1-4}$ alkyl- of $R^{c1}$ and $R^{d1}$ are each optionally substituted with 1 or 2 independently selected $R^A$ substituents;
  or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^A$ substituents; and
  each $R^A$ is independently selected from oxo, $C_{1-6}$ alkyl, $C_{1-6}$ haloalkyl, CN, and $OR^{a4}$, wherein the $C_{1-6}$ alkyl of $R^A$ is optionally substituted with 1 or 2 independently selected $R^D$ substituents.

In some embodiments, $R^2$ is $C(O)NR^{c1}R^{d1}$;
$R^{c1}$ is H;
$R^{d1}$ is selected from ethyl, propyl, isopropyl, butyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl and thianyl, wherein the ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl and thianyl of $R^{d1}$ are each optionally substituted with 1 or 2 independently selected $R^A$ substituents;

or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1 or 2 independently selected $R^A$ substituents; and each $R^A$ is independently selected from oxo, methyl, $CH_2F$, $CHF_2$, $CF_3$, $—OCH_3$, $—CH_2OH$, CN and OH.

In some embodiments, $R^2$ is $C(O)NR^{c1}R^{d1}$;
$R^{c1}$ is H;
$R^{d1}$ is selected from ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl and thianyl, wherein the ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrrolidinyl and thianyl of $R^{d1}$ are each optionally substituted with 1 or 2 independently selected $R^A$ substituents;

or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1 or 2 independently selected $R^A$ substituents; and each $R^A$ is independently selected from oxo, methyl, $CH_2F$, $CHF_2$, $CF_3$, $—OCH_3$, $—CH_2OH$, CN and OH.

In some embodiments, $R^2$ is $C(O)NR^{c1}R^{d1}$; $R^{c1}$ is H; and $R^{d1}$ is selected from 4-hydroxybicyclo[2.2.1]heptanyl and tetrahydropyranyl.

In some embodiments, $R^2$ is Cy, $C(O)NR^{c1}R^{d1}$ or $NR^{c1}C(O)R^{b1}$, wherein $R^{c1}$ is H; and $R^{b1}$ and $R^{d1}$ are each independently selected from $C_{1-6}$ alkyl, $C_{3-7}$ cycloalkyl, 4-10 membered heterocycloalkyl, $C_{3-10}$ cycloalkyl-$C_{1-6}$ alkyl-, and (4-10 membered heterocycloalkyl)-$C_{1-6}$ alkyl-, each of which is optionally substituted by 1, 2, 3, or 4 independently selected $R^A$ substituents.

In some embodiments, each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, of $R^{a1}$, $R^{b1}$, $R^{c1}$, and $R^{d1}$ are each optionally substituted with 1, 2, 3, 4, 5, 6, 7, or 8 independently selected $R^A$ substituents; and each $R^A$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each $R^{c1}$ and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, 4, 5, 6, 7, or 8 independently selected $R^A$ substituents;

or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, 4, 5, 6, 7, or 8 independently selected $R^A$ substituents.

In some embodiments, Cy is a $C_{3-14}$ cycloalkyl optionally substituted with 1, 2, 3, 4, 5, 6, 7, or 8 independently selected $R^A$ substituents.

In some embodiments, Cy is a $C_{3-10}$ cycloalkyl optionally substituted with 1, 2, 3, or 4 independently selected $R^A$ substituents.

In some embodiments, Cy is a $C_{3-6}$ cycloalkyl optionally substituted with 1, 2, 3, or 4 independently selected $R^A$ substituents.

In some embodiments, Cy is a 5-14 membered heteroaryl optionally substituted with 1, 2, 3, 4, 5, 6, 7, or 8 independently selected $R^A$ substituents.

In some embodiments, Cy is a 5-10 membered heteroaryl optionally substituted with 1, 2, 3, or 4 independently selected $R^A$ substituents.

In some embodiments, Cy is a 5-6 membered heteroaryl optionally substituted with 1, 2, 3, or 4 independently selected $R^A$ substituents.

In some embodiments, Cy is a 5 membered heteroaryl optionally substituted with 1, 2, or 3 independently selected $R^A$ substituents.

In some embodiments, Cy is a 5-14 membered heteroaryl optionally substituted with 1, 2, 3, 4, 5, 6, 7, or 8 independently selected $R^A$ substituents.

In some embodiments, Cy is a 4-14 membered heterocycloalkyl optionally substituted with 1, 2, 3, 4, 5, 6, 7, or 8 independently selected $R^A$ substituents.

In some embodiments, Cy is a 4-10 membered heterocycloalkyl optionally substituted with 1, 2, 3, or 4 independently selected $R^A$ substituents.

In some embodiments, Cy is a 4-6 membered heterocycloalkyl optionally substituted with 1, 2, 3, or 4 independently selected $R^A$ substituents.

In some embodiments, Cy is a 5 membered heterocycloalkyl optionally substituted with 1, 2, 3, or 4 independently selected $R^A$ substituents.

In some embodiments, Cy is selected from:

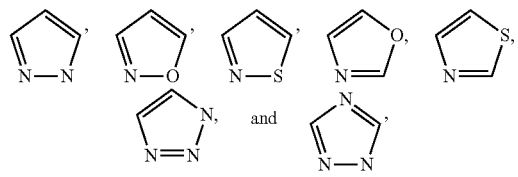

each of which is optionally substituted by 1 or 2 independently selected $R^A$ substituents.

In some embodiments, R² is selected from the following moieties:

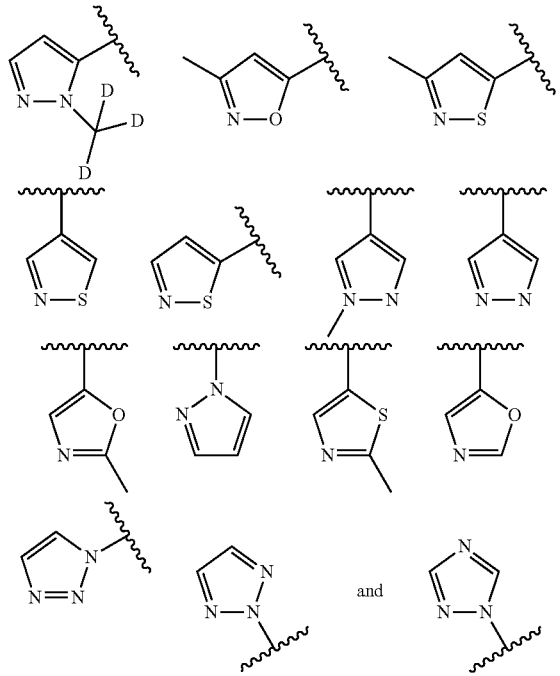

In some embodiments, Cy is selected from pyrazol-1-yl, pyrazol-4-yl, pyrazol-5-yl, isoxazol-5-yl, isothiazol-4-yl, isothizol-5-yl, oxazol-5-yl, thiazol-5-yl, 1,2,3-triazol-1-yl, 1,2,3-triazol-2-yl, and 1,2,4-triazol-1-yl, each of which is substituted by 1 $R^A$ substituent.

In some embodiments, each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_3$ 7 cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$, $R^{b4}$, $R^{c4}$, and $R^{d4}$ each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^A$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, and $C_{2-6}$ alkynyl of $R^A$ are each optionally substituted with 1, 2, 3, or 4 independently selected $R^D$ substituents;

each $R^{a4}$, $R^{b4}$, $R^{c4}$, and $R^{d4}$ is independently selected from H, $C_{1-6}$ alkyl, and $C_{1-6}$ haloalkyl, wherein the $C_{1-6}$ alkyl of $R^{a4}$, $R^{b4}$, $R^{c4}$, and $R^{d4}$ are each optionally substituted with 1, 2, 3, or 4 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^A$ is independently selected from D, halo, $C_{1-6}$ alkyl, $C_{1-6}$ haloalkyl, CN, $OR^{a4}$, and $NR^{c4}R^{d4}$; wherein the $C_{1-6}$ alkyl, $C_{2-6}$ alkenyl, and $C_{2-6}$ alkynyl of $R^A$ are each optionally substituted with 1, 2, 3, or 4 independently selected $R^D$ substituents;

each $R^{a4}$, $R^{c4}$, and $R^{d4}$ is independently selected from H, $C_{1-6}$ alkyl, $C_{1-6}$ haloalkyl, wherein the $C_{1-6}$ alkyl of $R^{a4}$, $R^{c4}$, and $R^{d4}$ are each optionally substituted with 1, 2, 3, or 4 independently selected $R^D$ substituents; and each $R^D$ is independently selected from D, OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each $R^A$ is independently selected from D, halo, $C_{1-6}$ alkyl, and $C_{1-6}$ haloalkyl, wherein the $C_{1-6}$ alkyl is optionally substituted with 1, 2, or 3 D.

In some embodiments, each $R^A$ is independently selected from methyl and $CD_3$.

In some embodiments, each $R^A$ is methyl.

In some embodiments, each $R^A$ is $CD_3$.

In some embodiments, $R^2$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with 1, 2, or 3 independently selected $R^A$ substituents.

In some embodiments, $R^2$ is $C_{1-6}$ alkyl, which is optionally substituted by 1, 2, or 3 independently selected $R^A$ groups.

In some embodiments, $R^2$ is $C_{1-6}$ alkyl.

In some embodiments, $R^2$ is propyl.

In some embodiments, $R^2$ is $C_{2-6}$ alkenyl, which is optionally substituted by 1, 2, or 3 independently selected $R^A$ groups.

In some embodiments, $R^2$ is $C_{2-6}$ alkenyl.

In some embodiments, $R^2$ is propenyl or butenyl.

In some embodiments, $R^2$ is prop-1-enyl or but-1-enyl.

In some embodiments, $R^2$ is $C_{2-6}$ alkynyl, which is optionally substituted with 1, 2 or 3 independently selected $R^A$ substituents.

In some embodiments, $R^2$ is ethynyl, propynyl, butynyl, or pentynyl, wherein the ethynyl is optionally substituted by $R^A$, and the propynyl, butynyl, and pentynyl groups are each optionally substituted by 1, 2, or 3 independently selected $R^A$ groups.

In some embodiments, $R^2$ is selected from ethynyl, prop-1-ynyl, but-1-ynyl, and pent-1-ynyl, wherein the ethynyl is substituted by $R^A$, and the prop-1-ynyl, but-1-ynyl, and pent-1-ynyl are each optionally substituted by 1, 2, or 3 independently selected $R^A$ groups.

In some embodiments, $R^2$ is selected from prop-1-ynyl, but-1-ynyl, and pent-1-ynyl, wherein the prop-1-ynyl, but-1-ynyl, and pent-1-ynyl are each optionally substituted by 1, 2, or 3 independently selected $R^A$ groups.

In some embodiments, $R^2$ is ethynyl, wherein the ethynyl is optionally substituted by 1, 2, or 3 independently selected $R^A$ groups.

In some embodiments, each $R^A$ is independently selected from H, D, $C_{1-6}$ alkyl, $C_{1-6}$ haloalkyl, $C_{6-10}$ aryl, $C_{3-12}$ cycloalkyl, 5-10 membered heteroaryl, 4-12 membered heterocycloalkyl, wherein the $C_{1-6}$ alkyl, $C_{6-10}$ aryl, $C_{3-12}$ cycloalkyl, 5-10 membered heteroaryl, and 4-12 membered heterocycloalkyl, are each optionally substituted with 1, 2, 3, 4, or 5 independently selected $R^D$ substituents.

In some embodiments, each $R^A$ is independently selected from H, D, $C_{1-6}$ alkyl, $C_{1-6}$ haloalkyl, $C_{6-10}$ aryl, $C_{3-12}$ cycloalkyl, 5-10 membered heteroaryl, 4-12 membered heterocycloalkyl, $C_{6-10}$ aryl-$C_{1-6}$ alkyl-, $C_{3-12}$ cycloalkyl-$C_{1-6}$ alkyl-, (5-10 membered heteroaryl)-$C_{1-6}$alkyl-, and (4-12 membered heterocycloalkyl)-$C_{1-6}$ alkyl-, wherein the $C_{1-6}$ alkyl, $C_{6-10}$ aryl, $C_{3-12}$ cycloalkyl, 5-10 membered heteroaryl, 4-12 membered heterocycloalkyl, $C_{6-10}$ aryl-$C_{1-6}$ alkyl-, $C_{3-12}$ cycloalkyl-$C_{1-6}$ alkyl-, (5-10 membered heteroaryl)-$C_{1-6}$ alkyl-, and (4-12 membered heterocycloalkyl)-$C_{1-6}$ alkyl- are each optionally substituted with 1, 2, 3, 4, or 5 independently selected $R^D$ substituents, and wherein the connection of $C_{6-10}$ aryl-$C_{1-6}$ alkyl-, $C_{3-12}$ cycloalkyl-$C_{1-6}$ alkyl-, (5-10 membered heteroaryl)-$C_{1-6}$ alkyl- and (4-12 membered heterocycloalkyl)-$C_{1-6}$ alkyl-groups to $R^2$ (e.g., to an alkynyl group of $R^2$) may occur through the aforementioned ring or the $C_{1-6}$ alkyl group.

In some embodiments, each $R^A$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups.

In some embodiments, each $R^{a4}$ is independently selected from H and $C_{1-6}$ alkyl.

In some embodiments, each $R^A$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups; and
each $R^{a4}$ is independently selected from H and $C_{1-6}$ alkyl.

In some embodiments, each $R^A$ is independently selected from $C_{1-6}$ alkyl, $C_{6-10}$ aryl, $C_{3-10}$ cycloalkyl, 5-10 membered heteroaryl, 4-10 membered heterocycloalkyl, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups.

In some embodiments, each $R^A$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, and imidazopyrazinyl of $R^A$ are each optionally substituted by 1 or 2 independently selected $R^D$ groups.

In some embodiments, each $R^D$ is independently selected from halo, $C_{1-6}$ alkyl, CN, cyano-$C_{1-6}$ alkyl, and $OR^{a5}$.

In some embodiments, each $R^{a5}$ is independently selected from H and $C_{1-6}$ alkyl.

In some embodiments, each $R^D$ is independently selected from halo, $C_{1-6}$ alkyl, CN, cyano-$C_{1-6}$ alkyl, and $OR^{a5}$; and
each $R^{a5}$ is independently selected from H and $C_{1-6}$ alkyl.

In some embodiments, each $R^A$ is independently selected from $C_{1-6}$ alkyl, $C_{6-10}$ aryl, $C_{3-10}$ cycloalkyl, 5-10 membered heteroaryl, 4-10 membered heterocycloalkyl, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups; and each $R^D$ is independently selected from halo, $C_{1-6}$ alkyl, CN, cyano-$C_{1-6}$ alkyl, and $OR^{a5}$.

In some embodiments, each $R^A$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, and imidazopyrazinyl of $R^A$ are each optionally substituted by 1 or 2 independently selected $R^D$ groups; and each $R^D$ is independently selected from methyl, cyano, cyanomethyl, and methoxy.

In some embodiments, $R^2$ is $C_{1-6}$ haloalkyl.

In some embodiments, $R^2$ is trifluoromethyl.

In some embodiments, $R^2$ is selected from $C_{3-6}$ cycloalkyl and 4-7 membered heterocycloalkyl, wherein the $C_{3-6}$ cycloalkyl and 4-7 membered heterocycloalkyl are each optionally substituted with 1, 2, or 3 independently selected $R^A$ substituents.

In some embodiments, each $R^A$ is independently selected from D, halo, oxo, $C_{1-6}$ alkyl, $C_{6-10}$ aryl, $C_{3-6}$ cycloalkyl, 5-10 membered heteroaryl, $C(O)R^{b4}$, $C(O)OR^{a4}$, $C(O)NR^{c4}R^{d4}$, and $S(O)_2R^{b4}$, wherein the $C_{1-6}$ alkyl, $C_{6-10}$ aryl, $C_{3-6}$ cycloalkyl, and 5-10 membered heteroaryl of $R^A$ are each optionally substituted with 1 or 2 independently selected $R^D$ substituents.

In some embodiments, each $R^{a4}$, $R^{b4}$, $R^{c4}$, and $R^{d4}$ is independently selected from H, $C_{1-6}$ alkyl, phenyl, $C_{3-6}$ cycloalkyl, 5-10 membered heteroaryl, and 4-10 membered heterocycloalkyl, wherein the $C_{1-6}$ alkyl, phenyl, $C_{3-6}$ cycloalkyl, 5-10 membered heteroaryl, and 4-10 membered heterocycloalkyl of $R^{a4}$ and $R^{b4}$ are each optionally substituted with 1 or 2 independently selected $R^D$ substituents.

In some embodiments, $R^{c4}$ and $R^{d4}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^D$ substituents.

In some embodiments, each $R^D$ is independently selected from OH, CN, $C_{1-6}$ alkyl, $C_{1-6}$ alkoxy, $C_{1-6}$ haloalkyl, and phenyl.

In some embodiments, $R^2$ is selected from $C_{3-12}$ cycloalkyl and 4-12 membered heterocycloalkyl, wherein the $C_{3-12}$ cycloalkyl and 4-12 membered heterocycloalkyl are each optionally substituted with 1, 2, or 3 independently selected $R^A$ substituents; and
  each $R^A$ is independently selected from D, halo, oxo, $C_{1-6}$ alkyl, $C_{6-10}$ aryl, $C_{3-6}$ cycloalkyl, 5-10 membered heteroaryl, $C(O)R^{b4}$, $C(O)OR^{a4}$, $C(O)NR^{c4}R^{d4}$ and $S(O)_2 R^{b4}$, wherein the $C_{1-6}$ alkyl, $C_{6-10}$ aryl, $C_{3-6}$ cycloalkyl, and 5-10 membered heteroaryl of $R^A$ are each optionally substituted with 1 or 2 independently selected $R^D$ substituents.

In some embodiments, $R^2$ is selected from $C_{3-6}$ cycloalkyl and 4-7 membered heterocycloalkyl, wherein the $C_{3-6}$ cycloalkyl and 4-7 membered heterocycloalkyl of $R^2$ are each optionally substituted with 1, 2, or 3 independently selected $R^A$ substituents; and
  each $R^A$ is independently selected from $C_{1-3}$ alkyl, $C(O)R^{b4}$, $C(O)OR^{a4}$, $C(O)NR^{c4}R^{d4}$ and $S(O)_2 R^{b4}$, wherein the $C_{1-3}$ alkyl of $R^A$ are each optionally substituted with 1 or 2 independently selected $R^D$ substituents.

In some embodiments, $R^2$ is selected from $C_{3-6}$ cycloalkyl and 4-7 membered heterocycloalkyl, wherein the $C_{3-6}$ cycloalkyl and 4-7 membered heterocycloalkyl are each optionally substituted with 1, 2, or 3 independently selected $R^A$ substituents;
  each $R^A$ is independently selected from D, halo, oxo, $C_{1-6}$ alkyl, $C_{6-10}$ aryl, $C_{3-6}$ cycloalkyl, 5-10 membered heteroaryl, $C(O)R^{b4}$, $C(O)OR^{a4}$, $C(O)NR^{c4}R^{d4}$ and $S(O)_2 R^{b4}$, wherein the $C_{1-6}$ alkyl, $C_{6-10}$ aryl, $C_{3-6}$ cycloalkyl, and 5-10 membered heteroaryl of $R^A$ are each optionally substituted with 1 or 2 independently selected $R^D$ substituents; and
  each $R^{a4}$, $R^{b4}$, $R^{c4}$, and $R^{d4}$ is independently selected from H, $C_{1-6}$ alkyl, phenyl, $C_{3-6}$ cycloalkyl, 5-10 membered heteroaryl, and 4-10 membered heterocycloalkyl, wherein the $C_{1-6}$ alkyl, phenyl, $C_{3-6}$ cycloalkyl, 5-10 membered heteroaryl, and 4-10 membered heterocycloalkyl of $R^{a4}$, $R^{b4}$, $R^{c4}$, and $R^{d4}$ are each optionally substituted with 1 or 2 independently selected $R^D$ substituents.

In some embodiments, $R^2$ is selected from $C_{3-6}$ cycloalkyl and 4-7 membered heterocycloalkyl, wherein the $C_{3-6}$ cycloalkyl and 4-7 membered heterocycloalkyl are each optionally substituted with 1, 2, or 3 independently selected $R^A$ substituents;
  each $R^A$ is independently selected from D, halo, oxo, $C_{1-6}$ alkyl, $C_{6-10}$ aryl, $C_{3-6}$ cycloalkyl, 5-10 membered heteroaryl, $C(O)R^{b4}$, $C(O)OR^{a4}$, $C(O)NR^{c4}R^{d4}$, and $S(O)_2 R^{b4}$, wherein the $C_{1-6}$ alkyl, $C_{6-10}$ aryl, $C_{3-6}$ cycloalkyl, and 5-10 membered heteroaryl of $R^A$ are each optionally substituted with 1 or 2 independently selected $R^D$ substituents;
  each $R^{a4}$, $R^{b4}$, $R^{c4}$, and $R^{d4}$ is independently selected from H, $C_{1-6}$ alkyl, phenyl, $C_{3-6}$ cycloalkyl, 5-10 membered heteroaryl, and 4-10 membered heterocycloalkyl, wherein the $C_{1-6}$ alkyl, phenyl, $C_{3-6}$ cycloalkyl, 5-10 membered heteroaryl, and 4-10 membered heterocycloalkyl of $R^{a4}$, $R^{b4}$, $R^{c4}$, and $R^{d4}$ are each optionally substituted with 1 or 2 independently selected $R^D$ substituents;
  $R^{c4}$ and $R^{d4}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^D$ substituents; and
  each $R^D$ is independently selected from OH, CN, $C_{1-6}$ alkyl, $C_{1-6}$ alkoxy, $C_{1-6}$ haloalkyl, and phenyl.

In some embodiments, $R^2$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^2$ are each optionally substituted with 1, 2, or 3 independently selected $R^A$ substituents.

In some embodiments, $R^2$ is selected from azetidinyl and cyclobutyl, wherein the azetidinyl and cyclobutyl of $R^2$ are each optionally substituted with 1, 2, or 3 independently selected $R^A$ substituents.

In some embodiments, $R^2$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^2$ are each optionally substituted with 1, 2, or 3 independently selected $R^A$ substituents; and
  each $R^A$ is independently selected from oxo, $C_{1-6}$ alkyl, phenyl, $C_{3-6}$ cycloalkyl, 5-10 membered heteroaryl, $C(O)R^{b4}$, $C(O)OR^{a4}$, $C(O)NR^{c4}R^{d4}$ and $S(O)_2 R^{b4}$, wherein the $C_{1-6}$ alkyl, phenyl, $C_{3-6}$ cycloalkyl, and 5-10 membered heteroaryl, of $R^A$ are each optionally substituted with 1 or 2 independently selected $R^D$ substituents.

In some embodiments, $R^2$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^2$ are each optionally substituted with 1, 2, or 3 independently selected $R^A$ substituents;
  each $R^A$ is independently selected from oxo, $C_{1-6}$ alkyl, phenyl, $C_{3-6}$ cycloalkyl, 5-10 membered heteroaryl, $C(O)R^{b4}$, $C(O)OR^{a4}$, $C(O)NR^{c4}R^{d4}$, and $S(O)_2 R^{b4}$, wherein the $C_{1-6}$ alkyl, phenyl, $C_{3-6}$ cycloalkyl, and 5-10 membered heteroaryl, of $R^A$ are each optionally substituted with 1 or 2 independently selected $R^D$ substituents; and
  each $R^{a4}$, $R^{b4}$, $R^{c4}$, and $R^{d4}$ is independently selected from H, $C_{1-6}$ alkyl, phenyl, $C_{3-6}$ cycloalkyl, 5-7 membered heteroaryl, and 4-7 membered heterocycloalkyl, wherein the $C_{1-6}$ alkyl, $C_{3-6}$ cycloalkyl, 5-7 membered heteroaryl, and 4-7 membered heterocycloalkyl of $R^{a4}$, $R^{b4}$, $R^{c4}$, and $R^{d4}$ are each optionally substituted with 1 or 2 independently selected $R^D$ substituents.

In some embodiments, $R^2$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^2$ are each optionally substituted with 1, 2, or 3 independently selected $R^A$ substituents;

each $R^A$ is independently selected from $C_{1-3}$ alkyl, $C(O)R^{b4}$, $C(O)OR^{a4}$, $C(O)NR^{c4}R^{d4}$, and $S(O)_2R^{b4}$, wherein the $C_{1-3}$ alkyl of $R^A$ are each optionally substituted with 1 or 2 independently selected $R^D$ substituents;

each $R^{a4}$, $R^{b4}$, $R^{c4}$, and $R^{d4}$ is independently selected from H, $C_{1-6}$ alkyl, phenyl, $C_{3-6}$ cycloalkyl, 5-7 membered heteroaryl, and 4-7 membered heterocycloalkyl, wherein the $C_{1-6}$ alkyl, $C_{3-6}$ cycloalkyl, 5-7 membered heteroaryl, and 4-7 membered heterocycloalkyl of $R^{a4}$, $R^{b4}$, $R^{c4}$, and $R^{d4}$ are each optionally substituted with 1 or 2 independently selected $R^D$ substituents;

or, any $R^{c4}$ and $R^{d4}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^D$ substituents; and each $R^D$ is independently selected from OH, CN, $C_{1-6}$ alkyl, $C_{1-6}$ alkoxy, $C_{1-6}$ haloalkyl, and phenyl.

In some embodiments, $R^2$ is selected from azetidinyl and cyclobutyl, wherein the azetidinyl and cyclobutyl of $R^2$ are each optionally substituted with 1, 2, or 3 $R^A$ substituents independently selected from (1-methyl-1H-pyrazol-4-yl)sulfonyl, ethylcarboxylate, oxo, cyclopropyl, butyl, acetyl, cyclopropanecarbonyl, phenyl, methylphenyl, dimethylphenyl, pyridinyl, thiazolyl, trifluoromethylphenyl, cyanophenyl, hydroxyphenyl, hydroxymethyl, cyanoethyl, oxohexahydropyrrolo[1,2-a]pyrazine-2-yl, furan-2-carbonyl, cyanopyrazinyl, and ethoxyphenyl.

In some embodiments, $R^3$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D.

In some embodiments, $R^3$ is $C_{1-6}$ alkyl, wherein $C_{1-6}$ alkyl is optionally substituted with 1, 2, or 3 D.

In some embodiments, $R^3$ is methyl or $CD_3$.

In some embodiments, $R^3$ is methyl.

In some embodiments, $R^3$ is $CD_3$.

In some embodiments, $R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D.

In some embodiments, $R^4$ is H, D or $C_{1-6}$ alkyl, wherein $C_{1-6}$ alkyl is optionally substituted with 1, 2, or 3 D.

In some embodiments, $R^4$ is H.

In some embodiments, $R^4$ is D.

In some embodiments, $R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D.

In some embodiments, $R^5$ is H, D or $C_{1-6}$ alkyl, wherein $C_{1-6}$ alkyl is optionally substituted with 1, 2, or 3 D.

In some embodiments, $R^5$ is H.

In some embodiments, $R^5$ is D.

In some embodiments, $R^4$ and R are each H.

In some embodiments, $R^6$ is selected from H, D, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OH, COOH and $NH_2$, wherein $C_{1-6}$ alkyl is optionally substituted with 1, 2, or 3 D.

In some embodiments, $R^6$ is selected from H, D, halo, $C_{1-6}$ alkyl, $C_{2-6}$ alkenyl, $C_{2-6}$ alkynyl, $C_{1-6}$ haloalkyl, CN, $NO_2$, OH, COOH and $NH_2$, wherein $C_{1-6}$ alkyl is optionally substituted with 1, 2, or 3 D.

In some embodiments, $R^6$ is H, D or $C_{1-6}$ alkyl, wherein $C_{1-6}$ alkyl is optionally substituted with 1, 2, or 3 D.

In some embodiments, $R^6$ is methyl.

In some embodiments, $R^6$ is $CD_3$.

In some embodiments, $R^6$ is H.

In some embodiments, $R^6$ is D.

In some embodiments, $R^6$ is $C_{1-6}$ haloalkyl, wherein each halogen is F, wherein the haloalkyl is optionally substituted with 1 or 2 independently selected Y substituents, wherein each Y is independently selected from D, halo, $C_{1-6}$ alkyl, and $C_{1-6}$ haloalkyl. In other embodiments, each Y is independently selected from halo and $C_{1-6}$ haloalkyl.

In some embodiments, $R^6$ is H, $CH_2F$, $CHF_2$ or $CF_3$.

In some embodiments, $R^6$ is selected from $CF_3$, $CCl_3$, $CF_2H$, $CCl_2H$, $CF_2Y$, $CCl_2Y$, $CFH_2$, $CClH_2$, CFHY, CClHY, $CF(Y)_2$ and $CCl(Y)_2$.

In some embodiments, $R^6$ is selected from $CF_3$, $CF_2H$, $CF_2Y$, $CFH_2$, CFHY, and $CF(Y)_2$.

In some embodiments, $R^6$ is $C_{1-6}$ haloalkyl, wherein each halogen is F.

In some embodiments, $R^6$ is $C_{1-6}$ haloalkyl, wherein each halogen is Cl.

In some embodiments, $R^6$ is selected from $CH_2F$, $CHF_2$, $CF_3$, and $CF_2CF_3$.

In some embodiments, $R^6$ is $CH_2F$, $CHF_2$, or $CF_3$.

In some embodiments, $R^6$ is $CF_3$.

In some embodiments, $R^6$ is $CH_2F$.

In some embodiments, $R^6$ is $CHF_2$.

In some embodiments, $R^6$ is $CF_2CF_3$.

In some embodiments, $R^7$ is selected from H, D, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OH, COOH and $NH_2$.

In some embodiments, $R^7$ is selected from H, D, halo, $C_{1-6}$ alkyl, $C_{2-6}$ alkenyl, $C_{2-6}$ alkynyl, $C_{1-6}$ haloalkyl, CN, $NO_2$, OH, COOH and $NH_2$.

In some embodiments, $R^7$ is H, D or $C_{1-6}$ alkyl.

In some embodiments, $R^7$ is methyl or ethyl.

In some embodiments, $R^7$ is $CD_3$.

In some embodiments, $R^7$ is H.

In some embodiments, $R^7$ is D.

In some embodiments, $R^8$ is selected from H, D, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OH, COOH and $NH_2$, wherein the $C_{1-6}$ alkyl is optionally substituted with 1, 2, or 3 D.

In some embodiments, $R^8$ is selected from H, D, halo, $C_{1-6}$ alkyl, $C_{2-6}$ alkenyl, $C_{2-6}$ alkynyl, $C_{1-6}$ haloalkyl, CN, $NO_2$, OH, COOH and $NH_2$, wherein the $C_{1-6}$ alkyl is optionally substituted with 1, 2, or 3 D.

In some embodiments, $R^8$ is H, D or $C_{1-6}$ alkyl, wherein the $C_{1-6}$ alkyl is optionally substituted with 1, 2, or 3 D.

In some embodiments, $R^8$ is methyl or ethyl.

In some embodiments, $R^8$ is $CD_3$.

In some embodiments, $R^8$ is H.

In some embodiments, $R^8$ is D.

In some embodiments, $R^7$ and $R^8$ are each H.

In some embodiments, $R^7$ and $R^8$, together with the C atom to which they are attached, form a cyclopropyl or cyclobutyl.

In some embodiments, $R^7$ and $R^8$, together with the C atom to which they are attached, form a cyclopropyl.

In some embodiments, each $R^D$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{b5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{c5})R^{b5}$, $C(=NOH)R^{b5}$, $C(=NCN)R^{b5}$, $C(=NR^{c5})NR^{c5}R^{d5}$, $NR^{c5}C(=NR^{c5})NR^{c5}R^{d5}$, $NR^{c5}C(=NR^{c5})R^{b5}$, $NR^{c5}C(=NOH)NR^{c5}R^{d5}$, $NR^{c5}C(=NCN)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{c5}$, $S(O)_2NR^{c5}R^{d5}$, $OS(O)(=NR^{c5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, or 4 independently selected $R^E$ substituents.

In some embodiments, each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, or 4 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents.

In some embodiments, each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}C(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$ and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, or 4 independently selected $R^G$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, and $R^{d6}$ are each optionally substituted with 1, 2, 3, or 4 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^G$ substituents.

In some embodiments, the compound is a compound of Formula (II):

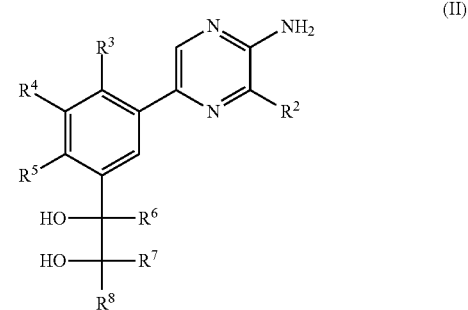

or a pharmaceutically acceptable salt thereof.

In some embodiments, the compound is a compound of Formula (III):

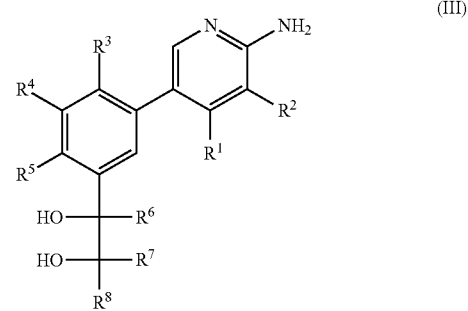

or a pharmaceutically acceptable salt thereof.

In some embodiments, the compound is a compound of Formula (IV):

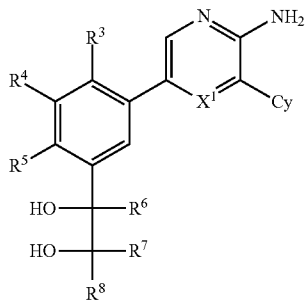

(IV)

or a pharmaceutically acceptable salt thereof.

In some embodiments, the compound is a compound of Formula (V):

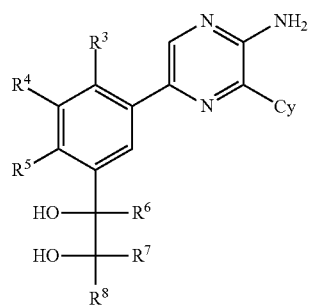

(V)

or a pharmaceutically acceptable salt thereof.

In some embodiments, X is N or $CR^1$;

$R^1$ is H, D or $C_{1-6}$ alkyl;

$R^2$ is Cy, $C(O)NR^{c1}R^{d1}$ or $NR^cC(O)R^{b1}$;

Cy is 5-14 membered heteroaryl, which is optionally substituted with 1, 2, 3, 4, 5, 6, 7, or 8 independently selected $R^A$ substituents;

$R^3$, $R^4$, and $R^5$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D;

$R^6$, $R^7$ and $R^8$ are each independently selected from H, D, halo, $C_{1-6}$ alkyl, $C_{2-6}$ alkenyl, $C_{2-6}$ alkynyl, $C_{1-6}$ haloalkyl, CN, OH, and $NH_2$, wherein $C_{1-6}$ alkyl is optionally substituted with 1, 2, or 3 D;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{b4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;

each $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b1}$, $R^{c1}$, and $R^{d1}$ are each optionally substituted with 1, 2, 3, or 4 independently selected $R^D$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, groups $X^1$, $R^1$, $R^{b1}$, $R^{c1}$, $R^{d1}$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is Cy.

In some embodiments, groups $X^1$, $R^1$, $R^{b1}$, $R^{c1}$, $R^{d1}$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is $C(O)NR^{c1}R^{d1}$.

In some embodiments, groups $X^1$, $R^1$, $R^{b1}$, $R^{c1}$, $R^{d1}$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is $NR^{c1}C(O)R^{b1}$.

In some embodiments, $X^1$ is N or $CR^1$;

$R^1$ is H, D or $C_{1-6}$ alkyl;

$R^2$ is Cy, $C(O)NR^{c1}R^{d1}$ or $NR^{c1}C(O)R^{b1}$;

Cy is 5-6 membered heteroaryl, which is optionally substituted with 1, 2, 3, or 4 independently selected $R^A$ substituents;

$R^3$, $R^4$, and $R^5$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D;

$R^6$, $R^7$ and $R^8$ are each independently selected from H, D, halo, $C_{1-6}$ alkyl, $C_{2-6}$ alkenyl, $C_{2-6}$ alkynyl, $C_{1-6}$ haloalkyl, CN, OH, and $NH_2$, wherein $C_{1-6}$ alkyl is optionally substituted with 1, 2, or 3 D;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;

each $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b1}$, $R^{c1}$, and $R^{d1}$ are each optionally substituted with 1, 2, 3, or 4 independently selected $R^D$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, groups $X^1$, $R^1$, $R^{b1}$, $R^{c1}$, $R^{d1}$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is Cy.

In some embodiments, groups $X^1$, $R^1$, $R^{b1}$, $R^d$, $R^1$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is $C(O)NR^{c1}R^{d1}$.

In some embodiments, groups $X^1$, $R^1$, $R^{b1}$, $R^{c1}$, $R^{d1}$, Cy, $R^A$, $R^3$, $R^4$, $R^5$, $R^6$, $R^7$, $R^8$, $R^{a4}$, $R^{b4}$, $R^{c4}$, $R^{d4}$, and $R^D$ are as defined above, and $R^2$ is $NR^cC(O)R^{b1}$.

In some embodiments:

$X^1$ is N or CH;

$R^2$ is $C(O)NR^{c1}R^{d1}$;

each $R^{c1}$ and $R^{d1}$ is independently selected from H, $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, or 4 independently selected $R^A$ substituents;

or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^A$ substituents;

each $R^A$ is independently selected from D, halo, oxo, $C_{1-6}$ alkyl, $C_{1-6}$ haloalkyl, $C_{2-6}$ alkenyl, $C_{2-6}$ alkynyl, CN, $NO_2$, and $OR^{a4}$, wherein the $C_{1-6}$ alkyl, $C_{2-6}$ alkenyl, and $C_{2-6}$ alkynyl of $R^A$ is optionally substituted with 1, 2 or 3 independently selected $R^D$ substituents;

each $R^{a4}$ is independently selected from H and $C_{1-6}$ alkyl, wherein the $C_{1-6}$ alkyl is optionally substituted by CN, $NO_2$, or OH;

each $R^D$ is OH;

each $R^3$, $R^4$ and $R^5$ is independently selected from H, D, halo, CN, OH, $C_{1-3}$ alkyl, and $C_{1-3}$ haloalkyl, wherein the $C_{1-6}$ alkyl is optionally substituted by 1, 2, 3, 4, 5, or 6 D; and each $R^6$, $R^7$, and $R^8$ is independently selected from H, D, $C_{1-6}$ alkyl and $C_{1-6}$ haloalkyl.

In some embodiments:
$X^1$ is N;
$R^2$ is $C(O)NR^{c1}R^{d1}$;
$R^{c1}$ is H;
$R^{d1}$ is selected from ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrorolidinyl and thianyl, wherein the ethyl, propyl, isopropyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclopbutyl, methyl-phenyl, ethyl-phenyl, oxetanyl, tetrahydrofuranyl, tetrahydropyranyl, pyrorolidinyl and thianyl of $R^{d1}$ is optionally substituted with 1 or 2 independently selected $R^A$ substituents;
or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1 or 2 independently selected $R^A$ substituents;
each $R^A$ is independently selected from oxo, methyl, $CH_2F$, $CHF_2$, $CF_3$, $-OCH_3$, $-CH_2OH$, CN, and OH;
$R^3$ is selected from H, methyl, and $CD_3$.
$R^4$ and $R^5$ are each H;
$R^6$ is selected from $CH_2F$, $CHF_2$, and $CF_3$; and
$R^7$ and $R^8$ are each H.
In some embodiments:
$X^1$ is N or CH;
$R^2$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with 1, 2, or 3 independently selected $R^A$ substituents;
each $R^A$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups;
each $R^{a4}$ is independently selected from H and $C_{1-6}$ alkyl;
each $R^D$ is independently selected from halo, $C_{1-6}$ alkyl, CN, cyano-$C_{1-6}$ alkyl, and $OR^{a5}$;
each $R^{a5}$ is independently selected from H and $C_{1-6}$ alkyl;
each $R^3$, $R^4$ and $R^5$ is independently selected from H, D, halo, CN, OH, $C_{1-3}$ alkyl, and $C_{1-3}$ haloalkyl, wherein the $C_{1-6}$ alkyl is optionally substituted by 1, 2, 3, 4, 5, or 6 D; and
each $R^6$, $R^7$, and $R^8$ is independently selected from H, D, $C_{1-6}$ alkyl, and $C_{1-6}$ haloalkyl.
In some embodiments:
$X^1$ is N or CH;
$R^2$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with 1 or 2 independently selected $R^A$ substituents;
each $R^A$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups;

each $R^{a4}$ is independently selected from H and $C_{1-6}$ alkyl;
each $R^D$ is independently selected from halo, $C_{1-6}$ alkyl, CN, cyano-$C_{1-6}$ alkyl, and $OR^{a5}$;
each $R^{a5}$ is independently selected from H and $C_{1-6}$ alkyl;
$R^3$ is selected from H and $C_{1-6}$ alkyl;
$R^4$ is selected from H and $C_{1-6}$ alkyl;
$R^5$ is selected from H and $C_{1-6}$ alkyl;
$R^6$ is a $C_{1-3}$ haloalkyl, wherein each halogen of the $C_{1-3}$ haloalkyl is independently selected from F and Cl; and
each $R^7$ and $R^8$ is independently selected from H, D, $C_{1-6}$ alkyl, and $C_{1-6}$ haloalkyl.
In some embodiments:
$X^1$ is N;
$R^2$ is selected from trifluoromethyl, propyl, propenyl, ethynyl, propynyl, butynyl, and pentynyl, wherein the ethynyl is optionally substituted by $R^A$, and the propynyl, butynyl, and pentynyl groups are each optionally substituted by 1, 2, or 3 independently selected $R^A$ groups;
each $R^A$ is independently selected from $C_{1-6}$ alkyl, $C_{6-10}$ aryl, $C_{3-10}$ cycloalkyl, 5-10 membered heteroaryl, 4-10 membered heterocycloalkyl, and $OR^{a4}$, wherein the $C_{1-6}$ alkyl, $C_{6-10}$ aryl, $C_{3-10}$ cycloalkyl, 5-10 membered heteroaryl, and 4-10 membered heterocycloalkyl of $R^A$ are each optionally substituted by 1 or 2 independently selected $R^D$ groups;
each $R^{a4}$ is independently selected from H and $C_{1-6}$ alkyl;
each $R^D$ is independently selected from halo, $C_{1-6}$ alkyl, CN, cyano-$C_{1-6}$ alkyl, and $OR^{a5}$;
each $R^{a5}$ is independently selected from H and $C_{1-6}$ alkyl;
$R^3$ is $C_{1-6}$ alkyl;
$R^4$ is H;
$R^5$ is H;
$R^6$ is a $C_{1-3}$ haloalkyl, wherein each halogen of the $C_{1-3}$ haloalkyl is independently selected from F and Cl;
$R^7$ is H; and
$R^8$ is H.
In some embodiments:
$X^1$ is N;
$R^2$ is selected from trifluoromethyl, propyl, propenyl, ethynyl, propynyl, butynyl, and pentynyl, wherein the ethynyl is optionally substituted by $R^A$, and the propynyl, butynyl, and pentynyl groups are each optionally substituted by 1, 2, or 3 independently selected $R^A$ groups;
each $R^A$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, and imidazopyrazinyl of $R^A$ are each optionally substituted by 1 or 2 independently selected $R^D$ groups;
each $R^D$ is independently selected from methyl, cyano, cyanomethyl, and methoxy;
$R^3$ is $C_{1-6}$ alkyl;
$R^4$ is H;
$R^5$ is H;
$R^6$ is $CHF_2$ or $CF_3$;
$R^7$ is H; and
$R^8$ is H.
In some embodiments:
$X^1$ is N or CH;
$R^2$ is selected from $C_{3-12}$ cycloalkyl and 4-12 membered heterocycloalkyl, wherein the $C_{3-12}$ cycloalkyl and 4-12 membered heterocycloalkyl are each optionally substituted with 1, 2, or 3 independently selected $R^A$ substituents;

each $R^A$ is independently selected from D, halo, oxo, $C_{1-6}$ alkyl, $C_{6-10}$ aryl, $C_{3-6}$ cycloalkyl, 5-10 membered heteroaryl, $C(O)R^{b4}$, $C(O)OR^{a4}$, $C(O)NR^{c4}R^{d4}$, and $S(O)_2R^{b4}$, wherein the $C_{1-6}$ alkyl, $C_{6-10}$ aryl, $C_{3-6}$ cycloalkyl, and 5-10 membered heteroaryl of $R^A$ are each optionally substituted with 1 or 2 independently selected $R^D$ substituents;

each $R^{a4}$, $R^{b4}$, $R^{c4}$ and $R^{d4}$ is independently selected from H, $C_{1-6}$ alkyl, phenyl, $C_{3-6}$ cycloalkyl, 5-10 membered heteroaryl, and 4-10 membered heterocycloalkyl, wherein the $C_{1-6}$ alkyl, phenyl, $C_{3-6}$ cycloalkyl, 5-10 membered heteroaryl, and 4-10 membered heterocycloalkyl of $R^{a4}$ and $R^{b4}$ are each optionally substituted with 1 or 2 independently selected $R^D$ substituents;

or, any $R^{c4}$ and $R^{d4}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^D$ substituents;

each $R^3$, $R^4$ and $R^5$ is independently selected from H, D, halo, CN, OH, $C_{1-3}$ alkyl, and $C_{1-3}$ haloalkyl, wherein the $C_{1-6}$ alkyl is optionally substituted by 1, 2, 3, 4, 5, or 6 D; and each $R^6$, $R^7$ and $R^8$ is independently selected from H, D, $C_{1-6}$ alkyl, and $C_{1-6}$ haloalkyl.

In some embodiments:

$X^1$ is N or CH;

$R^2$ is selected from $C_{3-6}$ cycloalkyl and 4-7 membered heterocycloalkyl, wherein the $C_{3-6}$ cycloalkyl and 4-7 membered heterocycloalkyl are each optionally substituted with 1, 2, or 3 $R^A$ substituents;

each $R^A$ is independently selected from $C_{1-3}$ alkyl, $C(O)R^{b4}$, $C(O)OR^{a4}$, $C(O)NR^{c4}R^{d4}$, and $S(O)_2R^{b4}$, wherein the $C_{1-3}$ alkyl of $R^A$ are each optionally substituted with 1 or 2 independently selected $R^D$ substituents;

each $R^{a4}$, $R^{b4}$, $R^{c4}$, and $R^{d4}$ is independently selected from H, $C_{1-6}$ alkyl, phenyl, $C_{3-6}$ cycloalkyl, 5-7 membered heteroaryl, and 4-7 membered heterocycloalkyl, wherein the $C_{1-6}$ alkyl, $C_{3-6}$ cycloalkyl, 5-7 membered heteroaryl, and 4-7 membered heterocycloalkyl of $R^{a4}$, $R^{b4}$, $R^{c4}$, and $R^{d4}$ are each optionally substituted with 1 or 2 independently selected $R^D$ substituents;

or, any $R^{c4}$ and $R^{d4}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^D$ substituents;

each $R^D$ is independently selected from OH, CN, $C_{1-6}$ alkyl, $C_{1-6}$ alkoxy, $C_{1-6}$ haloalkyl and phenyl;

$R^3$ is selected from H, methyl and $CD_3$;

$R^4$ and $R^5$ are each H;

$R^6$ is selected from $CH_2F$, $CHF_2$, and $CF_3$; and $R^7$ and $R^8$ are each H.

In some embodiments:

$X^1$ is N;

$R^2$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^2$ are each optionally substituted with 1, 2, or 3 $R^A$ substituents independently selected from (1-methyl-1H-pyrazol-4-yl)sulfonyl, ethylcarboxylate, oxo, cyclopropyl, butyl, acetyl, cyclopropanecarbonyl, phenyl, methylphenyl, dimethylphenyl, pyridinyl, thiazolyl, trifluoromethylphenyl, cyanophenyl, hydroxyphenyl, hydroxymethyl, cyanoethyl, oxohexahydropyrrolo[1,2-a]pyrazine-2-yl, furan-2-carbonyl, cyanopyrazinyl, and ethoxyphenyl;

$R^3$ is selected from H, methyl and $CD_3$;

$R^4$ and $R^5$ are each H;

$R^6$ is selected from $CH_2F$, $CHF_2$, and $CF_3$; and $R^7$ and $R^8$ are each H.

In some embodiments, $X^1$ is N or $CR^1$;

$R^1$ is H;

$R^2$ is Cy, $C(O)NR^{c1}R^{d1}$ or $NR^{c1}C(O)R^{b1}$;

Cy is 5-membered heteroaryl, which is optionally substituted with 1, 2, or 3 independently selected $R^A$ substituents;

$R^3$, $R^4$, and $R^5$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D;

$R^6$, $R^7$ and $R^8$ are each independently selected from H, D, halo, $C_{1-6}$ alkyl, $C_{2-6}$ alkenyl, $C_{2-6}$ alkynyl, $C_{1-6}$ haloalkyl, CN, OH, and $NH_2$, wherein $C_{1-6}$ alkyl is optionally substituted with 1, 2, or 3 D;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;

each $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b1}$, $R^{c1}$, and $R^{d1}$ are each optionally substituted with 1, 2, 3, or 4 independently selected $R^D$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-C$_{1-6}$ alkyl- of R$^{a4}$, R$^{b4}$, R$^{c4}$, and R$^{d4}$ are each optionally substituted with 1, 2, 3, 4, 5, 6, 7, or 8 independently selected R$^D$ substituents;

or, any R$^{c4}$ and R$^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^D$ substituents; and each R$^D$ is independently selected from D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-4}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, groups X$^1$, R$^1$, R$^{b1}$, R$^{c1}$, R$^{d1}$, Cy, R$^A$, R$^3$, R$^4$, R$^5$, R$^6$, R$^7$, R$^8$, R$^{a4}$, R$^{b4}$, R$^{c4}$, R$^{d4}$, and R$^D$ are as defined above, and R$^2$ is Cy.

In some embodiments, groups X$^1$, R$^1$, R$^{b1}$, R$^{c1}$, R$^{d1}$, Cy, R$^A$, R$^3$, R$^4$, R$^5$, R$^6$, R$^7$, R$^8$, R$^{a4}$, R$^{b4}$, R$^{c4}$, R$^{d4}$, and R$^D$ are as defined above, and R$^2$ is C(O)NR$^{c1}$R$^{d1}$.

In some embodiments, groups X$^1$, R$^1$, R$^{b1}$, R$^{c1}$, R$^{d1}$, Cy, R$^A$, R$^3$, R$^4$, R$^5$, R$^6$, R$^7$, R$^8$, R$^{a4}$, R$^{b4}$, R$^{c4}$, R$^{d4}$, and R$^D$ are as defined above, and R$^2$ is NR$^c$C(O)R$^{b1}$.

In some embodiments, the compound is a compound of Formula (V):

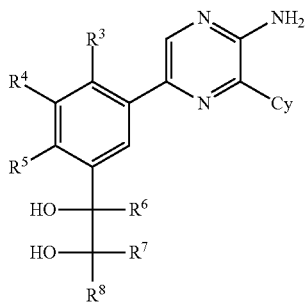

(V)

or a pharmaceutically acceptable salt thereof, wherein:

X$^1$ is N or CR$^1$;

R$^1$ is H, D or C$_{1-6}$ alkyl;

Cy is 5-14 membered heteroaryl, which is optionally substituted with 1, 2, 3, 4, 5, 6, 7, or 8 independently selected R$^A$ substituents;

R$^3$, R$^4$, and R$^5$ are each independently selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, CN, OH, and NH$_2$, wherein C$_{1-6}$ alkyl is optionally substituted with 1, 2, or 3 D;

R$^6$, R$^7$ and R$^8$ are each independently selected from H, D, halo, C$_{1-6}$ alkyl, C$_{2-6}$ alkenyl, C$_{2-6}$ alkynyl, C$_{1-6}$ haloalkyl, CN, OH, and NH$_2$, wherein C$_{1-6}$ alkyl is optionally substituted with 1, 2, or 3 D;

each R$^A$ is independently selected from D, halo, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a4}$, SR$^{a4}$, NHOR$^{a4}$, C(O)R$^{b4}$, C(O)NR$^{c4}$R$^{d4}$, C(O)NR$^{c4}$(OR$^{b4}$), C(O)OR$^{a4}$, OC(O)R$^{b4}$, OC(O)NR$^{c4}$R$^{d4}$, NR$^{c4}$R$^{d4}$, NR$^{c4}$NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)NR$^{c4}$R$^{d4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, and OS(O)$_2$R$^{b4}$, wherein the C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-6}$ alkyl-, C$_{3-7}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^A$ are each optionally substituted with 1, 2, 3, 4, 5, 6, 7, or 8 independently selected R$^D$ substituents;

each R$^{a4}$, R$^{b4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a4}$, R$^{b4}$, R$^{c4}$, and R$^{d4}$ are each optionally substituted with 1, 2, 3, 4, 5, 6, 7, or 8 independently selected R$^D$ substituents;

or, any R$^{c4}$ and R$^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected R$^D$ substituents; and each R$^D$ is independently selected from D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-4}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the compound is a compound of Formula (V):

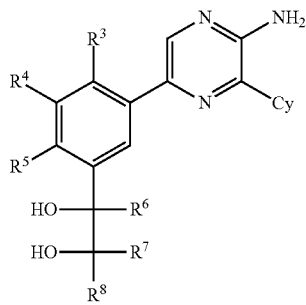

or a pharmaceutically acceptable salt thereof, wherein:
$X^1$ is N or $CR^1$;
$R^1$ is H, D or $C_{1-6}$ alkyl;
Cy is 5-6 membered heteroaryl, which is optionally substituted with 1, 2, 3, or 4 independently selected $R^A$ substituents;
$R^3$, $R^4$, and $R^5$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D;
$R^6$, $R^7$ and $R^8$ are each independently selected from H, D, halo, $C_{1-6}$ alkyl, $C_{2-6}$ alkenyl, $C_{2-6}$ alkynyl, $C_{1-6}$ haloalkyl, CN, OH, and $NH_2$, wherein $C_{1-6}$ alkyl is optionally substituted with 1, 2, or 3 D;
each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;
each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents; and
each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound is a compound of Formula (V):

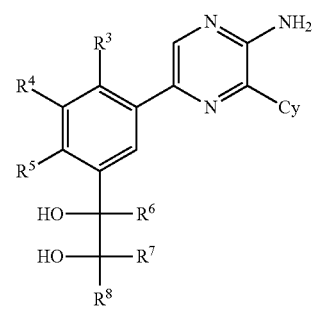

or a pharmaceutically acceptable salt thereof, wherein:
$X^1$ is N or $CR^1$;
$R^1$ is H;
Cy is 5-membered heteroaryl, which is optionally substituted with 1, 2, or 3 independently selected $R^A$ substituents;
$R^3$, $R^4$, and $R^5$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein $C_{1-6}$ alkyl is optionally substituted with 1, 2, or 3 D;
$R^6$, $R^7$ and $R^8$ are each independently selected from H, D, halo, $C_{1-6}$ alkyl, $C_{2-6}$ alkenyl, $C_{2-6}$ alkynyl, $C_{1-6}$ haloalkyl, CN, OH, and $NH_2$, wherein $C_{1-6}$ alkyl is optionally substituted with 1, 2, or 3 D;
each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, 4, 5, 6, 7, or 8 independently selected $R^D$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound is a compound of Formula (V):

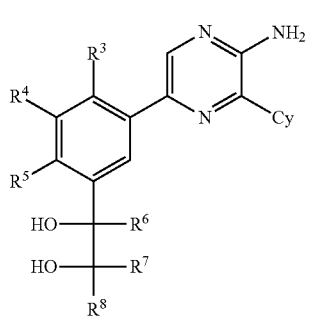

(V)

or a pharmaceutically acceptable salt thereof, wherein:
Cy is selected from 5 membered heteroaryl, which is optionally substituted with 1, 2, or 3 independently selected $R^4$ substituents;

$R^3$ is $C_{1-6}$ alkyl, which is optionally substituted with 1, 2, or 3 D;

$R^4$ and $R^5$ are each independently H, D or $C_{1-6}$ alkyl, wherein the $C_{1-6}$ alkyl is optionally substituted with 1, 2, or 3 D;

$R^6$ is H, D, $C_{1-6}$ alkyl or $C_{1-6}$ haloalkyl, wherein each halogen is F, wherein the haloalkyl is optionally substituted with 1 or 2 independently selected Y substituents, wherein each Y substituent is independently selected from D, halo, $C_{1-6}$ alkyl, and $C_{1-6}$ haloalkyl;

$R^7$ and $R^8$ are each independently H, D or $C_{1-6}$ alkyl, wherein the $C_{1-6}$ alkyl is optionally substituted with 1, 2, or 3 D;

each $R^A$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, and $C_{2-6}$ alkynyl of $R^A$ are each optionally substituted with 1, 2, 3, or 4 independently selected $R^D$ substituents;

each $R^{a4}$, $R^{b4}$, $R^{c4}$, and $R^{d4}$ is independently selected from H, $C_{1-6}$ alkyl, and $C_{1-6}$ haloalkyl, wherein the $C_{1-6}$ alkyl of $R^{a4}$, $R^{b4}$, $R^{c4}$, and $R^{d4}$ are each optionally substituted with 1, 2, 3, or 4 independently selected $R^D$ substituents; and each $R^D$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound is a compound of Formula (V):

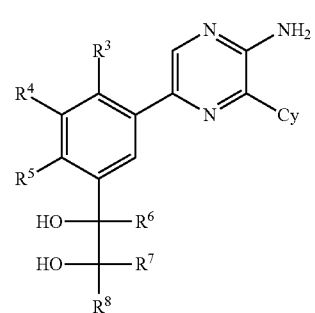

(V)

or a pharmaceutically acceptable salt thereof, wherein:
Cy is selected from 5 membered heteroaryl, which is optionally substituted with 1, 2, or 3 independently selected $R^4$ substituents;

R³ is C₁₋₆ alkyl, which is optionally substituted with 1, 2, or 3 D;

R⁴ and R⁵ are each independently H, D or C₁₋₆ alkyl, wherein the C₁₋₆ alkyl is optionally substituted with 1, 2, or 3 D;

R⁶ is H, D, C₁₋₆ alkyl or C₁₋₆ haloalkyl, wherein each halogen is F, wherein the haloalkyl is optionally substituted with 1 or 2 independently selected Y substituents, wherein each Y substituent is independently selected from D, halo, C₁₋₆ alkyl, and C₁₋₆ haloalkyl;

R⁷ and R⁸ are each independently H, D or C₁₋₆ alkyl, wherein the C₁₋₆ alkyl is optionally substituted with 1, 2, or 3 D;

each $R^A$ is independently selected from D, halo, C₁₋₆ alkyl, C₁₋₆ haloalkyl, CN, $OR^{a4}$, and $NR^{c4}R^{d4}$; wherein the C₁₋₆ alkyl of $R^A$ are each optionally substituted with 1, 2, 3, or 4 independently selected $R^D$ substituents;

each $R^{a4}$, $R^{c4}$, and $R^{d4}$ is independently selected from H, D, C₁₋₆ alkyl, and C₁₋₆ haloalkyl, wherein the C₁₋₆ alkyl of $R^{a4}$, $R^{c4}$, and $R^{d4}$ are each optionally substituted with 1, 2, 3, or 4 independently selected $R^D$ substituents; and each $R^D$ is independently selected from D, OH, CN, halo, C₁₋₆ alkyl, C₁₋₆ haloalkyl, C₁₋₆ alkoxy, C₁₋₆ haloalkoxy, amino, C₁₋₆ alkylamino, and di(C₁₋₆ alkyl)amino.

In some embodiments, the compound is a compound of Formula (V):

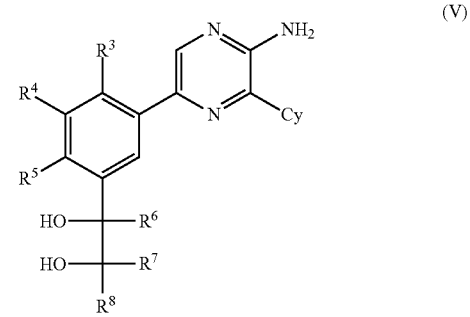

(V)

or a pharmaceutically acceptable salt thereof, wherein:

Cy is selected from:

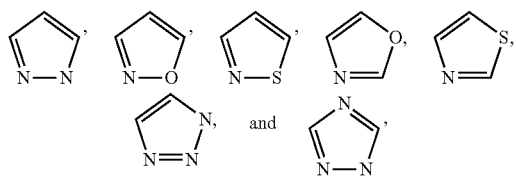

each of which is optionally substituted by 1 or 2 independently selected $R^A$ substituents;

R³ is methyl or CD₃;

R⁴ and R⁵ are each H;

R⁶ is C₁₋₆ haloalkyl, wherein each halogen is F;

R⁷ and R⁸ are each H; and each $R^A$ is methyl or CD₃.

In some embodiments, the compound is compound of Formula (VI), (VIb), or (VIc):

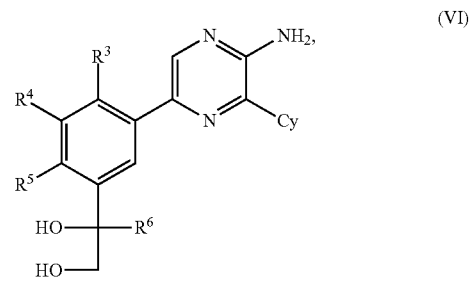

(VI)

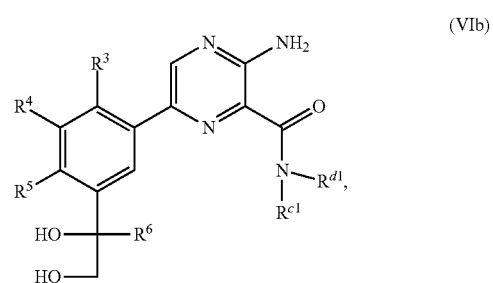

(VIb)

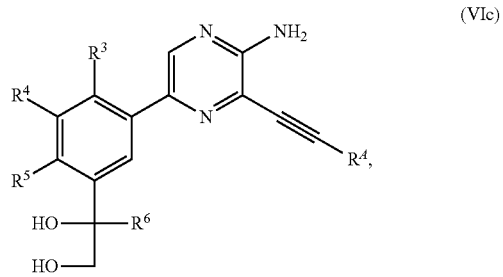

(VIc)

or a pharmaceutically acceptable salt thereof.

In some embodiments, the compound is compound of Formula (VII), (VIIb), or (VIIc):

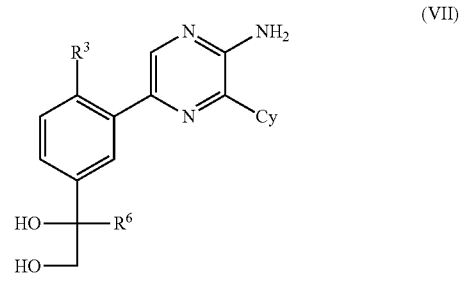

(VII)

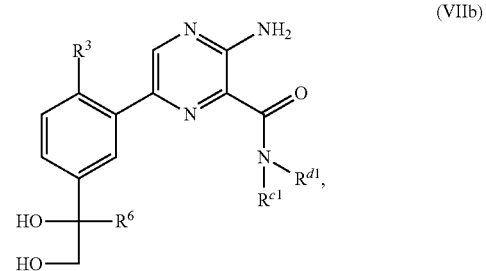

(VIIb)

-continued

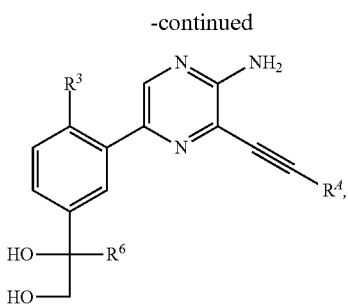
(VIIc)

or a pharmaceutically acceptable salt thereof.

In some embodiments, the compound is compound of Formula (VIII), (VIIIb), or (VIIIc):

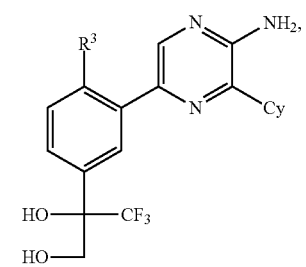
(VIII)

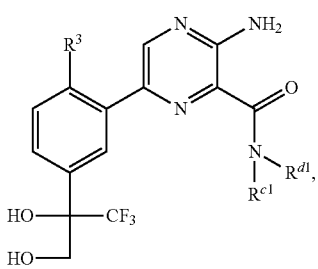
(VIIIb)

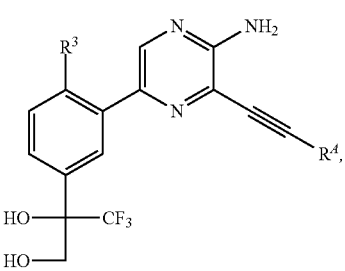
(VIIIc)

or a pharmaceutically acceptable salt thereof.

In some embodiments, the compound is selected from:

2-(3-(5-Amino-6-(1-(methyl-d₃)-1H-pyrazol-5-yl)pyrazin-2-yl)-4-methylphenyl)-3,3,3-trifluoropropane-1,2-diol;
2-(3-(5-Amino-6-(1-methyl-1H-pyrazol-4-yl)pyrazin-2-yl)-4-methylphenyl)-3,3,3-trifluoropropane-1,2-diol;
2-(3-(5-Amino-6-(1H-pyrazol-4-yl)pyrazin-2-yl)-4-methylphenyl)-3,3,3-trifluoropropane-1,2-diol;
2-(3-(5-Amino-6-(3-methylisoxazol-5-yl)pyrazin-2-yl)-4-methylphenyl)-3,3,3-trifluoropropane-1,2-diol;
2-(3-(5-Amino-6-(isothiazol-4-yl)pyrazin-2-yl)-4-methylphenyl)-3,3,3-trifluoropropane-1,2-diol;
2-(3-(5-Amino-6-(isothiazol-5-yl)pyrazin-2-yl)-4-methylphenyl)-3,3,3-trifluoropropane-1,2-diol;
2-(3-(5-amino-6-(3-methylisothiazol-5-yl)pyrazin-2-yl)-4-methylphenyl)-3,3,3-trifluoropropane-1,2-diol;
2-(3-(5-Amino-6-(2-methyloxazol-5-yl)pyrazin-2-yl)-4-methylphenyl)-3,3,3-trifluoropropane-1,2-diol;
2-(3-(5-amino-6-(2-methylthiazol-5-yl)pyrazin-2-yl)-4-methylphenyl)-3,3,3-trifluoropropane-1,2-diol;
2-(3-(5-Amino-6-(oxazol-5-yl)pyrazin-2-yl)-4-methylphenyl)-3,3,3-trifluoropropane-1,2-diol;
2-(3-(5-Amino-6-(1H-pyrazol-1-yl)pyrazin-2-yl)-4-methylphenyl)-3,3,3-trifluoropropane-1,2-diol;
2-(3-(5-Amino-6-(1H-1,2,3-triazol-1-yl)pyrazin-2-yl)-4-methylphenyl)-3,3,3-trifluoropropane-1,2-diol;
(2-(3-(5-Amino-6-(2H-1,2,3-triazol-2-yl)pyrazin-2-yl)-4-methylphenyl)-3,3,3-trifluoropropane-1,2-diol;
2-(3-(5-Amino-6-(1H-1,2,4-triazol-1-yl)pyrazin-2-yl)-4-methylphenyl)-3,3,3-trifluoropropane-1,2-diol;
2-(3-(5-Amino-6-(2-methyloxazol-5-yl)pyrazin-2-yl)-4-(methyl-d₃)phenyl)-3,3,3-trifluoropropane-1,2-diol;
3-amino-6-(2-(methyl-d₃)-5-(1,1,1-trifluoro-2,3-dihydroxypropan-2-yl)phenyl)-N-(tetrahydro-2H-pyran-4-yl)pyrazine-2-carboxamide;
3-amino-6-(5-(1,1-difluoro-2,3-dihydroxypropan-2-yl)-2-(methyl-d₃)phenyl)-N-(4-hydroxybicyclo[2.2.1]heptan-1-yl)pyrazine-2-carboxamide;
3-amino-6-(2-(methyl-d₃)-5-(1,1,1-trifluoro-2,3-dihydroxybutan-2-yl)phenyl)-N-(tetrahydro-2H-pyran-4-yl)pyrazine-2-carboxamide;
2-(3-(5-amino-6-(3-methyl-1H-pyrazol-4-yl)pyrazin-2-yl)-4-(methyl-d₃)phenyl)-1,1,1,4,4,4-hexafluorobutane-2,3-diol;
2-(3-(5-amino-6-(3-methyl-1H-pyrazol-4-yl)pyrazin-2-yl)-4-(methyl-d₃)phenyl)-1,1,1,4,4,4-hexafluorobutane-2,3-diol;
3-amino-6-(2-methyl-5-(1,1,1-trifluoro-2,3-dihydroxy-3-methylbutan-2-yl)phenyl)-N-(tetrahydro-2H-pyran-4-yl)pyrazine-2-carboxamide;
2-(3-(5-amino-6-(1-((1-methyl-1H-pyrazol-3-yl)sulfonyl)azetidin-3-yl)pyrazin-2-yl)-4-methylphenyl)-3,3,3-trifluoropropane-1,2-diol;
(3-(3-amino-6-(2-methyl-5-(1,1,1-trifluoro-2,3-dihydroxypropan-2-yl)phenyl)pyrazin-2-yl)cyclobutyl)(3-hydroxyazetidin-1-yl)methanone;
3-amino-N-((1s,3R)-3-cyanocyclobutyl)-6-(2-(methyl-d₃)-5-((S)-1,1,1-trifluoro-2,3-dihydroxypropan-2-yl)phenyl)pyrazine-2-carboxamide;
3-amino-N-((1S,2S)-2-hydroxycyclohexyl)-6-(2-(methyl-d₃)-5-((S)-1,1,1-trifluoro-2,3-dihydroxypropan-2-yl)phenyl)pyrazine-2-carboxamide;
3-amino-N-((trans)-3-hydroxytetrahydro-2H-pyran-4-yl)-6-(2-(methyl-d₃)-5-((S)-1,1,1-trifluoro-2,3-dihydroxypropan-2-yl)phenyl)pyrazine-2-carboxamide;
3-amino-N-((1s,3R)-3-hydroxy-3-(trifluoromethyl)cyclobutyl)-6-(2-(methyl-d₃)-5-((S)-1,1,1-trifluoro-2,3-dihydroxypropan-2-yl)phenyl)pyrazine-2-carboxamide;
3-amino-N-((1s,3R)-3-hydroxy-1-methylcyclobutyl)-6-(2-(methyl-d₃)-5-((S)-1,1,1-trifluoro-2,3-dihydroxypropan-2-yl)phenyl)pyrazine-2-carboxamide;
(S)-3-amino-N-(4-(hydroxymethyl)bicyclo[2.1.1]hexan-1-yl)-6-(2-(methyl-d₃)-5-(1,1,1-trifluoro-2,3-dihydroxypropan-2-yl)phenyl)pyrazine-2-carboxamide;
(S)-3-amino-N-(3-(hydroxymethyl)bicyclo[1.1.1]pentan-1-yl)-6-(2-(methyl-d₃)-5-(1,1,1-trifluoro-2,3-dihydroxypropan-2-yl)phenyl)pyrazine-2-carboxamide;
3-amino-N—((S)-1-hydroxypropan-2-yl)-6-(2-(methyl-d₃)-5-((S)-1,1,1-trifluoro-2,3-dihydroxypropan-2-yl)phenyl)pyrazine-2-carboxamide;
(S)-3-amino-N-(2-cyano-2-methylpropyl)-6-(2-(methyl-d₃)-5-(1,1,1-trifluoro-2,3-dihydroxypropan-2-yl)phenyl)pyrazine-2-carboxamide;

(S)-3-amino-N-(4-hydroxybicyclo[2.2.1]heptan-1-yl)-6-(2-(methyl-d₃)-5-(1,1,1-trifluoro-2,3-dihydroxypropan-2-yl)phenyl)pyrazine-2-carboxamide;

3-amino-N—((R)-1-hydroxypropan-2-yl)-6-(2-(methyl-d₃)-5-((S)-1,1,1-trifluoro-2,3-dihydroxypropan-2-yl)phenyl)pyrazine-2-carboxamide;

(S)-3-amino-N-(4-hydroxybicyclo[2.1.1]hexan-1-yl)-6-(2-(methyl-d₃)-5-(1,1,1-trifluoro-2,3-dihydroxypropan-2-yl)phenyl)pyrazine-2-carboxamide;

3-amino-6-(5-((S)-1,1-difluoro-2,3-dihydroxypropan-2-yl)-2-(methyl-d₃)phenyl)-N-((1S,2S)-2-hydroxycyclohexyl)pyrazine-2-carboxamide;

3-amino-6-(5-((S)-1,1-difluoro-2,3-dihydroxypropan-2-yl)-2-(methyl-d₃)phenyl)-N-((1R,2R)-2-hydroxycyclohexyl)pyrazine-2-carboxamide;

(S)-3-amino-N-(4-cyanobicyclo[2.1.1]hexan-1-yl)-6-(5-(1,1-difluoro-2,3-dihydroxypropan-2-yl)-2-(methyl-d₃)phenyl)pyrazine-2-carboxamide;

(S)-3-amino-6-(5-(1,1-difluoro-2,3-dihydroxypropan-2-yl)-2-(methyl-d₃)phenyl)-N-(tetrahydro-2H-pyran-4-yl)pyrazine-2-carboxamide;

(S)-3-amino-6-(5-(1,1-difluoro-2,3-dihydroxypropan-2-yl)-2-methylphenyl)-N-(tetrahydro-2H-pyran-4-yl)pyrazine-2-carboxamide;

3-amino-6-(5-((S)-1,1-difluoro-2,3-dihydroxypropan-2-yl)-2-methylphenyl)-N—((S)-1-hydroxypropan-2-yl)pyrazine-2-carboxamide;

3-amino-6-(5-(1,1-difluoro-2,3-dihydroxypropan-2-yl)-2-methylphenyl)-N-(4-hydroxybicyclo[2.2.1]heptan-1-yl)pyrazine-2-carboxamide;

(3-amino-6-(5-((S)-1,1-difluoro-2,3-dihydroxypropan-2-yl)-2-methylphenyl)pyrazin-2-yl)((R)-2-(hydroxymethyl)pyrrolidin-1-yl)methanone;

(S)-3-amino-6-(5-(1,1-difluoro-2,3-dihydroxypropan-2-yl)-2-methylphenyl)-N-isopropylpyrazine-2-carboxamide;

3-amino-N-(4-cyanobicyclo[2.1.1]hexan-1-yl)-6-(5-(1,1-difluoro-2,3-dihydroxypropan-2-yl)-2-methylphenyl)pyrazine-2-carboxamide;

3-amino-6-(5-((S)-1,1-difluoro-2,3-dihydroxypropan-2-yl)-2-methylphenyl)-N-(3-methyltetrahydrofuran-3-yl)pyrazine-2-carboxamide; and 2-(3-(5-amino-6-(trifluoromethyl)pyrazin-2-yl)-4-methylphenyl)-3,3,3-trifluoropropane-1,2-diol;

or an enantiomer, diastereomer or tautomer thereof;

or a pharmaceutically acceptable salt thereof. In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof. In some embodiments, the invention includes all stereoisomers of the aforementioned compounds.

In some embodiments, the compound is a compound of Formula (I):

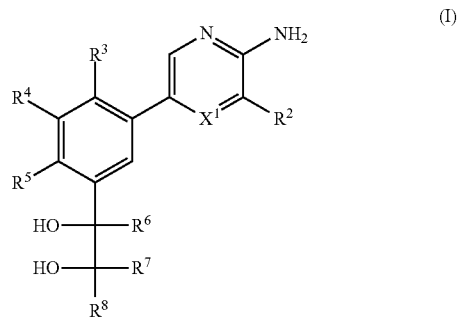

or a pharmaceutically acceptable salt thereof, wherein:
$X^1$ is N or $CR^1$;
$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;
$R^2$ is selected from $C(O)NR^{c1}R^{d1}$;
$R^3$, $R^4$ and $R^5$ are each independently selected from H, D, halo, CN, OH, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, amino, $C_{1-6}$ alkylamino, di($C_{1-6}$ alkyl)amino, and $C(O)NR^cR^d$, wherein the $C_{1-6}$ alkyl is optionally substituted by 1, 2, 3, 4, 5, or 6 D;
$R^6$, $R^7$ and $R^8$ are each independently selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b3}$, $C(O)NR^{c3}R^{d3}$, $C(O)NR^{c3}(OR^{a3})$, $C(O)OR^{a3}$, $C(=NR^{e3})R^{b3}$, $C(=NOH)R^{b3}$, $C(=NCN)R^{b3}$, and $C(=NR^{e3})NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$, $R^7$, and $R^8$ are each optionally substituted with 1, 2, 3, 4, 5, 6, 7, or 8 independently selected $R^B$ substituents; and wherein the $C_{1-6}$ haloalkyl of $R^6$, $R^7$, or $R^8$ is optionally substituted by 1, 2, 3, or 4 independently selected Y substituents;
each Y is independently selected from D, halo, $C_{1-6}$ alkyl, and $C_{1-6}$ haloalkyl;
or $R^6$ and $R^7$ substituents, together with the ring atoms to which they are attached, form a $C_{3-10}$ cycloalkyl or 4-7 membered heterocycloalkyl, each of which is optionally substituted with 1, 2, 3, or 4 independently selected $R^B$ substituents;
or $R^7$ and $R^8$ substituents, together with the ring atoms to which they are attached, form a $C_{3-10}$ cycloalkyl or 4-7 membered heterocycloalkyl, each of which is optionally substituted with 1, 2, 3, or 4 independently selected $R^B$ substituents;
$R^c$ and $R^d$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^c$ and $R^d$, are each optionally substituted with 1, 2, 3, 4, 5, 6, 7, or 8 independently selected $R^M$ substituents;

each $R^{c1}$ and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, 4, 5, 6, 7, or 8 independently selected $R^A$ substituents;

or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, 4, 5, 6, 7, or 8 independently selected $R^A$ substituents;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{b3}$, $R^{c3}$, and $R^{d3}$ are each optionally substituted with 1, 2, 3, 4, 5, 6, 7, or 8 independently selected $R^B$ substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^B$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, C(O)$R^{b4}$, C(O)$NR^{c4}R^{d4}$, C(O)$NR^{c4}(OR^{b4})$, C(O)$OR^{a4}$, OC(O)$R^{b4}$, OC(O)$NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, C(=$NR^{e4}$)$R^{b4}$, C(=NOH)$R^{b4}$, C(=NCN)$R^{b4}$, C(=$NR^{e4}$)$NR^{c4}R^{d4}$, $NR^{c4}C$(=$NR^{e4}$)$NR^{c4}R^{d4}$, $NR^{c4}C$(=$NR^{e4}$)$R^{b4}$, $NR^{c4}C$(=NOH)$NR^{c4}R^{d4}$, $NR^{c4}C$(=NCN)$NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, S(O)$NR^{c4}R^{d4}$, $S(O)_2R^{b4}$, $S(O)_2NR^{c4}R^{d4}$, OS(O)(=$NR^{c4}$)$R^{b4}$, $OS(O)_2R^{b4}$, $SF_5$, $P(O)R^{f1}R^{g4}$, OP(O)($OR^{h4}$)($OR^{i4}$), $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ is optionally substituted with 1, 2, 3, 4, 5, 6, 7, or 8 independently selected $R^D$ substituents;

each $R^B$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, C(O)$R^{b2}$, C(O)$NR^{c2}R^{d2}$, C(O)$NR^{c2}(OR^{b2})$, C(O)$OR^{a2}$, OC(O)$R^{b2}$, OC(O)$NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, C(=$NR^{e2}$)$R^{b2}$, C(=NOH)$R^{b2}$, C(=NCN)$R^{b2}$, C(=$NR^{e2}$)$NR^{c2}R^{d2}$, $NR^{c2}C$(=$NR^{e2}$)$NR^{c2}R^{d2}$, $NR^{c2}C$(=$NR^{e2}$)$R^{b2}$, $NR^{e2}C$(=NOH)$NR^{c2}R^{d2}$, $NR^{e2}C$(=NCN)$NR^{c2}R^{d2}$, $NR^{c2}S(O)R^{b2}$, $NR^{c2}S(O)NR^{c2}R^{d2}$, $NR^{c2}S(O)_2R^{b2}$, $NR^{c2}S(O)_2NR^{c2}R^{d2}$, $S(O)R^{b2}$, S(O)$NR^{c2}R^{d2}$, $S(O)_2R^{b2}$, $S(O)_2NR^{c2}R^{d2}$, OS(O)(=$NR^{e2}$)$R^{b2}$, $OS(O)_2R^{b2}$, $SF_5$, $P(O)R^{h2}R^{g2}$, OP(O)($OR^{h2}$)($OR^{i2}$), $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ is optionally substituted with 1, 2, 3, 4, 5, 6, 7, or 8 independently selected $R^M$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$, and $R^{d2}$ are each optionally substituted with 1, 2, 3, 4, 5, 6, 7, or 8 independently selected $R^M$ substituents;

or, any $R^{c2}$ and $R^{d2}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^M$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{b5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{c5})R^{b5}$, $C(=NOH)R^{b5}$, $C(=NCN)R^{b5}$, $C(=NR^{c5})NR^{c5}R^{d5}$, $NR^{c5}C(=NR^{c5})NR^{c5}R^{d5}$, $NR^{c5}C(=NR^{c5})R^{b5}$, $NR^{c5}C(=NOH)NR^{c5}R^{d5}$, $NR^{c5}C(=NCN)NR^{c5}R^{d1}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{c5}$, $S(O)_2NR^{c5}R^{d5}$, $OS(O)(=NR^{c5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, or 4 independently selected $R^E$ substituents;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, or 4 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}C(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, 4, 5, 6, 7, or 8 independently selected $R^G$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, and $R^{d6}$ are each optionally substituted with 1, 2, 3, 4, 5, 6, 7, or 8 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^G$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^G$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl; and each $R^M$ is independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 14 carbon atoms. In some embodiments, the aryl group has from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atom. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-$C_{1-6}$ alkyl" refers to a group of formula —($C_{1-6}$ alkylene)-CN.

As used herein, the term "HO—$C_{1-6}$ alkyl" refers to a group of formula —($C_{1-6}$ alkylene)-OH.

As used herein, the term "HO—$C_{1-3}$ alkyl" refers to a group of formula —($C_{1-3}$ alkylene)-OH.

As used herein, the term "$C_{1-6}$ alkoxy-$C_{1-6}$ alkyl" refers to a group of formula —($C_{1-6}$ alkylene)-O($C_{1-3}$ alkyl).

As used herein, the term "$C_{1-6}$ alkoxy-$C_{1-3}$ alkyl" refers to a group of formula —($C_{1-6}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "aminocarbonyloxy" refers to a group of formula —OC(O)NH$_2$.

As used herein, the term "$C_{1-3}$ alkylcarbonyloxy" refers to a group of formula —OC(O)($C_{1-3}$ alkyl).

As used herein, the term "$C_{1-3}$ alkylaminocarbonyloxy" refers to a group of formula —OC(O)NH($C_{1-3}$ alkyl).

As used herein, the term "di($C_{1-3}$ alkyl)aminocarbonyloxy" refers to a group of formula —OC(O)N($C_{1-3}$ alkyl)$_2$, wherein the two alkyl groups each has, independently, 1 to 3 carbon atoms.

As used herein, "cycloalkyl" refers to non-aromatic cyclic hydrocarbons including cyclized alkyl and alkenyl groups. Cycloalkyl groups can include mono- or polycyclic (e.g., having 2, 3, or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons (i.e., $C_{3-14}$). In some embodiments, the cycloalkyl is a $C_{3-14}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S and B, wherein any ring forming N is optionally an N-oxide group. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-14 membered monocyclic, bicyclic heteroaryl, or tricyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a five-membered or six-membered heteroaryl ring. In some embodiments, the heteroaryl group contains 3 to 14, 4 to 14, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b]thiazole, purine, triazine, thieno[3,2-b]pyridine, imidazo[1,2-a]pyridine, 1,5-naphthyridine, 1H-pyrazolo[4, 3-b]pyridine and the like.

A five-membered heteroaryl is a heteroaryl group having five ring-forming atoms wherein one or more (e.g., 1, 2, or 3) of the ring-forming atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl is a heteroaryl group with a ring having six ring-forming atoms wherein one or more (e.g., 1, 2, or 3) of the ring-forming atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated), wherein one or more of the ring-forming carbon atoms is replaced by a heteroatom selected from N, O, S and B, and wherein the ring-forming carbon atoms and heteroatoms can be optionally substituted by one or more oxo or sulfide (e.g., C(O), S(O), C(S), or S(O)$_2$, etc.). Heterocycloalkyl groups include monocyclic and polycyclic (e.g., having 2, 3, or 4 fused rings) systems. Included in heterocycloalkyl are monocyclic and polycyclic 3-14- or 4-14- or 3-12- or 4-12-, or 3-10-, or 4-10- or 3-7- or 4-7- or 5-6-membered heterocycloalkyl groups. Heterocycloalkyl groups can also include spirocycles and bridged rings (e.g., a 5-14 membered bridged biheterocycloalkyl ring optionally substituted with 0 to 2 additional heteroatoms independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 14 ring-forming atoms, 4 to 14 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 4-10 membered heterocycloalkyl having 1, 2, 3, or 4 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent, e.g., $R^M$ or $R^A$, are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as R-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula (I) can be prepared as shown in Scheme 1. Suitable starting materials 1-1, where $Y^1$ and $Y^2$ are independently a halogen (e.g., Cl, Br, or I) or pseudohalogen (e.g., OTf or OMs), can be converted to an appropriate substituted metal 1-2 (e.g., $M^1$ is $B(OH)_2$, Bpin, $BF_3K$, $Sn(Bu)_3$, or Zn) under standard conditions (e.g., in the presence of a diboron reagent such as bis(pinacolato) diboron, a palladium catalyst, such as dichlorobis(triphenylphosphine)palladium(II), or bis(diphenylphosphino)ferrocene]dichloropalladium(II), complex with dichloromethane, and a base, such as potassium acetate) and then coupled to 1-3 where $Y^6$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II), complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis(triphenylphosphine)palladium (0) or [1,1'-bis(diphenylphosphino)ferrocene] dichloropalladium (II)) to give to give compound 1-4.

Intermediate 1-4 can be converted to diol-containing intermediate 1-5 by exposure to reagents for dihydroxylation (e.g., osmium tetroxide and a re-oxidant such as N-methylmorpholine-N-oxide, or AD-mix α or AD-mix β). Intermediate 1-5 can be converted to an appropriate substituted metal 1-6 (e.g., $M^2$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichlorobis(triphenylphosphine)palladium(II), bis (diphenylphosphino)ferrocene]dichloropalladium(II), complex with dichloromethane, or $Pd_2(dba)_3$ and a ligand (such as 2-dicyclohexylphosphino-2',4',6'-tri-iso-propyl-1,1'-biphenyl) and a base, such as potassium acetate) and then coupled to 1-7 where $Y^3$ and $Y^7$ are independently a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene] dichloropalladium (II)) to give to give compound 1-8.

Intermediate 1-8 can be converted to compounds of Formula (I) by cross-coupling with an appropriate metal $R^2$-M (where M is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II), complex with dichloromethane and a base (e.g., a carbonate base such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene] dichloropalladium (II)). Alternatively, compounds of Formula (I) can be prepared from intermediate 1-8 by reacting with a nucleophile under SNAr conditions (e.g., by heating in the presence of a carbonate base, such as $Cs_2CO_3$).

One skilled in the art would recognize that compounds of Formula (I) can also be prepared by reversing the order of the last two steps of Scheme 1. Beginning with a suitably substituted intermediate 1-7, where $Y^3$ and $Y^7$ are independently a halogen (e.g., Cl, Br, or I) or pseudohalogen (e.g., OTf or OMs), coupling to install $R^2$ can be performed before coupling with intermediate 1-6, to afford compounds of Formula (I).

Scheme 1.

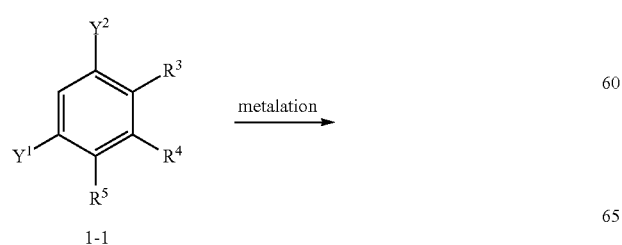

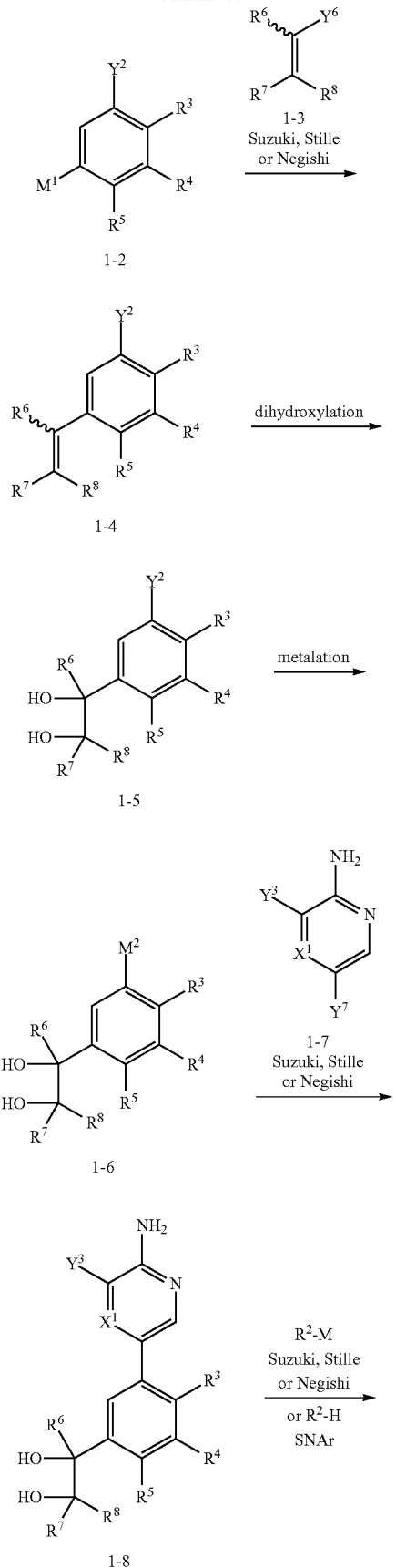

-continued

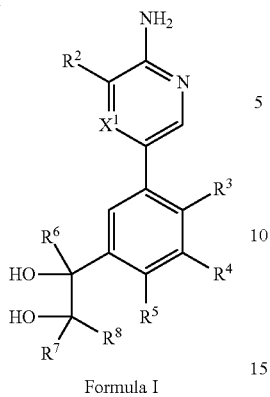

Formula I

Compounds of Formula (I) can be prepared as shown in Scheme 2. Beginning with an appropriately substituted 1,4-dibromobenzene 2-1, sequential reaction with strong base (e.g., nBuLi) at low temperature (e.g., −78° C.), followed by reaction with a carboxylic acid derivative $R^6C(O)-L^1$, such as an ester (methyl or ethyl ester) (e.g., methyl trifluoroacetate or ethyl trifluoroacetate) or a Weinreb amide (e.g., 2,2-difluoro-N-methoxy-N-methylacetamide), followed by in situ treatment with a second equivalent of strong base (e.g., nBuLi) at low temperature (e.g., −78° C.), followed by a second electrophile $R^3-L^2$ (wherein $L^2$ is a suitable leaving group (e.g., halogen, such as Cl, Br or I or a mesylate or tosylate)) affords ketone intermediate 2-2. It will be appreciated by one skilled in the art that the order of the two steps can be reversed and the two steps can also be performed separately, stepwise. Intermediate 2-2 can be halogenated by exposure to halogenating conditions to introduce $Y^2$ (e.g., bromine in the presence of $AlCl_3$ and mild heating), or N-halo-succinimide (e.g., N-bromosuccinimide) and sulfuric acid in acetic acid at elevated temperature (e.g., 80° C.)) to afford intermediate 2-3. Intermediate 2-3 can be olefinated to afford intermediate 2-5 under standard conditions for olefination (e.g., Wittig conditions with an ylide such as 2-4, where $Y^9$ can be a phenyl, generated by reacting a phosphonium salt with a strong base (e.g., n-BuLi, potassium tert-butoxide or NaHMDS) or generated by a method similar to that found in *Organic Letters*, Vol. 4, No. 10, 1671-1674, 2002 (e.g., in situ generation of methylenetriphenylphosphorane from the rhodium(I)-catalyzed decomposition of trimethylsilyldiazomethane in the presence of triphenylphosphine and 2-propanol)). Intermediate olefin 2-5 can be converted to compounds of Formula (I) by the methods outlined in Scheme 1.

Scheme 2.

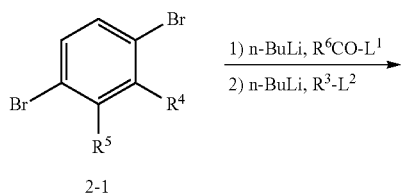

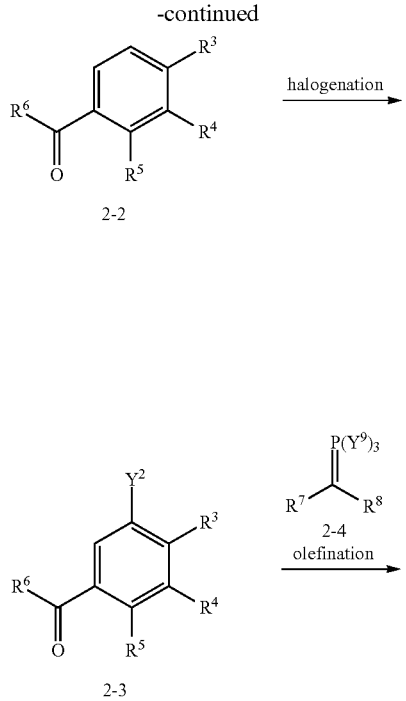

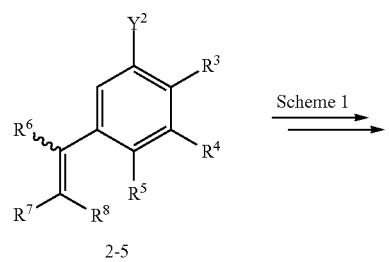

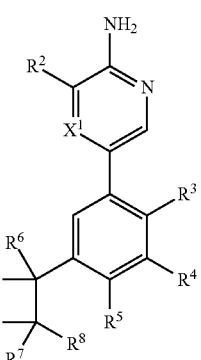

Formula I

Compounds of Formula (I) can also be prepared as shown in Scheme 3. Appropriate starting materials 3-1, where $Y^3$ is a halogen (e.g., Cl, Br, or I) or pseudohalogen (e.g., OTf or OMs), can be coupled with an appropriately substituted metal $R^2$-M (where M is $B(OH)_2$, Bpin, $BF_3K$, $Sn(Bu)_3$, Zn or ZnX (where X is a halogen such as iodide)) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II), complex with dichloromethane and a base (e.g., a carbonate base such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene] dichloropalladium (II) optionally in the presence of an additive such as copper(I)iodide) to afford intermediate 3-2. Intermediate 3-2 can then be halogenated by reaction with a reagent suitable for introducing the halogen $Y^7$ (e.g., N-halosuccinimide such as N-iodosuccinimide, N-bromosuccinimide or N-chlorosuccinimide). Intermediate 3-3 bearing a suitable halogen $Y^7$ (e.g., Cl, Br or I) can be elaborated to provide compounds of Formula (I) as shown in Scheme 1.

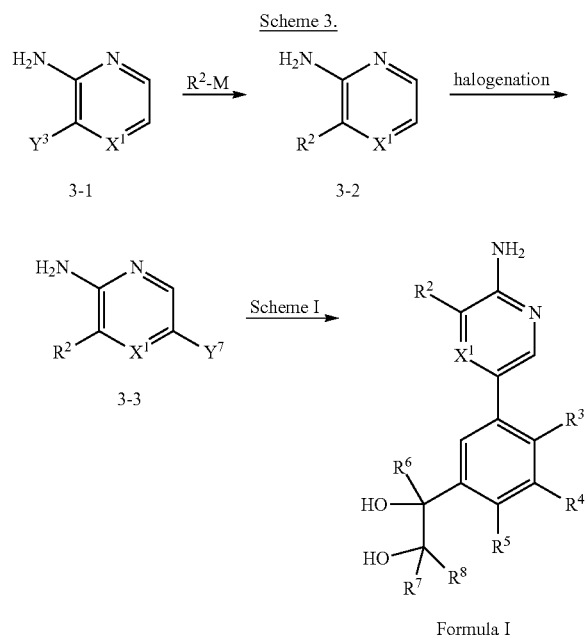

Compounds of Formula (I) wherein $R^2$ is an amide or a heterocycle can also be prepared as shown in Scheme 4. The group $Y^3$ of halo-substituted intermediate 4-1 (wherein $Y^3$ is Cl, Br or I) can be converted to a nitrile group via nucleophilic displacement with a cyanide source (e.g., heating in the presence of NaCN) or by coupling with a cyanide source under standard Negishi conditions (e.g., heating with $Zn(CN)_2$ in the presence of a palladium catalyst, such as tetrakis(triphenylphosphine)palladium(0) or [1,1'-bis(diphenylphosphino)ferrocene]dichloropalladium (II)) to afford intermediate 4-2. The nitrile substituent of intermediate 4-2 can be converted to heterocycle-substituted compounds of Formula (I) by methods known to one skilled in the art (e.g., heating an appropriately substituted acyl hydrazide in the presence of an alkoxide base in an alcoholic solvent (e.g., NaOMe in MeOH or NaOEt in EtOH) to form a triazole; heating with an azide source such as $NaN_3$ to form a tetrazole). Nitrile containing intermediates 4-2 can also be converted to amide intermediates 4-4 (compounds of Formula (I) wherein $R^2$ is an amide group) by hydrolysis (e.g., heating in the presence of aqueous acid; or with KOH in tBuOH) followed by coupling of the resulting acid with $R^{c1}R^{d1}NH$ using standard amide coupling conditions (e.g., HATU).

The group $Y^3$ of halo-substituted intermediate 4-1 (wherein $Y^3$ is Cl, Br or I) can be converted to an ester intermediate 4-3 under standard conditions for carbonylation (e.g., in the presence of a palladium catalyst, such as [1,1'-bis(diphenylphosphino)ferrocene]dichloropalladium, carbon monoxide, and an alcohol $R^{a1}OH$ such as methanol or ethanol). Ester 4-3 can be converted to amide 4-4 (compounds of Formula (I) wherein $R^2$ is an amide group) using amination conditions (e.g., by reacting with an amine such as $R^{c1}R^{d1}NH$ in the presence of $AlMe_3$). Alternatively, ester 4-3 can be converted to amide 4-4 under standard conditions for hydrolysis, such as exposure to hydroxide base (e.g., LiOH, NaOH, KOH in water and a cosolvent such as THF, MeOH or EtOH) to furnish a carboxylic acid, followed by coupling of the resulting acid with $R^{c1}R^{d1}NH$ using standard amide coupling conditions (e.g., HATU). Alternatively, the group $Y^3$ of halo-substituted intermediate 4-1 can be converted directly to an amide 4-4 under standard conditions for carbonylation (e.g., in the presence of a palladium catalyst, such as [1,1'-bis(diphenylphosphino)ferrocene]dichloropalladium, carbon monoxide, and an amine $R^{c1}R^{d1}NH$). Suitable amides 4-4 can be converted to compounds of Formula (I) wherein $R^2$ is a heterocycle by methods known to one skilled in the art (e.g., when amide 4-4 is a hydrazide, it may be reacted with N-(triphenylphosphoranylidene)isocyanamide or with p-toluenesulfonic acid and an orthoester (e.g., triethylorthoformate) to form an 1,3,4-oxadiazole; an appropriately substituted amide can be reacted with an α-halocarbonyl compound (e.g., chloracetaldehyde) to afford an oxazole; an appropriately substituted amide can be reacted with 1,1-dimethoxy-N,N-dimethylmethanamine and hydroxylamine to form an 1,2,4-oxadiazole; conversion of the amide to a thioamide (e.g., using $P_2S_5$ or Lawesson's reagent) before subjecting to the aforementioned reagents, would result in the corresponding thiadiazoles or thiazoles rather than oxadiazoles and oxazoles).

Scheme 4.

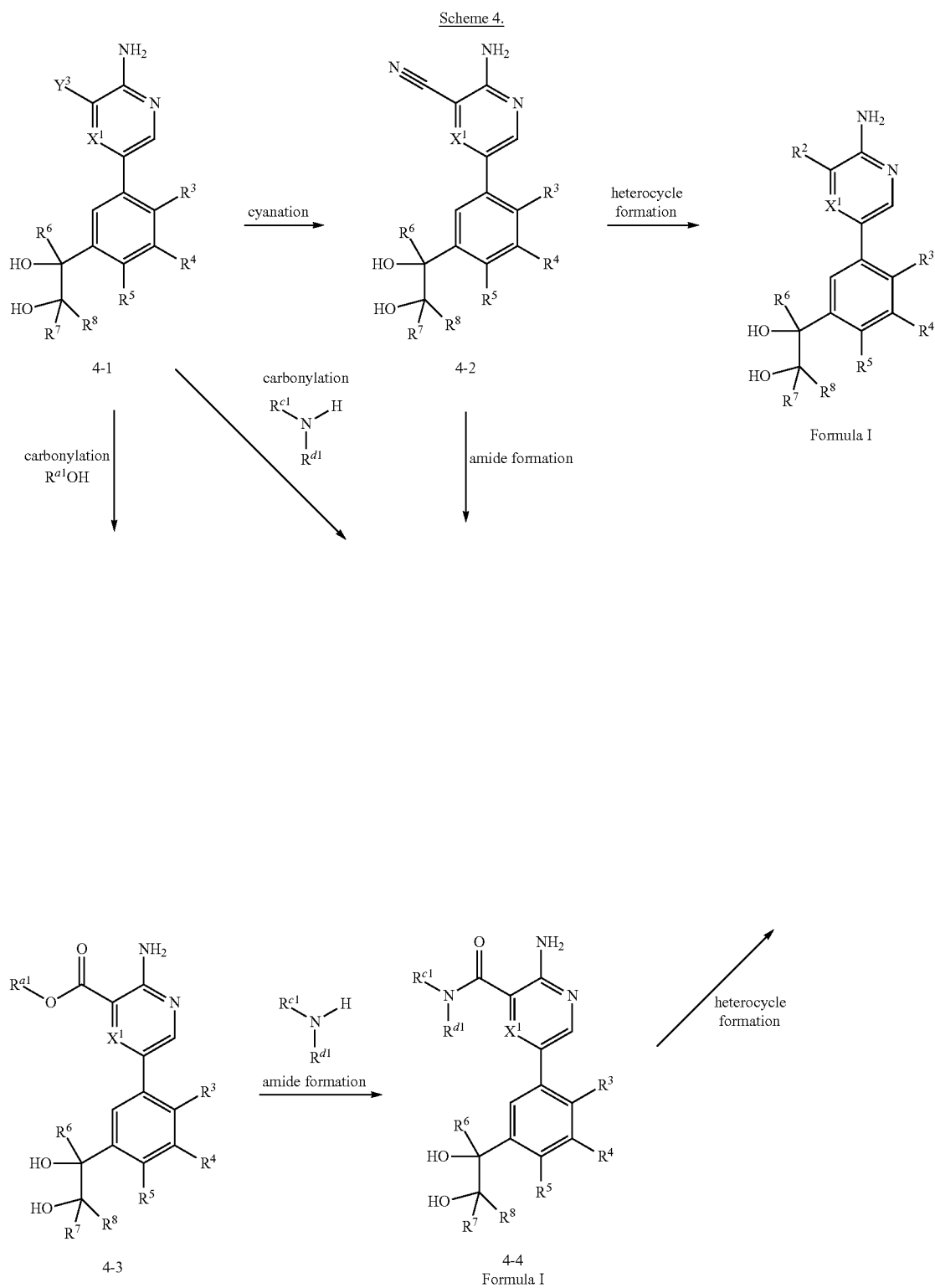

As shown in Scheme 5, the steps of Scheme 4 can be performed on appropriate starting materials 5-1 prior to coupling with intermediate 1-6 from Scheme 1. This also affords intermediates useful in the preparation of compounds of Formula (I) wherein $R^2$ is an amide or a heterocycle. Carboxylic acid intermediate 5-4 (e.g., $R^{a1}$=H and $Y^7$=an appropriate halogen such as Cl, Br or I) can be converted to amide intermediate 5-5 by reacting with an amine ($R^{c1}R^{d1}$NH) under standard conditions for amide formation (e.g., using a coupling reagent such as HATU, in the presence of a base, such as diisopropylethylamine).

Scheme 5.
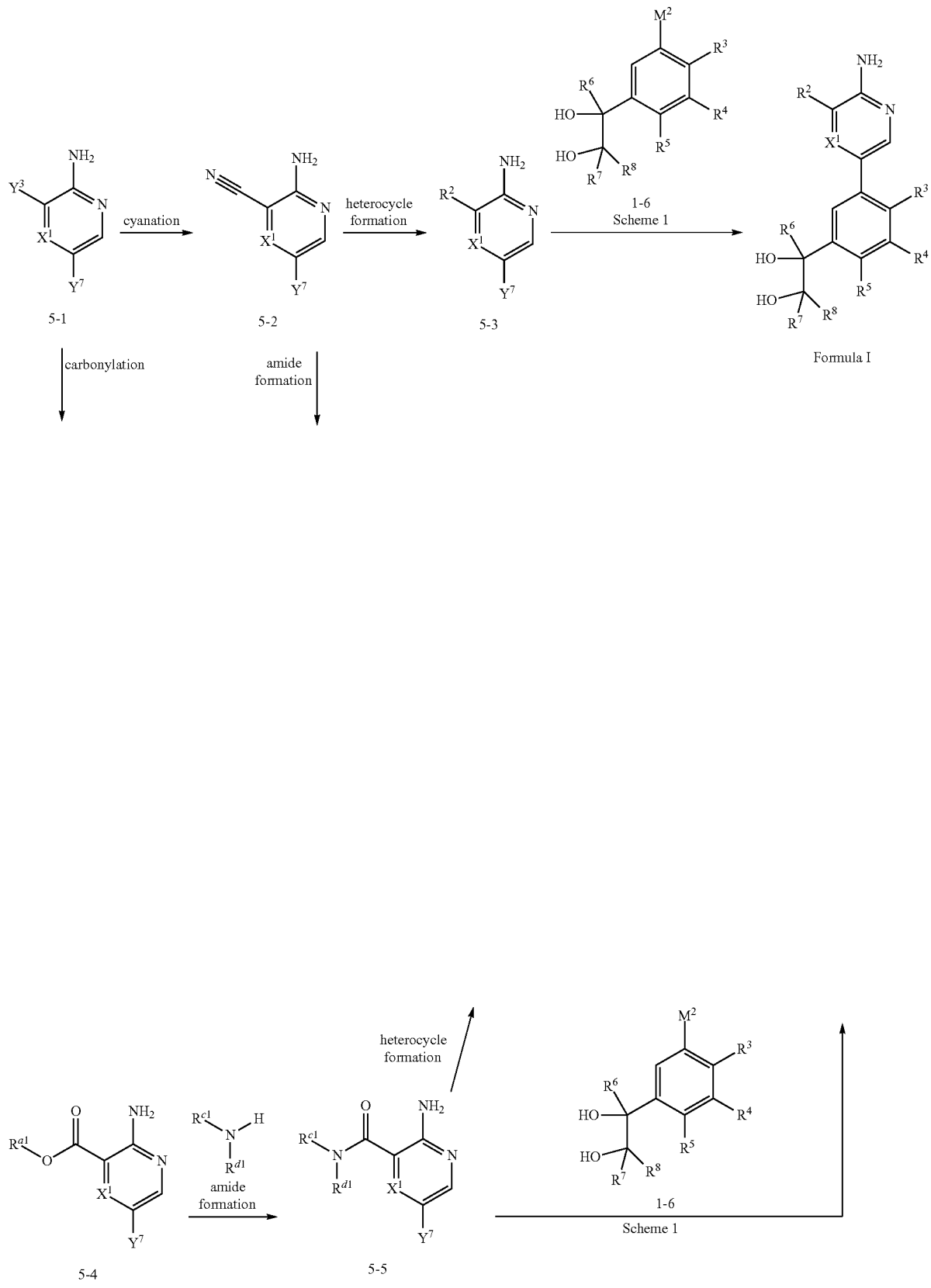

Compounds of Formula (I) can be prepared as shown in Scheme 6. Suitable starting materials 6-1, wherein $Y^3$ and $Y^7$ are suitable halogen atoms (e.g., Cl, Br, or I) or pseudo-halogens (e.g., OTf or OMs), can be converted to intermediate 6-3 by coupling with an organozinc species formed from a suitable optionally protected halide 6-2 wherein $Y^1$ is a halogen (e.g., Cl, Br, or I) under standard Negishi conditions (e.g., in the presence of Zn (which can be activated by agents such as 1,2-dibromoethane and TMSCl) and in the presence of a suitable palladium catalyst, (e.g., dichloro[1,1'-bis(diphenylphosphino)ferrocene]palladium (II) dichloromethane adduct and copper (I)iodide)). Intermediate 6-3 wherein $Y^7$ is a halogen (e.g., Cl, Br, or I) or pseudohalogen (e.g., OTf or OMs) can be coupled with an appropriately substituted metal 6-4 (e.g., $M^2$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane and a base (e.g., a carbonate base such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds 6-5, which themselves may be compounds of Formula (I), or if protected (with a protecting group P, e.g., Boc), may be deprotected to afford compounds 6-6 using conditions suitable for removal of the protecting group which are also suitable in terms of compatibility with other functional groups that may be present in the molecule. Intermediates 6-6 may optionally be reacted with an electrophile $R^4\text{-}L^1$ (wherein $L^1$ is a leaving group (e.g., halogen, such as Cl, Br or I or a mesylate or tosylate), or $R^4\text{-}L^1$ may be a carboxylic acid activated by exposure to a coupling reagent (e.g., DCC, EDC or HATU)) in the presence of a base (e.g., diisopropylethylamine or triethylamine) to furnish compounds of Formula (I).

Scheme 6.

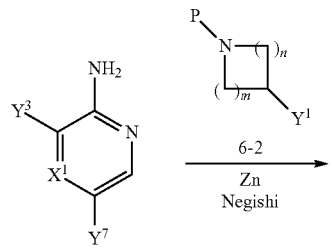

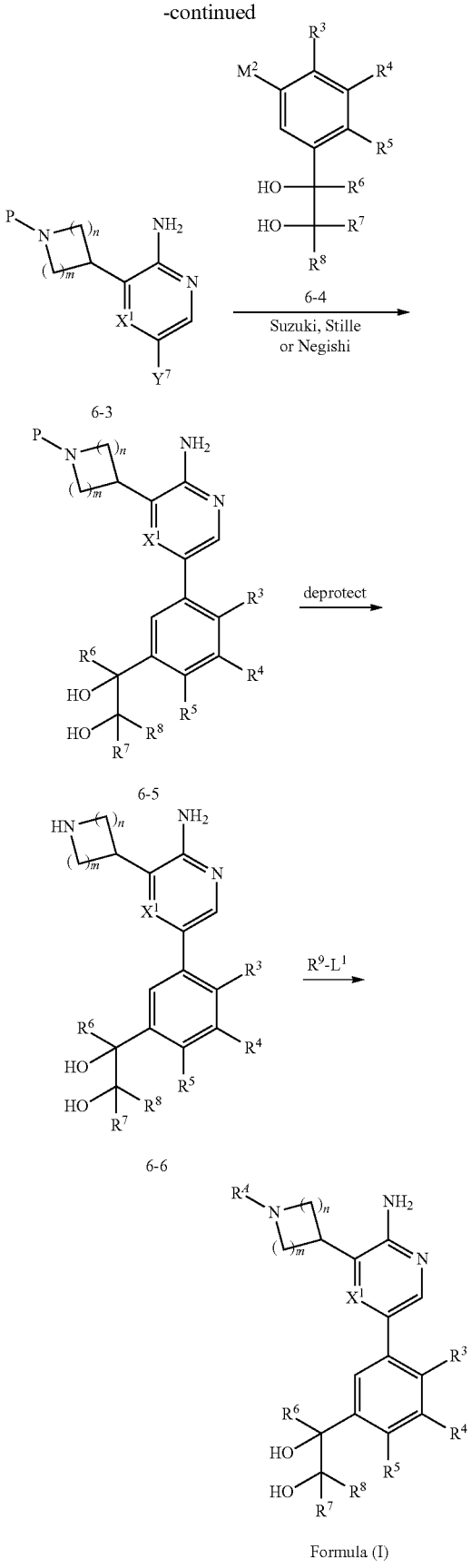

Compounds of Formula (I) can be prepared as shown in Scheme 7. Suitable starting materials 7-1, wherein $Y^7$ is a halogen (e.g., Cl, Br, or I) or pseudohalogen (e.g., OTf or OMs), can be converted to intermediates 7-3 by coupling with an appropriately substituted metal 7-2 (e.g., $M^2$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)). Halogen-containing intermediate 7-4 can be prepared by reacting intermediate 7-3 with a reagent suitable for introducing the halogen $Y^3$ (e.g., N-halosuccinimide such as N-iodosuccinimide, N-bromosuccinimide or N-chlorosuccinimide). Intermediate 7-4 bearing a suitable halogen $Y^3$ (e.g., Cl, Br or I) can be coupled with an organozinc derived from a suitable starting material 7-5 wherein $Y^1$ is a suitable halogen (e.g., Br or I) under standard Negishi conditions (e.g., in the presence of Zn (which can be activated by agents such as 1,2-dibromoethane and TMSCl) and in the presence of a suitable palladium catalyst, (e.g., [1,3-bis(2,6-diisopropylphenyl)imidazol-2-ylidene](3-chloropyridyl)palladium(II) dichloride)) to furnish compounds of Formula (I).

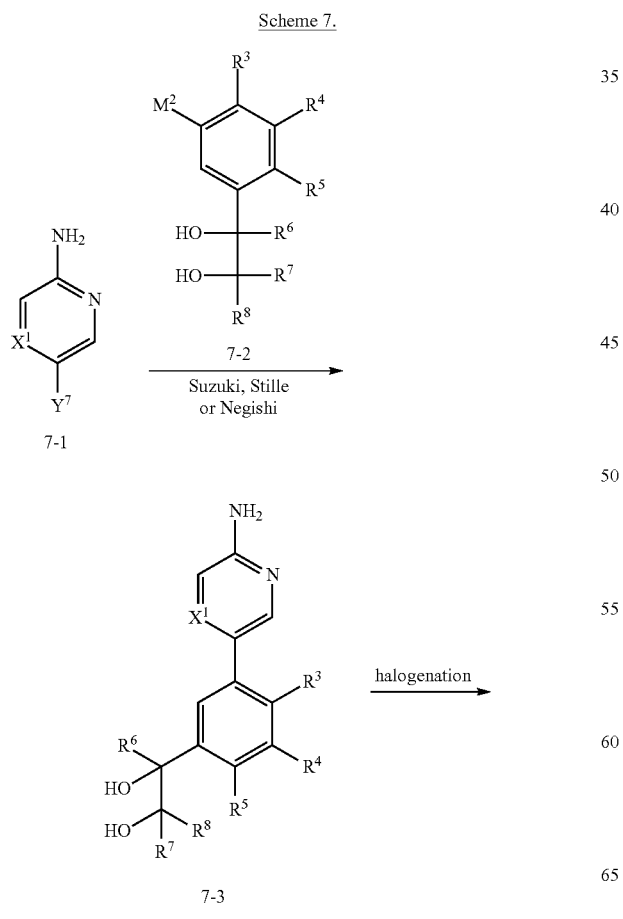

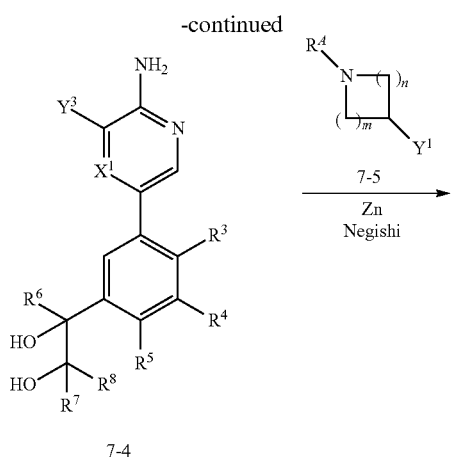

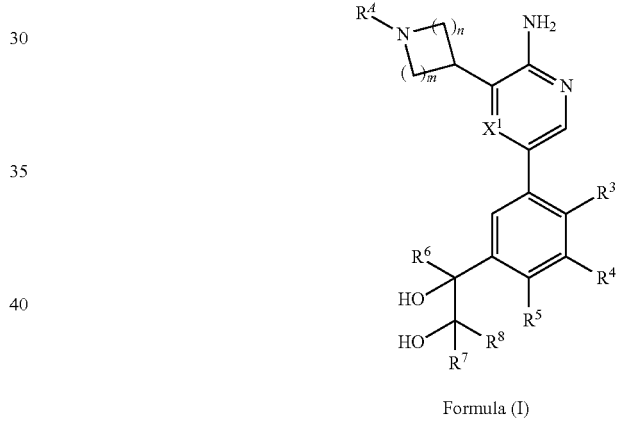

Formula (I)

Compounds of Formula (I) can be prepared as shown in Scheme 8. Intermediates 8-1 which contain an ester (e.g., R is methyl or ethyl) can be hydrolyzed by exposure to hydroxide base (e.g., LiOH, NaOH, KOH in water and a cosolvent such as THF, MeOH or EtOH) to furnish carboxylic acid intermediates 8-2. Carboxylic acid containing intermediates can be coupled with an amine 8-3 in the presence of an amide coupling reagent (e.g., DCC, EDC and HATU) and in the presence of a suitable base (e.g., diisopropylethylamine or triethylamine) to furnish compounds of Formula (I). Alternatively, ester containing intermediates can be converted directly to amide-containing compounds of Formula (I) by reaction at elevated temperature (e.g., 80° C.) with an amine 8-3 in the presence of a Lewis acid catalyst (e.g., $AlMe_3$).

Scheme 8.

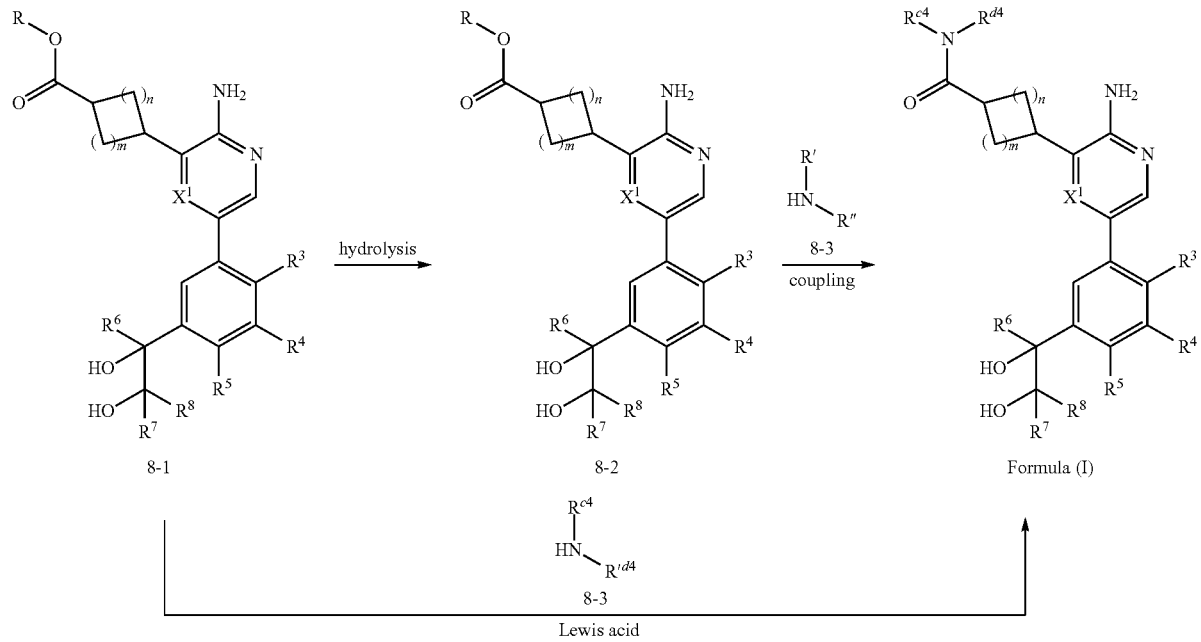

Compounds of Formula (I) can be prepared as shown in Scheme 9. Diol-containing intermediate 9-4 can be elaborated to carboxylic acid intermediate 9-1 by reaction with a suitable oxidizing agent (e.g., by reaction with oxygen or air over a metal, such as Pt). Carboxylic acid containing intermediate 9-1 can be subjected to conditions for esterification (e.g., refluxing in an alcoholic solvent such as methanol or ethanol in the presence of an acid, such as sulfuric acid) to provide ester intermediate 9-2. Exposure of 9-2 to an organometallic reagent $R^7$-$M^1$ (e.g., a Grignard reagent such as methylmagnesium bromide) can provide substituted diol intermediate 9-3. Alternatively, diol-containing intermediate 9-4 can be converted to an aldehyde intermediate 9-5 by treatment with an appropriate oxidizing agent (e.g., sulfur trioxide-pyridine complex or Dess-Martin periodinane). Exposure of aldehyde 9-5 to an appropriate nucleophile (e.g., an organometallic reagent $R^7$-$M^1$ such as a Grignard reagent (e.g., methylmagnesium bromide) or reagents providing a source of a fluorinated carbon nucleophile (e.g., an appropriately substituted silane such as trimethyl(trifluoromethyl)silane or trimethyl(difluoromethyl)silane in the presence of TBAF)) can provide substituted diol intermediate 9-6. Intermediate 9-6 can be oxidized to ketone 9-7 by reaction with an appropriate oxidizing agent (e.g., Dess Martin periodinane or PCC) and the product ketone 9-7 can be reacted with an appropriate nucleophile (e.g., an organometallic reagent $R^8$-$M^2$ such as a Grignard reagent (e.g., methylmagnesium bromide) or reagents providing a source of a fluorinated carbon nucleophile (e.g., an appropriately substituted silane such as trimethyl(trifluoromethyl)silane or trimethyl(difluoromethyl)silane in the presence of TBAF)) to provide substituted diol-containing intermediate 9-8. Intermediates 9-3, 9-6, and 9-8 are useful for the synthesis of compounds of Formula (I) according to the methods of Scheme 1.

Scheme 9.

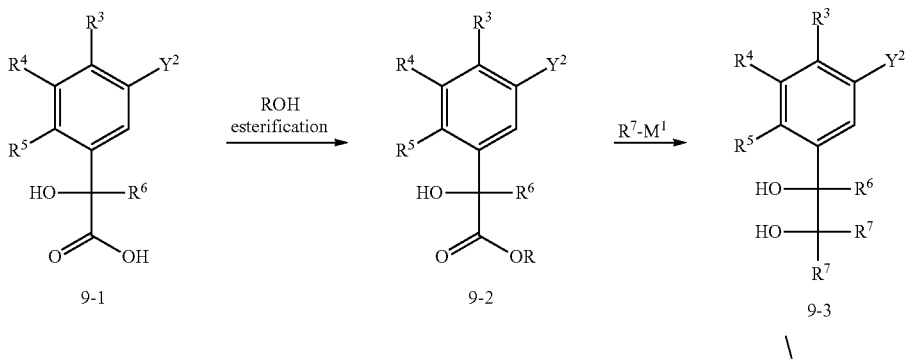

-continued

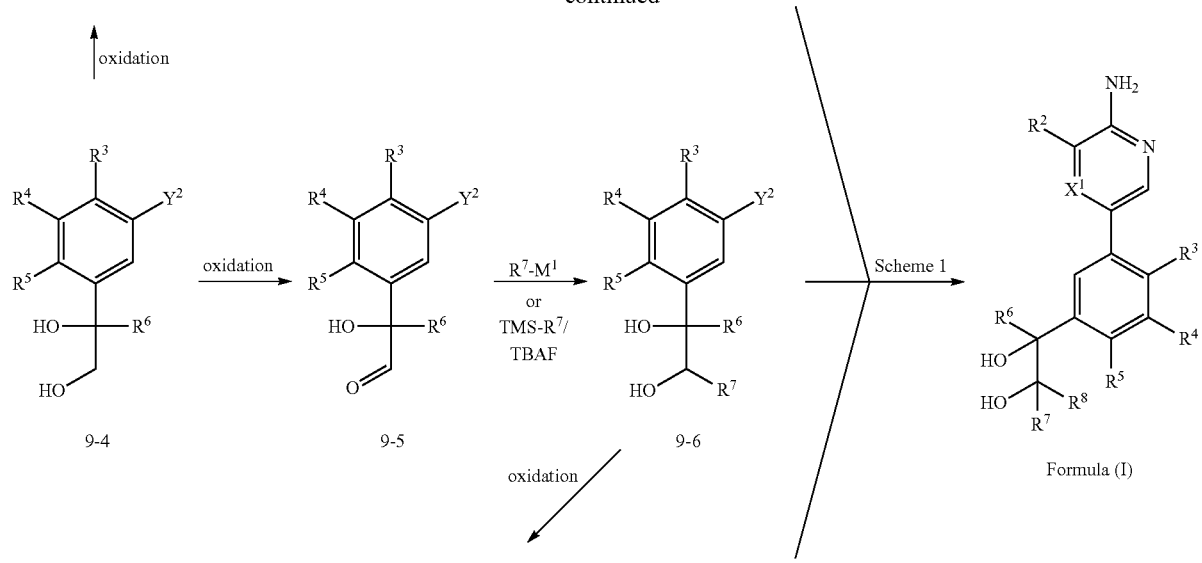

Compounds of Formula (I) can be prepared as shown in Scheme 10. Appropriate starting material 10-1, wherein $Y^1$ and $Y^2$ are independently suitable halogens (e.g., Cl, Br or I) or pseudohalogens (e.g., OTf), can be converted to ketone intermediate 10-2 by formation of a Grignard reagent (e.g., by reacting 10-1 with magnesium in the presence of dibromoethane), and reaction of the Grignard reagent with a suitable electrophile ($R^6CO-L^1$), wherein $L^1$ is a suitable leaving group (e.g., $R^6CO-L^1$ is a Weinreb amide ($L^1$= NMeOMe), such as 2,2-difluoro-N-methoxy-N-methylacetamide). Intermediate 10-2 can be converted to an appropriately substituted olefin 10-3 via known methods (e.g., by reaction with trimethylsilyldiazomethane in the presence of a catalyst such as tris(triphenylphosphine)rhodium(I) chloride and triphenylphosphine in a mixture containing 2-propanol; or via Peterson olefination, e.g., reaction with ((trimethylsilyl)methyl)magnesium chloride followed by reaction with trimethylsilyl trifluoromethanesulfonate)). Intermediate 10-3 can be converted to compounds of Formula (I) as shown in Scheme 1.

Scheme 10.

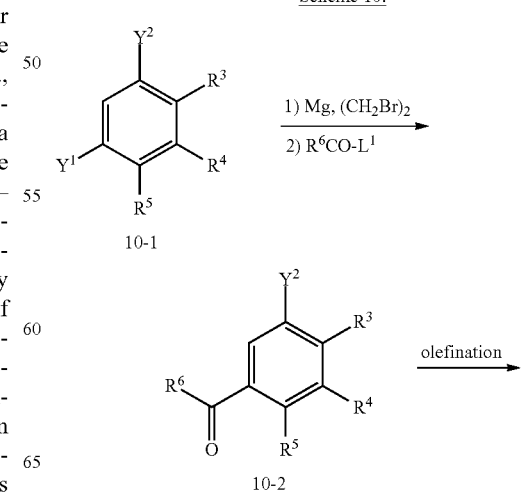

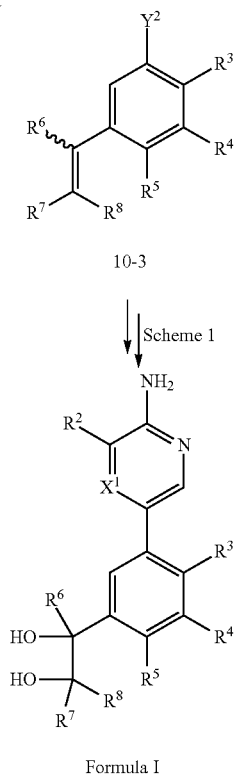

Formula I

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 μM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

In some embodiments, the disease or disorder is acute myeloid leukemia (e.g., acute monocytic leukemia), small lymphocytic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogeneous group of immune cells from the myeloid lineage (a family of cells that originate from bone marrow stem cells). MDSCs strongly expand in pathological situations such as chronic infections and cancer, as a result of an altered hematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the non-Hodgkin's lymphoma (NHL) is relapsed NHL, refractory NHL, recurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma. In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g., allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertrophy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertrophy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

It is believed that compounds of provided herein (e.g., compounds of Formula (I), or pharmaceutically acceptable salts thereof) or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors such as, for example, those described in WO 2006/056399. Other agents such as therapeutic antibodies can be used in combination with the compounds of the present disclosure for treatment of diseases, disorders, or conditions, particularly PI3K-associated diseases, disorders, or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™ (gefitinib), TARCEVA™ (erlotinib), antibodies to EGFR, GLEEVEC™ (imatinib mesylate), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADET™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotiib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is MGA012, nivolumab or pembrolizumab. In some embodiments, the anti-PD1 antibody is MGA012. In some embodiments, the anti-PD1 antibody is nivolumab. In some embodiments, the anti-PD1 antibody is pembrolizumab. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A or MED14736.

In some embodiments, the PI3Kγ inhibitors provided herein can be used alone, or in combination an anti-PD-1, for the treatment melanoma (PD-1 refractory), NSCLC (PD-1 refractory), HNSCC (PD-1 refractory), triple negative breast cancer (PD-1 naïve), mesothelioma, adrenocarcinoma or tumors with high level of MDSC.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, PI3K-gamma inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, BMS-986205, PF-06840003, IOM2983, RG-70099, LY338196, and NGL919.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, *Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, polio virus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion) Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1, 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any alkyl, alkenyl, alkynyl, aryl, phenyl, cycloalkyl, heterocycloalkyl, or heteroaryl substituents, or —$C_{1-6}$ alkyl-linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label*

Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J Combi. Chem.*, 6, 874-883 (2004)).

The purified compounds were typically subjected to analytical liquid chromatography mass spectrometry (LCMS) for purity analysis under one or both of the following conditions: Instrument=Agilent 1260 LC/MSD; pH 2 method: column=Waters Sunfire C18, 5 μm particle size, 2.1×50 mm, mobile phase: A=0.025% TFA in water and B=acetonitrile, gradient=2% to 90% B in 4 minutes with flow rate 2.0 mL/minute; pH 10 method: column=Waters XBridge C18, 5 μm particle size, 2.1×50 mm, mobile phase: A=0.05% NH$_4$OH in water and B=acetonitrile, gradient=2% to 90% B in 4 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C$_{18}$ 5 μm, 30×100 mm or Waters XBridge™ C$_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ C$_{18}$ 5 μm, 30×100 mm column, eluting with mobile phase A: 0.10% NH$_4$OH in water and mobile phase B: acetonitrile; the flow rate was 60 mL/minute, the separating gradient was optimized for each compound using the Compound Specific Method Optimization protocol as described in the literature (see e.g., Blom et al.).

Stereochemical Rationale

The Sharpless asymmetric dihydroxylation of olefins has been studied extensively, and its basis as a model for enantioselectivity is well established (Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.*, 1992, 57, 2768-2771; and Kolb, H. C.; VanNieuwenhze, M. S.; Sharpless, K. B. *Chem. Rev.*, 1994, 94, 2483-2547. Briefly, the application of AD-mix-α (containing (DHQ)$_2$-PHAL) in the dihydroxylation of prop-1-en-2-ylbenzene affords (S)-2-phenylpropane-1,2-diol. Application of AD-mix-β (containing (DHQD)$_2$-PHAL) in the dihydroxylation of prop-1-en-2-ylbenzene affords (R)-2-phenylpropane-1,2-diol (Sharpless and Kolb, supra). Moreno-Dorado et al. extended the method to the trifluoromethyl case (e.g., (3,3,3-trifluoroprop-1-en-2-yl)benzene affords (S)-3,3,3-trifluoro-2-phenylpropane-1,2-diol when treated with AD-mix-α and affords (R)-3,3,3-trifluoro-2-phenylpropane-1,2-diol when treated with AD-mix-β) and the stereochemical outcome was verified by subsequent conversion to well-known compounds whose specific rotations were found to be in agreement with the literature values (Moreno-Dorado, F. J.; Guerra, F. M.; Ortega, M. J.; Zubia, E.; Massanet, G. M. Tetrahedron: *Asymmetry*, 2003, 14, 503-510). While not wishing to be bound by any one theory, in the dihydroxylations performed on vinyl arenes in the Examples, we expect to obtain the (S)-configuration with AD-mix-α and the (R)-configuration with AD-mix-β.

Example 1a. 2-(3-(5-Amino-6-(1-(methyl-d₃)-1H-pyrazol-5-yl)pyrazin-2-yl)-4-methylphenyl)-3,3,3-trifluoropropane-1,2-diol trifluoroacetate salt (Single Enantiomer Isolated)

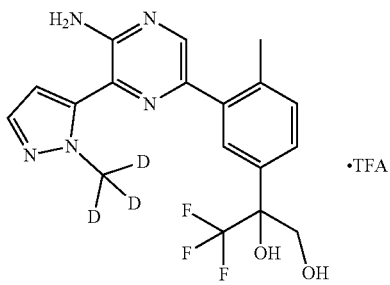 [SMILES: [2H]C([2H])([2H])n1nccc1-c1nc(-c2cc(C(O)(CO)C(F)(F)F)ccc2C)cnc1N]

Step 1. 2-(3-Chloro-4-methylphenyl)-4,4,5,5-tetramethyl-1,3,2-dioxaborolane

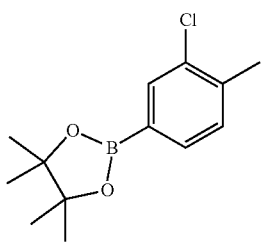

A degassed mixture of 4-bromo-2-chloro-1-methylbenzene (12.0 g, 58.4 mmol, Aldrich), potassium acetate (17.2 g, 175 mmol), bis(pinacolato)diboron (16.3 g, 64.2 mmol), and PdCl₂(dppf)-CH₂Cl₂ adduct (1.91 g, 2.34 mmol) in dioxane (120 mL) was heated at 75° C. overnight. After cooling to room temperature, the reaction mixture was diluted with EtOAc, filtered, and solvent was removed in vacuo. Purification via flash chromatography, eluting with a gradient of 0-5% EtOAc in hexanes, afforded product as a white solid (11.7 g, 80%). LCMS for $C_{13}H_{19}BClO_2$ (M+H)⁺: calculated m/z=253.1; found 253.0.

Step 2. 2-Chloro-1-methyl-4-(3,3,3-trifluoroprop-1-en-2-yl)benzene

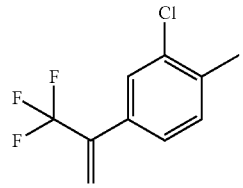

A degassed mixture of 2-(3-chloro-4-methylphenyl)-4,4,5,5-tetramethyl-1,3,2-dioxaborolane (11.7 g, 46.6 mmol), 2-bromo-3,3,3-trifluoroprop-1-ene (11.4 g, 65.2 mmol, Aldrich), K₂CO₃ (1.0 M in water, 140 mL, 140 mmol), and Pd(PPh₃)₂Cl₂ (1.63 g, 2.33 mmol) in THF (300 mL) was heated at 65° C. under N₂ for 3 hours. Upon cooling to room temperature, the reaction mixture was diluted with water and extracted with EtOAc. The organic layer was washed with water, followed by brine, dried over Na₂SO₄, filtered, and solvent was removed in vacuo. Purification via flash chromatography, eluting with hexanes, afforded product as a yellow oil (8.56 g, 83%). ¹H NMR (400 MHz, CDCl₃) δ 7.47 (s, 1H), 7.27 (s, 2H), 6.00-5.96 (m, 1H), 5.81-5.76 (m, 1H), 2.42 (s, 3H). ¹⁹F NMR (376 MHz, CDCl₃) δ −64.93 (s).

Step 3. 2-(3-Chloro-4-methylphenyl)-3,3,3-trifluoropropane-1,2-diol (Enriched in One Enantiomer)

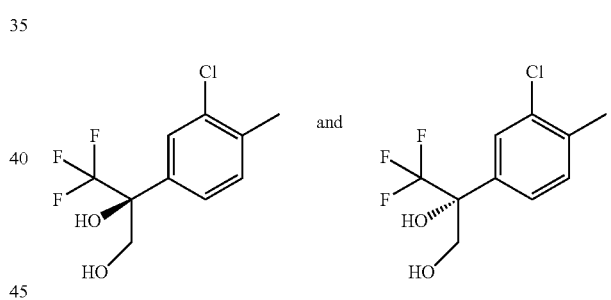

To a suspension of AD-mix-α (54.4 g, 116 mmol) in water (100 mL) at 0° C. was added a solution of 2-chloro-1-methyl-4-(3,3,3-trifluoroprop-1-en-2-yl)benzene (8.56 g, 38.8 mmol) in t-BuOH (100 mL). The mixture was then stirred at 6° C. for 46 hours. The reaction was cooled in an ice bath to 0° C., and sodium sulfite (18 g) was added. The reaction mixture was warmed to room temperature and stirred for 30 minutes. tert-Butanol was removed in vacuo and the aqueous mixture was extracted twice with EtOAc. The combined organic extracts were dried over Na₂SO₄, filtered, and solvent was removed in vacuo. Purification via flash chromatography, eluting with a gradient of 0-40% EtOAc in hexanes afforded product as a colorless oil (8.7 g, 88%). Due to use of AD-mix-α, it is believed that the product was enriched in the (S)-enantiomer (see stereochemical rationale supra). ¹H NMR (400 MHz, CDCl₃) δ 7.59 (s, 1H), 7.36 (d, J=8.0 Hz, 1H), 7.30 (d, J=8.0 Hz, 1H), 4.31 (dd, J=11.9, 6.1 Hz, 1H), 3.91-3.84 (m, 1H), 3.70 (s, 1H), 2.41 (s, 3H), 1.88-1.79 (dd, J=7.1, 6.3 Hz, 1H). ¹⁹F NMR (376 MHz, CDCl₃) δ −77.25 (s).

Step 4. 3,3,3-Trifluoro-2-(4-methyl-3-(4,4,5,5-tetramethyl-1,3,2-dioxaborolan-2-yl)phenyl)propane-1,2-diol (Enriched in One Enantiomer)

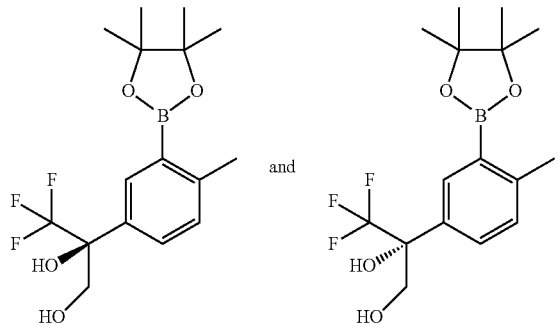 [SMILES: Cc1ccc([C@](O)(CO)C(F)(F)F)cc1B1OC(C)(C)C(C)(C)O1 ; Cc1ccc([C@@](O)(CO)C(F)(F)F)cc1B1OC(C)(C)C(C)(C)O1]

A degassed mixture of 2-(3-chloro-4-methylphenyl)-3,3,3-trifluoropropane-1,2-diol (from Step 3, enriched in one isomer (believed to be the (S)-enantiomer), 1.00 g, 3.93 mmol), bis(pinacolato)diboron (2.99 g, 11.8 mmol), potassium acetate (2.31 g, 23.6 mmol), Pd$_2$(dba)$_3$ (0.180 g, 0.196 mmol) and 2-dicyclohexylphosphino-2',4',6'-tri-iso-propyl-1,1'-biphenyl (0.374 g, 0.785 mmol) in dioxane (12 mL) was heated in a sealed vial in an oil bath held at 120° C. for 2 hours. Upon cooling to room temperature, the reaction mixture was diluted with EtOAc, filtered through Celite®, and solvent was removed in vacuo. The product was purified via flash chromatography, eluting with a gradient of 0-40% EtOAc in hexanes to afford product as an oil (1.0 g, 73%). LCMS for C$_{16}$H$_{26}$BF$_3$NO$_4$ (M+NH$_4$)$^+$: calculated m/z=364.2; found 364.2 (pH 10 analytical condition).

Step 5. 2-(3-(5-amino-6-chloropyrazin-2-yl)-4-methylphenyl)-3,3,3-trifluoropropane-1,2-diol (Single Enantiomers Isolated)

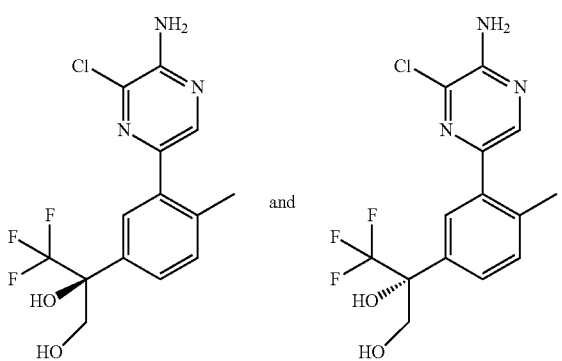 [SMILES: Cc1ccc([C@](O)(CO)C(F)(F)F)cc1-c1cnc(N)c(Cl)n1 ; Cc1ccc([C@@](O)(CO)C(F)(F)F)cc1-c1cnc(N)c(Cl)n1]

A degassed mixture of 5-bromo-3-chloropyrazin-2-amine (0.163 g, 0.780 mmol, Ark Pharm), 3,3,3-trifluoro-2-(4-methyl-3-(4,4,5,5-tetramethyl-1,3,2-dioxaborolan-2-yl)phenyl)propane-1,2-diol (0.300 g, 0.867 mmol enriched in one isomer (believed to be the (S)-enantiomer) from Step 4), Na$_2$CO$_3$ (0.276 g, 2.60 mmol) and PdCl$_2$(dppf)-CH$_2$Cl$_2$ adduct (0.035 g, 0.043 mmol) in dioxane (10 mL) and water (2 mL) was heated to 100° C. overnight. Upon cooling to room temperature, the reaction mixture was diluted with water and EtOAc, and the biphasic mixture was filtered through Celite®. The layers were separated and the aqueous layer was extracted with another portion of EtOAc. The combined organic layers were washed with brine, dried over MgSO$_4$, filtered, and concentrated. Purification via flash chromatography, eluting with a gradient of 0-70% EtOAc/hexanes afforded product as an oil. LCMS for C$_{14}$H$_{14}$ClF$_3$N$_3$O$_2$ (M+H)$^+$: calculated m/z=348.1; found 348.1. The enantiomers were separated by chiral chromatography (Phenomenex Lux Amylose-1, 21.2×250 mm, 5 µM, loading: 75 mg in 5.0 mL EtOH, eluting with 45% EtOH in hexanes at 20 mL/min for 10 minutes). Peak 1 retention time: 6.5 min, Peak 2 retention time: 8.9 min. Peak 1 was believed to be the (S)-enantiomer, while Peak 2 was believed to be the (R)-enantiomer. Peak 1 was used in Step 6. Peak 1: $^1$H NMR (400 MHz, CDCl$_3$) δ 8.05 (s, 1H), 7.56 (s, 1H), 7.47 (d, J=7.9 Hz, 1H), 7.31 (d, J=8.0 Hz, 1H), 5.12 (s, 2H), 4.26 (d, J=11.9 Hz, 1H), 3.93 (d, J=11.6 Hz, 1H), 2.39 (s, 3H). Peak 2: $^1$H NMR (400 MHz, CDCl$_3$) δ 8.07 (s, 1H), 7.56 (d, J=1.2 Hz, 1H), 7.50-7.43 (m, 1H), 7.32 (d, J=8.1 Hz, 1H), 5.09 (br s, 2H), 4.28 (d, J=11.9 Hz, 1H), 3.93 (d, J=11.9 Hz, 1H), 3.84 (br s, 1H), 2.40 (s, 3H), 2.15 (br s, 1H).

Step 6. 2-(3-(5-Amino-6-(1-(methyl-d$_3$)-1H-pyrazol-5-yl)pyrazin-2-yl)-4-methylphenyl)-3,3,3-trifluoropropane-1,2-diol trifluoroacetate salt (Single Enantiomer Prepared)

A degassed mixture of 2-(3-(5-amino-6-chloropyrazin-2-yl)-4-methylphenyl)-3,3,3-trifluoropropane-1,2-diol (0.120 g, 0.345 mmol, Peak 1 from Step 5), 1-(methyl-d$_3$)-5-(4,4,5,5-tetramethyl-1,3,2-dioxaborolan-2-yl)-1H-pyrazole (219 mg, 1.04 mmol, prepared as in *Journal of Labelled Compounds and Radiopharmaceuticals* (2012), 55(13), pp. 467-469), and PdCl$_2$(dppf)-CH$_2$Cl$_2$ adduct (28 mg, 0.035 mmol) in Na$_2$CO$_3$ solution (1.0 M in water, 1.04 mL, 1.04 mmol) and dioxane (3.0 mL) was heated to 100° C. for 5 hours. The mixture was cooled to room temperature, filtered and purified by preparative HPLC-MS (pH=2). Lyophilization of the eluent afforded product as a white solid (0.200 g, 44%). The product was believed to be the (S)-enantiomer, (S)-2-(3-(5-Amino-6-(1-(methyl-d3)-1H-pyrazol-5-yl)pyrazin-2-yl)-4-methylphenyl)-3,3,3-trifluoropropane-1,2-diol, for the reasons detailed above. LCMS calculated for C$_{18}$H$_{16}$D$_3$F$_3$N$_5$O$_2$ (M+H)$^+$: m/z=397.2, found: 397.1. $^1$H NMR (600 MHz, DMSO-d$_6$) δ 8.20 (s, 1H), 7.66 (s, 1H), 7.57 (s, 1H), 7.50 (d, J=8.1 Hz, 1H), 7.32 (d, J=8.1 Hz, 1H), 6.72 (s, 1H), 6.39 (br s, 2H), 3.90 (s, 2H), 2.39 (s, 3H).

Example 1b. 2-(3-(5-Amino-6-(1-(methyl-d$_3$)-1H-pyrazol-5-yl)pyrazin-2-yl)-4-methylphenyl)-3,3,3-trifluoropropane-1,2-diol trifluoroacetate salt (Single Enantiomer Isolated)

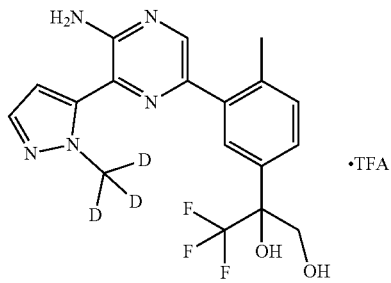 [SMILES: [2H]C([2H])([2H])n1nccc1-c1nc(-c2cc(C(O)(CO)C(F)(F)F)ccc2C)cnc1N]

The procedure of Example 1a, Step 6, was followed, using Peak 2 from Example 1a, Step 5. A degassed mixture of 2-(3-(5-amino-6-chloropyrazin-2-yl)-4-methylphenyl)-3,3,3-trifluoropropane-1,2-diol (0.020 g, 0.058 mmol, Peak 2 from Example 1a, Step 5) and 1-(methyl-d$_3$)-5-(4,4,5,5-tetramethyl-1,3,2-dioxaborolan-2-yl)-1H-pyrazole (36.4 mg, 0.173 mmol, prepared as in *Journal of Labelled Compounds and Radiopharmaceuticals* (2012), 55(13), pp. 467-469), and PdCl$_2$(dppf)-CH$_2$Cl$_2$adduct (4.7 mg, 5.7 µmol) in dioxane (2 mL) and Na$_2$CO$_3$ solution (1.0 M, 0.173 mL, 0.173 mmol) was heated to 100° C. for 5 hours. Upon cooling to room temperature, the reaction mixture was filtered and purified via preparative HPLC-MS (pH=2) to afford product as a white solid (8.0 mg, 27%). The product was believed to be the (R)-enantiomer, (R)-2-(3-(5-Amino-6-(1-(methyl-d3)-1H-pyrazol-5-yl)pyrazin-2-yl)-4-methylphenyl)-3,3,3-trifluoropropane-1,2-diol, for the reasons detailed above in Example 1a, Step 5. LCMS calculated for C$_{18}$H$_{16}$D$_3$F$_3$N$_5$O$_2$ (M+H)$^+$: m/z=397.2, found: 397.1. $^1$H NMR (400 MHz, DMSO-d$_6$) δ 8.20 (s, 1H), 7.66 (d, J=1.2 Hz, 1H), 7.57 (d, J=1.9 Hz, 1H), 7.50 (dd, J=7.9, 1.2 Hz, 1H), 7.32 (d, J=8.2 Hz, 1H), 6.72 (d, J=1.9 Hz, 1H), 6.37 (br s, 2H), 3.91 (s, 2H), 2.39 (s, 3H).

Examples 2-7

Unless otherwise indicated, the compounds in Table 1 were synthesized according to the procedure described for Example 1a, utilizing the appropriate boronic esters or boronic acids. As detailed above, a single enantiomer was isolated and was believed to be the (S)-enantiomer (see stereochemical rationale supra).

TABLE 1

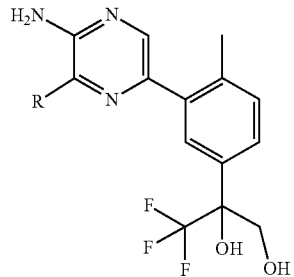

| Example No. | Compound Name | R | LCMS |
|---|---|---|---|
| 2 | 2-(3-(5-Amino-6-(1-methyl-1H-pyrazol-4-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(1-methyl-1H-pyrazol-4-yl)pyrazin-2-yl)-4-methylphenyl)-3,3,3-trifluoropropane-1,2-diol) | 1-methyl-1H-pyrazol-4-yl | Calculated for C$_{18}$H$_{19}$F$_3$N$_5$O$_2$ (M + H)$^+$: m/z = 394.1, found: 394.1 |
| 3 | 2-(3-(5-Amino-6-(1H-pyrazol-4-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(1H-pyrazol-4-yl)pyrazin-2-yl)-4-methylphenyl)-3,3,3-trifluoropropane-1,2-diol) | 1H-pyrazol-4-yl | Calculated for C$_{17}$H$_{17}$F$_3$N$_5$O$_2$ (M + H)$^+$: m/z = 380.1, found: 380.0 |
| 4 | 2-(3-(5-Amino-6-(3-methylisoxazol-5-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(3-methylisoxazol-5-yl)pyrazin-2-yl)-4-methylphenyl)-3,3,3-trifluoropropane-1,2-diol) | 3-methylisoxazol-5-yl | Calculated for C$_{18}$H$_{18}$F$_3$N$_4$O$_3$ (M + H)$^+$: m/z = 395.1, found: 395.1 |
| 5 | 2-(3-(5-Amino-6-(isothiazol-4-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(isothiazol-4-yl)pyrazin-2-yl)-4-methylphenyl)-3,3,3-trifluoropropane-1,2-diol) | isothiazol-4-yl | Calculated for C$_{17}$H$_{16}$F$_3$N$_4$O$_2$S (M + H)$^+$: m/z = 397.1, found: 397.1 |
| 6 | 2-(3-(5-Amino-6-(isothiazol-5-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(isothiazol-5-yl)pyrazin-2-yl)-4-methylphenyl)-3,3,3-trifluoropropane-1,2-diol, trifluoroacetate salt) | isothiazol-5-yl | Calculated for C$_{17}$H$_{16}$F$_3$N$_4$O$_2$S (M + H)$^+$: m/z = 397.1, found: 397.1 |

TABLE 1-continued

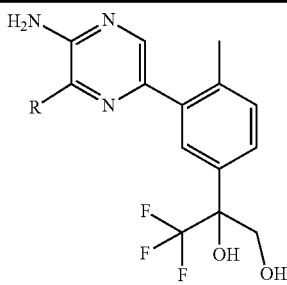

| Example No. | Compound Name | R | LCMS |
|---|---|---|---|
| 7 | 2-(3-(5-amino-6-(3-methylisothiazol-5-yl)pyrazin-2-yl)-4-methylphenyl)-3,3,3-trifluoropropane-1,2-diol, trifluoroacetate salt (single enantiomer isolated, believed to be (S)-2-(3-(5-amino-6-(3-methylisothiazol-5-yl)pyrazin-2-yl)-4-methylphenyl)-3,3,3-trifluoropropane-1,2-diol) | 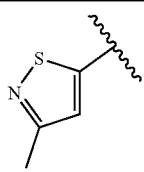 | Calculated for $C_{18}H_{18}F_3N_4O_2S$ $(M + H)^+$: m/z = 411.1, found: 411.1 |

Example 9. 2-(3-(5-Amino-6-(2-methyloxazol-5-yl)pyrazin-2-yl)-4-methylphenyl)-3,3,3-trifluoropropane-1,2-diol, trifluoroacetate salt (Single Enantiomer Prepared)

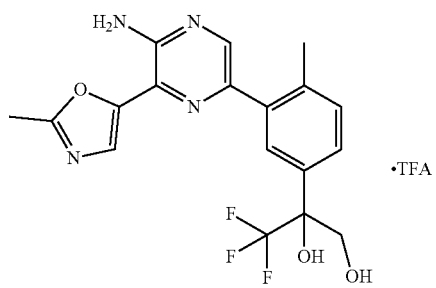 [SMILES: Cc1ncc(-c2nc(-c3cc(C(O)(CO)C(F)(F)F)ccc3C)cnc2N)o1]

Step 1. 2-(3-Chloro-4-methylphenyl)-3,3,3-trifluoropropane-1,2-diol (Racemic Mixture Prepared)

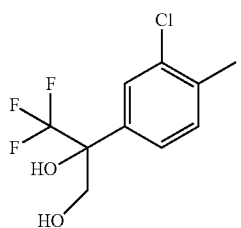 [SMILES: Cc1ccc(C(O)(CO)C(F)(F)F)cc1Cl]

To a solution of 2-chloro-1-methyl-4-(3,3,3-trifluoroprop-1-en-2-yl)benzene (3.00 g, 13.6 mmol, prepared as in Example 1a, Step 2) in acetone (30 mL) and water (30 mL) was added NMO (2.07 g, 17.7 mmol) and OsO$_4$ (4% in water, 5.19 mL, 0.816 mmol). The reaction was stirred for 5 hours. The reaction mixture was filtered and concentrated. The residue was partitioned between EtOAc and water. The aqueous layer was extracted with two additional portions of EtOAc. The combined organic layers were dried over Na$_2$SO$_4$, filtered and concentrated. Purification via flash chromatography, eluting with a gradient of 0-50% EtOAc in hexanes afforded product as an oil (2.86 g, 76%).

Step 2. 3,3,3-Trifluoro-2-(4-methyl-3-(4,4,5,5-tetramethyl-1,3,2-dioxaborolan-2-yl)phenyl)propane-1,2-diol (Racemic Mixture Prepared)

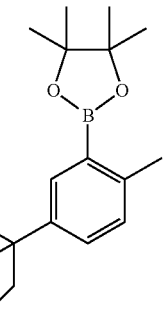

A degassed mixture of 2-(3-chloro-4-methylphenyl)-3,3,3-trifluoropropane-1,2-diol (racemic mixture from Step 1, 1.00 g, 3.93 mmol), bis(pinacolato)diboron (2.99 g, 11.8 mmol), potassium acetate (2.31 g, 23.6 mmol), Pd$_2$(dba)$_3$ (0.180 g, 0.196 mmol) and 2-dicyclohexylphosphino-2',4',6'-tri-iso-propyl-1,1'-biphenyl (0.374 g, 0.785 mmol) in dioxane (12.0 mL) was heated in a sealed vial in an oil bath at 120° C. for 1.5 hours. Upon cooling to room temperature, the reaction mixture was diluted with EtOAc, filtered through Celite®, and the solvent was removed in vacuo. The product was purified via flash chromatography, eluting with a gradient of 0-40% EtOAc in hexanes to afford product as an oil (1.0 g, 73%). LCMS for $C_{16}H_{26}BF_3NO_4$ (M+NH$_4$)$^+$: calculated m/z=364.2; found 364.2 (pH 10 analytical condition).

Step 3. (S)-2-(3-(5-Amino-6-chloropyrazin-2-yl)-4-methylphenyl)-3,3,3-trifluoropropane-1,2-diol and (R)-2-(3-(5-Amino-6-chloropyrazin-2-yl)-4-methylphenyl)-3,3,3-trifluoropropane-1,2-diol (Single Enantiomers Isolated)

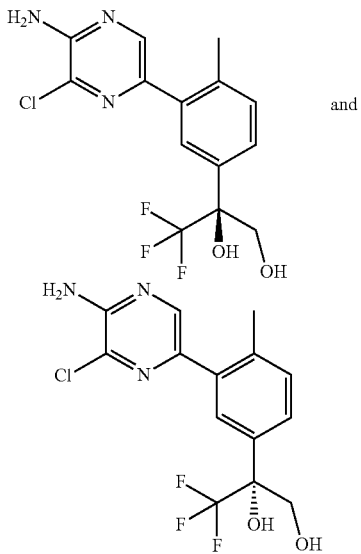

A vial was charged with 5-bromo-3-chloropyrazin-2-amine (0.379 g, 1.82 mmol, Ark Pharm), and 3,3,3-trifluoro-2-(4-methyl-3-(4,4,5,5-tetramethyl-1,3,2-dioxaborolan-2-yl)phenyl)propane-1,2-diol (0.700 g, 2.02 mmol) and dioxane (30 mL). The reaction was degassed, a mixture of $Na_2CO_3$ (0.643 g, 6.07 mmol) in water (10 mL) was added, followed by $PdCl_2(dppf)\text{-}CH_2Cl_2$ adduct (0.083 g, 0.101 mmol), and the mixture was degassed again. The reaction was heated to 100° C. overnight. Upon cooling to room temperature, the reaction mixture was diluted and extracted twice with EtOAc. The combined organic extracts were washed with brine, dried over $MgSO_4$, filtered, and solvent was removed in vacuo. Purification via flash chromatography, eluting with a gradient of 0-100% EtOAc in hexanes afforded product as a light yellow oil (506 mg, 72%). The enantiomers were separated by chiral chromatography (Phenomenex Lux Amylose-1, 21.2×250 mm, 5 μM, loading: 45 mg in 1.8 mL EtOH, eluting with 45% EtOH in hexanes at 20 mL/min for 10 minutes). Peak 1 retention time: 6.0 min, Peak 2 retention time: 7.7 min. Peak 1 was used in Step 4. Peak 1 was believed to be the (S)-enantiomer, based on the same separation conditions that were used in Example 1a, Step 5. LCMS for $C_{14}H_{14}ClF_3N_3O_2$ $(M+H)^+$: calculated m/z=348.1; found 348.1.

Step 4. 2-(3-(5-Amino-6-(2-methyloxazol-5-yl)pyrazin-2-yl)-4-methylphenyl)-3,3,3-trifluoropropane-1,2-diol trifluoroacetate salt (Single Enantiomer Prepared)

A degassed mixture of 2-(3-(5-amino-6-chloropyrazin-2-yl)-4-methylphenyl)-3,3,3-trifluoropropane-1,2-diol (100 mg, 0.288 mmol, Peak 1 from Step 3), 2-methyl-5-(4,4,5,5-tetramethyl-1,3,2-dioxaborolan-2-yl)oxazole (0.180 g, 0.863 mmol, Ark Pharm) and $PdCl_2(dppf)\text{-}CH_2Cl_2$ adduct (23.5 mg, 0.029 mmol) in dioxane (3 mL) and $Na_2CO_3$ solution (1.0 M in water, 0.86 mL, 0.86 mmol) was heated in a sealed vial in an oil bath held overnight at 120° C. Based on the determination in Step 3, the product is believed to be the (S)-enantiomer. Preparative HPLC-MS (pH=2) afforded product as a light yellow solid (0.080 g, 54%). The product is believed to be the (S)-enantiomer, (S)-2-(3-(5-Amino-6-(2-methyloxazol-5-yl)pyrazin-2-yl)-4-methylphenyl)-3,3,3-trifluoropropane-1,2-diol. LCMS calculated for $C_{18}H_{18}F_3N_4O_3(M+H)^+$: m/z=395.1, found: 395.1. $^1$H NMR (500 MHz, DMSO-$d_6$) δ 8.15 (s, 1H), 7.64 (s, 1H), 7.61 (s, 1H), 7.50 (d, J=7.6 Hz, 1H), 7.32 (d, J=8.1 Hz, 1H), 3.92 (s, 2H), 2.54 (s, 3H), 2.36 (s, 3H).

Examples 10 and 11

Unless otherwise indicated, the compounds in Table 2 were synthesized according to the procedure described for Example 9, utilizing the appropriate boronic esters or boronic acids. While not wishing to be bound by any theory, it is thought that the compounds below are the (S)-enantiomer.

TABLE 2

| Example No. | Compound Name | $^1$H NMR | R | LCMS |
|---|---|---|---|---|
| 10 | 2-(3-(5-Amino-6-(2-methylthiazol-5-yl)pyrazin-2-yl)-4-methylphenyl)-3,3,3-trifluoropropane-1,2-diol trifluoroacetate salt (single enantiomer isolated, believed to be (S)-2-(3-(5-Amino-6-(2-methylthiazol-5-yl)pyrazin-2-yl)-4-methylphenyl)-3,3,3-trifluoropropane-1,2-diol) | | 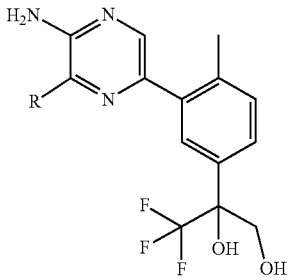 | Calculated for $C_{18}H_{18}F_3N_4O_2S$ $(M + H)^+$: m/z = 411.1, found: 411.1 |

TABLE 2-continued

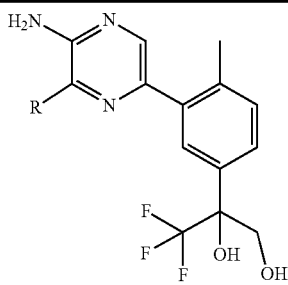

| Example No. | Compound Name  ¹H NMR | R | LCMS |
|---|---|---|---|

¹H NMR (600 MHz, DMSO-d₆) δ 8.27 (s, 1H), 8.14 (s, 1H), 7.63 (s, 1H), 7.50 (d, J = 8.0 Hz, 1H), 7.32 (d, J = 8.1 Hz, 1H), 6.61 (s, 2H), 3.92 (s, 2H), 2.68 (s, 3H), 2.40 (s, 3H).

| 11 | 2-(3-(5-Amino-6-(oxazol-5-yl)pyrazin-2-yl)-4-methylphenyl)-3,3,3-trifluoropropane-1,2-diol trifluoroacetate salt (single enantiomer isolated, believed to be (S)-2-(3-(5-Amino-6-(oxazol-5-yl)pyrazin-2-yl)-4-methylphenyl)-3,3,3-trifluoropropane-1,2-diol) | 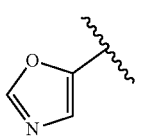 [SMILES: *c1cnco1] | Calculated for $C_{17}H_{16}F_3N_4O_3$ (M + H)⁺: m/z = 381.1, found: 381.1 |

¹H NMR (500 MHz, DMSO-d₆) δ 8.56 (s, 1H), 8.20 (s, 1H), 7.81 (s, 1H), 7.64 (s, 1H), 7.51 (d, J = 8.3 Hz, 1H), 7.33 (d, J = 8.1 Hz, 1H), 3.92 (s, 2H), 2.38 (s, 3H).

Example 12. 2-(3-(5-Amino-6-(1H-pyrazol-1-yl)pyrazin-2-yl)-4-methylphenyl)-3,3,3-trifluoropropane-1,2-diol, trifluoroacetate salt (Single Enantiomer Prepared)

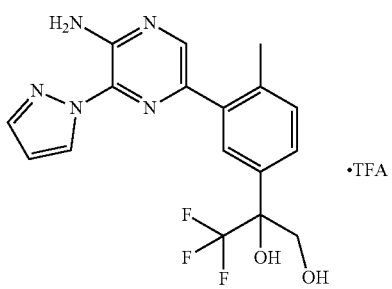 [SMILES: Cc1ccc(C(O)(CO)C(F)(F)F)cc1-c1cnc(N)c(-n2cccn2)n1]

A mixture of 2-(3-(5-amino-6-chloropyrazin-2-yl)-4-methylphenyl)-3,3,3-trifluoropropane-1,2-diol (17 mg, 0.049 mmol, Peak 1 from Example 1a, Step 5; due to use of AD-mix-α in Step 3 of Example 1a that later produced Peak 1 of Example 1a, Step 5, it is believed that the reactant here is the (S)-enantiomer of 2-(3-(5-amino-6-chloropyrazin-2-yl)-4-methylphenyl)-3,3,3-trifluoropropane-1,2-diol (see stereochemical rationale supra), 1H-pyrazole (10.0 mg, 0.147 mmol), and cesium carbonate (48 mg, 0.15 mmol) in dioxane (1 mL) was heated in an oil bath held at 120° C. overnight. Upon cooling to room temperature, the mixture was diluted with MeOH and filtered. Purification via preparative HPLC-MS (pH 2) afforded the desired product as a white solid (5.0 mg, 20%). The product is believed to be the (S)-enantiomer, (S)-2-(3-(5-Amino-6-(1H-pyrazol-1-yl)pyrazin-2-yl)-4-methylphenyl)-3,3,3-trifluoropropane-1,2-diol. LCMS calculated for $C_{17}H_{17}F_3N_5O_2$(M+H)⁺: m/z=380.1, found: 380.1. ¹H NMR (400 MHz, DMSO-d₆) δ 8.63 (dd, J=2.6, 0.5 Hz, 1H), 8.19 (s, 1H), 7.94-7.92 (m, 1H), 7.69 (d, J=1.5 Hz, 1H), 7.51 (dd, J=8.0, 1.4 Hz, 1H), 7.34 (d, J=8.1 Hz, 1H), 6.66 (dd, J=2.5, 1.9 Hz, 1H), 3.93 (s, 2H), 2.43 (s, 3H). ¹⁹F NMR (376 MHz, DMSO-d₆) δ −74.79 (s), −75.54 (s).

Examples 13-15

Unless otherwise indicated, the compounds in Table 3 were synthesized according to the procedure described for Example 12, utilizing the appropriate heterocycles. As detailed above, due to use of AD-mix-α in Step 3 of Example 1a that later produced Peak 1 of Example 1a, Step 5, it is believed the products in the table below are the (S)-enantiomer.

TABLE 3

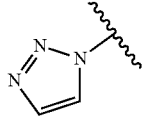

| Example No. | Compound Name | R | LCMS |
|---|---|---|---|
| 13 | 2-(3-(5-Amino-6-(1H-1,2,3-triazol-1-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(1H-1,2,3-triazol-1-yl)pyrazin-2-yl)-4-methylphenyl)-3,3,3-trifluoropropane-1,2-diol) | 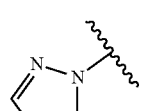 | Calculated for $C_{16}H_{16}F_3N_6O_2$ $(M + H)^+$: m/z = 381.1, found: 381.1 |
| 14 | 2-(3-(5-Amino-6-(1H-1,2,3-triazol-2-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(2H-1,2,3-triazol-2-yl)pyrazin-2-yl)-4-methylphenyl)-3,3,3-trifluoropropane-1,2-diol) | 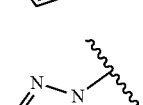 | Calculated for $C_{16}H_{16}F_3N_6O_2$ $(M + H)^+$: m/z = 381.1, found: 381.1 |
| 15 | 2-(3-(5-Amino-6-(1H-1,2,4-triazol-1-yl)pyrazin-2-yl)-4-methylphenyl)-3,3,3-trifluoropropane-1,2-diol, trifluoroacetate salt (single enantiomer isolated, believed to be (S)-2-(3-(5-Amino-6-(1H-1,2,3-triazol-1-yl)pyrazin-2-yl)-4-methylphenyl)-3,3,3-trifluoropropane-1,2-diol) | 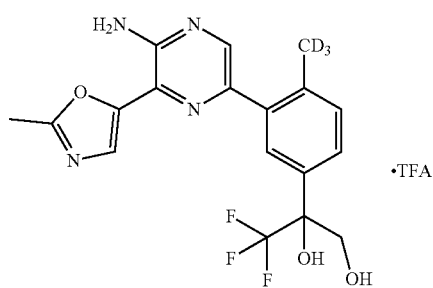 | Calculated for $C_{16}H_{16}F_3N_6O_2$ $(M + H)^+$: m/z = 381.1, found: 381.1 |

Example 16. 2-(3-(5-Amino-6-(2-methyloxazol-5-yl)pyrazin-2-yl)-4-(methyl-$d_3$)phenyl)-3,3,3-trifluoropropane-1,2-diol trifluoroacetate salt (Single Enantiomer Prepared)

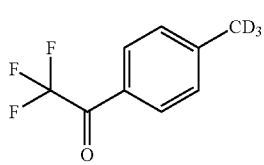 [SMILES: [2H]C([2H])([2H])c1ccc(C(=O)C(F)(F)F)cc1]

Step 1. 2,2,2-Trifluoro-1-(4-(methyl-$d_3$)phenyl)ethan-1-one

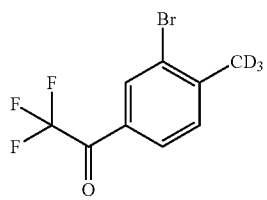 [SMILES: [2H]C([2H])([2H])c1ccc(C(=O)C(F)(F)F)cc1Br]

1,4-Dibromobenzene (10.0 g, 42.4 mmol, Aldrich) in THF (94 mL) and diethyl ether (94 mL) at −78° C. was treated dropwise with n-butyllithium (1.6 M in hexanes, 26.5 mL, 42.4 mmol). Ethyl 2,2,2-trifluoroacetate (6.02 g, 42.4 mmol, Aldrich) was then added, and the reaction was stirred for 30 minutes. A further portion of n-butyllithium (1.6 M in hexanes, 26.5 mL, 42.4 mmol) was added, and after stirring for 10 minutes, iodomethane-$d_3$ (6.76 g, 46.6 mmol, Aldrich) was added. After stirring for 30 minutes, a precooled solution of conc. HCl (12.5 mL) in EtOH (6.25 mL) was added. The reaction mixture was then poured into 2 N HCl (250 mL). The layers were separated and the organic layer was dried over MgSO$_4$, filtered and concentrated to afford product, which was used without further purification. Yield: 7.2 g, 89%. $^1$H NMR (400 MHz, CDCl$_3$) δ 8.00 (d, J=7.7 Hz, 1H), 7.37 (d, J=8.4 Hz, 1H). $^{19}$F NMR (376 MHz, CDCl$_3$) δ −71.33 (s).

Step 2. 1-(3-Bromo-4-(methyl-$d_3$)phenyl)-2,2,2-trifluoroethan-1-one

A solution of 2,2,2-trifluoro-1-(4-(methyl-$d_3$)phenyl)ethan-1-one (7.20 g, 37.7 mmol) in 1,2-dichloroethane (10 mL) was added slowly dropwise to a mixture of aluminum chloride (11.0 g, 82.9 mmol) in 1,2-dichloroethane (25 mL).

The reaction mixture was then heated to 35° C. and was stirred for 5 minutes. Bromine (1.94 mL, 37.7 mmol) was then added dropwise to the heated mixture. The reaction was stirred at 35° C. for 1.5 hours, then at 45° C. for 7 hours. Upon cooling to room temperature, the reaction was quenched by slowly pouring into a mixture of ice-cold DCM and 1 N HCl. The layers were separated, and the aqueous layer was extracted with two further portions of DCM. The combined organic extracts were washed with sat. NaHCO$_3$ solution, followed by brine, dried over Na$_2$SO$_4$, filtered and concentrated to afford product, which was used without further purification. (Yield: 9.9 g, 98%). $^1$H NMR (400 MHz, CDCl$_3$) δ 8.28-8.22 (m, 1H), 7.96-7.89 (m, 1H), 7.44 (d, J=8.0 Hz, 1H). $^{19}$F NMR (376 MHz, CDCl$_3$) δ −71.50(s).

Step 3. 2-Bromo-1-(methyl-d$_3$)-4-(3,3,3-trifluoro-prop-1-en-2-yl)benzene

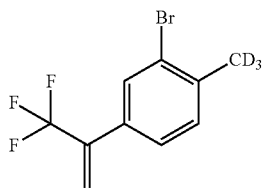 [SMILES: [2H]C([2H])([2H])c1ccc(C(=C)C(F)(F)F)cc1Br]

A mixture of methyltriphenylphosphonium bromide (12.4 g, 34.7 mmol) in THF (30 mL) at 0° C. was treated with n-butyllithium (1.6 M in hexanes, 20.8 mL, 33.3 mmol) added dropwise, and the reaction was stirred for 20 minutes. A solution of 1-(3-bromo-4-(methyl-d$_3$)phenyl)-2,2,2-trifluoroethan-1-one (7.50 g, 27.8 mmol) in THF (15 mL) was added dropwise, and the cooling bath was removed. The mixture was allowed to reach room temperature and stir for 2.5 hours. The reaction mixture was diluted with water and extracted three times with DCM. The combined organic extracts were dried over Na$_2$SO$_4$, filtered and solvent was removed in vacuo. Purification via flash chromatography (eluting with a slow gradient from 0-10% EtOAc in hexanes) afforded product as a yellow oil (2.3 g, 23%). $^1$H NMR (400 MHz, CDCl$_3$) δ 7.65 (d, J=1.3 Hz, 1H), 7.34-7.30 (m, 1H), 7.27 (d, J=7.9 Hz, 1H), 5.98 (q, J=1.2 Hz, 1H), 5.78 (q, J=1.5 Hz, 1H). $^{19}$F NMR (376 MHz, CDCl$_3$) δ −64.93 (s).

Step 4. 2-(3-Bromo-4-(methyl-d$_3$)phenyl)-3,3,3-trifluoropropane-1,2-diol (Enriched in One Enantiomer)

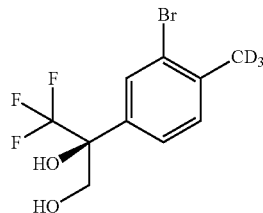 and

To a suspension of AD-mix-α (18.1 g, 38.7 mmol) in water (36 mL) at 0° C. was added a solution of 2-bromo-1-(methyl-d$_3$)-4-(3,3,3-trifluoroprop-1-en-2-yl)benzene (3.46 g, 12.9 mmol) in tBuOH (36 mL). The mixture was stirred at 6° C. for 88 hours. The reaction was warmed to room temperature and sodium sulfite (6.0 g) was added. After stirring for 15 minutes, tBuOH was removed in vacuo. The aqueous mixture was then extracted twice with EtOAc. The combined organic extracts were dried over Na$_2$SO$_4$, filtered and solvent was removed in vacuo. Purification via flash chromatography, eluting with a gradient of 0-40% EtOAc in hexanes, afforded product (3.2 g, 82%). Due to use of AD-mix-α, it is believed that the product is enriched in the (S)-enantiomer (see stereochemical rationale supra). $^1$H NMR (400 MHz, CDCl$_3$) δ 7.78 (d, J=1.4 Hz, 1H), 7.42-7.38 (m, 1H), 7.29 (d, J=7.9 Hz, 1H), 4.29 (dd, J=11.9, 6.1 Hz, 1H), 3.91-3.82 (m, 1H), 3.77 (s, 1H), 2.00 (t, J=6.7 Hz, 1H). $^{19}$F NMR (376 MHz, CDCl$_3$) δ −77.24 (s).

Step 5. 3,3,3-Trifluoro-2-(4-(methyl-d$_3$)-3-(4,4,5,5-tetramethyl-1,3,2-dioxaborolan-2-yl)phenyl)propane-1,2-diol (Enriched in One Enantiomer)

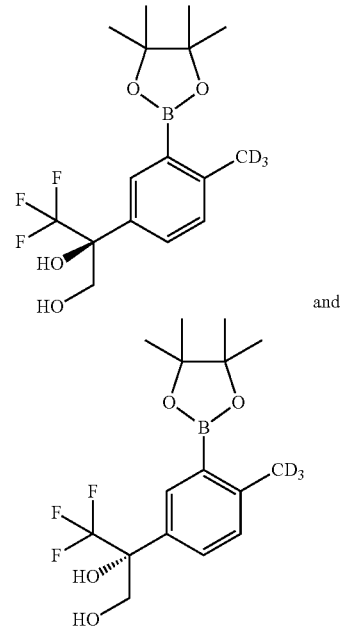

A degassed mixture of 2-(3-bromo-4-(methyl-d$_3$)phenyl)-3,3,3-trifluoropropane-1,2-diol (enriched in one enantiomer, believed to be the (S)-isomer as detailed above) from Step 4, 0.50 g, 1.6 mmol), bis(pinacolato)diboron (1.05 g, 4.14 mmol), potassium acetate (0.975 g, 9.93 mmol) and triphenylphosphine palladium chloride (0.070 g, 0.099 mmol) in THF (6.1 mL) was heated in a sealed vial in an oil bath held at 120° C. for 3 hours. Upon cooling to room temperature, the reaction mixture was diluted with EtOAc and water and filtered. The layers of the filtrate were separated and the organic layer was dried over Na$_2$SO$_4$, filtered, and concentrated. Purification via flash chromatography, eluting with a gradient of 0-40% EtOAc/hexanes afforded product (0.39 g, 67%). LCMS for C$_{16}$H$_{23}$D$_3$BF$_3$NO$_4$ (M+NH$_4$)$^+$: calculated m/z=367.2; found 367.2 (pH 10 analytical condition). LCMS for C$_{16}$H$_{19}$D$_3$BF$_3$NaO$_4$ (M+Na)$^+$: calculated m/z=372.2; found 372.1 (pH 10 analytical condition). $^1$H NMR (400 MHz, CDCl$_3$) δ 7.92 (d, J=1.7 Hz, 1H), 7.54 (dd, J=8.1, 1.8 Hz, 1H), 7.24 (d, J=8.1 Hz, 1H), 4.31 (d, J=11.5 Hz, 1H), 3.97 (d, J=11.6 Hz, 1H), 3.64 (s, 1H), 1.37 (s, 12H).

Step 6. 2-(3-(5-Amino-6-chloropyrazin-2-yl)-4-(methyl-d3)phenyl)-3,3,3-trifluoropropane-1,2-diol (Enriched in One Enantiomer)

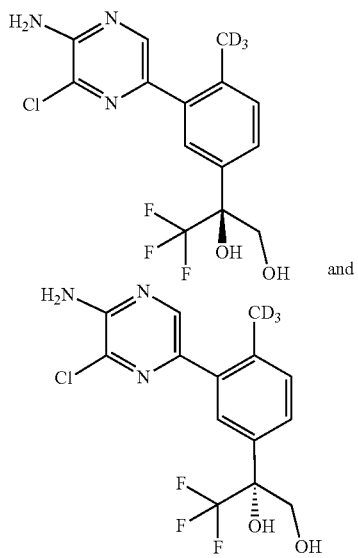

A degassed mixture of 5-bromo-3-chloropyrazin-2-amine (291 mg, 1.40 mmol, Ark Pharm), and 3,3,3-trifluoro-2-(4-(methyl-d$_3$)-3-(4,4,5,5-tetramethyl-1,3,2-dioxaborolan-2-yl)phenyl)propane-1,2-diol (a mixture enriched in one enantiomer, believed to be the (S)-isomer from Step 5, 390 mg, 1.11 mmol) in dioxane (16 mL) was treated with Na$_2$CO$_3$ solution (1.0 M, 4.2 mL, 4.2 mmol) and PdCl$_2$(dppf)-CH$_2$Cl$_2$ adduct (57 mg, 0.070 mmol). The mixture was degassed again and then heated to 100° C. for 3 hours. Upon cooling to room temperature, the reaction mixture was partitioned between water and EtOAc, and the layers were separated. The aqueous layer was extracted with two additional portions of EtOAc and the combined organic extracts were washed with brine, dried over Na$_2$SO$_4$, filtered, and concentrated. Purification via flash chromatography, eluting with a gradient of 0-80% EtOAc/hexanes afforded product (0.217 g, 56%). LCMS for C$_{14}$H$_{11}$D$_3$ClF$_3$N$_3$O$_2$ (M+H)$^+$: calculated m/z=351.1; found 351.0. $^1$H NMR (400 MHz, CDCl$_3$) δ 8.03 (s, 1H), 7.56 (d, J=1.6 Hz, 1H), 7.50 (dd, J=8.1, 1.3 Hz, 1H), 7.32 (d, J=8.1 Hz, 1H), 5.25 (s, 2H), 4.21 (d, J=11.9 Hz, 1H), 3.97 (d, J=11.9 Hz, 1H). $^{19}$F NMR (376 MHz, CDCl$_3$) δ −77.27 (s). The enantiomers were separated by chiral chromatography (Phenomenex Lux Amylose-1, 21.2×250 mm, 5 μM, loading: 90 mg in 1.9 mL EtOH, eluting with 30% EtOH in hexanes at 20 mL/min for 20 minutes). Peak 1 retention time: 8.7 min, Peak 2 retention time: 13.5 min. Peak 1 was used in Step 7. Peak 1 was believed to be the (S)-enantiomer (see previous steps).

Step 7. 2-(3-(5-Amino-6-(2-methyloxazol-5-yl)pyrazin-2-yl)-4-(methyl-d$_3$)phenyl)-3,3,3-trifluoropropane-1,2-diol trifluoroacetate salt (Single Enantiomer Prepared)

The title compound was prepared according to the procedure of Example 9, Step 4, using Peak 1 from Step 6 of Example 16. LCMS for C$_{18}$H$_{15}$D$_3$F$_3$N$_4$O$_3$ (M+H)$^+$: calculated m/z=398.1; found 398.1. The product is believed to be the (S)-enantiomer, (S)-2-(3-(5-Amino-6-(2-methyloxazol-5-yl)pyrazin-2-yl)-4-(methyl-d3)phenyl)-3,3,3-trifluoropropane-1,2-diol. $^1$H NMR (400 MHz, MeOD) δ 8.14 (s, 1H), 7.67 (d, J=1.7 Hz, 1H), 7.64 (s, 1H), 7.57 (dd, J=7.9, 1.5 Hz, 1H), 7.36 (d, J=8.1 Hz, 1H), 4.09 (d, J=11.7 Hz, 1H), 4.01 (d, J=11.7 Hz, 1H), 2.61 (s, 3H).

Example 17. 3-Amino-6-(2-(methyl-d$_3$)-5-(1,1,1-trifluoro-2,3-dihydroxypropan-2-yl)phenyl)-N-(tetrahydro-2H-pyran-4-yl)pyrazine-2-carboxamide, trifluoroacetate salt (Single Enantiomer Prepared)

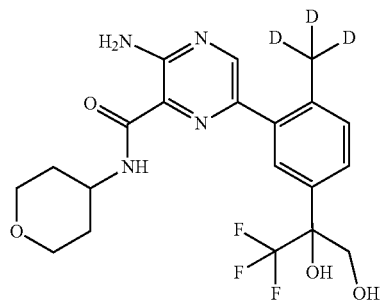

Step 1. Ethyl 3-amino-6-(2-(methyl-d$_3$)-5-(1,1,1-trifluoro-2,3-dihydroxypropan-2-yl)phenyl)pyrazine-2-carboxylate

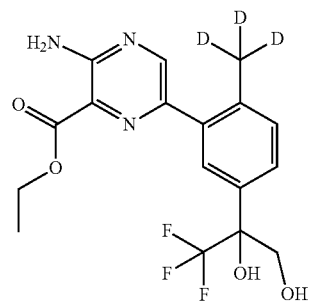 [SMILES: [2H]C([2H])([2H])c1ccc(C(O)(CO)C(F)(F)F)cc1-c1cnc(N)c(C(=O)OCC)n1]

2-(3-(5-Amino-6-chloropyrazin-2-yl)-4-(methyl-d$_3$)phenyl)-3,3,3-trifluoropropane-1,2-diol (0.200 g, 0.570 mmol; from Example 16, Peak 1 from Step 6, believed to be the (S)-isomer), ethanol (3 mL), triethylamine (0.32 mL, 2.3 mmol) and dichloro[1,1'-bis(diphenylphosphino)ferrocene] palladium (II) dichloromethane adduct (47 mg, 0.057 mmol) were combined in a sealable reaction vessel. Carbon monoxide was bubbled through the reaction mixture subsurface for 5 minutes, then the reaction was sealed and a balloon of CO was affixed. The reaction mixture was heated at 80° C. under an atmosphere of CO for 2 hours. The volatiles were removed in vacuo and the resulting residue was purified via flash chromatography (eluting with a gradient from 0-80% in EtOAc in hexanes) to provide product as a colorless oil (0.15 g, 67%). LCMS for $C_{17}H_{16}D_3F_3N_3O_4$ (M+H)$^+$: calculated m/z=389.1; found 389.1.

Step 2. 3-Amino-6-(2-(methyl-d₃)-5-(1,1,1-trifluoro-2,3-dihydroxypropan-2-yl)phenyl)pyrazine-2-carboxylic acid

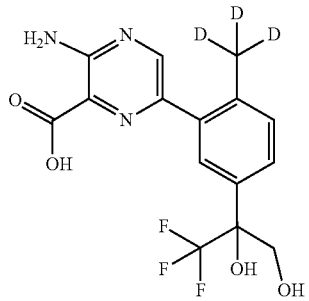 [SMILES: [2H]C([2H])([2H])c1ccc(C(O)(CO)C(F)(F)F)cc1-c1cnc(N)c(C(=O)O)n1]

To a solution of ethyl 3-amino-6-(2-(methyl-d₃)-5-(1,1,1-trifluoro-2,3-dihydroxypropan-2-yl)phenyl)pyrazine-2-carboxylate (0.150 g, 0.386 mmol) in methanol (3 mL) was added lithium hydroxide (46 mg, 1.9 mmol) in water (3.0 mL). The reaction mixture was stirred for 2 hours, and then methanol was removed in vacuo. 1.0 N HCl solution was added to achieve pH=7 and the resulting mixture was extracted with two portions of EtOAc. The combined organic extracts were dried over MgSO₄, filtered, and concentrated to afford product, which was used without further purification (0.14 mg crude, 100%). LCMS for $C_{15}H_{12}D_3F_3N_3O_4$ (M+H)$^+$: calculated m/z=361.1; found 361.1.

Step 3. 3-Amino-6-(2-(methyl-d₃)-5-(1,1,1-trifluoro-2,3-dihydroxypropan-2-yl)phenyl)-N-(tetrahydro-2H-pyran-4-yl)pyrazine-2-carboxamide, trifluoroacetate salt To a solution of 3-amino-6-(2-(methyl-d₃)-5-(1,1,1-trifluoro-2,3-dihydroxypropan-2-yl)phenyl)pyrazine-2-carboxylic acid (0.050 mg, 0.14 mmol) in DMF (4 mL) was added HATU (79 mg, 0.21 mmol) and DIEA (0.048 mL, 0.28 mmol). To this mixture was added tetrahydro-2H-pyran-4-amine (17 mg, 0.17 mmol, Combi-Blocks). The reaction mixture was stirred for 1 hour, then was diluted with water and extracted with two portions of EtOAc. The combined organic extracts were evaporated and the resulting residue was purified via preparative HPLC-MS (pH=2) to afford product as a light yellow solid (0.030 g, 38%). The product is believed to be the (S)-isomer (see stereochemical rationale supra). LCMS for $C_{20}H_{21}D_3F_3N_4O_4$ (M+H)$^+$: calculated m/z=444.2; found 444.4. $^1$H NMR (500 MHz, DMSO) δ 8.41-8.37 (s, 1H), 8.35-8.30 (d, J=8.3 Hz, 1H), 7.65-7.61 (d, J=2.0 Hz, 1H), 7.55-7.51 (dd, J=8.0, 2.0 Hz, 1H), 7.36-7.31 (d, J=8.0 Hz, 1H), 4.06-3.97 (m, 1H), 3.97-3.90 (m, 2H), 3.88-3.81 (m, 2H), 3.44-3.35 (td, J=11.6, 2.3 Hz, 2H), 1.78-1.69 (m, 2H), 1.69-1.57 (qd, J=11.3, 4.3 Hz, 2H).

Example 18. 3-Amino-6-(5-(1,1-difluoro-2,3-dihydroxypropan-2-yl)-2-(methyl-d₃)phenyl)-N-(4-hydroxybicyclo[2.2.1]heptan-1-yl)pyrazine-2-carboxamide trifluoroacetate salt (Single Enantiomer Prepared)

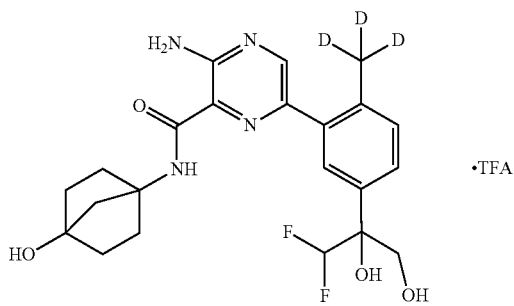 [SMILES: [2H]C([2H])([2H])c1ccc(C(O)(CO)C(F)F)cc1-c1cnc(N)c(C(=O)NC23CCC(O)(CC2)C3)n1]

Step 1. I-Bromo-4-(methyl-d3)benzene

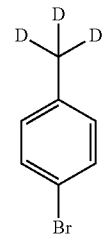

1,4-Dibromobenzene (15.0 g, 63.6 mmol, Aldrich) in THF (280 mL) at −78° C. was treated dropwise with n-butyllithium (1.6 M in hexanes, 39.7 mL, 63.6 mmol). The reaction mixture was stirred for 30 minutes, followed by the addition of iodomethane-d₃ (10.1 g, 69.9 mmol, Oakwood). After stirring for 30 minutes, the reaction mixture was warmed to room temperature and diluted with diethyl ether. The mixture was washed with water (2×), followed by brine (1×). The organic layer was dried over MgSO₄, filtered, and concentrated to afford product as a yellow oil, that was used without further purification (10.3 g, 93%). $^1$H NMR (400 MHz, CDCl₃) δ 7.42-7.37 (d, J=8.1 Hz, 2H), 7.10-7.05 (d, J=8.0 Hz, 2H).

Step 2. 2,2-Difluoro-1-(4-(methyl-d3)phenyl)ethan-1-one

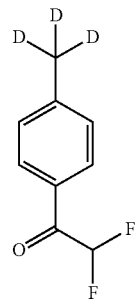 [SMILES: [2H]C([2H])([2H])c1ccc(C(=O)C(F)F)cc1]

To a well stirred mixture of Mg powder (1.9 g, 78 mmol, Aldrich) in THF (72.0 mL) was added 1,2-dibromoethane (two drops). After 10 minutes, a solution of 1-bromo-4-(methyl-d₃)benzene (12.4 g, 71.2 mmol, prepared by the method of Step 1) in THF (54.0 mL) was added dropwise. After complete addition, additional 1,2-dibromoethane was added (two drops). The mixture was stirred at ambient temperature for 1.5 hours, and the mixture was then cooled to 0° C. 2,2-Difluoro-N-methoxy-N-methylacetamide (9.0 g, 65 mmol, Oakwood) in THF (36.0 mL) was added dropwise and after stirring the mixture at 0° C. for 10 minutes, the ice bath was removed. After 40 minutes, the reaction was quenched by the addition of 2.0 N HCl (315 mL). After quenching, the reaction was stirred for 15 minutes. Et₂O was added and the resulting layers were separated. The aqueous portion was extracted once with Et₂O. The combined organic extracts were dried over Na₂SO₄, filtered, and concentrated. The product was purified via flash chromatography, eluting with a gradient from 0-10% EtOAc in hexanes to afford product as an off-white solid (8.85 g, 79%). ¹H NMR (400 MHz, CDCl₃) δ 8.03-7.95 (d, J=8.4 Hz, 2H), 7.38-7.33 (d, J=8.3 Hz, 2H), 6.45-6.02 (t, J=53.6 Hz, 1H).

Step 3. 1-(3-Bromo-4-(methyl-d₃)phenyl)-2,2-difluoroethan-1-one

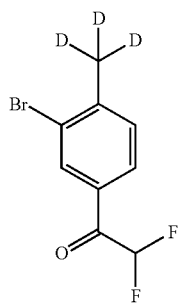

2,2-Difluoro-1-(4-(methyl-d₃)phenyl)ethan-1-one (8.45 g, 48.8 mmol) was cooled to 0° C. and concentrated H₂SO₄ (26.0 mL, 488 mmol) was slowly added. The reaction mixture was maintained at 0° C., and was treated with N-bromosuccinimide (9.12 g, 51.2 mmol) added portion wise, and was stirred for 1 hour. Separately, a mixture of water and MTBE (1:1) was cooled to 0° C., then added slowly to the reaction mixture at 0° C. The aqueous layer was separated and was extracted with two additional portions of MTBE. The combined organic extracts were washed with 10% Na₂S₂O₃ and brine, dried over MgSO₄, filtered and concentrated. The product was purified via flash chromatography, eluting with a gradient of 0-5% EtOAc in hexanes to afford product as a light yellow oil (10.2 g, 83%). ¹H NMR (400 MHz, CDCl₃) δ 8.27-8.23 (s, 1H), 7.97-7.89 (d, J=7.9 Hz, 1H), 7.43-7.39 (d, J=8.0 Hz, 1H), 6.41-6.10 (t, J=53.4 Hz, 1H).

Step 4. 2-Bromo-4-(3,3-difluoroprop-1-en-2-yl)-1-(methyl-d3)benzene

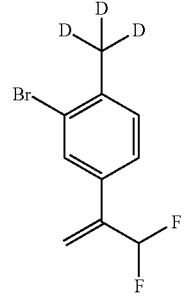

Following a similar procedure as found in *Organic Letters* Vol. 4, No. 10, 1671-1674, 2002, to a solution of tris(triphenylphosphine)rhodium(I) chloride (3.17 g, 3.42 mmol) and triphenylphosphine (19.2 g, 73.0 mmol) in THF (140 mL) under N₂ was added 2-propanol (5.62 mL, 73.0 mmol, dried over molecular sieves), followed by 1-(3-bromo-4-(methyl-d₃)phenyl)-2,2-difluoroethan-1-one (11.5 g, 45.6 mmol) in THF (42 mL). Then trimethylsilyldiazomethane (2.0 M in ether, 39 mL, 78 mmol) was slowly added to the mixture. After a stirring for 1.5 hours, the mixture was quenched by the dropwise addition of acetic acid (5.2 mL, 91 mmol). The mixture was stirred for 30 minutes and volatiles were then evaporated on a rotary evaporator. The product was purified via flash chromatography, eluting with 100% hexanes, to afford a mixture of product and PPh₃, which was further purified via flash chromatography (eluting with 100% hexanes) to afford product as a light yellow oil (5.80 g, 51%). ¹H NMR (400 MHz, CDCl₃) δ 7.72-7.62 (d, J=1.9 Hz, 1H), 7.37-7.31 (dd, J=8.0, 1.8 Hz, 1H), 7.30-7.23 (m, 1H), 6.55-6.19 (t, J=55.2 Hz, 1H), 5.75-5.72 (t, J=1.9 Hz, 1H), 5.69-5.64 (t, J=2.3 Hz, 1H).

Step 5. 2-(3-Bromo-4-(methyl-d3)phenyl)-3,3-difluoropropane-1,2-diol (Enriched in One Enantiomer)

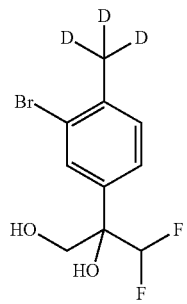 [SMILES: [2H]C([2H])([2H])c1ccc(C(O)(CO)C(F)F)cc1Br]

2-Bromo-4-(3,3-difluoroprop-1-en-2-yl)-1-(methyl-d₃)benzene (5.8 g, 23 mmol) in ᵗBuOH (60.0 mL) was added to a suspension of AD-mix-alpha (32.5 g, 69.6 mmol) in water (60.0 mL) at 0° C. The mixture was then stirred at 3-6° C. for 48 hours. The reaction was then quenched by the addition of sodium sulfite (10 g). The mixture was stirred for 10 minutes, then was concentrated via rotary evaporation to remove ᵗBuOH. The aqueous mixture was diluted with water and extracted with EtOAc (3×). The combined organic extracts were dried over Na$_2$SO$_4$, filtered, and concentrated. The product was purified via flash chromatography, eluting with a gradient of 0-40% EtOAc in hexanes, to afford product as a colorless oil (5.8 g, 87%). The product is believed to be enriched in the (S)-isomer (see stereochemical rationale supra). LCMS for C$_{10}$H$_8$D$_3$BrF$_2$NaO$_2$ (M+Na)$^+$: calculated m/z=306.1; found 306.1. $^1$H NMR (400 MHz, CDCl$_3$) δ 7.75-7.73 (d, J=1.9 Hz, 1H), 7.39-7.34 (m, 1H), 7.30-7.25 (d, J=8.0 Hz, 1H), 6.08-5.74 (t, J=55.8 Hz, 1H), 4.22-4.15 (dd, J=12.1, 4.8 Hz, 1H), 3.88-3.80 (dd, J=12.9, 3.7 Hz, 1H), 3.47-3.08 (s, 1H).

Step 6. 3,3-Difluoro-2-(4-(methyl-d$_3$)-3-(4,4,5,5-tetramethyl-1,3,2-dioxaborolan-2-yl)phenyl)propane-1,2-diol (Enriched in One Enantiomer)

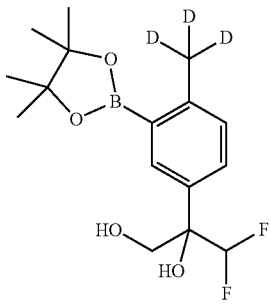 [SMILES: [2H]C([2H])([2H])c1ccc(C(O)(CO)C(F)F)cc1B1OC(C)(C)C(C)(C)O1]

A degassed mixture of 2-(3-bromo-4-(methyl-d$_3$)phenyl)-3,3-difluoropropane-1,2-diol (2.0 g, 7.0 mmol), bis(pinacolato)diboron (3.22 g, 12.7 mmol), potassium acetate (2.07 g, 21.1 mmol), and dichlorobis(triphenylphosphine)palladium (II) (0.395 g, 0.563 mmol) in THF (40.0 mL) was heated in a sealed tube in an oil bath held at 120° C. for 1.5 hours. Upon cooling, the reaction mixture was diluted with EtOAc, filtered through Celite©, and was concentrated. The product was purified by flash chromatography, eluting with a gradient from 0-40% EtOAc in hexanes to afford product as a light yellow oil (2.3 g, 99%). LCMS for C$_{16}$H$_{19}$D$_3$BF$_2$O$_3$ (M+H–H$_2$O)$^+$: calculated m/z=314.2; found 314.2.

Step 7. 2-(3-(5-Amino-6-chloropyrazin-2-yl)-4-(methyl-d$_3$)phenyl)-3,3-difluoropropane-1,2-diol (Single Enantiomer Isolated, Believed to be the (S)-Isomer)

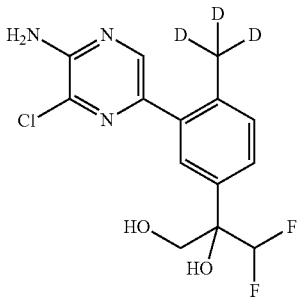 [SMILES: [2H]C([2H])([2H])c1ccc(C(O)(CO)C(F)F)cc1-c1cnc(N)c(Cl)n1]

A degassed mixture of 5-bromo-3-chloropyrazin-2-amine (2.01 g, 9.63 mmol), 3,3-difluoro-2-(4-(methyl-d$_3$)-3-(4,4,5,5-tetramethyl-1,3,2-dioxaborolan-2-yl)phenyl)propane-1,2-diol (2.9 g, 8.7 mmol, prepared as in Step 6) and PdCl$_2$(dppf)-CH$_2$Cl$_2$ adduct (0.358 g, 0.438 mmol) in Na$_2$CO$_3$ solution (1.0 M, 26.3 mL, 26.3 mmol), and dioxane (90.0 mL) was heated to 100° C. in a flask equipped with reflux condenser for 1 hour. Upon cooling to room temperature, the reaction mixture was partitioned between water and EtOAc. The layers were separated and the aqueous layer was extracted with two further portions of EtOAc. The combined organic extracts were washed with brine, dried over MgSO$_4$, filtered, and concentrated. The product was purified via flash chromatography, eluting with a gradient of 0-70% EtOAc in hexanes, to afford product as a light yellow solid (1.84 g, 58%). The enantiomers were separated by chiral chromatography (Phenomenex Lux Amylose-1, 21.2×250 mm, 5 µM, loading: 90 mg in 9.0 mL EtOH, eluting with 45% EtOH in hexanes at 20 mL/min for 16 minutes). Peak 1 retention time: 9.4 min, Peak 2 retention time: 14.1 min. Peak 1 was believed to be the (S)-enantiomer (see stereochemical rationale supra), while Peak 2 was believed to be the (R)-enantiomer. Peak 1 (1.01 g obtained) was used in Step 8. LCMS for C$_{14}$H$_{12}$D$_3$ClF$_2$N$_3$O$_2$ (M+H)$^+$: calculated m/z=333.1; found 333.1.

Step 8. 3-Amino-6-(5-(1,1-difluoro-2,3-dihydroxypropan-2-yl)-2-(methyl-d$_3$)phenyl)pyrazine-2-carboxylic acid (Single Enantiomer Prepared)

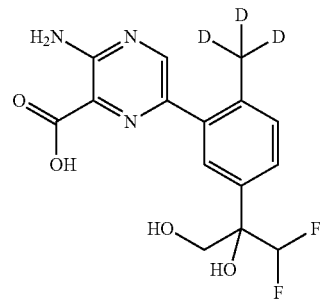 [SMILES: [2H]C([2H])([2H])c1ccc(C(O)(CO)C(F)F)cc1-c1cnc(N)c(C(=O)O)n1]

2-(3-(5-Amino-6-chloropyrazin-2-yl)-4-(methyl-d$_3$)phenyl)-3,3-difluoropropane-1,2-diol (0.500 g, 1.50 mmol, peak 1 from Step 7), ethanol (20.0 mL), triethylamine (0.838 mL, 6.01 mmol), and dichloro[1,1'-bis(diphenylphosphino)ferrocene]palladium (II) dichloromethane adduct (123 mg, 0.150 mmol) were combined in a sealable vessel. Carbon monoxide was bubbled through the reaction mixture subsurface for 5 minutes, then the reaction was sealed and a balloon of CO was affixed. The reaction mixture was heated at 80° C. under an atmosphere of CO for 3.5 hours. The volatiles were removed in vacuo and the resulting residue was purified via flash chromatography (eluting with a gradient from 0-70% in EtOAc in hexanes) to provide desired product ester as an oil (0.440 g). LCMS for C$_{17}$H$_{17}$D$_3$F$_2$N$_3$O$_4$ (M+H)$^+$: calculated m/z=371.2; found 371.1. The ester was then dissolved in MeOH (10.0 mL), and LiOH (0.180 g, 7.51 mmol) in water (10.0 mL) was added. After stirring for 1.5 hours, MeOH was removed in vacuo. The aqueous mixture was treated with 1.0 N HCl to adjust to pH=3. Solid NaCl was added to saturate the solution, and the mixture was extracted with EtOAc (4×). The combined organic extracts were dried over Na$_2$SO$_4$, filtered, and concentrated to afford product as a brown solid (386 mg, 75%). LCMS for C$_{15}$H$_{13}$D$_3$F$_2$N$_3$O$_4$ (M+H)$^+$: calculated m/z=343.1; found 343.1.

Step 9. 3-Amino-6-(5-(1,1-difluoro-2,3-dihydroxypropan-2-yl)-2-(methyl-d₃)phenyl)-N-(4-hydroxybicyclo[2.2.1]heptan-1-yl)pyrazine-2-carboxamide trifluoroacetate salt (Single Enantiomer Prepared)

To a solution of 3-amino-6-(5-(1,1-difluoro-2,3-dihydroxypropan-2-yl)-2-(methyl-d₃)phenyl)pyrazine-2-carboxylic acid (5.0 mg, 0.015 mmol) in DMF (0.20 mL) was added HATU (8.3 mg, 0.022 mmol) and DIEA (0.013 mL, 0.073 mmol). To this mixture was added 4-aminobicyclo[2.2.1]heptan-1-ol (2.2 mg, 0.018 mmol). After stirring for 30 minutes, the reaction mixture was diluted with acetonitrile and methanol, filtered, and the product was purified via preparative HPLC-MS (pH=2). The product is believed to be the (S)-enantiomer (see stereochemical rationale supra). Yield: 6.6 mg. LCMS for $C_{22}H_{24}D_3F_2N_4O_4$ (M+H)⁺: calculated m/z=452.2; found 452.2. ¹H NMR (400 MHz, DMSO-d₆) δ 8.41-8.38 (s, 1H), 8.23-8.20 (s, 1H), 7.60-7.57 (d, J=1.9 Hz, 1H), 7.49-7.43 (dd, J=7.9, 2.0 Hz, 1H), 7.32-7.25 (d, J=8.0 Hz, 1H), 6.42-5.99 (t, J=55.6 Hz, 1H), 3.78 (d, J=11.6 Hz, 1H), 3.69 (d, J=11.6 Hz, 1H), 2.07-1.94 (m, 2H), 1.91-1.79 (m, 4H), 1.77-1.63 (m, 2H), 1.62-1.48 (m, 2H). ¹⁹F{¹H}NMR (376 MHz, DMSO-d₆) δ −74.15 (s), −129.17--130.48 (d, $J_{F-F}$=277.2 Hz), −133.80--135.42 (d, $J_{F-F}$=277.4 Hz).

Example 19. 3-Amino-6-(2-(methyl-d₃)-5-(1,1,1-trifluoro-2,3-dihydroxybutan-2-yl)phenyl)-N-(tetrahydro-2H-pyran-4-yl)pyrazine-2-carboxamide (Single Isomer Prepared)

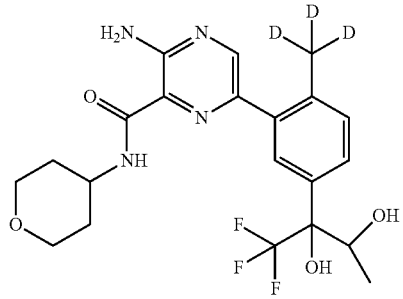 [SMILES: [2H]C([2H])([2H])c1ccc(C(O)(C(C)O)C(F)(F)F)cc1-c1cnc(N)c(C(=O)NC2CCOCC2)n1]

Step 1. 2-(3-Bromo-4-(methyl-d₃)phenyl)-3,3,3-trifluoro-2-hydroxypropanal

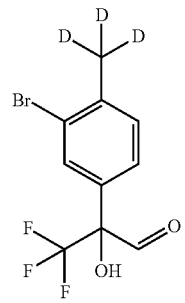

2-(3-Bromo-4-(methyl-d₃)phenyl)-3,3,3-trifluoropropane-1,2-diol (5.0 g, 14.9 mmol, from Example 16, Step 4, before chiral separation (enriched in one enantiomer, believed to be the (S)-enantiomer (see stereochemical rationale supra)) in DCM (80 mL) was treated with triethylamine (27.0 mL, 194 mmol) and the mixture was cooled to 0° C. Sulfur trioxide-Pyridine complex (9.48 g, 59.6 mmol) dissolved in DMSO (67 mL) was added. The reaction mixture was stirred for 10 minutes, the bath was removed, the mixture was warmed to room temperature, and was stirred for 3.5 hours. The mixture was then concentrated via rotary evaporation to remove DCM and triethylamine, and the remaining aqueous mixture was immersed in a water bath and was treated with saturated NaHCO₃ solution until gas evolution ceased. The mixture was saturated with solid NaCl and additional brine was added. The mixture was extracted with one portion of EtOAc (300 mL). The EtOAc extraction was washed with brine, dried over Na₂SO₄, filtered, and concentrated. The residue was mixed with 100 mL acetonitrile and filtered to remove the small amount of solid precipitate. The acetonitrile filtrate was concentrated via rotary evaporation to give 5.20 g of crude product as a light brown foam. Theoretical yield was assumed and the product was used without further purification.

Step 2. 2-(3-Bromo-4-(methyl-d₃)phenyl)-1,1,1-trifluorobutane-2,3-diol (Two Separate Diastereomers were Isolated that were Each Subsequently Separated into Single Enantiomers)

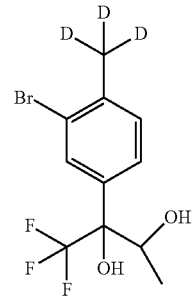 [SMILES: [2H]C([2H])([2H])c1ccc(C(O)(C(C)O)C(F)(F)F)cc1Br]

Methylmagnesium bromide (3.0 M in Et₂O, 27.8 mL, 83 mmol) was added dropwise to a solution of 2-(3-bromo-4-(methyl-d₃)phenyl)-3,3,3-trifluoro-2-hydroxypropanal (4.9 g, 14 mmol) in THF (100 mL) at 0° C. The mixture was warmed to room temperature and was stirred for 4.5 hours. The mixture was then cooled in an ice-water bath and quenched by addition of 1.0 N HCl. After gas evolution ceased, the bath was removed and 1.0 N HCl was added to adjust to pH=3. The mixture was stirred for 30 minutes, then was extracted with EtOAc (2×). The combined organic extracts were dried over Na₂SO₄, filtered, and concentrated. The product was purified via flash chromatography, eluting with 100% hexanes, then a gradient of 0-15% EtOAc in hexanes to afford two diastereomers: Peak 1, major diastereomer (first to elute): 1.84 g. Peak 2, minor diastereomer (second to elute): 0.62 g.

Each diastereomer (each enriched in one enantiomer believed to be the (S)-configuration at the tertiary alcohol, supra) was submitted separately for chiral purification, and only the major enantiomer in each chiral separation (believed to be the (S)-configuration at the tertiary alcohol, supra) was collected.

The first diastereomer to elute during the flash chromatography was subjected to chiral HPLC to separate the enantiomers (Phenomenex Lux Amylose-1, 21.2×250 mm, 5

μM, loading: 50 mg in 1.0 mL EtOH, eluting with 5% EtOH in hexanes at 20 mL/min for 17 minutes). Peak 1 retention time: 11.3 min, Peak 2 retention time: 12.5 min. Peak 2 was the major enantiomer, and is thus believed to be the (S)-configuration at the tertiary alcohol (see stereochemical rationale supra). This single enantiomer was subsequently used in Step 3.

The second diastereomer to elute during the flash chromatography was subjected to chiral HPLC to separate the enantiomers (Phenomenex Lux Amylose-1, 21.2×250 mm, 5 μM, loading: 30 mg in 0.9 mL EtOH, eluting with 30% EtOH in hexanes at 20 mL/min for 12 minutes). Peak 1 retention time: 6.25 min, Peak 2 retention time: 10.5 min. Peak 1 was the major enantiomer, and is thus believed to be the (S)-configuration at the tertiary alcohol (see stereochemical rationale supra).

Step 3. 1,1,1-Trifluoro-2-(4-(methyl-d$_3$)-3-(4,4,5,5-tetramethyl-1,3,2-dioxaborolan-2-yl)phenyl)butane-2,3-diol (Single Isomer Prepared)

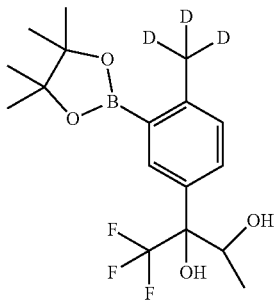 [SMILES: [2H]C([2H])([2H])c1ccc(C(O)(C(C)O)C(F)(F)F)cc1B1OC(C)(C)C(C)(C)O1]

A degassed mixture of 2-(3-bromo-4-(methyl-d$_3$)phenyl)-1,1,1-trifluorobutane-2,3-diol (0.500 g, 1.58 mmol, peak 2 from chiral separation of the first eluting diastereomer from flash chromatography in Step 2), bis(pinacolato)diboron (723 mg, 2.85 mmol), potassium acetate (466 mg, 4.74 mmol) and triphenylphosphine palladium chloride (89 mg, 0.13 mmol) in THF (10.0 mL) was heated in a sealed tube in an oil bath held at 120° C. for 1.5 hours. Upon cooling to room temperature, the reaction mixture was diluted with EtOAc, filtered through Celite®, and concentrated. The product was purified by flash chromatography, eluting with a gradient from 0-20% EtOAc in hexanes to afford product as a light yellow oil. Theoretical yield assumed and the product was used in Step 4.

Step 4. 2-(3-(5-Amino-6-chloropyrazin-2-yl)-4-(methyl-d$_3$)phenyl)-1,1,1-trifluorobutane-2,3-diol (Single Isomer Prepared)

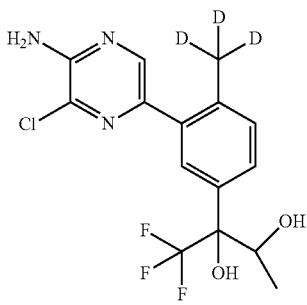 [SMILES: [2H]C([2H])([2H])c1ccc(C(O)(C(C)O)C(F)(F)F)cc1-c1cnc(N)c(Cl)n1]

A degassed mixture of 5-bromo-3-chloropyrazin-2-amine (362 mg, 1.74 mmol, Ark Pharm), 1,1,1-trifluoro-2-(4-(methyl-d$_3$)-3-(4,4,5,5-tetramethyl-1,3,2-dioxaborolan-2-yl)phenyl)butane-2,3-diol (574 mg, 1.58 mmol, from Step 3) and PdCl$_2$(dppf)-CH$_2$Cl$_2$ adduct (64 mg, 0.079 mmol) in dioxane (15.0 mL) and Na$_2$CO$_3$ solution (1.0 M, 4.74 mL, 4.74 mmol) was heated to 100° C. for 2 hours. Additional PdCl$_2$(dppf)-CH$_2$Cl$_2$ adduct (64 mg, 0.079 mmol) was added and the mixture was heated for 1.5 hours at 100° C. Upon cooling to room temperature, the reaction mixture was partitioned between water and EtOAc then the biphasic mixture was filtered through Celite® to remove solids. The layers of the filtrate were separated. The aqueous layer was extracted with EtOAc and the combined organic layers were washed with brine, dried over MgSO$_4$, filtered, and concentrated. The product was purified via flash chromatography, eluting with a gradient from 0-60% EtOAc in hexanes, to afford product as a light yellow solid (466 mg, 81%). LCMS for $C_{15}H_{13}D_3ClF_3N_3O_2$ (M+H)$^+$: calculated m/z=365.1; found 365.2.

Step 5. 3-Amino-6-(2-(methyl-d$_3$)-5-(1,1,1-trifluoro-2,3-dihydroxybutan-2-yl)phenyl)-N-(tetrahydro-2H-pyran-4-yl)pyrazine-2-carboxamide (Single Isomer Prepared)

The title compound was prepared by following the procedures found in Example 17, Steps 1 through 3, using 2-(3-(5-amino-6-chloropyrazin-2-yl)-4-(methyl-d$_3$)phenyl)-1,1,1-trifluorobutane-2,3-diol from Step 4. The product was purified via preparative HPLC-MS (pH=10). The product is believed to be the (S)-enantiomer (see stereochemical rationale supra). LCMS for $C_{21}H_{23}D_3F_3N_4O_4$ (M+H)$^+$: calculated m/z=458.2; found 458.2. $^1$H NMR (500 MHz, DMSO) δ 8.38-8.35 (s, 1H), 8.35-8.30 (d, J=8.3 Hz, 1H), 7.72-7.57 (br s, 1H), 7.57-7.54 (d, J=2.0 Hz, 1H), 7.48-7.41 (dd, J=8.0, 2.0 Hz, 1H), 7.37-7.28 (d, J=8.0 Hz, 1H), 6.39-5.77 (br s, 1H), 5.54-4.78 (br s, 1H), 4.45-4.37 (q, J=6.3 Hz, 1H), 4.07-3.94 (m, 1H), 3.89-3.79 (dt, J=11.4, 3.6 Hz, 2H), 3.47-3.36 (td, J=11.5, 2.3 Hz, 2H), 1.80-1.70 (m, 2H), 1.70-1.57 (m, 2H), 0.90-0.79 (d, J=6.3 Hz, 3H). $^{19}$F NMR (471 MHz, DMSO) δ −69.03−−75.88 (s).

Example 20. 2-(3-(5-Amino-6-(3-methyl-1H-pyrazol-4-yl)pyrazin-2-yl)-4-(methyl-d$_3$)phenyl)-1,1,1,4,4,4-hexafluorobutane-2,3-diol, trifluoroacetate salt, (a Single Diastereomer Enriched in One Enantiomer was Prepared)

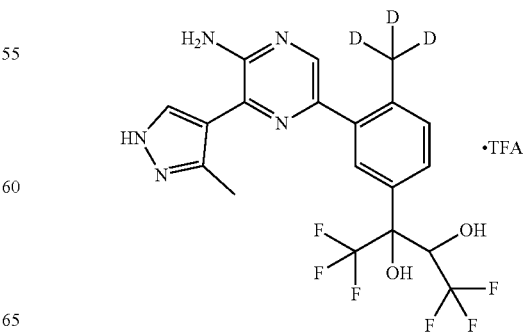

Step 1. 2-(3-Bromo-4-(methyl-d₃)phenyl)-1,1,1,4,4,4-hexafluorobutane-2,3-diol (Two Diastereomers Isolated, Each Enriched in One Enantiomer)

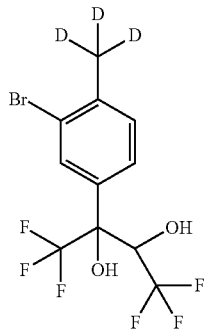 [SMILES: [2H]C([2H])([2H])c1ccc(C(O)(C(O)C(F)(F)F)C(F)(F)F)cc1Br]

A solution of 2-(3-bromo-4-(methyl-d₃)phenyl)-3,3,3-trifluoro-2-hydroxypropanal (0.30 g, 0.85 mmol, from Example 19, Step 1) in dry THF (1.7 mL) was cooled to 0° C. and trimethyl(trifluoromethyl)silane (0.31 mL, 2.1 mmol) was added. The yellow mixture was treated with TBAF (1.0 M in THF, 0.017 mL, 0.017 mmol) at 0° C. The reaction was stirred for a few minutes at 0° C., the ice bath was removed, and the resulting reaction mixture was stirred for 40 minutes, with warming to room temperature. The reaction was re-cooled to 0° C., and water (0.17 mL, 9.4 mmol) and TBAF (1.0 M in THF, 0.17 mL, 0.17 mmol) were added. The ice bath was removed and the mixture was stirred for 30 minutes at ambient temperature. The reaction mixture was diluted with brine (20 mL), and was extracted with EtOAc (50 mL). The organic layer was washed with 1.0 N HCl (2×25 mL), followed by brine, dried over Na₂SO₄, filtered, and concentrated to afford a yellow oil. The product was purified via flash chromatography, eluting with a gradient from 0-15% EtOAc in hexanes to afford two separate diastereomers (each enriched in one enantiomer believed to be the (S)-configuration at the tertiary alcohol (see stereochemical rationale supra)). Peak 1 (first to elute): 92 mg, 29%. Peak 2 (second to elute): 68 mg, 22%.

Step 2. 1,1,1,4,4,4-hexafluoro-2-(4-(methyl-d3)-3-(4,4,5,5-tetramethyl-1,3,2-dioxaborolan-2-yl)phenyl)butane-2,3-diol (a Single Diastereomer Enriched in One Enantiomer was Prepared)

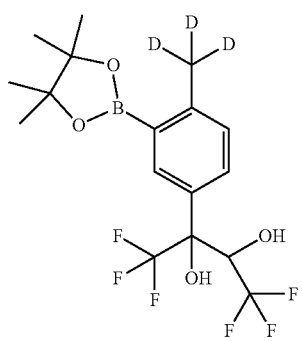 [SMILES: [2H]C([2H])([2H])c1ccc(C(O)(C(O)C(F)(F)F)C(F)(F)F)cc1B1OC(C)(C)C(C)(C)O1]

The title product was prepared using the procedure of Example 19, Step 3, using 2-(3-bromo-4-(methyl-d₃)phenyl)-1,1,1,4,4,4-hexafluorobutane-2,3-diol (92 mg, 0.20 mmol, Peak 1 from Step 1), to afford the title compound (15 mg). LCMS for $C_{17}H_{23}D_3BF_6NO_4$ $(M+NH_4)^+$: calculated m/z=435.2; found 435.2.

Step 3. 5-Chloro-3-(3-methyl-1H-pyrazol-4-yl)pyrazin-2-amine

A flask was charged with 3-bromo-5-chloropyrazin-2-amine (0.24 g, 1.2 mmol, D-L Chiral Chemicals), 3-methyl-4-(4,4,5,5-tetramethyl-1,3,2-dioxaborolan-2-yl)-1H-pyrazole (0.24 g, 1.2 mmol, Aldrich), bis(di-tert-butyl(4-dimethylaminophenyl)phosphine)dichloropalladium(II) (0.041 g, 0.058 mmol), and cesium fluoride (0.53 g, 3.5 mmol). tert-Butyl alcohol (6.1 mL) and water (1.6 mL) were added, and the mixture was degassed and heated to 60° C. for 1.5 hours, then at 70° C. overnight, then at 100° C. for 1.5 hours. Upon cooling, the reaction mixture was partitioned between water and EtOAc, and the layers were separated. The aqueous layer was extracted with two additional portions of EtOAc and the combined organic layers were washed with brine, dried over MgSO₄, filtered, and concentrated. The product was purified by flash chromatography, eluting with a gradient of 0-10% MeOH in DCM to afford a pale yellow solid (0.14 g, 58%). LCMS for $C_8H_9ClN_5$ $(M+H)^+$: calculated m/z=210.1; found 210.1.

Step 4. 2-(3-(5-Amino-6-(3-methyl-1H-pyrazol-4-yl)pyrazin-2-yl)-4-(methyl-d3)phenyl)-1,1,1,4,4,4-hexafluorobutane-2,3-diol, trifluoroacetate salt (a Single Diastereomer Enriched in One Enantiomer was Prepared)

A microwave vial was charged with 1,1,1,4,4,4-hexafluoro-2-(4-(methyl-d₃)-3-(4,4,5,5-tetramethyl-1,3,2-dioxaborolan-2-yl)phenyl)butane-2,3-diol (15 mg, 0.029 mmol, from Step 2, a single diastereomer enriched in one enantiomer), 5-chloro-3-(3-methyl-1H-pyrazol-4-yl)pyrazin-2-amine (9.1 mg, 0.043 mmol, from Step 3) and dichloro[1,1'-bis(diphenylphosphino)ferrocene]palladium (II) dichloromethane adduct (4.7 mg, 5.8 μmol). THF (0.5 mL) was added, followed by K₂CO₃ solution (1.0 M, 0.086 mL, 0.086 mmol). The reaction mixture was degassed by bubbling a stream of nitrogen through the solution for 5 minutes, and then was heated in the microwave at 130° C. for 30 minutes. The reaction mixture was diluted with acetonitrile and methanol, was filtered and purified via preparative HPLC-MS (pH=2) to afford product as the TFA salt (3.7 mg). The product is believed to be enriched in the (S)-enantiomer at the tertiary alcohol (see stereochemical rationale supra). LCMS for $C_{19}H_{15}D_3F_6N_5O_2$ $(M+H)^+$: calculated m/z=465.2; found 465.1. ¹H NMR (400 MHz, MeOD) δ 8.04-8.00 (s, 1H), 7.95-7.92 (s, 1H), 7.74-7.70 (s, 1H), 7.60-7.54 (d, J=7.3 Hz, 1H), 7.38-7.34 (d, J=8.2 Hz, 1H), 4.83-4.76 (q, J=7.2 Hz, 1H), 2.46 (s, 3H). ¹⁹F NMR (376 MHz, MeOD) δ −72.13--−72.41 (s), −75.50--−75.75 (s), −77.24--−77.60 (s).

141

Example 21. 2-(3-(5-Amino-6-(3-methyl-1H-pyrazol-4-yl)pyrazin-2-yl)-4-(methyl-d₃)phenyl)-1,1,1,4,4,4-hexafluorobutane-2,3-diol, trifluoroacetate salt (a Single Diastereomer Enriched in One Enantiomer was Prepared)

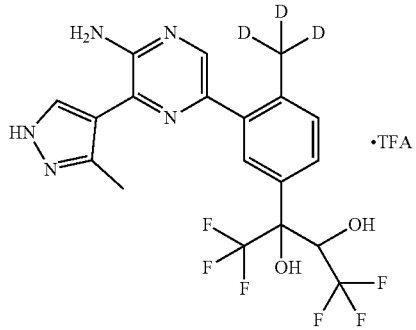 [SMILES: [2H]C([2H])([2H])c1ccc(C(O)(C(O)C(F)(F)F)C(F)(F)F)cc1-c1cnc(N)c(-c2c[nH]nc2C)n1]

The title product was prepared using the procedure of Example 20, Steps 2-4, using Peak 2 from Example 20, Step 1 to afford the title compound as a single diastereomer enriched in one enantiomer. The product is believed to be enriched in the (S)-enantiomer at the tertiary alcohol (see stereochemical rationale supra). LCMS for $C_{19}H_{15}D_3F_6N_5O_2$ (M+H)⁺: calculated m/z=465.2; found 465.1. ¹H NMR (400 MHz, MeOD) δ 8.02-8.01 (s, 1H), 7.95-7.94 (s, 1H), 7.91-7.88 (s, 1H), 7.79-7.74 (d, J=8.1 Hz, 1H), 7.34-7.30 (d, J=8.2 Hz, 1H), 4.70-4.47 (q, J=7.0 Hz, 1H), 2.55-2.33 (s, 3H). ¹⁹F NMR (376 MHz, MeOD) δ −72.71−−73.13 (s), −77.33−−77.52 (s), −77.58−−78.04 (s).

Example 22. 3-Amino-6-(2-methyl-5-(1,1,1-trifluoro-2,3-dihydroxy-3-methylbutan-2-yl)phenyl)-N-(tetrahydro-2H-pyran-4-yl)pyrazine-2-carboxamide, trifluoroacetate salt, (Enriched in One Enantiomer)

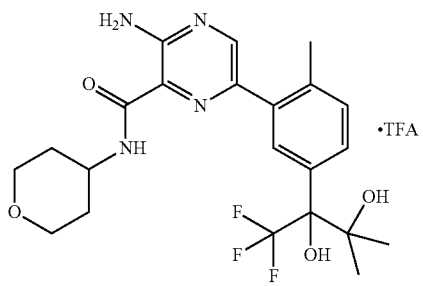 [SMILES: Cc1ccc(C(O)(C(C)(C)O)C(F)(F)F)cc1-c1cnc(N)c(C(=O)NC2CCOCC2)n1]

142

Step 1. 2-(3-Chloro-4-methylphenyl)-3,3,3-trifluoro-2-hydroxypropanoic acid (Enriched in One Enantiomer)

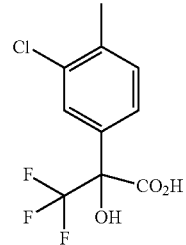

A procedure similar to that disclosed in *Tetrahedron: Asymmetry* Vol. 5, No. 8, pp. 1413-1476, 1994 was performed as follows: to a mixture of 2-(3-chloro-4-methylphenyl)-3,3,3-trifluoropropane-1,2-diol (0.70 g, 2.8 mmol, Example 1a, Step 3 (enriched in one enantiomer, believed to be the (S)-enantiomer, see stereochemical rationale supra)), NaHCO₃ (0.346 g, 4.12 mmol), and Platinum (5% on carbon, 1.07 g, 0.275 mmol) in water (50.0 mL) was added one drop of Antifoam A concentrate, 100% (Aldrich catalog #A5633). The mixture was then heated at 75° C. overnight while a gentle flow of air (pulled into the reaction flask by vacuum) was bubbled through the solution. Additional Platinum (5% on carbon, 0.644 g, 0.165 mmol) was added and the mixture was stirred under the same conditions for a total of 40 hours. Upon cooling to room temperature, the mixture was filtered through Celite© and rinsed with water. 1.0 N HCl was added to achieve pH=2, and the aqueous mixture was extracted with EtOAc (3×). The combined organic extracts were washed with water, followed by brine, dried over MgSO₄, filtered and evaporated. The product was purified via flash chromatography, eluting with a gradient from 0-100% EtOAc in hexanes to afford a light yellow solid contaminated with unreacted diol.

Step 2. Ethyl 2-(3-chloro-4-methylphenyl)-3,3,3-trifluoro-2-hydroxypropanoate (Enriched in One Enantiomer)

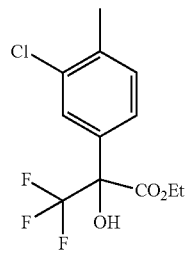 [SMILES: CCOC(=O)C(O)(c1ccc(C)c(Cl)c1)C(F)(F)F]

2-(3-Chloro-4-methylphenyl)-3,3,3-trifluoro-2-hydroxypropanoic acid (0.50 g, 1.5 mmol, the mixture from Step 1) in EtOH (4.0 mL) was treated with concentrated H₂SO₄ (0.079 mL, 1.5 mmol) was added. The mixture was sealed and heated to 80° C. overnight. Upon cooling to room temperature, the reaction mixture was neutralized by the addition saturated NaHCO₃ solution. The mixture was extracted with EtOAc and the organic layer was dried over Na₂SO₄, filtered and concentrated. The product was purified via flash chromatography, eluting with a gradient of 0-15% EtOAc in hexanes to afford the product as a colorless oil (0.33 g, 42% over two steps). LCMS for $C_{12}H_{11}ClF_3O_2(M+H-H_2O)^+$: calculated m/z=279.0; found 278.9.

Step 3. 2-(3-Chloro-4-methylphenyl)-1,1,1-trifluoro-3-methylbutane-2,3-diol (Enriched in One Enantiomer)

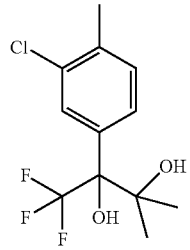

Methylmagnesium bromide (3.0 M in Et$_2$O, 1.85 mL, 5.56 mmol) dropwise to a solution of ethyl 2-(3-chloro-4-methylphenyl)-3,3,3-trifluoro-2-hydroxypropanoate (0.33 g, 1.1 mmol) in THF (10 mL) at 0° C. The mixture was then raised to ambient temperature and was stirred for 1.5 hours. Additional methylmagnesium bromide (3.0 M in Et$_2$O, 0.185 mL, 0.556 mmol) was added. The mixture was stirred for 30 minutes, then was cooled with an ice-water bath and quenched by the cautious addition of 1.0 N HCl. When gas evolution ceased, additional 1.0 N HCl was added to adjust to pH=3. The mixture was stirred for 30 minutes at room temperature, then was extracted with EtOAc (2×). The combined organic extracts were dried over Na$_2$SO$_4$, filtered and concentrated. The product was purified via flash chromatography, eluting with a gradient of 0-20% EtOAc in hexanes to afford product as a colorless oil (0.22 g, 70%). LCMS for $C_{12}H_{13}ClF_3O$ $(M+H-H_2O)^+$: calculated m/z=265.1; found 265.0.

Step 4. 3-Amino-6-(2-methyl-5-(1,1,1-trifluoro-2,3-dihydroxy-3-methylbutan-2-yl)phenyl)-N-(tetrahydro-2H-pyran-4-yl)pyrazine-2-carboxamide, trifluoroacetate salt (Enriched in One Enantiomer)

The title compound was prepared by following the procedure of Example 1a, Steps 4-5, followed by the procedure of Example 17, Steps 1-3, using 2-(3-chloro-4-methylphenyl)-1,1,1-trifluoro-3-methylbutane-2,3-diol (enriched in one enantiomer, believed to be (S)—, see stereochemical rationale supra). LCMS for $C_{22}H_{28}F_3N_4O_4$ (M+H)$^+$: calculated m/z=469.2; found 469.2. $^1$H NMR (400 MHz, MeOD) δ 8.36-8.30 (s, 1H), 7.80-7.71 (d, J=2.0 Hz, 1H), 7.69-7.61 (dd, J=7.9, 2.0 Hz, 1H), 7.36-7.30 (d, J=8.1 Hz, 1H), 4.17-4.05 (m, 1H), 4.02-3.93 (dt, J=11.8, 3.5 Hz, 2H), 3.62-3.51 (td, J=11.6, 2.3 Hz, 2H), 2.46-2.38 (s, 3H), 1.96-1.85 (m, 2H), 1.75-1.60 (m, 2H), 1.31-1.28 (s, 3H), 1.28-1.24 (s, 3H).

Example 23. 2-(3-(5-Amino-6-(1-((1-methyl-1H-pyrazol-3-yl)sulfonyl)azetidin-3-yl)pyrazin-2-yl)-4-methylphenyl)-3,3,3-trifluoropropane-1,2-diol (Enriched in One Enantiomer)

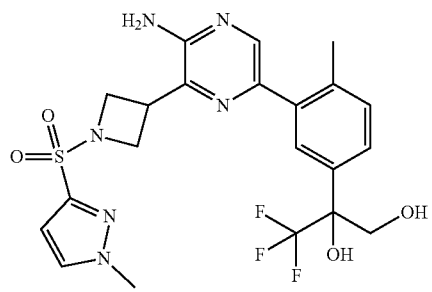 [SMILES: Cc1ccc(C(O)(CO)C(F)(F)F)cc1-c1cnc(N)c(C2CN(S(=O)(=O)c3ccn(C)n3)C2)n1]

Step 1. tert-Butyl 3-(3-amino-6-chloropyrazin-2-yl)azetidine-1-carboxylate

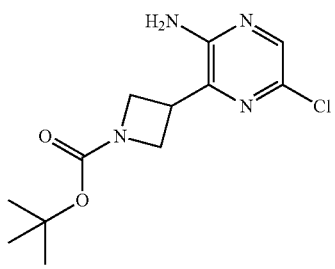 [SMILES: CC(C)(C)OC(=O)N1CC(c2nc(Cl)cnc2N)C1]

Zinc dust (activated by the procedure found in WO2011/143365, the disclosure of which is incorporated herein by reference in its entirety) (0.627 g, 9.59 mmol) was charged to a dry flask and suspended in DMA (2.5 mL). 1,2-Dibromoethane (0.031 mL, 0.36 mmol) and TMSCl (0.092 mL, 0.72 mmol) were added and the reaction was stirred for 25 min. tert-Butyl 3-iodoazetidine-1-carboxylate (2.04 g, 7.20 mmol, Oakwood) in DMA (6.0 mL) was added slowly to the mixture which was immersed in a water bath to keep the temperature below 65° C. The mixture was stirred for 1 hour and was degassed by bubbling a stream of nitrogen through the mixture for 5 minutes.

A separate flask was charged with 3-bromo-5-chloropyrazin-2-amine (0.50 g, 2.4 mmol, D-L Chiral Chemicals), dichloro[1,1'-bis(diphenylphosphino)ferrocene]palladium (II) dichloromethane adduct (0.118 g, 0.144 mmol) and copper(I) iodide (0.057 g, 0.30 mmol). DMA (6.0 mL) was added, and the mixture was degassed by bubbling a stream of nitrogen through the mixture for 5 minutes. The solution containing the organozinc in DMA was added, excluding any remaining zinc solids. The reaction mixture was then heated at 80° C. for 30 min. Upon cooling to room temperature, the reaction mixture was partitioned between water and EtOAc. The aqueous layer was extracted with two additional portions of EtOAc. The combined organic extracts were washed with water and brine, dried over sodium sulfate, filtered, and concentrated. The product was purified by flash chromatography, eluting with a gradient from 0-100% EtOAc in hexanes to afford product (0.62 g, 90%). LCMS calculated for $C_{12}H_{18}ClN_4O_2(M+H)^+$: m/z=285.1, found: 285.1. $^1$H NMR (400 MHz, CDCl$_3$) δ

7.96-7.90 (s, 1H), 4.78-4.65 (s, 2H), 4.35-4.22 (m, 4H), 3.79-3.69 (p, J=7.4 Hz, 1H), 1.48-1.44 (s, 9H).

Step 2. tert-Butyl 3-(3-amino-6-(2-methyl-5-(1,1,1-trifluoro-2,3-dihydroxypropan-2-yl)phenyl)pyrazin-2-yl)azetidine-1-carboxylate (Enriched in One Enantiomer)

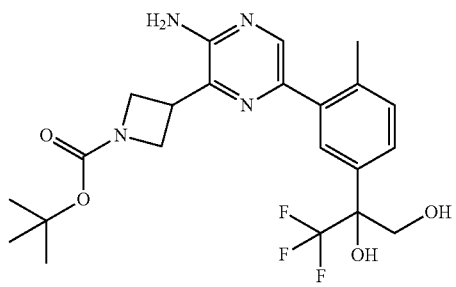 [SMILES: Cc1ccc(C(O)(CO)C(F)(F)F)cc1-c1cnc(N)c(C2CN(C(=O)OC(C)(C)C)C2)n1]

A degassed mixture of tert-butyl 3-(3-amino-6-chloropyrazin-2-yl)azetidine-1-carboxylate (0.615 g, 2.16 mmol), 3,3,3-trifluoro-2-(4-methyl-3-(4,4,5,5-tetramethyl-1,3,2-dioxaborolan-2-yl)phenyl)propane-1,2-diol (0.748 g, 2.16 mmol, enriched in one enantiomer believed to be (S)—, supra), and $PdCl_2(dppf)\cdot CH_2Cl_2$ adduct (0.088 g, 0.11 mmol) in dioxane (10.8 mL) and $Na_2CO_3$ (1.0 M in water, 6.5 mL, 6.5 mmol) was heated in a sealed vial in an oil bath held at 120° C. for 3 hours. Upon cooling to room temperature, the reaction mixture was diluted with EtOAc and sufficient water to dissolve solids. The layers were separated and the aqueous layer was extracted with two further portions of EtOAc. The combined organic extracts were dried over $Na_2SO_4$, filtered, and concentrated. The product was purified by flash chromatography, eluting with a slow gradient from 0-100% EtOAc in hexanes (yield: 400 mg, 40%). LCMS calculated for $C_{22}H_{28}F_3N_4O_4$ (M+H)$^+$: m/z=469.2, found: 469.1. $^1$H NMR (400 MHz, CDCl$_3$) δ 8.12-7.99 (s, 1H), 7.68-7.57 (s, 1H), 7.53-7.47 (d, J=7.3 Hz, 1H), 7.39-7.33 (d, J=8.1 Hz, 1H), 4.66-4.56 (s, 2H), 4.45-4.25 (m, 4H), 4.07-3.93 (m, 2H), 3.87-3.78 (m, 1H), 2.48-2.40 (s, 3H), 1.49-1.41 (s, 9H).

Step 3. 2-(3-(5-Amino-6-(azetidin-3-yl)pyrazin-2-yl)-4-methylphenyl)-3,3,3-trifluoropropane-1,2-diol, HCl salt (Enriched in One Enantiomer)

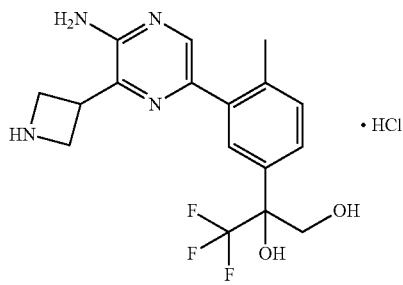 [SMILES: Cc1ccc(C(O)(CO)C(F)(F)F)cc1-c1cnc(N)c(C2CNC2)n1 ; "· HCl"]

A solution of tert-butyl 3-(3-amino-6-(2-methyl-5-(1,1,1-trifluoro-2,3-dihydroxypropan-2-yl)phenyl)pyrazin-2-yl)azetidine-1-carboxylate (0.32 g, 0.68 mmol) was treated with HCl (1.25 M in MeOH (generated by diluting a HCl solution with MeOH), 10.0 mL, 12.5 mmol) and the reaction was stirred at room temperature for 48 hours. Additional HCl (1.25 M in MeOH, 10.0 mL, 12.5 mmol) was added and the reaction was stirred for 72 hours. Volatiles were evaporated to afford the HCl salt, and the product was used without further purification.

Step 4. 2-(3-(5-Amino-6-(1-((1-methyl-1H-pyrazol-3-yl)sulfonyl)azetidin-3-yl)pyrazin-2-yl)-4-methylphenyl)-3,3,3-trifluoropropane-1,2-diol (Enriched in One Enantiomer)

2-(3-(5-Amino-6-(azetidin-3-yl)pyrazin-2-yl)-4-methylphenyl)-3,3,3-trifluoropropane-1,2-diol hydrochloride salt (0.010 g, 0.025 mmol) in DCM (0.25 mL) was treated with DIPEA (0.026 mL, 0.15 mmol) and 1-methyl-1H-pyrazole-3-sulfonyl chloride (4.5 mg, 0.025 mmol, Maybridge). After 1 hour, the reaction was quenched by the addition of a small quantity of water and ammonium hydroxide solution. The mixture was concentrated via rotary evaporation to remove DCM and the mixture was diluted with MeOH and purified by preparative HPLC-MS (pH=10) to afford the title compound (enriched in one enantiomer, believed to be (S)—, see stereochemical rationale supra) (5 mg, 40%). LCMS calculated for $C_{21}H_{24}F_3N_6O_4S$ (M+H)$^+$: m/z=513.2, found: 513.1. $^1$H NMR (400 MHz, MeOD) δ 7.93-7.90 (s, 1H), 7.63-7.59 (d, J=2.0 Hz, 1H), 7.59-7.55 (d, J=8.0 Hz, 1H), 7.40-7.35 (m, 2H), 6.84-6.50 (d, J=2.3 Hz, 1H), 4.28-4.24 (m, 4H), 4.14-4.09 (d, J=11.8 Hz, 1H), 4.09-4.05 (d, J=11.8 Hz, 1H), 4.03-3.94 (p, J=8.1 Hz, 1H), 3.56-3.46 (s, 3H), 2.36-2.14 (s, 3H). $^{19}$F NMR (376 MHz, MeOD) δ −78.08-−78.59 (s).

Example 24. (3-(3-Amino-6-(2-methyl-5-(1,1,1-trifluoro-2,3-dihydroxypropan-2-yl)phenyl)pyrazin-2-yl)cyclobutyl)(3-hydroxyazetidin-1-yl)methanone trifluoroacetate salt (Single Enantiomer Prepared)

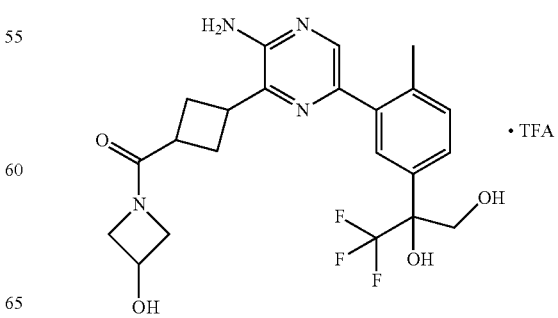

147

Step 1. Ethyl 3-(3-amino-6-chloropyrazin-2-yl)cyclobutane-1-carboxylate (Mixture of Cis and Trans Isomers Prepared)

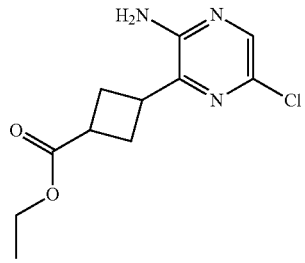 [SMILES: CCOC(=O)C1CC(c2nc(Cl)cnc2N)C1]

A mixture of 3-bromo-5-chloropyrazin-2-amine (545 mg, 2.61 mmol, D-L Chiral Chemicals) and [1,3-bis(2,6-diisopropylphenyl)imidazol-2-ylidene](3-chloropyridyl)palladium(II) dichloride (178 mg, 0.261 mmol) in DMA (18.2 mL) was degassed.

Separately, a vial was charged with zinc (freshly activated and dried according to the procedure found in WO2011/143365, 1.49 g, 22.8 mmol) and the vial was flushed with $N_2$ and heated with a heat gun, then cooled. Dry THF (20 mL) was added. 1,2-Dibromoethane (0.20 mL, 2.4 mmol) was added and the mixture was heated with a heat gun to reflux, and then cooled to room temperature. This heating and cooling cycle was performed three times. TMSCl (0.60 mL, 4.7 mmol) was added. The mixture was heated to 50° C. in an oil bath, and ethyl 3-iodocyclobutane-1-carboxylate (2.0 g, 7.9 mmol, prepared as described in WO2014/200882, the disclosure of which is incorporated herein by reference in its entirety) in THF (10 mL) was added dropwise. The mixture was maintained at 50° C. for about 1 hour, then was cooled to room temperature and degassed by bubbling a stream of nitrogen through the mixture for 5 min. This mixture was then added to the solution of 3-bromo-5-chloropyrazin-2-amine above, excluding zinc solids. The reaction was heated to 50° C. for 1.75 hours, then to 80° C. for 45 minutes. Upon cooling to room temperature, the reaction mixture was partitioned between EtOAc and water. The aqueous layer was extracted again with EtOAc. The combined organic extracts were washed with brine, dried over $Na_2SO_4$, filtered, and concentrated. The product was purified via flash chromatography, eluting with a gradient from 0-75% EtOAc in hexanes to afford product (0.35 g, 52%). The cis- and trans-isomers are partially separable, however the product was carried as a mixture to the following step. LCMS calculated for $C_{11}H_{15}ClN_3O_2(M+H)^+$: m/z=256.1, found: 256.0.

First diastereomer to elute: $^1$H NMR (400 MHz, CDCl$_3$) δ 7.97-7.73 (s, 1H), 4.64-4.32 (s, 2H), 4.29-4.14 (q, J=7.1 Hz, 2H), 3.72-3.52 (m, 1H), 3.27-3.10 (m, 1H), 2.80-2.51 (m, 4H), 1.35-1.25 (t, J=7.1 Hz, 3H).

Second diastereomer to elute: $^1$H NMR (400 MHz, CDCl$_3$) δ 7.98-7.78 (s, 1H), 4.59-4.45 (s, 2H), 4.21-4.12 (q, J=7.1 Hz, 2H), 3.47-3.35 (p, J=8.8 Hz, 1H), 3.26-3.15 (m, 1H), 2.77-2.57 (m, 4H), 1.31-1.25 (t, J=7.2 Hz, 3H).

148

Step 2. 3-(3-Amino-6-(2-methyl-5-(1,1,1-trifluoro-2,3-dihydroxypropan-2-yl)phenyl)pyrazin-2-yl)cyclobutane-1-carboxylic acid (Two Diastereomers Isolated; (Cis & Trans); Each Prepared as a Single Enantiomer)

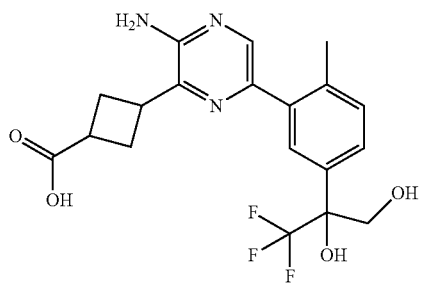 [SMILES: Cc1ccc(C(O)(CO)C(F)(F)F)cc1-c1cnc(N)c(C2CC(C(=O)O)C2)n1]

The product of Example 1a, Step 3 (2-(3-chloro-4-methylphenyl)-3,3,3-trifluoropropane-1,2-diol) was subjected to chiral HPLC (Phenomenex Lux Amylose-1, 21.2×250 mm, 5 µM, loading: 55 mg in 1.0 mL EtOH, eluting with 5% EtOH in hexanes at 20 mL/min for 25 minutes). Peak 1 retention time: 19.3 min, Peak 2 retention time: 22.3 min. Peak 1 was believed to be the (S)-enantiomer (see stereochemical rationale supra), while Peak 2 was believed to be the (R)-enantiomer. Peak 1 was collected and converted to 3,3,3-trifluoro-2-(4-methyl-3-(4,4,5,5-tetramethyl-1,3,2-dioxaborolan-2-yl)phenyl)propane-1,2-diol according to the procedure of Example 1a, Step 4. A degassed mixture of 3,3,3-trifluoro-2-(4-methyl-3-(4,4,5,5-tetramethyl-1,3,2-dioxaborolan-2-yl)phenyl)propane-1,2-diol so produced (0.322 g, 0.931 mmol), ethyl 3-(3-amino-6-chloropyrazin-2-yl)cyclobutane-1-carboxylate (0.119 g, 0.465 mmol, a mixture of cis and trans isomers from Step 1) and PdCl$_2$(dppf)-CH$_2$Cl$_2$ adduct (0.019 g, 0.023 mmol) in dioxane (2.3 mL) and Na$_2$CO$_3$ (1.0 M in water, 1.4 mL, 1.4 mmol) was heated in a sealed vial held in an oil bath at 120° C. for 3 hours. Additional 3,3,3-trifluoro-2-(4-methyl-3-(4,4,5,5-tetramethyl-1,3,2-dioxaborolan-2-yl)phenyl)propane-1,2-diol and PdCl$_2$(dppf)-CH$_2$Cl$_2$ adduct (same amounts) were added as a degassed solution in dioxane (2.3 mL) and heating was continued for 3 hours. Upon cooling to room temperature, the reaction mixture was diluted with water and MeCN, filtered and purified by preparative HPLC-MS (pH=2, Waters Xbridge C18, 30×100 mm, 5 µM particle size, 60 mL/min, Mobile phase A: Aq (0.1% TFA), Mobile phase B: MeCN, 16.6-42.2% B in 12 min). Two diastereomers of carboxylic acid product were isolated separately. Peak 2 was subsequently used in Step 3.

Peak 1 (first to elute, retention time: 5.9 min). LCMS calculated for $C_{19}H_{21}F_3N_3O_4$ (M+H)$^+$: m/z=412.1, found: 412.3.

Peak 2 (second to elute, retention time: 6.7 min). LCMS calculated for $C_{19}H_{21}F_3N_3O_4$ (M+H)$^+$: m/z=412.1, found: 412.3. Peak 2 was used in Step 3.

Step 3. (3-(3-Amino-6-(2-methyl-5-(1,1,1-trifluoro-2,3-dihydroxypropan-2-yl)phenyl)pyrazin-2-yl)cyclobutyl)(3-hydroxyazetidin-1-yl)methanone (Single Enantiomer Prepared)

To 3-(3-amino-6-(2-methyl-5-(1,1,1-trifluoro-2,3-dihydroxypropan-2-yl)phenyl)pyrazin-2-yl)cyclobutane-1-carboxylic acid (0.011 g, 0.027 mmol, from Peak 2 of Step 2), azetidin-3-ol hydrochloride (3.6 mg, 0.053 mmol, Oakwood) and DIPEA (0.023 mL, 0.13 mmol) in DMF (1.0 mL) was added HATU (0.015 g, 0.040 mmol). The reaction was stirred for 30 minutes, diluted with MeOH and purified by preparative HPLC-MS (pH=2). The product is believed to be the (S)-configuration at the tertiary alcohol, supra). LCMS calculated for $C_{22}H_{26}F_3N_4O_4(M+H)^+$: m/z=467.2, found: 467.1. $^1$H NMR (400 MHz, MeOD) δ 7.90-7.82 (s, 1H), 7.75-7.66 (s, 1H), 7.62-7.52 (d, J=8.2 Hz, 1H), 7.41-7.28 (d, J=8.1 Hz, 1H), 4.63-4.53 (m, 1H), 4.39-4.31 (m, 1H), 4.29-4.19 (m, 1H), 4.14-4.06 (d, J=11.8 Hz, 1H), 4.06-3.98 (d, J=11.8 Hz, 1H), 3.95-3.84 (m, 1H), 3.84-3.71 (m, 2H), 2.75-2.62 (m, 4H), 2.50-2.46 (s, 3H). $^{19}$F NMR (376 MHz, MeOD) δ −77.26--−77.60 (s), −78.10--−78.35 (s).

Example 25. 2-(3-(5-Amino-6-(trifluoromethyl)pyrazin-2-yl)-4-methylphenyl)-3,3,3-trifluoropropane-1,2-diol (Single Enantiomer Prepared)

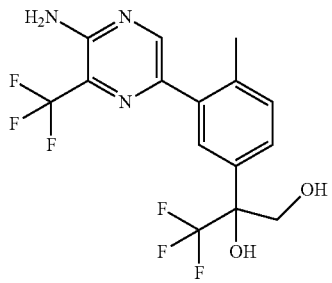 [SMILES: Cc1ccc(C(O)(CO)C(F)(F)F)cc1-c1cnc(N)c(C(F)(F)F)n1]

Step 1. 5-Bromo-3-(trifluoromethyl)pyrazin-2-amine

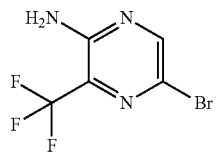

To 3-(trifluoromethyl)pyrazin-2-amine (0.020 g, 0.12 mmol, Oakwood) in $CH_2Cl_2$ (0.5 mL) was added N-bromosuccinimide (0.022 g, 0.12 mmol) and the reaction was stirred overnight. The reaction mixture was partitioned between DCM and water, and the aqueous portion was extracted with three portions of DCM. The combined organic extracts were dried over $Na_2SO_4$, filtered, and concentrated. The product was purified by flash chromatography, eluting with a gradient from 0-25% EtOAc in hexanes to afford a white crystalline solid (0.013 g, 44%). $^1$H NMR (400 MHz, CDCl$_3$) δ 8.44-8.23 (s, 1H), 5.22-4.98 (s, 2H). $^{19}$F NMR (376 MHz, CDCl$_3$) δ −65.04--−69.69 (s).

Step 2. 2-(3-(5-Amino-6-(trifluoromethyl)pyrazin-2-yl)-4-methylphenyl)-3,3,3-trifluoropropane-1,2-diol (Single Enantiomer Prepared)

A degassed mixture of 5-bromo-3-(trifluoromethyl)pyrazin-2-amine (0.030 g, 0.12 mmol, prepared as in Step 1), 3,3,3-trifluoro-2-(4-methyl-3-(4,4,5,5-tetramethyl-1,3,2-dioxaborolan-2-yl)phenyl)propane-1,2-diol (0.043 g, 0.124 mmol, single enantiomer obtained as described in Example 24, Step 2) and PdCl$_2$(dppf)-CH$_2$Cl$_2$ adduct (5.0 mg, 6.2 μmol) in dioxane (0.6 mL) and Na$_2$CO$_3$, (1.0 M in water, 0.37 mL, 0.37 mmol) was heated in a sealed vial in an oil bath held at 120° C. for 3 hours. Upon cooling to room temperature, the reaction mixture was diluted with EtOAc and water sufficient to dissolve solids. The layers were separated and the aqueous layer was extracted with two further portions of EtOAc. The combined organic extracts were dried over Na$_2$SO$_4$, filtered and concentrated. The product was purified by preparative HPLC-MS (pH=10). The product is believed to be the (S)-configuration at the tertiary alcohol, (see stereochemical rationale supra)). LCMS for $C_{15}H_{14}F_6N_3O_2(M+H)^+$: m/z=382.1, found: 382.1. $^1$H NMR (400 MHz, CDCl$_3$) δ 8.43-8.37 (s, 1H), 7.68-7.57 (s, 1H), 7.53-7.44 (d, J=7.9 Hz, 1H), 7.42-7.32 (d, J=8.1 Hz, 1H), 5.19-5.08 (s, 2H), 4.38-4.28 (d, J=11.8 Hz, 1H), 3.99-3.91 (d, J=11.9 Hz, 1H), 3.85-3.63 (br s, 1H), 2.49-2.30 (s, 3H). $^{19}$F NMR (376 MHz, CDCl$_3$) δ −65.20--−70.41 (s), −74.01--−80.34 (s).

Examples 26-37

Compounds in Table 4 were prepared by the method of Example 17, using the appropriate amines instead of tetrahydro-2H-pyran-4-amine in Step 3. Where the compound was isolated as the TFA salt, preparative HPLC-MS (pH=2) conditions were used for purification. Where the compound was isolated as the free base, preparative HPLC-MS (pH=10) conditions were used for purification.

TABLE 4

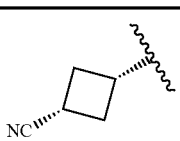

| Example No. | Compound Name / ¹H NMR | R | LCMS |
|---|---|---|---|
| 26 | 3-Amino-N-((1s,3R)-3-cyanocyclobutyl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | 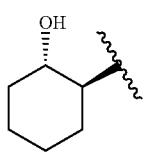 | Calculated for $C_{20}H_{18}D_3F_3N_5O_3$ $(M + H)^+$: m/z = 439.2, found: 439.4 |

¹H NMR (500 MHz, DMSO-d₆) δ 8.99 (d, J = 8.8 Hz, 1H), 8.35 (s, 1H), 7.89-7.25 (br s, 2H), 7.60 (d, J = 2.0 Hz, 1H), 7.54 (dd, J = 8.0, 2.0 Hz, 1H), 7.35 (d, J = 8.0 Hz, 1H), 4.49 (h, J = 8.6 Hz, 1H), 3.94 (s, 2H), 3.05 (tt, J = 10.0, 8.1 Hz, 1H), 2.62-2.53 (m, 4H).

| 27 | 3-Amino-N-((1S,2S)-2-hydroxycyclohexyl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | 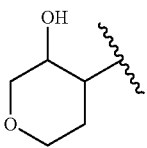 [SMILES: *C1CCOCC1O] | Calculated for $C_{21}H_{23}D_3F_3N_4O_4$ $(M + H)^+$: m/z = 458.2, found: 458.1 |

¹H NMR (400 MHz, CD₃OD) δ 8.32 (d, J = 0.9 Hz, 1H), 7.69 (d, J = 1.1 Hz, 1H), 7.57 (d, J = 8.1 Hz, 1H), 7.36 (dd, J = 8.1, 1.0 Hz, 1H), 4.09 (d, J = 11.8 Hz, 1H), 4.02 (d, J = 11.8 Hz, 1H), 3.74 (td, J = 9.8, 4.1 Hz, 1H), 3.49 (td, J = 9.8, 4.2 Hz, 1H), 2.15-1.98 (m, 2H), 1.86-1.61 (m, 2H), 1.53-1.23 (m, 4H).

| 28 | 3-Amino-N-((trans)-3-hydroxytetrahydro-2H-pyran-4-yl)-6-(2-(methyl-d₃)-5-((S)-1,1,1-trifluoro-2,3-dihydroxypropan-2-yl)phenyl)pyrazine-2-carboxamide (single enantiomer) | 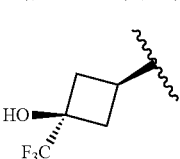 | Calculated for $C_{20}H_{21}D_3F_3N_4O_5$ $(M + H)^+$: m/z = 460.2, found: 460.1 |

¹H NMR (500 MHz, DMSO-d₆) δ 8.38 (s, 1H), 8.31 (d, J = 8.2 Hz, 1H), 7.73-7.52 (br s, 2H), 7.63 (d, J = 2.0 Hz, 1H), 7.53 (dd, J = 8.1, 2.0 Hz, 1H), 7.34 (d, J = 8.0 Hz, 1H), 6.43 (s, 1H), 5.17 (t, J = 5.8 Hz, 1H), 4.99 (d, J = 5.7 Hz, 1H), 3.98-3.88 (m, 2H), 3.85-3.74 (m, 3H), 3.56-3.48 (m, 1H), 3.37-3.33 (m, 1H), 3.04 (dd, J = 11.1, 9.8 Hz, 1H), 1.92-1.83 (m, 1H), 1.66-1.54 (m, 1H).

| 29 | 3-Amino-N-((1s,3R)-3-hydroxy-3-(trifluoromethyl)cyclobutyl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | 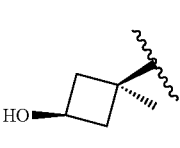 [SMILES: *[C@]1(C)C[C@H](O)C1] | Calculated for $C_{20}H_{18}D_3F_6N_4O_4$ $(M + H)^+$: m/z = 498.2, found: 498.1 |

¹H NMR (600 MHz, DMSO-d₆) δ 8.84 (d, J = 7.9 Hz, 1H), 8.36 (s, 1H), 7.74-7.49 (br s, 2H), 7.61 (d, J = 2.0 Hz, 1H), 7.53 (dd, J = 8.0, 2.0 Hz, 1H), 7.35 (d, J = 8.1 Hz, 1H), 6.56 (s, 1H), 6.46 (s, 1H), 5.19 (t, J = 5.3 Hz, 1H), 4.22-4.12 (m, 1H), 3.98-3.89 (m, 2H), 2.82-2.70 (m, 2H), 2.45-2.33 (m, 2H).

| 30 | 3-Amino-N-((1s,3R)-3-hydroxy-1-methylcyclobutyl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | | Calculated for $C_{20}H_{21}D_3F_3N_4O_4$ $(M + H)^+$: m/z = 442.2, found: 442.1 |

¹H NMR (400 MHz, CD₃OD) δ 8.32 (s, 1H), 7.68 (d, J = 2.0 Hz, 1H), 7.57 (dd, J = 7.9, 1.7 Hz, 1H), 7.36 (d, J = 8.1 Hz, 1H), 4.17 (p, J = 7.2 Hz, 1H), 4.09 (d, J = 11.8 Hz, 1H), 4.02 (d, J = 11.7 Hz, 1H), 2.67-2.55 (m, 2H), 2.33-2.18 (m, 2H), 1.49 (s, 3H).

TABLE 4-continued

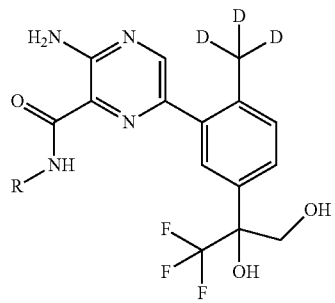

| Example No. | Compound Name / ¹H NMR | R | LCMS |
|---|---|---|---|
| 31 | (S)-3-Amino-N-(4-(hydroxymethyl)bicyclo[2.1.1]hexan-1-yl)-6-(2-(methyl-d₃)-5-(1,1,1-trifluoro-2,3-dihydroxypropan-2-yl)phenyl)pyrazine-2-carboxamide (single enantiomer) | bicyclo[2.1.1]hexane with CH₂OH | Calculated for $C_{22}H_{23}D_3F_3N_4O_4$ $(M + H)^+$: m/z = 470.2, found: 470.1 |

¹H NMR (500 MHz, DMSO-d₆) δ 8.62 (s, 1H), 8.37 (s, 1H), 7.69-7.54 (br s, 2H), 7.63 (d, J = 2.0 Hz, 1H), 7.52 (dd, J = 8.1, 1.9 Hz, 1H), 7.33 (d, J = 8.0 Hz, 1H), 6.43 (s, 1H), 5.16 (t, J = 5.8 Hz, 1H), 4.46 (t, J = 5.5 Hz, 1H), 3.97-3.84 (m, 2H), 3.49 (d, J = 5.4 Hz, 2H), 1.94-1.85 (m, 2H), 1.81-1.74 (m, 2H), 1.55-1.49 (m, 2H), 1.49-1.41 (m, 2H).

| 32 | (S)-3-Amino-N-(3-(hydroxymethyl)bicyclo[1.1.1]pentan-1-yl)-6-(2-(methyl-d₃)-5-(1,1,1-trifluoro-2,3-dihydroxypropan-2-yl)phenyl)pyrazine-2-carboxamide (single enantiomer) | bicyclo[1.1.1]pentane with CH₂OH | Calculated for $C_{21}H_{21}D_3F_3N_4O_4$ $(M + H)^+$: m/z = 456.2, found: 456.1 |

¹H NMR (500 MHz, DMSO-d₆) δ 8.86 (s, 1H), 8.34 (s, 1H), 7.59 (d, J = 2.0 Hz, 1H), 7.52 (dd, J = 8.1, 2.0 Hz, 1H), 7.33 (d, J = 8.0 Hz, 1H), 6.43 (s, 1H), 5.17 (t, J = 5.8 Hz, 1H), 4.51 (t, J = 5.6 Hz, 1H), 3.93 (d, J = 5.8 Hz, 2H), 3.48 (d, J = 5.7 Hz, 2H), 1.95 (s, 6H).

| 33 | 3-Amino-N-((S)-1-hydroxypropan-2-yl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | CH(CH₃)CH₂OH (S) | Calculated for $C_{18}H_{19}D_3F_3N_4O_4$ $(M + H)^+$: m/z = 418.2, found: 418.3 |
| 34 | (S)-3-Amino-N-(2-cyano-2-methylpropyl)-6-(2-(methyl-d₃)-5-(1,1,1-trifluoro-2,3-dihydroxypropan-2-yl)phenyl)pyrazine-2-carboxamide (single enantiomer) | C(CH₃)₂CN-CH₂ | Calculated for $C_{20}H_{20}D_3F_3N_5O_3$ $(M + H)^+$: m/z = 441.2, found: 441.1 |

¹H NMR (500 MHz, DMSO-d₆) δ 8.76 (t, J = 6.8 Hz, 1H), 8.43 (s, 1H), 7.68-7.54 (br s, 2H), 7.64 (d, J = 2.0 Hz, 1H), 7.53 (dd, J = 8.1, 1.9 Hz, 1H), 7.35 (d, J = 8.0 Hz, 1H), 6.43 (br s, 1H), 5.17 (br s, 1H), 3.94 (s, 2H), 3.50 (d, J = 6.8 Hz, 2H), 1.33 (s, 6H).

| 35 | (S)-3-Amino-N-(4-hydroxybicyclo[2.2.1]heptan-1-yl)-6-(2-(methyl-d₃)-5-(1,1,1-trifluoro-2,3-dihydroxypropan-2-yl)phenyl)pyrazine-2-carboxamide, trifluoroacetate salt (single enantiomer) | bicyclo[2.2.1]heptane with OH | Calculated for $C_{22}H_{23}D_3F_3N_4O_4$ $(M + H)^+$: m/z = 470.2, found: 470.1 |
| 36 | 3-Amino-N-((R)-1-hydroxypropan-2-yl)-6-(2-(methyl-d₃)-5-((S)-1,1,1-trifluoro-2,3-dihydroxypropan-2-yl)phenyl)pyrazine-2-carboxamide, trifluoroacetate salt (single enantiomer) | CH(CH₃)CH₂OH (R) | Calculated for $C_{18}H_{19}D_3F_3N_4O_4$ $(M + H)^+$: m/z = 418.2, found: 418.3 |

¹H NMR (500 MHz, DMSO-d₆) δ 8.39 (s, 1H), 8.21 (d, J = 8.4 Hz, 1H), 7.89-7.40 (br s, 2H), 7.62 (d, J = 2.0 Hz, 1H), 7.55-7.50 (m, 1H), 7.34 (d, J = 8.0 Hz, 1H), 4.04-3.96 (m, 1H), 3.96-3.85 (m, 2H), 3.51-3.36 (m, 2H), 1.15 (d, J = 6.6 Hz, 3H).

TABLE 4-continued

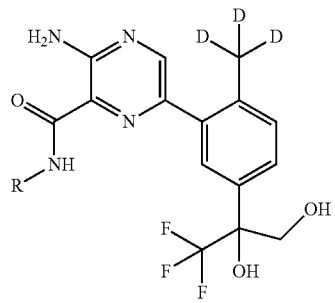

| Example No. | Compound Name | R <br> $^1$H NMR | LCMS |
|---|---|---|---|
| 37 | (S)-3-Amino-N-(4-hydroxybicyclo[2.1.1]hexan-1-yl)-6-(2-(methyl-d₃)-5-(1,1,1-trifluoro-2,3-dihydroxypropan-2-yl)phenyl)pyrazine-2-carboxamide, trifluoroacetate salt (single enantiomer) | 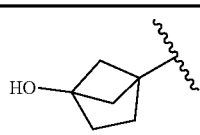 | Calculated for $C_{21}H_{21}D_3F_3N_4O_4$ $(M + H)^+$: m/z = 456.2, found: 456.1 |
| | $^1$H NMR (500 MHz, DMSO-d₆) δ 8.59 (s, 1H), 8.37 (s, 1H), 7.79-7.45 (br s, 2H), 7.62 (d, J = 2.0 Hz, 1H), 7.52 (dd, J = 7.8, 1.7 Hz, 1H), 7.33 (d, J = 8.0 Hz, 1H), 6.46 (s, 1H), 5.69 (s, 1H), 5.19 (t, J = 5.9 Hz, 1H), 4.03-3.83 (m, 2H), 1.88-1.83 (m, 2H), 1.83-1.80 (m, 2H), 1.80-1.75 (m, 2H), 1.63-1.56 (m, 2H). | | |

The amine required for synthesis of Example 37 was prepared as described in WO2017/223414, the disclosure of which is incorporated herein by reference in its entirety.

Compounds in Table 5 were prepared by the method of Example 18, using the appropriate amines instead of 4-aminobicyclo[2.2.1]heptan-1-ol in Step 9. Where the compound was isolated as the TFA salt, preparative HPLC-MS (pH=2) conditions were used for purification. Where the compound was isolated as the free base, preparative HPLC-MS (pH=10) conditions were used for purification.

TABLE 5

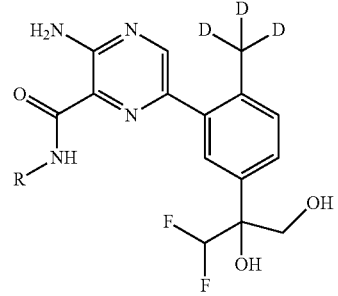

| Example No. | Compound Name | R <br> $^1$H NMR | LCMS |
|---|---|---|---|
| 38 | 3-Amino-6-(5-((S)-1,1-difluoro-2,3-dihydroxypropan-2-yl)-2-(methyl-d₃)phenyl)-N-((1S,2S)-2-hydroxycyclohexyl)pyrazine-2-carboxamide, trifluoroacetate salt (single enantiomer) | 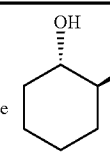 | Calculated for $C_{21}H_{24}D_3F_2N_4O_4$ $(M + H)^+$: m/z = 440.2, found: 440.2 |
| | $^1$H NMR (400 MHz, DMSO-d₆) δ 8.38 (s, 1H), 8.15 (d, J = 8.2 Hz, 1H), 7.57 (d, J = 1.9 Hz, 1H), 7.46 (dd, J = 8.0, 2.0 Hz, 1H), 7.30 (d, J = 8.0 Hz, 1H), 6.21 (t, J = 55.6 Hz, 1H), 3.78 (d, J = 10.7 Hz, 1H), 3.69 (d, J = 10.6 Hz, 1H), 3.62-3.48 (m, 2H), 1.99-1.80 (m, 2H), 1.69-1.54 (m, 2H), 1.35-1.10 (m, 4H). <br> $^{19}$F{$^1$H} NMR (376 MHz, DMSO-d₆) δ −74.05 (s), −129.75 (d, $J_{F-F}$ = 277.6 Hz), −134.32 (d, $J_{F-F}$ = 277.2 Hz). | | |
| 39 | 3-Amino-6-(5-((S)-1,1-difluoro-2,3-dihydroxypropan-2-yl)-2-(methyl-d₃)phenyl)-N-((1R,2R)-2-hydroxycyclohexyl)pyrazine-2-carboxamide, trifluoroacetate salt (single enantiomer) | 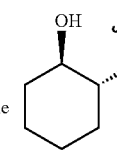 | Calculated for $C_{21}H_{24}D_3F_2N_4O_4$ $(M + H)^+$: m/z = 440.2, found: 440.3 |

TABLE 5-continued

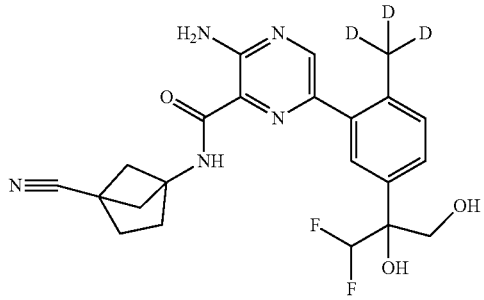 [SMILES: [2H]C([2H])([2H])c1ccc(C(O)(CO)C(F)F)cc1-c1cnc(N)c(C(=O)NC23CCC(C#N)(C2)C3)n1]

| Example No. | Compound Name ¹H NMR | R | LCMS |
|---|---|---|---|

¹H NMR (400 MHz, DMSO-d₆) δ 8.38 (s, 1H), 8.15 (d, J = 8.3 Hz, 1H), 7.57 (d, J = 2.0 Hz, 1H), 7.46 (dd, J = 8.0, 2.0 Hz, 1H), 7.30 (d, J = 8.0 Hz, 1H), 6.21 (t, J = 55.6 Hz, 1H), 3.78 (d, J = 11.6 Hz, 1H), 3.69 (d, J = 11.0 Hz, 1H), 3.61-3.50 (m, 1H), 3.47-3.30 (m, 1H), 2.01-1.80 (m, 2H), 1.71-1.52 (m, 2H), 1.37-1.12 (m, 4H). ¹⁹F{¹H} NMR (376 MHz, DMSO-d₆) δ −74.45 (s), −129.80 (d, $J_{F\text{-}F}$ = 277.4 Hz), −134.32 (d, $J_{F\text{-}F}$ = 277.4 Hz).

Example 40. (S)-3-Amino-N-(4-cyanobicyclo[2.1.1]hexan-1-yl)-6-(5-(1,1-difluoro-2,3-dihydroxypropan-2-yl)-2-(methyl-d₃)phenyl)pyrazine-2-carboxamide (Single Enantiomer Prepared)

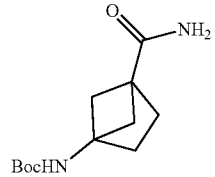 [SMILES: CC(C)(C)OC(=O)NC12CCC(C(N)=O)(C1)C2]

Step 1. tert-Butyl (4-carbamoylbicyclo[2.1.1]hexan-1-yl)carbamate

A solution of 4-((tert-butoxycarbonyl)amino)bicyclo[2.1.1]hexane-1-carboxylic acid (250 mg, 1.0 mmol) (Spirochem catalog #SPC-a643) and triethylamine (0.17 mL, 1.2 mmol) in THF (5.0 mL) at −15° C. was treated with ethyl chloroformate (0.11 mL, 1.1 mmol) and the reaction was stirred for 1 hour. To the mixture was added ammonium hydroxide (15 M, 7.0 mL, 52 mmol) and the reaction mixture was stirred at room temperature overnight. The solvent was removed in vacuo. The residue was partitioned between water and EtOAc. The aqueous layer was extracted with two further portions of EtOAc. The combined organic extracts were dried over Na₂SO₄, filtered and concentrated to afford the title compound as a white solid (220 mg, 88%). LCMS for $C_{12}H_{21}N_2O_3$ (M+H)⁺: calculated m/z=241.2, found 241.3. ¹H NMR (400 MHz, DMSO-d₆) δ 7.30 (br s, 1H), 7.07 (s, 1H), 6.83 (s, 1H), 1.93 (br, 2H), 1.70 (s, 4H), 1.49 (s, 2H), 1.38 (s, 9H).

Step 2. tert-Butyl (4-cyanobicyclo[2.1.1]hexan-1-yl)carbamate

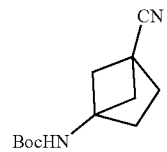 [SMILES: CC(C)(C)OC(=O)NC12CCC(C#N)(C1)C2]

Trichloroacetyl chloride (0.54 mL, 4.8 mmol) was added to a solution of tert-butyl (4-carbamoylbicyclo[2.1.1]hexan-1-yl)carbamate (290 mg, 1.2 mmol, prepared according to the method of Step 1) and triethylamine (1.4 mL, 9.7 mmol) in DCM (20 mL) at 0° C. After 40 minutes, the reaction was quenched by the addition of saturated NaHCO₃ solution, and the aqueous mixture was extracted with DCM. The organic extract was dried over MgSO₄, filtered, and concentrated. The product was purified by flash column chromatography (eluting with a gradient of 0-20% EtOAc/hexanes) to afford the title compound as a white solid (230 mg, 86%). LCMS for $C_{12}H_{19}N_2O_2$ (M+H)⁺: calculated m/z=223.1, found 223.1. ¹H NMR (400 MHz, CD₃OD) δ 2.35 (br, 2H), 2.06-1.98 (m, 2H), 1.90-1.82 (m, 2H), 1.82-1.78 (m, 2H), 1.45 (s, 9H).

Step 3. 4-Aminobicyclo[2.1.1]hexane-1-carbonitrile, hydrochloric acid salt

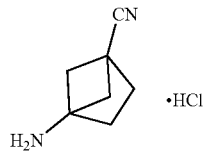

tert-Butyl (4-cyanobicyclo[2.1.1]hexan-1-yl)carbamate (0.99 g, 4.5 mmol, prepared by the method of Step 2) was dissolved in DCM (50 mL) and HCl in dioxane (4.0 M, 11 mL, 44 mmol) was added. The mixture was stirred overnight and volatiles were removed in vacuo to afford the title compound as a white solid (0.7 g, 100%). LCMS for $C_7H_{11}N_2$ $(M+H)^+$: calculated m/z=123.1, found 123.2. $^1H$ NMR (500 MHz, DMSO-$d_6$) δ 9.03 (s, 3H), 2.26-2.20 (m, 2H), 2.11-2.06 (m, 2H), 1.89-1.82 (m, 4H).

Step 4. 3-Amino-N-(4-cyanobicyclo[2.1.1]hexan-1-yl)-6-(5-(1,1-difluoro-2,3-dihydroxypropan-2-yl)-2-(methyl-$d_3$)phenyl)pyrazine-2-carboxamide (Single Enantiomer Prepared)

To a solution of 3-amino-6-(5-(1,1-difluoro-2,3-dihydroxypropan-2-yl)-2-(methyl-$d_3$)phenyl)pyrazine-2-carboxylic acid (believed to be the (S)-enantiomer, 50 mg, 0.15 mmol, from Example 18, Step 8) in DMF (1.5 mL) was added HATU (72 mg, 0.19 mmol) and N,N-diisopropylethylamine (0.10 mL, 0.58 mmol). To this mixture was added 4-aminobicyclo[2.1.1]hexane-1-carbonitrile, HCl salt (28 mg, 0.18 mmol), and the reaction mixture was stirred for 1 hour. The reaction mixture was diluted with EtOAc and the organic mixture was washed with water (2×). The combined aqueous layers were extracted with EtOAc (2×) and combined with the initial organic extract. The combined organic extracts were washed with brine, dried over sodium sulfate, filtered and concentrated. The product was purified via preparative HPLC-MS (pH 10) to afford the title compound (22 mg, 34%). The product is believed to be the (S)-enantiomer (see stereochemical rationale vide supra). LCMS for $C_{22}H_{21}D_3F_2N_5O_3$ $(M+H)^+$: m/z=447.2, found: 447.1. $^1H$ NMR (500 MHz, DMSO-$d_6$) δ 8.93 (s, 1H), 8.36 (s, 1H), 7.66-7.50 (br s, 2H), 7.55 (d, J=1.8 Hz, 1H), 7.46 (dd, J=8.0, 1.8 Hz, 1H), 7.29 (d, J=8.0 Hz, 1H), 6.20 (t, J=55.6 Hz, 1H), 5.81 (s, 1H), 5.09 (t, J=6.0 Hz, 1H), 3.78 (dd, J=11.8, 5.9 Hz, 1H), 3.69 (dd, J=11.5, 5.5 Hz, 1H), 2.38-2.30 (m, 2H), 2.08-1.99 (m, 2H), 1.99-1.96 (m, 2H), 1.96-1.90 (m, 2H).

Example 41. (S)-3-Amino-6-(5-(1,1-difluoro-2,3-dihydroxypropan-2-yl)-2-(methyl-$d_3$)phenyl)-N-(tetrahydro-2H-pyran-4-yl)pyrazine-2-carboxamide (Single Enantiomer Prepared)

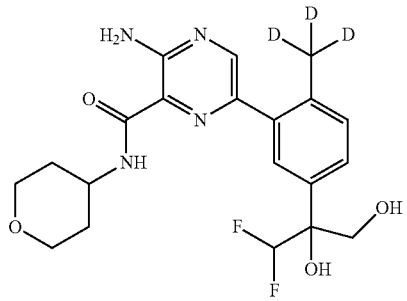 [SMILES: [2H]C([2H])([2H])c1ccc(C(O)(CO)C(F)F)cc1-c1cnc(N)c(C(=O)NC2CCOCC2)n1]

Carbon monoxide was bubbled through a mixture of (S)-2-(3-(5-amino-6-chloropyrazin-2-yl)-4-(methyl-$d_3$)phenyl)-3,3-difluoropropane-1,2-diol (160 mg, 0.48 mmol, Peak 1 from Example 18, Step 7 believed to be the (S)-enantiomer), tetrahydro-2H-pyran-4-amine (0.40 mL, 3.9 mmol, Combi-Blocks #AM-1004), triethylamine (0.54 mL, 3.9 mmol), and dichloro[1,1'-bis(diphenylphosphino)ferrocene]palladium(II) dichloromethane adduct (79 mg, 0.096 mmol) in dioxane (9.6 mL) for 5 minutes. The reaction was heated at 90° C. under 1 atm of CO overnight.

The volatiles were removed in vacuo, and the residue was diluted with EtOAc and saturated $NH_4Cl$ solution. After stirring for 15 minutes, the biphasic mixture was filtered through Celite®, and the layers of the filtrate were separated. The aqueous layer was extracted with EtOAc (2×). The combined organic extracts were dried over $Na_2SO_4$, filtered and concentrated. Flash chromatography, eluting with a gradient from 0-100% in EtOAc in hexanes, afforded the desired product. The product was further purified via preparative HPLC-MS (pH=10) to afford the title compound (0.13 g, 63%). The product is believed to be the (S)-enantiomer (see stereochemical rationale supra). LCMS for $C_{20}H_{22}D_3F_2N_4O_4$ $(M+H)^+$: m/z=426.2, found: 426.2. $^1H$ NMR (500 MHz, DMSO-$d_6$) δ 8.38 (s, 1H), 8.32 (d, J=8.3 Hz, 1H), 7.71-7.52 (br s, 1H), 7.58 (d, J=2.0 Hz, 1H), 7.46 (dd, J=8.0, 2.0 Hz, 1H), 7.30 (d, J=8.0 Hz, 1H), 6.21 (t, J=55.5 Hz, 1H), 5.82 (s, 1H), 5.09 (s, 1H), 4.06-3.95 (m, 1H), 3.85 (dt, J=11.4, 3.5 Hz, 2H), 3.78 (d, J=11.2 Hz, 1H), 3.69 (d, J=11.1 Hz, 1H), 3.40 (td, J=11.6, 2.3 Hz, 2H), 1.77-1.71 (m, 2H), 1.64 (qd, J=12.5, 11.9, 4.4 Hz, 2H).

Example 42. (S)-3-Amino-6-(5-(1,1-difluoro-2,3-dihydroxypropan-2-yl)-2-methylphenyl)-N-(tetrahydro-2H-pyran-4-yl)pyrazine-2-carboxamide (Single Enantiomer Prepared)

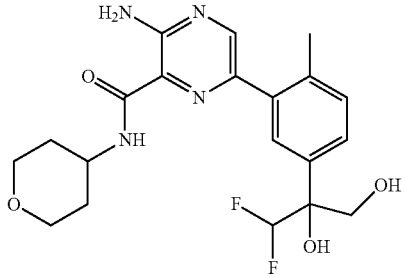 [SMILES: Cc1ccc(C(O)(CO)C(F)F)cc1-c1cnc(N)c(C(=O)NC2CCOCC2)n1]

Step 1. 1-(3-Chloro-4-methylphenyl)-2,2-difluoroethan-1-one

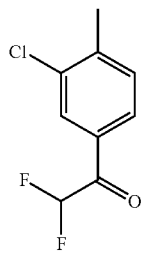

1,2-Dibromoethane (2 drops) was added to a vigorously-stirred mixture of Mg powder (1.2 g, 0.050 mol) in THF (40.0 mL) in a flask that was immersed in a room temperature water bath. After 10 minutes, 4-bromo-2-chloro-1-methylbenzene (8.9 g, 43 mmol, Aldrich 528889) in THF (30 mL) was added dropwise. After complete addition, two more drops of 1,2-dibromoethane were added. After stirring for 2 h, the reaction mixture was cooled to 0° C., stirred for 5 min, and a solution of 2,2-difluoro-N-methoxy-N-methylacetamide (5.0 g, 36 mmol, Oakwood 034757) in THF (20 mL) was then added dropwise. The reaction mixture was stirred for 10 min at 0° C. The ice bath was removed, and the mixture was allowed to warm to room temperature. The reaction was carefully quenched by the addition of 2.0 N HCl (170 mL), and the reaction mixture was stirred for 15 min. The layers of the mixture were separated. The aqueous layer was extracted with MTBE (3×120 mL). The combined organic extracts were washed successively with 1.0 N HCl, water, and brine. The organic layer was dried over $Na_2SO_4$, filtered and concentrated. Purification via flash chromatography, eluting with a gradient from 0-5% EtOAc in hexanes, afforded the title compound (7.0 g, 95%). $^1H$ NMR (400 MHz, $CDCl_3$) δ 8.09-8.04 (m, 1H), 7.93-7.84 (m, 1H), 7.42 (d, J=7.9 Hz, 1H), 6.26 (t, J=53.5 Hz, 1H), 2.50 (s, 3H). $^{19}F\{^1H\}$ NMR (376 MHz, $CDCl_3$) δ −121.72 (s).

Step 2. 2-Chloro-4-(3,3-difluoroprop-1-en-2-yl)-1-methylbenzene

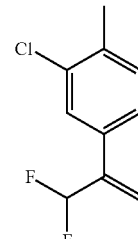

To a solution of tris(triphenylphosphine)rhodium(I) chloride (2.4 g, 2.6 mmol) and triphenylphosphine (14 g, 55 mmol) in THF (140 mL) under $N_2$, was added dry 2-propanol (4.2 mL, 55 mmol), followed by a solution of 1-(3-chloro-4-methylphenyl)-2,2-difluoroethan-1-one (7.0 g, 34 mmol) in THF (42 mL). Trimethylsilyldiazomethane (2.0 M in ether, 34 mL, 68 mmol) was added to the mixture, and the reaction was stirred at ambient temperature for 1.5 h. The reaction mixture was quenched by the dropwise addition of acetic acid (3.9 mL, 68 mmol), and the mixture was stirred for 30 min. Volatiles were removed in vacuo. Purification via flash chromatography, eluting with 100% hexanes, afforded the title compound (3.8 g, 55%). $^1H$ NMR (400 MHz, $CDCl_3$) δ 7.49 (d, J=1.8 Hz, 1H), 7.30 (dd, J=7.7, 1.5 Hz, 1H), 7.25 (d, J=8.0 Hz, 1H), 6.38 (t, J=55.2 Hz, 1H), 5.74 (t, J=1.9 Hz, 1H), 5.68 (t, J=2.3 Hz, 1H), 2.41 (s, 3H). $^{19}F\{^1H\}$ NMR (376 MHz, $CDCl_3$) δ −113.20 (s).

Step 3. 2-(3-Chloro-4-methylphenyl)-3,3-difluoropropane-1,2-diol (Enriched in One Enantiomer)

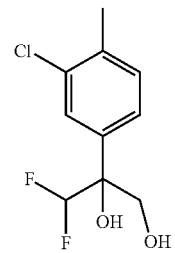

To a suspension of AD-mix-alpha (26.3 g, 56.3 mmol) in water (50.0 mL) at 0° C. was added a solution of 2-chloro-4-(3,3-difluoroprop-1-en-2-yl)-1-methylbenzene (3.80 g, 18.8 mmol) in t-BuOH (50.0 mL). The reaction was stirred at 3-6° C. for 40 h. The reaction was quenched by the addition of sodium sulfite (8 g). The reaction was stirred for 10 min, then was concentrated via rotary evaporation to remove t-BuOH. The aqueous mixture was diluted with water and extracted with EtOAc (3×). The combined organic extracts were dried over $Na_2SO_4$, filtered and concentrated. The product was purified via flash chromatography, eluting with a gradient of 0-40% EtOAc in hexanes, to afford the title compound (3.82 g, 86%). The product is believed to be enriched in the (S)-isomer (see stereochemical rationale supra). $^1H$ NMR (400 MHz, $CDCl_3$) δ 7.56 (d, J=1.8 Hz, 1H), 7.32 (dd, J=8.1, 1.8 Hz, 1H), 7.28 (d, J=8.1 Hz, 1H), 5.91 (t, J=55.8 Hz, 1H), 4.19 (ddd, J=11.6, 6.4, 1.3 Hz, 1H), 3.91-3.75 (m, 1H), 3.29 (s, 1H), 2.40 (s, 3H), 1.88 (t, J=6.3 Hz, 1H). $^{19}F\{^1H\}$ NMR (376 MHz, CDCl$_3$) δ −128.20 (d, $J_{F-F}$=284.4 Hz), −132.44 (d, $J_{F-F}$=284.3 Hz).

Step 4. 3,3-Difluoro-2-(4-methyl-3-(4,4,5,5-tetramethyl-1,3,2-dioxaborolan-2-yl)phenyl)propane-1,2-diol (Enriched in One Enantiomer)

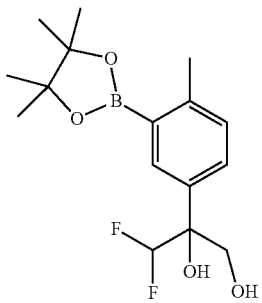 [SMILES: Cc1ccc(C(O)(CO)C(F)F)cc1B1OC(C)(C)C(C)(C)O1]

A mixture of 2-(3-chloro-4-methylphenyl)-3,3-difluoropropane-1,2-diol (from Step 3, believed to be enriched in the (S)-enantiomer, 2.4 g, 10.mmol), bis(pinacolato)diboron (7.7 g, 30 .mmol), potassium acetate (6.0 g, 61 mmol), Pd$_2$(dba)$_3$ (0.46 g, 0.51 mmol) and 2-dicyclohexylphosphino-2',4',6'-tri-iso-propyl-1,1'-biphenyl (0.97 g, 2.0 mmol) in dioxane (80 mL) was degassed by sparging with N$_2$ for 5 min. The reaction mixture was heated in a sealed vial at 120° C. for 3.5 h. Upon cooling to room temperature, the reaction mixture was diluted with EtOAc, filtered through Celite©, and concentrated under rotary evaporation. Purification via flash chromatography, eluting with a gradient of 0-40% EtOAc in hexanes, afforded the title compound (4.0 g, theoretical yield assumed). LCMS for C$_{16}$H$_{27}$BF$_2$NO$_4$ (M+NH$_4$)$^+$: m/z=346.2, found: 346.2.

Step 5. 2-(3-(5-Amino-6-chloropyrazin-2-yl)-4-methylphenyl)-3,3-difluoropropane-1,2-diol (Single Enantiomer Isolated, Believed to be the (S)-Isomer)

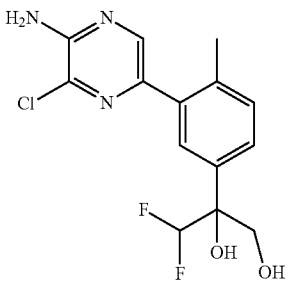 [SMILES: Cc1ccc(C(O)(CO)C(F)F)cc1-c1cnc(N)c(Cl)n1]

A mixture of 5-bromo-3-chloropyrazin-2-amine (2.3 g, 11 mmol), and 3,3-difluoro-2-(4-methyl-3-(4,4,5,5-tetramethyl-1,3,2-dioxaborolan-2-yl)phenyl)propane-1,2-diol (from Step 4, believed to be enriched in the (S)-enantiomer, 3.3 g, 10 .mmol) in dioxane (100 mL) was degassed by sparging with N$_2$ for 5 min. To the reaction mixture was added Na$_2$CO$_3$ solution (30 .mL, 30 .mmol) and PdCl$_2$ (dppf)-CH$_2$Cl$_2$ adduct (0.41 g, 0.51 mmol), and the mixture was degassed with N$_2$ for 2 min. The reaction mixture was heated at 100° C. for 3 h. Upon cooling, the reaction mixture was partitioned between water and EtOAc, and the biphasic mixture was filtered through Celite®. The layers were separated, and the aqueous layer was extracted with EtOAc (3×). The combined organic extracts were washed with brine, dried over MgSO$_4$, filtered, and concentrated. Purification via flash chromatography, eluting with a gradient from 0-70% EtOAc in hexanes, afforded the title compound (1.3 g, 38% yield over two steps). The enantiomers were separated via chiral HPLC (Phenomenex Lux Amylose-1, 21.2×250 mm, 5 μM, loading: 90 mg in 1.4 mL EtOH, eluting with 45% EtOH in hexanes at 20 mL/min). Peak 1 retention time: 8.2 min, Peak 2 retention time: 13.2 min. Peak 1 was the major enantiomer and was believed to be the (S)-enantiomer (see stereochemical rationale supra) and was used in Step 6 (0.80 g). LCMS for C$_{14}$H$_{15}$ClF$_2$N$_3$O$_2$ (M+H)$^+$: m/z=330.1, found: 330.0. $^1$H NMR (500 MHz, DMSO-d$_6$) δ 8.12 (s, 1H), 7.53 (d, J=1.9 Hz, 1H), 7.43 (dd, J=7.9, 2.0 Hz, 1H), 7.27 (d, J=8.0 Hz, 1H), 6.88 (s, 2H), 6.19 (t, J=55.6 Hz, 1H), 5.81 (s, 1H), 5.07 (t, J=5.5 Hz, 1H), 3.79-3.73 (m, 1H), 3.70-3.62 (m, 1H), 2.33 (s, 3H).

Step 6. 3-Amino-6-(5-(1,1-difluoro-2,3-dihydroxypropan-2-yl)-2-methylphenyl)pyrazine-2-carboxylic acid (Single Enantiomer Prepared)

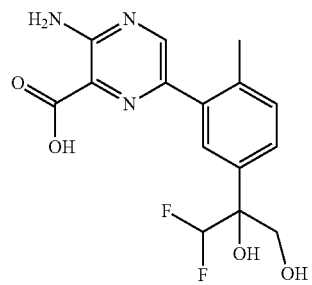 [SMILES: Cc1ccc(C(O)(CO)C(F)F)cc1-c1cnc(N)c(C(=O)O)n1]

Triethylamine (0.17 mL, 1.2 mmol) and dichloro[1,1'-bis(diphenylphosphino)ferrocene]palladium(II) dichloromethane adduct (25 mg, 0.031 mmol) were added to a solution of 2-(3-(5-amino-6-chloropyrazin-2-yl)-4-methylphenyl)-3,3-difluoropropane-1,2-diol (Peak 1 from Step 5, believed to be the (S)-enantiomer, 0.10 g, 0.31 mmol) in ethanol (6.0 mL). Carbon monoxide was bubbled through the solution for 10 min. The reaction mixture was heated at 80° C. under 1 atm of CO for 1.5 h. Volatiles were removed in vacuo. Flash chromatography, eluting with a gradient from 0-70% EtOAc in hexanes, afforded ethyl 3-amino-6-(5-(1,1-difluoro-2,3-dihydroxypropan-2-yl)-2-methylphenyl)pyrazine-2-carboxylate (0.10 g). LCMS for C$_{17}$H$_{20}$F$_2$N$_3$O$_4$ (M+H)$^+$: m/z=368.1, found: 368.1.

A solution of ethyl 3-amino-6-(5-(1,1-difluoro-2,3-dihydroxypropan-2-yl)-2-methylphenyl)pyrazine-2-carboxylate (0.10 g, 0.28 mmol) in MeOH (2.0 mL) was treated with a solution of LiOH (37 mg, 1.5 mmol) in water (2.0 mL). The mixture was stirred for 25 min, and MeOH was removed in vacuo. The aqueous mixture was acidified to pH=3 by the addition of 1.0 N HCl, saturated with NaCl, and extracted with EtOAc (4×). The combined organic extracts were dried over Na$_2$SO$_4$, filtered and concentrated to afford the title compound, which was used without further purification (91 mg, 87%). LCMS for C$_{15}$H$_{16}$F$_2$N$_3$O$_4$(M+H)$^+$: m/z=340.1, found: 340.1.

Step 7. 3-Amino-6-(5-(1,1-difluoro-2,3-dihydroxypropan-2-yl)-2-methylphenyl)-N-(tetrahydro-2H-pyran-4-yl)pyrazine-2-carboxamide (Single Enantiomer Prepared)

To a solution of 3-amino-6-(5-(1,1-difluoro-2,3-dihydroxypropan-2-yl)-2-methylphenyl)pyrazine-2-carboxylic acid (from Step 6, believed to be the (S)-enantiomer, 58 mg, 0.17 mmol) in DMF (2.0 mL) was added HATU (84 mg, 0.22 mmol), diisopropylethylamine (0.090 mL, 0.51 mmol), and tetrahydro-2H-pyran-4-amine (21 mg, 0.21 mmol, Combi-Blocks #AM-1004). The reaction mixture was stirred for 30 min, was diluted with EtOAc, and washed twice with water. The aqueous layers were combined and extracted with EtOAc (2×). The combined organic extracts were washed with brine, dried over $Na_2SO_4$, filtered and concentrated. Flash chromatography, eluting with a gradient of 0-100% EtOAc on hexanes, afforded 80 mg of oil. The oil was purified via preparative HPLC-MS (pH=10) and lyophilized to afford the title compound as a white powder (36 mg, 50%). The product is believed to be the (S)-enantiomer (see stereochemical rationale supra). LCMS for $C_{20}H_{25}F_2N_4O_4(M+H)^+$: m/z=423.2, found: 423.2. $^1$H NMR (500 MHz, DMSO-$d_6$) δ 8.38 (s, 1H), 8.32 (d, J=8.2 Hz, 1H), 7.71-7.50 (br s, 2H), 7.58 (d, J=1.5 Hz, 1H), 7.46 (dd, J=7.8, 2.2 Hz, 1H), 7.30 (d, J=8.0 Hz, 1H), 6.21 (t, J=55.6 Hz, 1H), 5.82 (s, 1H), 5.09 (s, 1H), 4.06-3.95 (m, 1H), 3.90-3.81 (m, 2H), 3.78 (d, J=11.2 Hz, 1H), 3.69 (d, J=11.1 Hz, 1H), 3.44-3.37 (m, 2H), 2.36 (s, 3H), 1.79-1.70 (m, 2H), 1.64 (qd, J=11.4, 4.3 Hz, 2H).

Compounds in Table 6 were prepared by the method of Example 42, using the appropriate amines instead of tetrahydro-2H-pyran-4-amine in Step 7. Where the compound was isolated as the TFA salt, preparative HPLC-MS (pH=2) conditions were used for purification. Where the compound was isolated as the free base, preparative HPLC-MS (pH=10) conditions were used for purification.

TABLE 6

| Example No. | Compound Name / 1H NMR | R | LCMS |
|---|---|---|---|
| 43 | 3-Amino-6-(5-((S)-1,1-difluoro-2,3-dihydroxypropan-2-yl)-2-methylphenyl)-N-((S)-1-hydroxypropan-2-yl)pyrazine-2-carboxamide, trifluoroacetate salt (single enantiomer) | HO-CH2-CH(CH3)-NH- | Calculated for $C_{18}H_{23}F_2N_4O_4$ $(M + H)^+$: m/z = 397.2, found: 397.1 |

$^1$H NMR (400 MHz, DMSO-$d_6$) δ 8.38 (s, 1H), 8.20 (d, J = 8.2 Hz, 1H), 7.80-7.49 (br s, 2H), 7.57 (d, J = 2.0 Hz, 1H), 7.46 (dd, J = 8.1, 2.0 Hz, 1H), 7.30 (d, J = 8.0 Hz, 1H), 6.21 (t, J = 55.5 Hz, 1H), 4.06-3.95 (m, 1H), 3.78 (d, J = 11.1 Hz, 1H), 3.69 (d, J = 11.1 Hz, 1H), 3.48-3.36 (m, 2H), 2.35 (s, 3H), 1.15 (d, J = 6.6 Hz, 3H).

| Example No. | Compound Name | R | LCMS |
|---|---|---|---|
| 44 | 3-Amino-6-(5-(1,1-difluoro-2,3-dihydroxypropan-2-yl)-2-methylphenyl)-N-(4-hydroxybicyclo[2.2.1]heptan-1-yl)pyrazine-2-carboxamide, trifluoroacetate salt (single enantiomer) | 4-hydroxybicyclo[2.2.1]heptan-1-yl-NH- | Calculated for $C_{22}H_{27}F_2N_4O_4$ $(M + H)^+$: m/z = 449.2, found: 449.1 |

$^1$H NMR (400 MHz, DMSO-$d_6$) δ 8.40 (s, 1H), 8.21 (s, 1H), 7.72-7.48 (br s, 2H), 7.59 (d, J = 2.0 Hz, 1H), 7.46 (dd, J = 7.9, 2.0 Hz, 1H), 7.30 (d, J = 8.1 Hz, 1H), 6.21 (t, J = 55.5 Hz, 1H), 3.82-3.73 (m, 1H), 3.73-3.65 (m, 1H), 2.36 (s, 3H), 2.09-1.94 (m, 2H), 1.93-1.79 (m, 4H), 1.78-1.63 (m, 2H), 1.63-1.39 (m, 2H).

| Example No. | Compound Name | R | LCMS |
|---|---|---|---|
| 45 | (3-Amino-6-(5-((S)-1,1-difluoro-2,3-dihydroxypropan-2-yl)-2-methylphenyl)pyrazin-2-yl)((R)-2-(hydroxymethyl)pyrrolidin-1-yl)methanone, trifluoroacetate salt (single enantiomer) | (R)-2-(hydroxymethyl)pyrrolidin-1-yl | Calculated for $C_{20}H_{25}F_2N_4O_4$ $(M + H)^+$: m/z = 423.2, found: 423.1 |
| 46 | (S)-3-Amino-6-(5-(1,1-difluoro-2,3-dihydroxypropan-2-yl)-2-methylphenyl)-N-isopropylpyrazine-2-carboxamide, trifluoroacetate salt (single enantiomer) | isopropyl-NH- | Calculated for $C_{18}H_{23}F_2N_4O_3$ $(M + H)^+$: m/z = 381.2, found: 381.1 |

TABLE 6-continued

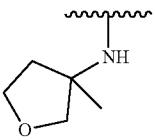 [SMILES: *NC1(C)CCOC1]

| Example No. | Compound Name 1H NMR | R | LCMS |
|---|---|---|---|

¹H NMR (400 MHz, DMSO-d₆) δ 8.37 (s, 1H), 8.16 (d, J = 8.4 Hz, 1H), 7.78-7.40 (br s, 2H), 7.57 (d, J = 2.0 Hz, 1H), 7.46 (dd, J = 7.9, 1.9 Hz, 1H), 7.30 (d, J = 8.0 Hz, 1H), 6.21 (t, J = 55.6 Hz, 1H), 4.16-4.00 (m, 1H), 3.78 (dd, J = 11.3, 2.2 Hz, 1H), 3.69 (dd, J = 11.2, 2.0 Hz, 1H), 2.35 (s, 3H), 1.18 (d, J = 6.6 Hz, 6H).

| 47 | 3-amino-6-(5-((S)-1,1-difluoro-2,3-dihydroxypropan-2-yl)-2-methylphenyl)-N-(3-methyltetrahydrofuran-3-yl)pyrazine-2-carboxamide, trifluoroacetate salt (mixture of two diastereomers) | 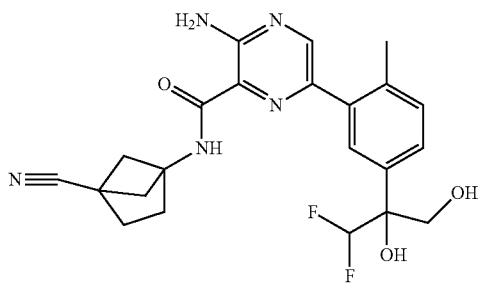 | Calculated for $C_{20}H_{25}F_2N_4O_4$ $(M + H)^+$: m/z = 423.2, found: 423.1 |

Example 48. 3-Amino-N-(4-cyanobicyclo[2.1.1]hexan-1-yl)-6-(5-(1,1-difluoro-2,3-dihydroxypropan-2-yl)-2-methylphenyl)pyrazine-2-carboxamide (Single Enantiomer Prepared)

Step 1. 2-(3-Chloro-4-methylphenyl)-1,1-difluoro-3-(trimethylsilyl)propan-2-ol

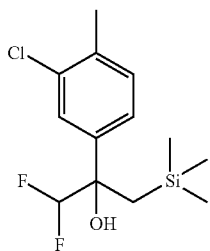 [SMILES: Cc1ccc(C(O)(C[Si](C)(C)C)C(F)F)cc1Cl]

A solution of ((trimethylsilyl)methyl)magnesium chloride (1.0 M in Et₂O, 67 mL, 67 mmol, Aldrich) was added dropwise to 1-(3-chloro-4-methylphenyl)-2,2-difluoroethan-1-one (9.1 g, 45 mmol, prepared as in Example 42, Step 1) in diethyl ether (56 ml) at 0° C. After complete addition of the organomagnesium solution, the mixture was stirred for 10 minutes at 0° C., then the reaction mixture was allowed to warm to ambient temperature and was stirred for 1.5 hours. The reaction mixture was cooled to 0° C. and was quenched by the dropwise addition of aq. HCl solution (2.0 N, 36 mL, 72 mmol). The mixture was warmed to room temperature and was diluted with water (100 mL) and extracted with MTBE (100 mL). The aqueous layer was separated and was extracted again with MTBE (3×50 mL). The combined organic extracts were washed successively with 2.0 N HCl, water, and brine, then dried over sodium sulfate, filtered and concentrated. The product was used without further purification (13 g, 99%). ¹H NMR (400 MHz, CDCl₃) δ 7.48 (d, J=1.8 Hz, 1H), 7.25 (dd, J=8.1, 1.8 Hz, 1H), 7.22 (d, J=8.1 Hz, 1H), 5.56 (t, J=57.1 Hz, 1H), 2.37 (s, 3H), 1.40 (dt, J=15.0, 1.2 Hz, 1H), 1.32 (d, J=15.1 Hz, 1H), −0.14 (s, 9H).

Step 2. 2-Chloro-4-(3,3-difluoroprop-1-en-2-yl)-1-methylbenzene

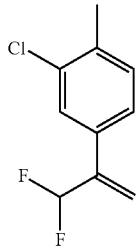

Trimethylsilyl trifluoromethanesulfonate (1.2 mL, 6.7 mmol) was added dropwise to a solution of 2-(3-chloro-4-methylphenyl)-1,1-difluoro-3-(trimethylsilyl)propan-2-ol (13 g, 45 mmol) in DCM (220 mL) at 0° C. The mixture was stirred for 10 minutes at 0° C., then was allowed to warm to ambient temperature and was stirred for 1.5 hours. The reaction flask was immersed in a water bath and saturated NaHCO₃ solution (120 mL) was introduced. The mixture was extracted with MTBE (180 mL). The aqueous layer was separated and extracted with additional MTBE (3×60 mL). The combined organic extracts were washed successively with saturated NaHCO₃ solution (120 mL), water (120 mL), and brine (140 mL), dried over $Na_2SO_4$, filtered and concentrated. The product was purified via flash column chromatography, eluting with 100% hexanes to afford the title compound (8.3 g, 92%). $^1$H NMR (400 MHz, $CDCl_3$) δ 7.47 (d, J=1.7 Hz, 1H), 7.28 (dd, J=8.1, 1.9 Hz, 1H), 7.23 (d, J=8.0 Hz, 1H), 6.35 (t, J=55.2 Hz, 1H), 5.72 (t, J=1.9 Hz, 1H), 5.66 (t, J=2.3 Hz, 1H), 2.39 (s, 3H). $^{19}$F{$^1$H} NMR (376 MHz, $CDCl_3$) δ −113.19 (s).

Step 3. 2-(3-Chloro-4-methylphenyl)-3,3-difluoropropane-1,2-diol (Enriched in One Enantiomer)

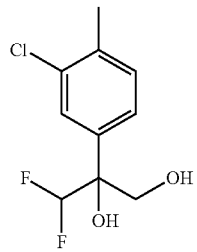

A solution of 2-chloro-4-(3,3-difluoroprop-1-en-2-yl)-1-methylbenzene (4.8 g, 24 mmol) in tert-butanol (64 mL) was added to a suspension of AD-mix-α (33 g, 72 mmol, Aldrich #392758) in water (63 mL) at 0° C. The mixture was then stirred at 3° C. for 3 days. Sodium sulfite (10 g) was added, and the resulting mixture was stirred for 10 minutes. Solvent was removed in vacuo, and the residue was partitioned between water and EtOAc. The layers were separated and the aqueous layer was extracted with two additional portions of EtOAc. The combined extracts were dried over $Na_2SO_4$, filtered and concentrated. Flash column chromatography, eluting with a gradient of 0-40% EtOAc in hexanes, afforded the title compound (5.0 g, 89%). The product is believed to be enriched in the (S)-isomer (see stereochemical rationale vide supra). $^1$H NMR (400 MHz, $CDCl_3$) δ 7.56 (d, J=1.8 Hz, 1H), 7.32 (dd, J=8.1, 1.7 Hz, 1H), 7.28 (d, J=8.0 Hz, 1H), 5.91 (t, J=55.8 Hz, 1H), 4.22-4.16 (m, 1H), 3.88-3.81 (m, 1H), 3.31 (s, 1H), 2.40 (s, 3H), 1.92 (t, J=6.4 Hz, 1H). $^{19}$F{$^1$H} NMR (376 MHz, $CDCl_3$) δ−128.19 (d, J=284.2 Hz), −132.47 (d, $J_{F\text{-}F}$=284.2 Hz).

Step 4. 3,3-Difluoro-2-(4-methyl-3-(4,4,5,5-tetramethyl-1,3,2-dioxaborolan-2-yl)phenyl)propane-1,2-diol (Enriched in One Enantiomer)

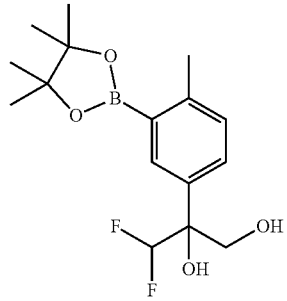 [SMILES: Cc1ccc(C(O)(CO)C(F)F)cc1B1OC(C)(C)C(C)(C)O1]

A degassed mixture of 2-(3-chloro-4-methylphenyl)-3,3-difluoropropane-1,2-diol (from Step 3, believed to be enriched in the (S)-enantiomer, 2.4 g, 10 mmol), bis(pinacolato)diboron (7.7 g, 30 mmol), potassium acetate (6.0 g, 61 mmol), $Pd_2(dba)_3$ (0.46 g, 0.51 mmol) and 2-dicyclohexylphosphino-2',4',6'-tri-iso-propyl-1,1'-biphenyl (0.97 g, 2.0 mmol) in dioxane (80 mL) was heated in a sealed vial at 120° C. for 3.5 hours. Upon cooling, the reaction mixture was diluted with EtOAc, filtered through Celite®, and concentrated. The product was purified via flash column chromatography, eluting with a gradient of 0-40% EtOAc in hexanes, to afford the title compound which was used without further purification in Step 5. Theoretical yield was assumed. LCMS for $C_{16}H_{27}BF_2NO_4$ $(M+NH_4)^+$: m/z=346.2, found: 346.2.

Step 5. 2-(3-(5-Amino-6-chloropyrazin-2-yl)-4-methylphenyl)-3,3-difluoropropane-1,2-diol (Single Enantiomer Isolated, Believed to be the (S)-Isomer)

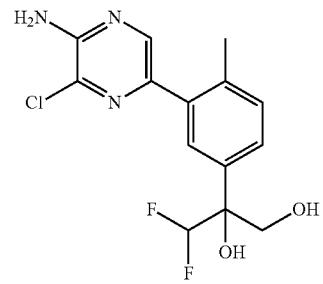 [SMILES: Cc1ccc(C(O)(CO)C(F)F)cc1-c1cnc(N)c(Cl)n1]

To a flask equipped with reflux condenser was added 5-bromo-3-chloropyrazin-2-amine (2.3 g, 11 mmol, Ark Pharm #AK-25099), 3,3-difluoro-2-(4-methyl-3-(4,4,5,5-tetramethyl-1,3,2-dioxaborolan-2-yl)phenyl)propane-1,2-diol (from Step 4, believed to be enriched in the (S)-enantiomer, 3.3 g, 10 mmol), and dioxane (100 mL). Sodium carbonate solution (30 mL, 30 mmol) and $PdCl_2(dppf)\text{-}CH_2Cl_2$ adduct (0.41 g, 0.51 mmol) were introduced, and the mixture was sparged with $N_2$ for 2 minutes. The reaction mixture was heated to 100° C. for 1 hour. Upon cooling to room temperature, saturated $NH_4Cl$ solution (100 mL) was added. The reaction mixture was stirred for 30 minutes and was extracted with EtOAc (3×). The combined organic extracts were dried over $MgSO_4$, filtered, and concentrated. The product was purified via flash column chromatography, eluting with a gradient of 0-70% EtOAc in hexanes, to afford the title compound. The enantiomers were separated via chiral HPLC (Phenomenex Lux Amylose-1, 21.2×250 mm, 5 μM, loading: 128 mg in 2.8 mL EtOH, eluting with 45% EtOH in hexanes at 20 mL/min). Peak 1 retention time: 8.3 min, Peak 2 retention time: 13.7 min. Peak 1 was the major enantiomer and was used in Step 6 (1.1 g, 33%). Peak 1 is believed to be the (S)-enantiomer (see stereochemical rationale vide supra). LCMS for $C_{14}H_{15}ClF_2N_3O_2$ $(M+H)^+$: monoisotopic m/z=330.1, found: 330.1.

Step 6. 3-Amino-6-(5-(1,1-difluoro-2,3-dihydroxy-propan-2-yl)-2-methylphenyl)pyrazine-2-carboxylic acid (Single Enantiomer Prepared)

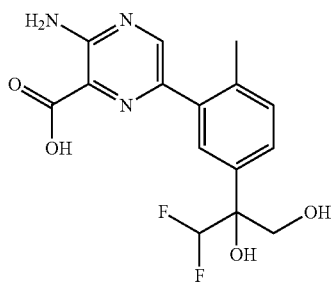

A solution of 2-(3-(5-amino-6-chloropyrazin-2-yl)-4-methylphenyl)-3,3-difluoropropane-1,2-diol (Peak 1 from Step 5, believed to be the (S)-enantiomer, 1.1 g, 3.3 mmol) in ethanol (44 mL) was treated with triethylamine (1.9 mL, 13 mmol) and $PdCl_2(dppf)\text{-}CH_2Cl_2$ adduct (0.27 g, 0.33 mmol). Carbon monoxide was bubbled through the mixture and the reaction was heated at 75° C. under an atmosphere of CO for 2.5 hours. Upon cooling to room temperature, the solvent was removed in vacuo. The product was purified via flash column chromatography, eluting with a gradient of 0-70% EtOAc in hexanes, to afford ethyl 3-amino-6-(5-(1,1-difluoro-2,3-dihydroxypropan-2-yl)-2-methylphenyl)pyrazine-2-carboxylate (1.0 g). LCMS for $C_{17}H_{20}F_2N_3O_4$ $(M+H)^+$: m/z=368.1, found: 368.1.

To a solution of ethyl 3-amino-6-(5-(1,1-difluoro-2,3-dihydroxypropan-2-yl)-2-methylphenyl)pyrazine-2-carboxylate (1.0 g, 2.7 mmol) in MeOH (22 mL) was added a solution of lithium hydroxide (0.40 g, 17 mmol) in water (22 mL). The reaction mixture was stirred for 1.5 hours and methanol was removed in vacuo. The aqueous mixture was acidified to pH=3 by the addition of 1.0 N HCl, saturated with NaCl, and extracted with EtOAc (4×). The combined organic extracts were dried over $Na_2SO_4$, filtered and concentrated to afford the title compound, which was used without further purification (1.0 g, 88%). LCMS for $C_{15}H_{16}F_2N_3O_4(M+H)^+$: m/z=340.1, found: 340.1.

Step 7. 3-Amino-N-(4-cyanobicyclo[2.1.1]hexan-1-yl)-6-(5-(1,1-difluoro-2,3-dihydroxypropan-2-yl)-2-methylphenyl)pyrazine-2-carboxamide (Single Enantiomer Prepared)

To a solution of 3-amino-6-(5-(1,1-difluoro-2,3-dihydroxypropan-2-yl)-2-methylphenyl)pyrazine-2-carboxylic acid (from Step 6, believed to be the (S)-enantiomer, 1.0 g, 2.9 mmol) in DMF (31 mL) was added HATU (1.5 g, 4.0 mmol) and N,N-diisopropylethylamine (2.2 mL, 12 mmol). To this mixture was added 4-aminobicyclo[2.1.1]hexane-1-carbonitrile, HCl salt (0.59 g, 3.7 mmol, from Example 40, Step 3). The reaction was stirred for 30 minutes and the mixture was diluted with EtOAc. The organic solution was washed with water (2×). The combined aqueous layers were extracted with EtOAc (2×). The combined organic extracts were washed with brine, dried over sodium sulfate, filtered and concentrated. The product was purified via flash column chromatography, eluting with a gradient of 0-70% EtOAc in hexanes, to afford a yellow oil (1.1 g). This product was subjected to purification via preparative HPLC-MS (pH 10) and lyophilized to afford the title compound (0.68 g, 50%). The product is believed to be the (S)-enantiomer (see stereochemical rationale vide supra). LCMS for $C_{22}H_{24}F_2N_5O_3(M+H)^+$: m/z=444.2, found: 444.2. $^1$H NMR (500 MHz, DMSO-$d_6$) δ 8.92 (s, 1H), 8.35 (s, 1H), 7.57 (br s, 2H), 7.53 (d, J=1.9 Hz, 1H), 7.45 (dd, J=8.0, 1.9 Hz, 1H), 7.28 (d, J=8.0 Hz, 1H), 6.19 (t, J=55.6 Hz, 1H), 5.80 (s, 1H), 5.08 (s, 1H), 3.77 (d, J=11.2 Hz, 1H), 3.68 (d, J=11.0 Hz, 1H), 2.35-2.33 (m, 2H), 2.32 (s, 3H), 2.05-1.99 (m, 2H), 1.97-1.95 (m, 2H), 1.95-1.90 (m, 2H). $^{19}$F NMR (470 MHz, DMSO-$d_6$) δ -129.72 (dd, J=277.3, 55.1 Hz), -134.28 (dd, J=277.4, 56.1 Hz).

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, VA) and maintained in RPMI with 10% FBS (Gibco/Life Technologies, Carlsbad, CA). For the assay, THP-1 cells are serum starved overnight in RPMI, then plated in RPMI ($2\times10^5$ cells/well in 90 μL) into 96-well flat-bottom tissue culture treated plates (Corning, Corning, NY), in the presence or absence of a concentration range of test compounds. Covered plates are incubated for 2 hours at 37° C., 5% $CO_2$ then treated with or without 10 nM MCP-1(MYBioSource, San Diego, CA) for 15 minutes at 37° C., 5% $CO_2$. Plates are centrifuged at 1600 RPM and supernatants are removed. Cells are lysed in Lysis Buffer (Cell Signaling, Danvers, MA) with Protease Inhibitor (Calbiochem/EMD, Germany), PMSF (Sigma, St Louis MO), HALTS (Thermo Fisher, Rockford, IL) for 30 min on wet ice. Cell lysates are frozen at -80° C. before testing. The lysates are tested in the Human/Mouse/Rat Phospho-RPS6 ELISA (R&D Systems, Inc. Minn, MN). The plate is measured using a microplate reader (SpectraMax M5—Molecular Devices, LLC Sunnyvale, CA) set to 450 nm with a wavelength correction of 540. $IC_{50}$ determination is performed by fitting the curve of inhibitor percent inhibition versus the log of the inhibitor concentration using the GraphPad Prism 5.0 software.

Example B. PI3K-γ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kγ (p110γ) Recombinant Human Protein was purchased from Life technology (Grand Island, NY). ATP, $MgCl_2$, DTT, EDTA, MOPS and CHAPS were purchased from Sigma Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software.

Example C. PI3Kδ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) Recombinant Human Protein was purchased from Eurofins (St Charles, MO). ATP, MgCl$_2$, DTT, EDTA, MOPS and CHAPS were purchased from Sigma Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 Ci [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). IC$_{50}$ determination was performed by fitting the curve of percent of the solvent control activity versus the log of the inhibitor concentration using the GraphPad Prism 6.0 software.

The compounds of the Examples were tested in the assays described in Examples A, B, and C and found to have the IC$_{50}$s are shown in Table A.

TABLE A

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 1a | + | + | # |
| 1b | ++ | ++ | NA |
| 2 | + | + | # |
| 3 | + | + | # |
| 4 | + | + | # |
| 5 | + | + | # |
| 6 | + | + | # |
| 7 | + | + | # |
| 9 | + | + | # |
| 10 | + | + | # |
| 11 | + | + | # |
| 12 | + | + | # |
| 13 | + | + | # |
| 14 | + | + | # |
| 15 | + | + | ## |
| 16 | + | + | # |
| 17 | + | + | # |
| 18 | + | + | # |
| 19 | + | ++ | ## |
| 20 | + | ++ | NA |
| 21 | + | + | # |
| 22 | + | ++ | # |
| 23 | + | ++ | ## |
| 24 | + | ++ | ## |
| 25 | + | ++ | NA |
| 26 | + | + | # |
| 27 | + | ++ | # |
| 28 | + | ++ | # |
| 29 | + | + | # |
| 30 | + | + | # |
| 31 | + | + | # |
| 32 | + | + | # |
| 33 | + | + | # |
| 34 | + | + | # |
| 35 | + | + | # |
| 36 | + | + | ## |
| 37 | + | + | # |
| 38 | + | +++ | ## |
| 39 | + | +++ | ## |
| 40 | + | + | # |
| 41 | + | + | # |
| 42 | + | + | # |
| 43 | + | ++ | ## |
| 44 | + | + | # |
| 45 | + | +++ | ## |
| 46 | + | + | # |
| 47 | + | + | # |
| 48 | + | + | # |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
\# refers to IC$_{50}$ of ≤100 nM;
\#\# refers to IC$_{50}$ of ≤500 nM;
\#\#\# refers to IC$_{50}$ of <1000 nM;
\#\#\#\# refers to an IC$_{50}$ of ≥1000 nM.
NA refers to data not available.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease or disorder in a patient, wherein the disease or disorder is associated with abnormal expression or activity of PI3Kγ kinase and is selected from the group consisting of colon cancer, gastric cancer, endometrial cancer, pancreatic cancer, renal cancer, breast cancer, skin cancer, head and neck squamous cell carcinoma, liver cancer, bladder cancer, astrocytoma, glioma, pancreatic cancer, and triple negative breast cancer, the method comprising administering to the patient a therapeutically effective amount of a compound of Formula (I):

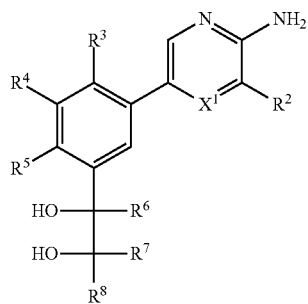

or a pharmaceutically acceptable salt thereof; wherein:
$X^1$ is N or $CR^1$;
$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;
$R^2$ is $C(O)NR^{c1}R^{d1}$;
$R^3$, $R^4$, and $R^5$ are each independently selected from H, D, halo, CN, OH, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, amino, $C_{1-6}$ alkylamino, di($C_{1-6}$ alkyl)amino, and $C(O)NR^cR^d$, wherein the $C_{1-6}$ alkyl is optionally substituted by 1, 2, 3, 4, 5, or 6 D;
$R^6$, $R^7$, and $R^8$ are each independently selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b3}$, $C(O)NR^{c3}R^{d3}$, $C(O)NR^{c3}(OR^{a3})$, $C(O)OR^{a3}$, $C(=NR^{e3})R^{b3}$, $C(=NOH)R^{b3}$, $C(=NCN)R^{b3}$, and $C(=NR^{e3})NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$, $R^7$, and $R^8$ are each optionally substituted with 1, 2, 3, 4, 5, 6, 7, or 8 independently selected $R^B$ substituents; and wherein the $C_{1-6}$ haloalkyl of $R^6$, $R^7$, or $R^8$ is optionally substituted by 1, 2, 3, or 4 independently selected Y substituents;
each Y is independently selected from D, halo, $C_{1-6}$ alkyl, and $C_{1-6}$ haloalkyl;
or $R^6$ and $R^7$ substituents, together with the ring atoms to which they are attached, form a $C_{3-10}$ cycloalkyl or 4-7 membered heterocycloalkyl, each of which is optionally substituted with 1, 2, 3, or 4 independently selected $R^B$ substituents;
or $R^7$ and $R^8$ substituents, together with the ring atoms to which they are attached, form a $C_{3-10}$ cycloalkyl or 4-7 membered heterocycloalkyl, each of which is optionally substituted with 1, 2, 3, or 4 independently selected $R^B$ substituents;
$R^c$ and $R^d$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^c$ and $R^d$, are each optionally substituted with 1, 2, 3, 4, 5, 6, 7, or 8 independently selected $R^M$ substituents;
each $R^{c1}$ and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, 4, 5, 6, 7, or 8 independently selected $R^A$ substituents;
or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, 4, 5, 6, 7, or 8 independently selected $R^A$ substituents;
each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{b3}$, $R^{c3}$, and $R^{d3}$ are each optionally substituted with 1, 2, 3, 4, 5, 6, 7, or 8 independently selected $R^B$ substituents;
or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^B$ substituents;
each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
each $R^A$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl- $C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{b4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOH)R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}C(=NOH)NR^{c4}R^{d4}$, $NR^{c4}C(=NCN)NR^{c4}R^{d4}$, $NR^{c4}S(O)R^{b4}$, $NR^{c4}$ $S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ is optionally substituted with 1, 2, 3, 4, 5, 6, 7, or 8 independently selected $R^D$ substituents;

each $R^B$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{b2},)$ $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}$ $C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}C(=NOH)NR^{c2}R^{d2}$, $NR^{c2}C(=NCN)NR^{c2}R^{d2}$, $NR^{c2}S(O)$ $R^{b2}$, $NR^{c2}S(O)NR^{c2}R^{d2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ is optionally substituted with 1, 2, 3, 4, 5, 6, 7, or 8 independently selected $R^M$ substituents;

each $R^{a2}$, $R^{b2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$, and $R^{d2}$ are each optionally substituted with 1, 2, 3, 4, 5, 6, 7, or 8 independently selected $R^M$ substituents;

or, any $R^{c2}$ and $R^{d2}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^M$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j2}$ and $R^{i2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$, and $R^{d4}$ are each optionally substituted with 1, 2, 3, 4, 5, 6, 7, or 8 independently selected $R^D$ substituents;

or, any $R^{c4}$ and $R^{d4}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^D$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{i4}$ and $R^{k4}$ is independently selected from OH, $C_{1-6}$ alkoxy, and $C_{1-6}$ haloalkoxy; or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{b5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOH)R^{b5}$, $C(=NCN)R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}C(=NOH)NR^{c5}R^{d5}$, $NR^{c5}C(=NCN)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{c5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^D$ are each optionally substituted with 1, 2, 3, or 4 independently selected $R^E$ substituents;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$, and $R^{d5}$ are each optionally substituted with 1, 2, 3, or 4 independently selected $R^E$ substituents;

or, any $R^{c5}$ and $R^{d5}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents; each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy; or any $R^{i5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^E$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{b6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}C(=NOH)NR^{c6}R^{d6}$, $NR^{c6}C(=NCN)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{c6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^E$ are each optionally substituted with 1, 2, 3, 4, 5, 6, 7, or 8 independently selected RG substituents;

each $R^{a6}$, $R^{b6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^G$ substituents;

or, any $R^{c6}$ and $R^{d6}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, 4, 5, 6, 7, or 8 independently selected $R^G$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{k6}$ is independently selected from OH, $C_{1-6}$ alkoxy, and $C_{1-6}$ haloalkoxy; or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl; and each $R^M$ is independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-7}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkyl aminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of claim 1, wherein each $R^A$ is independently selected from D, halo, $C_{1-6}$ alkyl, $C_{1-6}$ haloalkyl, CN, $OR^{a4}$, and $NR^{c4}R^{d4}$, wherein the $C_{1-6}$ alkyl, $C_{2-6}$ alkenyl, and $C_{2-6}$ alkynyl of $R^A$ are each optionally substituted with 1, 2, 3, or 4 independently selected $R^D$ substituents;

each $R^{a4}$, $R^{c4}$, and $R^{d4}$ is independently selected from H, $C_{1-6}$ alkyl, and $C_{1-6}$ haloalkyl, wherein the $C_{1-6}$ alkyl of $R^{a4}$, $R^{c4}$, and $R^{d4}$ are each optionally substituted with 1, 2, 3, or 4 independently selected $R^D$ substituents; and each $R^D$ is independently selected from D, OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

3. The method of claim 1, wherein each $R^{c1}$ and $R^{d1}$ is independently selected from H, $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, or 4 independently selected $R^A$ substituents;

or, any $R^{c1}$ and $R^{d1}$ attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^A$ substituents.

4. The method of claim 1, wherein $R^4$ is H, D, or $C_{1-6}$ alkyl, wherein the $C_{1-6}$ alkyl is optionally substituted with 1, 2, or 3 D.

5. The method of claim 1, wherein $R^5$ is H, D, or $C_{1-6}$ alkyl, wherein the $C_{1-6}$ alkyl is optionally substituted with 1, 2, or 3 D.

6. The method of claim 1, wherein $R^5$ is H.

7. The method of claim 1, wherein $R^6$ is H, D, $C_{1-6}$ alkyl, or $C_{1-6}$ haloalkyl, wherein each halogen is F, wherein the haloalkyl is optionally substituted with 1 or 2 independently selected Y substituents, and wherein each Y substituent is independently selected from D, halo, $C_{1-6}$ alkyl, and $C_{1-6}$ haloalkyl.

8. The method of claim 1, wherein $R^7$ is selected from H, D, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl is optionally substituted with 1, 2, or 3 D.

9. The method of claim 1, wherein $R^8$ is selected from H, D, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl is optionally substituted with 1, 2, or 3 D.

10. The method of claim 1, wherein $R^8$ is H.

11. The method of claim 1, wherein the compound of Formula (I) is a compound having Formula (II):

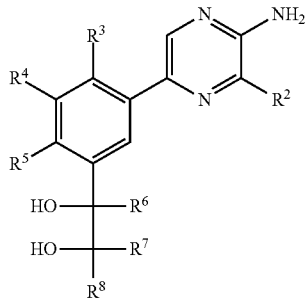

(II)

or a pharmaceutically acceptable salt thereof.

12. The method of claim 1, wherein:
$X^1$ is N or CH;
$R^2$ is $C(O)NR^{c1}R^{d1}$;
each $R^{c1}$ and $R^{d1}$ is independently selected from H, $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c1}$ and $R^{d1}$ are each optionally substituted with 1, 2, 3, or 4 independently selected $R^A$ substituents;
or, any $R^{c1}$ and $R^{d1}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1 or 2 independently selected $R^A$ substituents;
each $R^A$ is independently selected from D, halo, oxo, $C_{1-6}$ alkyl, $C_{1-6}$ haloalkyl, $C_{2-6}$ alkenyl, $C_{2-6}$ alkynyl, CN, $NO_2$ and $OR^{a4}$, wherein the $C_{1-6}$ alkyl, $C_{2-6}$ alkenyl, and $C_{2-6}$ alkynyl of $R^A$ is optionally substituted with 1 or 2 independently selected $R^D$ substituents;
each $R^{a4}$ is independently selected from H and $C_{1-6}$ alkyl, wherein the $C_{1-6}$ alkyl is optionally substituted CN, $NO_2$ or OH;
each $R^D$ is OH;
each $R^3$, $R^4$, and $R^5$ is independently selected from H, D, halo, CN, OH, Ci-3 alkyl, and Ci-3 haloalkyl, wherein the Ci-3 alkyl is optionally substituted by 1, 2, 3, 4, 5, or 6 D; and
each $R^6$, $R^7$, and $R^8$ is independently selected from H, D, $C_{1-6}$ alkyl and $C_{1-6}$ haloalkyl.

13. The method of claim 1, wherein:
$X^1$ is N;
$R^2$ is $C(O)NR^{c1}R^{d1}$;
$R^{c1}$ is H;
$R^{d1}$ is selected from ethyl, propyl, isopropyl, butyl, tert-butyl, cyclobutyl, cyclohexyl, bicyclo[1.1.1]pentanyl, bicyclo[2.1.1]hexanyl, bicyclo[2.2.1]heptanyl, methyl-cyclopropyl, methyl-cyclobutyl, methyl-phenyl, ethyl-phenyl, oxetanyl, tetrahydrofuranyl, tetrahydropyranyl, pyrrolidinyl, and thianyl, wherein the ethyl, propyl, isopropyl, tert-butyl, cyclobutyl, cyclohexyl, bicyclo [1.1.1]pentanyl, bicyclo[2.1.1]hexanyl, bicyclo[2.2.1]heptanyl, methyl-cyclopropyl, methyl-cyclobutyl, methyl-phenyl, ethyl-phenyl, oxetanyl, tetrahydrofuranyl, tetrahydropyranyl, pyrrolidinyl, and thianyl of $R^{d1}$ is optionally substituted with 1 or 2 independently selected $R^A$ substituents;
or, any $R^{c1}$ and $R^{d1}$, attached to the same N atom, together with the N atom to which they are attached, form an azetidinyl or pyrrolidinyl, wherein the azetidinyl or pyrrolidinyl is optionally substituted with 1 or 2 independently selected $R^A$ substituents;
each $R^A$ is independently selected from oxo, methyl, $CH_2F$, $CHF_2$, $CF_3$, $-OCH_3$, $-CH_2OH$, CN, and OH;
$R^3$ is selected from H, methyl, and $CD_3$;
$R^4$ and $R^5$ are each H;
$R^6$ is selected from $CH_2F$, $CHF_2$ and $CF_3$; and
$R^7$ and $R^8$ are each H.

14. The method of claim 1, wherein the compound of Formula (I) is selected from:
3-amino-6-(2-(methyl-$d_3$)-5-(1,1, 1-tri fluoro-2,3-dihydroxypropan-2-yl)phenyl)-N-(tetrahydro-2H-pyran-4-yl)pyrazine-2-carboxamide;
3-amino-6-(5-(1, 1-difluoro-2, 3-dihydroxypropan-2-yl)-2-(methyl-$d_3$)phenyl)-N-(4-hydroxybicyclo[2.2.1]heptan-1-yl)pyrazine-2-carboxamide;
3-amino-6-(2-(methyl-$d_3$)-5-(1, 1, 1-trifluoro-2,3-dihydroxybutan-2-yl)phenyl)-N-(tetrahydro-2H-pyran-4-yl)pyrazine-2-carboxamide;
3-amino-6-(2-methyl-5-(1, 1, 1-trifluoro-2, 3-dihydroxy-3-methylbutan-2-yl)phenyl)-N-(tetrahydro-2H-pyran-4-yl)pyrazine-2-carboxamide;
3-amino-N-((1 s,3R)-3-cyanocyclobutyl)-6-(2-(methyl-$d_3$)-5((S)-1, 1, 1-trifluoro-2,3-dihydroxypropan-2-yl) phenyl)pyrazine-2-carboxamide;
3-amino-N-((1s,2S)-2-hydroxycyclohexyl)-6-(2-(methyl-$d_3$)-5((S)-1, 1, 1-trifluoro-2, 3-dihydroxypropan-2-yl) phenyl)pyrazine-2-carboxamide;
3-amino-N-(trans)-3-hydroxytetrahydro-2H-pyran-4-yl)-6-(2-(methyl-$d_3$)-5((S)-1, 1, 1-trifluoro-2,3-dihydroxypropan-2-yl)phenyl)pyrazine-2-carboxamide;
3-amino-N(-1s,3R)-3-hydroxy-3-(trifluoromethyl)cyclobutyl)-6-(2-(methyl-$d_3$)-5-((S)-1,1, 1-trifluoro-2, 3-dihydroxypropan-2-yl)phenyl)pyrazine-2-carboxamide;
3-amino-N-(1s,3R)-3-hydroxy-1-methyl cyclobutyl)-6-(2-(methyl-$d_3$)-5((S)-1, 1, 1-trifluoro-2,3-dihydroxypropan-2-yl)phenyl)pyrazine-2-carboxamide;
(S)-3-amino-N-(4-(hydroxymethyl)bicyclo [2.1.1]hexan-1-yl)-6-(2-(methyl-$d_3$)-5-(1, 1, 1-trifluoro-2,3-dihydroxypropan-2-yl)phenyl)pyrazine-2-carboxamide;
(S)-3-amino-N-(3-(hydroxymethyl)bicyclo [1.1.1]pentan-1-yl)-6-(2-(methyl-$d_3$)-5-(1, 1, 1-trifluoro-2,3-dihydroxypropan-2-yl)phenyl)pyrazine-2-carboxamide;
3-amino-N—((S)-1-hydroxypropan-2-yl)-6-(2-(methyl-$d_3$)-5((S)-1, 1, 1-trifluoro-2, 3-dihydroxypropan-2-yl) phenyl)pyrazine-2-carboxamide;
(S)-3-amino-N-(2-cyano-2-methylpropyl)-6-(2-(methyl-$d_3$)-5-(1,1, 1-trifluoro-2,3-dihydroxypropan-2-yl)phenyl)pyrazine-2-carboxamide;
(S)-3-amino-N-(4-hydroxybicyclo [2.2.1]heptan-1-yl)-6-(2-(methyl-$d_3$)-5-(1, 1, 1-trifluoro-2,3-dihydroxypropan-2-yl)phenyl)pyrazine-2-carboxamide;
3-amino-N—((R)-1-hydroxypropan-2-yl)-6-(2-(methyl-$d_3$)-5((S)-1, 1, 1-trifluoro-2, 3-dihydroxypropan-2-yl) phenyl)pyrazine-2-carboxamide;

(S)-3-amino-N-(4-hydroxybicyclo[2.1.1]hexan-1-yl)-6-(2-(methyl-d$_3$)-5-(1, 1, 1-trifluoro-2,3-dihydroxypropan-2-yl)phenyl)pyrazine-2-carboxamide;

3-amino-6-(5-((S)-1,1-difluoro-2,3-dihydroxypropan-2-yl)-2-(methyl-d$_3$)phenyl)-N-((1S,2S)-2-hydroxycyclohexyl)pyrazine-2-carboxamide;

3-amino-6-(5-((S)-1,1-difluoro-2,3-dihydroxypropan-2-yl)-2-(methyl-d$_3$)phenyl)-N-((1R,2R)-2-hydroxycyclohexyl)pyrazine-2-carboxamide;

(S)-3-amino-N-(4-cyanobicyclo[2.1.1]hexan-1-yl)-6-(5-(1,1-difluoro-2,3-dihydroxypropan-2-yl)-2-(methyl-d$_3$)phenyl)pyrazine-2-carboxamide;

(S)-3-amino-6-(5-(1,1-difluoro-2,3-dihydroxypropan-2-yl)-2-(methyl-d$_3$)phenyl)-N-(tetrahydro-2H-pyran-4-yl)pyrazine-2-carb oxamide;

(S)-3-amino-6-(5-(1,1-difluoro-2,3-dihydroxypropan-2-yl)-2-methylphenyl)-N-(tetrahydro-2H-pyran-4-yl)pyrazine-2-carb oxamide;

3-amino-6-(5-((S)-1,1-difluoro-2,3-dihydroxypropan-2-yl)-2-methylphenyl)-N—((S)-1-hydroxypropan-2-yl)pyrazine-2-carboxamide;

3-amino-6-(5-(1,1-difluoro-2,3-dihydroxypropan-2-yl)-2-methylphenyl)-N-(4-hydroxybicyclo [2.2.1]heptan-1-yl)pyrazine-2-carboxamide;

(3-amino-6-(5-((S)-1,1-difluoro-2,3-dihydroxypropan-2-yl)-2-methylphenyl)pyrazin-2-yl)((R)-2-(hydroxymethyl)pyrrolidin-1-yl)methanone;

(S)-3-amino-6-(5-(1,1-difluoro-2,3-dihydroxypropan-2-yl)-2-methylphenyl)-N-isopropylpyrazine-2-carboxamide;

3-amino-6-(5-((S)-1,1-difluoro-2,3-dihydroxypropan-2-yl)-2-methylphenyl)-N-(3-methyltetrahydrofuran-3-yl)pyrazine-2-carb oxamide; and 3-amino-N-(4-cyanobicyclo[2.1.1]hexan-1-yl)-6-(5-(1,1-difluoro-2,3-dihydroxypropan-2-yl)-2-methylphenyl)pyrazine-2-carboxamide;

or an enantiomer, diastereomer or tautomer thereof;
or a pharmaceutically acceptable salt thereof.

15. The method of claim 1, wherein the compound of Formula (I) is (S)-3-amino-N-(4-cyanobicyclo[2.1.1]hexan-1-yl)-6-(5-(1,1-difluoro-2,3-dihydroxypropan-2-yl)-2-(methyl-d$_3$)phenyl)pyrazine-2-carboxamide; or an enantiomer, diastereomer or tautomer thereof; or a pharmaceutically acceptable salt thereof.

16. The method of claim 1, wherein the compound of Formula (I) is (S)-3-amino-6-(5-(1,1-difluoro-2,3-dihydroxypropan-2-yl)-2-methylphenyl)-N-(tetrahydro-2H-pyran-4-yl)pyrazine-2-carboxamide; or an enantiomer, diastereomer or tautomer thereof; or a pharmaceutically acceptable salt thereof.

17. The method of claim 1, wherein the disease or disorder is colon cancer.

18. The method of claim 1, wherein the disease or disorder is gastric cancer.

19. The method of claim 1, wherein the disease or disorder is endometrial cancer.

20. The method of claim 1, wherein the disease or disorder is pancreatic cancer.

21. The method of claim 1, wherein the disease or disorder is renal cancer.

22. The method of claim 1, wherein the disease or disorder is breast cancer.

23. The method of claim 1, wherein the disease or disorder is skin cancer.

24. The method of claim 1, wherein the disease or disorder is head and neck squamous cell carcinoma.

25. The method of claim 1, wherein the disease or disorder is liver cancer.

26. The method of claim 1, wherein the disease or disorder is bladder cancer.

27. The method of claim 1, wherein the disease or disorder is astrocytoma.

28. The method of claim 1, wherein the disease or disorder is glioma.

29. The method of claim 1, wherein the disease or disorder is pancreatic cancer.

30. The method of claim 1, wherein the disease or disorder is triple negative breast cancer.

* * * * *

UNITED STATES PATENT AND TRADEMARK OFFICE
CERTIFICATE OF CORRECTION

PATENT NO. : 11,926,616 B2
APPLICATION NO. : 17/540860
DATED : March 12, 2024
INVENTOR(S) : Stacey Shepard et al.

It is certified that error appears in the above-identified patent and that said Letters Patent is hereby corrected as shown below:

In the Claims

Column 175, Line 50: In Claim 1, delete "$R^7$ ," and insert -- $R^7$, --.

Column 177, Line 8: In Claim 1, before "$C(=NR^{e4})NR^{c4}R^{d4}$," insert -- $C(=NCN)R^{b4}$, --.

Column 177, Line 11: In Claim 1, delete "$NR^{c4}\ S(O)NR^{c4}R^{d4}$," and insert -- $NR^{c4}S(O)NR^{c4}R^{d4}$, --.

Column 177, Line 37: In Claim 1, delete "$NR^{c2}S(O)\ R^{b2}$," and insert -- $NR^{c2}S(O)R^{b2}$, --.

Column 178, Line 28: In Claim 1, delete "$R^{i2}$" and insert -- $R^{k2}$ --.

Column 178, Line 36: In Claim 1, delete "$R^{b4,}R^{c4}$," and insert -- $R^{b4}, R^{c4}$, --.

Column 179, Line 14: In Claim 1, delete "$R^{i4}$" and insert -- $R^{j4}$ --.

Column 179, Line 31: In Claim 1, delete "$NR^{c5}\ C(O)NR^{c5}R^{d5}$," and insert -- $NR^{c5}C(O)NR^{c5}R^{d5}$, --.

Column 179, Lines 35-36: In Claim 1, delete "$NR^{c5}\ S(O)NR^{c5}R^{d5}$," and insert -- $NR^{c5}S(O)NR^{c5}R^{d5}$, --.

Column 179, Line 43: In Claim 1, delete "$C_1$-6 alkyl-," and insert -- $C_{1-6}$ alkyl-, --.

Column 180, Line 26: In Claim 1, delete "$R^{i5}$" and insert -- $R^{j5}$ --.

Column 180, Line 42: In Claim 1, delete "$NR^{c6}C(O)NR^{c6}R^{d6}C(=NR^{e6})R^{b6}$," and insert -- $NR^{c6}C(O)NR^{c6}R^{d6}, C(=NR^{e6})R^{b6}$, --.

Column 180, Line 54: In Claim 1, delete "$C_1$-6 alkyl-," and insert -- $C_{1-6}$ alkyl-, --.

Signed and Sealed this
Twelfth Day of August, 2025

Coke Morgan Stewart
*Acting Director of the United States Patent and Trademark Office*

CERTIFICATE OF CORRECTION (continued)

U.S. Pat. No. 11,926,616 B2

Column 180, Line 58: In Claim 1, delete "RG" and insert -- $R^G$ --.

Column 180, Line 59: In Claim 1, delete "$R^{c6}$" and insert -- $R^{c6}$, --.

Column 181, Line 4: In Claim 1, delete "$R^{c6}$" and insert -- $R^{c6}$, --.

Column 181, Line 37: In Claim 1, delete "$R^{h6}$" and insert -- $R^{j6}$ --.

Column 182, Line 5: In Claim 2, delete "$NR^{c4}R^{d4}$," and insert -- $NR^{c4}R^{d4}$; --.

Column 182, Line 30: In Claim 3, delete "$R^{d1}$" and insert -- $R^{d1}$, --.

Column 183, Line 52: In Claim 12, delete "Ci-3 alkyl, and Ci-3 haloalkyl" and insert -- $C_{1-3}$ alkyl, and $C_{1-3}$ haloalkyl --.

Column 183, Line 53: In Claim 12, delete "Ci-3" and insert -- $C_{1-3}$ --.

Column 184, Line 21: In Claim 14, delete "(1,1, 1-tri fluoro" and insert -- (1,1,1-trifluoro --.

Column 184, Line 24: In Claim 14, delete "(1, 1" and insert -- (1,1 --.

Column 184, Line 24: In Claim 14, delete "2, 3" and insert -- 2,3 --.

Column 184, Lines 25-26: In Claim 14, delete "heptan- 1" and insert -- heptan-1 --.

Column 184, Line 27: In Claim 14, delete "(1, 1, 1" and insert -- (1,1,1 --.

Column 184, Line 30: In Claim 14, delete "(1, 1, 1" and insert -- (1,1,1 --.

Column 184, Line 30: In Claim 14, delete "2, 3" and insert -- 2,3 --.

Column 184, Line 34: In Claim 14, delete "((1 s,3R)" and insert -- ((1s,3R) --.

Column 184, Line 35: In Claim 14, delete "1, 1, 1" and insert -- 1,1,1 --.

Column 184, Line 37: In Claim 14, delete "((1s,2S)" and insert -- ((1S,2S) --.

Column 184, Line 38: In Claim 14, delete "1, 1, 1" and insert -- 1,1,1 --.

Column 184, Line 38: In Claim 14, delete "2, 3" and insert -- 2,3 --.

Column 184, Line 41: In Claim 14, delete "1, 1, 1" and insert -- 1,1,1 --.

Column 184, Line 43: In Claim 14, delete "N(-1s,3R)" and insert -- N-((1s,3R) --.

CERTIFICATE OF CORRECTION (continued)
U.S. Pat. No. 11,926,616 B2

Column 184, Line 44: In Claim 14, delete "1,1, 1" and insert -- 1,1,1 --.

Column 184, Line 47: In Claim 14, delete "methyl cyclobutyl)" and insert -- methylcyclobutyl) --.

Column 184, Line 48: In Claim 14, delete "1, 1, 1" and insert -- 1,1,1 --.

Column 184, Line 50: In Claim 14, delete "bicyclo [2.1.1]" and insert -- bicyclo[2.1.1] --.

Column 184, Line 51: In Claim 14, delete "(1, 1, 1" and insert -- (1,1,1 --.

Column 184, Line 53: In Claim 14, delete "bicyclo [1.1.1]" and insert -- bicyclo[1.1.1] --.

Column 184, Line 54: In Claim 14, delete "(1, 1, 1" and insert -- (1,1,1 --.

Column 184, Line 57: In Claim 14, delete "1, 1, 1" and insert -- 1,1,1 --.

Column 184, Line 57: In Claim 14, delete "2, 3" and insert -- 2,3 --.

Column 184, Line 60: In Claim 14, delete "(1,1, 1" and insert -- (1,1,1 --.

Column 184, Line 62: In Claim 14, delete "hydroxybicyclo [2.2.1]heptan- 1-yl)" and insert -- hydroxybicyclo[2.2.1]heptan-1-yl) --.

Column 184, Line 63: In Claim 14, delete "(1, 1, 1" and insert -- (1,1,1 --.

Column 184, Line 66: In Claim 14, delete "1, 1, 1" and insert -- 1,1,1 --.

Column 184, Line 66: In Claim 14, delete "2, 3" and insert -- 2,3 --.

Column 185, Line 2: In Claim 14, delete "(1, 1, 1" and insert -- (1,1,1 --.

Column 185, Line 15: In Claim 14, delete "carb oxamide;" and insert -- carboxamide; --.

Column 185, Line 18: In Claim 14, delete "carb oxamide;" and insert -- carboxamide; --.

Column 185, Line 23: In Claim 14, delete "(4-hydroxybicyclo [2.2.1]heptan-" and insert -- (4-hydroxybicyclo[2.2.1]heptan- --.

Column 185, Line 33: In Claim 14, delete "carb oxamide;" and insert -- carboxamide; --.